United States Patent
Thompson et al.

(10) Patent No.: US 9,944,637 B2
(45) Date of Patent: *Apr. 17, 2018

(54) P2X$_3$ AND/OR P2X$_{2/3}$ COMPOUNDS AND METHODS

(71) Applicant: Asana Biosciences, LLC, Bridgewater, NJ (US)

(72) Inventors: Scott K. Thompson, Phoenixville, PA (US); Aranapakam Venkatesan, Chadds Ford, PA (US); Tony Priestley, West Chester, PA (US); Mrinal Kundu, Kolkata (IN); Ashis Saha, Waltham, MA (US)

(73) Assignee: Asana Biosciences, LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/105,526

(22) PCT Filed: Dec. 16, 2014

(86) PCT No.: PCT/US2014/070497
§ 371 (c)(1),
(2) Date: Jun. 16, 2016

(87) PCT Pub. No.: WO2015/095128
PCT Pub. Date: Jun. 25, 2015

(65) Prior Publication Data
US 2016/0318927 A1    Nov. 3, 2016

Related U.S. Application Data

(60) Provisional application No. 61/916,499, filed on Dec. 16, 2013.

(51) Int. Cl.
| | | |
|---|---|---|
| C07D 471/04 | (2006.01) | |
| C07D 471/22 | (2006.01) | |
| A61K 31/437 | (2006.01) | |
| A61K 31/444 | (2006.01) | |
| A61K 31/4545 | (2006.01) | |
| A61K 31/496 | (2006.01) | |
| A61K 31/497 | (2006.01) | |
| A61K 31/506 | (2006.01) | |

(52) U.S. Cl.
CPC .......... *C07D 471/04* (2013.01); *A61K 31/437* (2013.01); *A61K 31/444* (2013.01); *A61K 31/4545* (2013.01); *A61K 31/496* (2013.01); *A61K 31/497* (2013.01); *A61K 31/506* (2013.01); *C07D 471/22* (2013.01)

(58) Field of Classification Search
None
See application file for complete search history.

(56) References Cited

U.S. PATENT DOCUMENTS

| | | |
|---|---|---|
| 4,906,474 A | 3/1990 | Langer et al. |
| 5,035,891 A | 7/1991 | Runkel et al. |
| 5,266,325 A | 11/1993 | Kuzma et al. |
| 5,292,515 A | 3/1994 | Moro et al. |
| 5,411,738 A | 5/1995 | Hind |
| 5,480,656 A | 1/1996 | Okada et al. |
| 5,575,815 A | 11/1996 | Slepian et al. |
| 5,633,002 A | 5/1997 | Sticker et al. |
| 5,827,528 A | 10/1998 | Kubo et al. |
| 6,036,976 A | 3/2000 | Takechi et al. |
| 6,039,967 A | 3/2000 | Ottoboni et al. |
| 6,432,937 B1 | 8/2002 | Hallgren |
| 6,464,688 B1 | 10/2002 | Harper et al. |
| 6,623,040 B1 | 9/2003 | Foley et al. |
| 6,709,406 B2 | 3/2004 | Laserow |
| 6,766,319 B1 | 7/2004 | Might |
| 6,894,071 B2 | 5/2005 | Nuijen et al. |
| 7,537,795 B2 | 5/2009 | Cormier et al. |
| 7,558,625 B2 | 7/2009 | Levin et al. |
| 7,736,665 B2 | 6/2010 | Patel et al. |
| 7,798,987 B2 | 9/2010 | Trautman et al. |
| 7,842,303 B2 | 11/2010 | Kuo et al. |
| 7,858,110 B2 | 12/2010 | Kuzma et al. |
| 9,238,647 B2 | 1/2016 | Burgey et al. |
| 2011/0046600 A1 | 2/2011 | Crank |
| 2011/0280922 A1 | 11/2011 | Ron et al. |
| 2012/0064181 A1 | 3/2012 | Burgey et al. |

FOREIGN PATENT DOCUMENTS

| | | |
|---|---|---|
| WO | 20070066068 A2 | 6/2007 |
| WO | 2010111058 A1 | 9/2010 |

OTHER PUBLICATIONS

International Search Report and Written Opinion for Application No. PCT/US2014/070497 dated Apr. 1, 2015.

(Continued)

*Primary Examiner* — Michael Barker
(74) *Attorney, Agent, or Firm* — DLA Piper LLP (US)

(57) ABSTRACT

The present application provides novel compounds and methods for preparing and using these compounds. In one embodiment, the compounds are of the structure of formula (I), wherein $R^1$-$R^4$ are defined herein. In a further embodiment, these compounds are useful in method for regulating one or both of the P2X$_3$ or P2X$_{2/3}$ receptors. In another embodiment, these compounds are useful for treating pain in patients by administering one or more of the compounds to a patient.

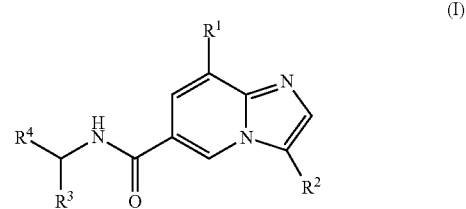

(I)

30 Claims, 8 Drawing Sheets

(56) References Cited

OTHER PUBLICATIONS

Binshtok, Anesthesiology, Jul. 2009, 111(1):127-137.
Ries, Anesthesiology, Jul. 2009, 111(1):122-126.
Gerner, Anesthesiology, Nov. 2008, 109(5):872-878.
Rautio, Nature Reviews Drug Discovery, 7:255-270 (2008).
Ettmayer, J. Med. Chem., 47:2393-2404 (2004).
Beaumont, Current Drug Metabolism, 4:461-485 (2003).
Simplicio, Molecules, 13:519-547 (2008).
Li, Bioorg. Med. Chem. Lett., 7:2909-2912 (1997).
Alexander, J. Med. Chem., 34:78-81 (1991).
Alexander, J. Med. Chem., 31:318-322 (1988).
Alexander, J. Med. Chem., 39:480-486 (1996).
Sagie & Kohane, "Prolonged Sensory-Selective Nerve Blockade", PNAS, 2010(8): 3740-3745, 2010.
Sullivan, "Dissolving Polymer Microneedle Patches for Influenza Vaccination", Nature Medicine, 16:915-920 (Jul. 18, 2010 online publication).
Lee, "Dissolving Microneedle Patch for Transdermal Delivery of Human Growth Hormone", Small, 7(4):531-539 (Jan. 4, 2011 online publication).
Sintov, "Radiofrequency-Driven Skin Microchanneling as a New Way for Electrically Assisted Transdermal Delivery of Hydrophilic Drugs", Controlled Release 89: 311-320 (2003).
Prausnitz and Langer, "Transdermal drug delivery", Nature Biotechnology, 26(11):1261-1268, Nov. 2006.
Witte, Naunyn-Schmeideberg's Arch. Pharmacol. 2011, 384:555-563.
Clouse, 2012, Urology 79:1410e1-1410e6.
Shimizu, 2000, British Journal of Pharmacology 131:610-616.
Sinshtok, Nature 449(4) 607-610, 2007.
Lilja, "Surfactant-Induced TRPVI activity—A Novel Mechanism for Eye Irritation?" Technological Sciences, 99 (1):174-180, 2007.
Hargreaves, "A new and sensitive method for measuring thermal nociception in cutaneous hyperalgesia", Pain 32: 77-88, 1988.
Burnstock, G. et al. (2012). "Purinergic Signaling in the Airways," *Pharmacological Reviews* 64(4): 834-868.
Thompson et al., U.S. Office Action dated Jan. 6, 2017, directed to U.S. Appl. No. 15/184,800; 11 pages.
Notification of the First Office Action dated Feb. 23, 2017, of corresponding Chinese Application No. 201480075680.1, along with an English translation.

P2X₃ AND/OR P2X₂/₃ COMPOUNDS AND METHODS

CROSS-REFERENCE TO PRIORITY APPLICATION

The present application is a national phase entry under 35 U.S.C § 371 of International Application No. PCT/US2014/070497 filed Dec. 16, 2014, which claims the benefit of the filing date of U.S. Provisional Application No. 61/916,499, filed Dec. 16, 2013, entitled P2X₃ and/or P2X₂/₃ Compounds and Methods, the disclosure of which are hereby incorporated herein by reference.

BACKGROUND

Adenosine triphosphate (ATP) is well-recognized as the primary energy currency of living cells, but has also emerged as a significant signaling molecule that can shape physiological and pathophysiological processes by interacting with any of several 'purinergic' membrane-associated receptor molecules. The purinergic receptor family comprises both G-protein-coupled (GPCR) receptors (assigned a P2Y nomenclature) and ligand-gated ion channel (P2X) variants. ATP elicits an excitatory effect on afferent sensory nerves via an interaction with receptors of the P2X subfamily. The consequence of such hyperexcitability may be interpreted as pain when the ATP effect is elicited in skin, bone or visceral tissues, as pain and/or cough in airway tissues, or as pain and/or instability when it occurs in the bladder. Two particular receptor variants within the P2X subfamily, designated P2X₃ and P2X₂/₃, have emerged as targets of particular interest in a variety of studies designed to measure nociception, airway or bladder function in rodents, since activation of these receptors by ATP is capable of generating the adverse events cited above.

Accordingly, there is a need for more potent and selective P2X₃/P2X₂/₃ modulators.

SUMMARY OF THE INVENTION

In one aspect, a compound of the structure of formula (I) is provided, wherein $R^1$-$R^4$ are described herein, or a pharmaceutically acceptable salt thereof.

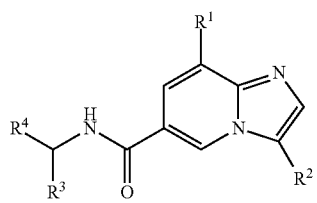

(I)

In another aspect, a compound of the structure of formula (II) is provided, which is embraced by formula (I), wherein $R^1$, $R^2$, and $R^4$ are described herein, or a pharmaceutically acceptable salt thereof.

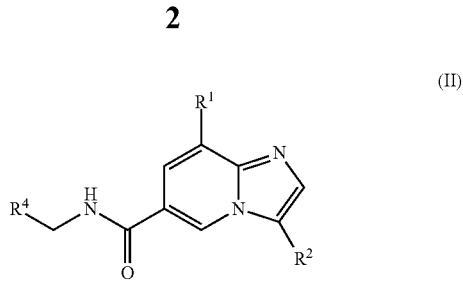

(II)

In a further aspect, a compound of the structure of formula (III) is provided, which is embraced by formula (I), wherein $R^1$, $R^2$, and $R^4$ are described herein, or a pharmaceutically acceptable salt or prodrug thereof.

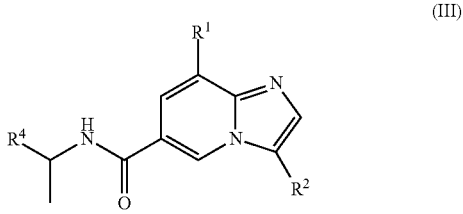

(III)

In yet another aspect, a compound of the structure of formula (IV) is provided, which is embraced by formula (I), wherein $R^2$ and $R^4$-$R^6$ are described herein, or a pharmaceutically acceptable salt thereof.

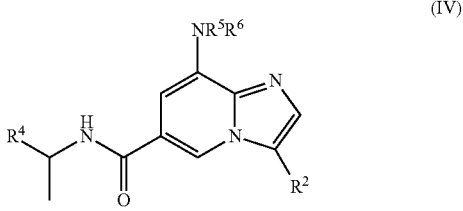

(IV)

In still a further aspect, a composition is provided and contains (i) a compound described herein and (ii) a pharmaceutically acceptable carrier.

In another aspect, a kit is provided and contains a compound described herein.

In yet a further aspect, a method for regulating activity of one or both of the P2X₃ or P2X₂/₃ receptors is provided and includes administering a compound described herein to a patient in need thereof. In one embodiment, the regulation is inhibition.

In a further aspect, a method for modulating one or both of the P2X₃ or P2X₂/₃ pathways is provided and includes administering a compound described herein to the patient.

In a still further aspect, a method for treating pain in a patient is provided and includes administering a compound described herein to the patient.

Other aspects and advantages of the invention will be readily apparent from the following detailed description of the invention.

DETAILED DESCRIPTION OF THE INVENTION

Figure 1A:
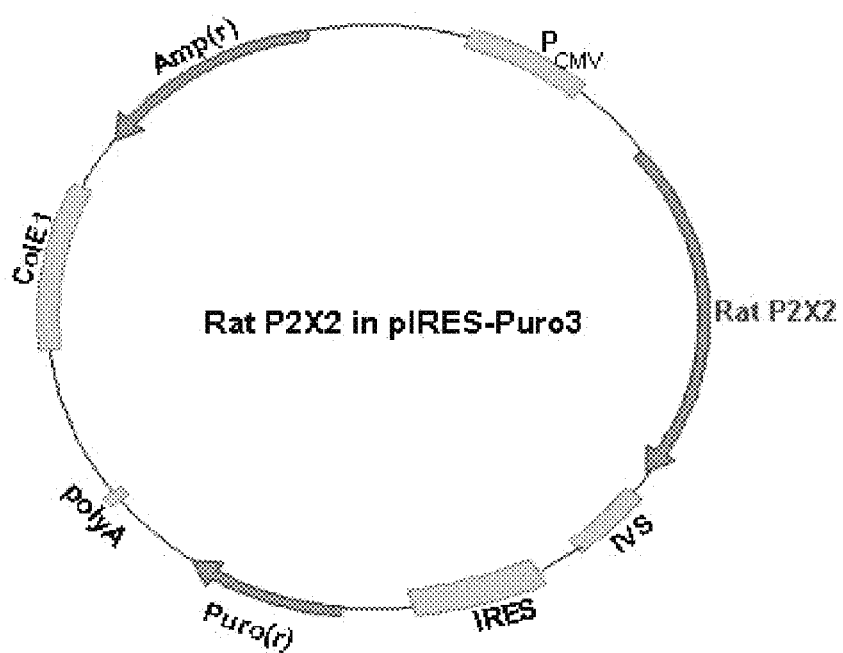
FIG. 1A is a map of a circular cloning plasmid pIRE-Spuro3 (Clontech Laboratories Inc., Mountain View, Calif.) into which the protein coding sequence of rat P2X2 has been cloned in the EcoRV-digested and dephosphorylated vector pIRES-puro3 within a multiple cloning site (MCS).

Discussed herein are novel compounds which have capabilities in modulating one or both of the $P2X_3$ or $P2X_{2/3}$ pathways. These compounds may be used to treat disease affected by a dysregulation of one or both of the $P2X_3$ or $P2X_{2/3}$ pathways.

The compounds discussed herein have the structure of formula (I).

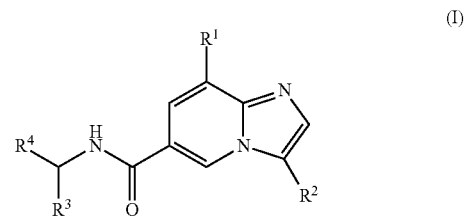

(I)

In this structure, $R^1$ is optionally substituted heteroaryl or $NR^5R^6$. In one aspect, $R^1$ is optionally substituted heteroaryl. In one embodiment, $R^1$ is optionally substituted heteroaryl. In another embodiment, $R^1$ is heteroaryl substituted with one or more halogen, $C_1$ to $C_6$ alkyl, $C_3$ to $C_6$ cycloalkyl, $C_3$ to $C_6$ cycloalkyl-$C_1$ to $C_6$ alkyl, $C_1$ to $C_6$ hydroxyalkyl, $C_1$ to $C_6$ alkoxy, $C_1$ to $C_6$ alkyl containing 1 to 3 fluorine atoms, or $CH_2CONH_2$. In a further embodiment, $R^1$ is oxadiazole, pyrazole, thiophene, or isoxazole. In yet another embodiment, $R^1$ is oxadiazole substituted with one or more $C_1$ to $C_6$ alkyl, pyrazole substituted with one or more $C_1$ to $C_6$ alkyl, pyrazole substituted with one or more $C_3$ to $C_6$ cycloalkyl-$C_1$ to $C_6$ alkyl, pyrazole substituted with one or more $C_1$ to $C_6$ alkyl containing 1 to 3 fluorine atoms, pyrazole substituted with one or more $CH_2CONH_2$ groups, thiophene substituted with one or more $C_1$ to $C_6$ alkyl, or isoxazole substituted with one or more $C_1$ to $C_6$ alkyl. In still a further embodiment, $R^1$ is oxadiazole substituted with one $C_1$ to $C_6$ alkyl, pyrazole substituted with one $C_1$ to $C_6$ alkyl, pyrazole substituted with one $C_3$ to $C_6$ cycloalkyl-$C_1$ to $C_6$ alkyl, pyrazole substituted with one $C_1$ to $C_6$ alkyl containing 1 fluorine atom, pyrazole substituted with one or more $CH_2CONH_2$ group, thiophene substituted with one $C_1$ to $C_6$ alkyl, or isoxazole substituted with one or two $C_1$ to $C_6$ alkyl. In another embodiment, $R^1$ is oxadiazole substituted with one ethyl, pyrazole substituted with one $CH_3$ or $CH_2CH_3$, pyrazole substituted with one —$CH_2$-cyclopropyl, pyrazole substituted with one $CH_2CH_2F$, pyrazole substituted with one or more $CH_2CONH_2$ group, thiophene substituted with one $CH_3$, or isoxazole substituted with two $CH_3$. In yet another embodiment, $R^1$ is 2-ethyl-1,3,4-oxadiazole, 1-methyl-pyrazole, 1-ethyl-pyrazole, 1-cyclopropylmethane-pyrazole, 1-fluoroethane-pyrazole, 1-carboxamidomethyl-pyrazole, 2-methyl-thiophene, or 3,5,-dimethyl-isoxazole.

In another aspect, $R^1$ is $NR^5R^6$. In one embodiment, $R^5$ and $R^6$ are, independently, chosen from H, optionally substituted $C_1$ to $C_6$ alkyl, $C_3$ or $C_6$ cycloalkyl, optionally substituted aryl, optionally substituted heteroaryl, or $CO(C_1$ to $C_6$ alkyl). In a further embodiment, $R^5$ and $R^6$ are optionally substituted phenyl. In another embodiment, $R^5$ and $R^6$ are phenyl substituted with fluorine or $C_1$ to $C_6$ alkoxy. In yet a further embodiment, one or both of $R^5$ and $R^6$ are optionally substituted thiazole. In still another embodiment, one or both of $R^5$ and $R^6$ are optionally substituted $C_1$ to $C_6$ alkyl or $C_3$ to $C_6$ cycloalkyl. In a further embodiment, one or both of $R^5$ and $R^6$ are 4-fluoro-phenyl or 2-methoxy-phenyl. In another embodiment, $R^5$ and $R^6$ are joined to form a 5 or 6-membered heterocyclic ring optionally substituted by one or more of halogen, $C_1$ to $C_6$ alkyl, $C_1$ to $C_6$ alkoxy, $C_1$ to $C_6$ hydroxyalkyl, $C_3$ to $C_6$ cycloalkyl, $C_3$ to $C_6$ cycloalkyl-$C_1$ to $C_6$ alkyl, $C_1$ to $C_6$ alkyl containing 1 to 3 fluorine atoms, or $CONH_2$. In a further embodiment, $R^5$ and $R^6$ are joined to form a heteroaryl. In still a further embodiment, $R^5$ and $R^6$ are joined to form an optionally substituted 5 or 6-membered heterocyclic ring. In yet another embodiment, $R^5$ and $R^6$ are joined to form an optionally substituted pyrrolidine, imidazole, pyrazole, tetrazole, triazole, piperidine, or piperazine. In a further embodiment, $R^5$ and $R^6$ are joined to form pyrrolidine optionally substituted with one or more $C_1$ to $C_6$ alkyl or $C_1$ to $C_6$ alkoxy. In another embodiment, $R^5$ and $R^6$ are joined to form imidazole substituted with one or more $C_1$ to $C_6$ alkyl. In still another embodiment, $R^5$ and $R^6$ are joined to form a pyrazole substituted with one or more $C_1$ to $C_6$ alkyl. In yet another embodiment, $R^5$ and $R^6$ are joined to form tetrazole substituted with one or more $C_3$ to $C_6$ cycloalkyl, $C_1$ to $C_6$ alkyl, $C_1$ to $C_6$ hydroxyalkyl, $C_1$ to $C_6$ alkyl containing 1-3 fluorine atoms, and $C_3$ to $C_6$ cycloalkyl-$C_1$ to $C_6$ alkyl. In a further embodiment, $R^5$ and $R^6$ are joined to form triazole substituted with one or more $C_3$ to $C_6$ cycloalkyl, $C_1$ to $C_6$ alkyl containing 1-3 fluorine atoms, and $C_1$ to $C_6$ alkyl. In another embodiment, $R^5$ and $R^6$ are joined to form piperidine substituted with one or more $C_1$ to $C_6$ alkoxy, halogen, $C_1$ to $C_6$ alkyl containing 1-3 fluorine atoms, $C_1$ to $C_6$ alkyl, or $CONH_2$. In yet another embodiment, $R^5$ and $R^6$ are joined to form piperazine substituted with $CONH_2$. In still a further embodiment, $R^5$ and $R^6$ are joined to form 3-methoxy-pyrrolidine, 3-methyl-3-methoxy-pyrrolidine, 2,5-dimethyl-imidazole, 5-ethyl-pyrazole, 5-propyl-tetrazole, 5-cyclopropyl-tetrazole, 5-propyl-tetrazole, 5-isopropyl-tetrazole, 5-ethyl-tetrazole, 5-cyclobutyl-tetrazole, 5-cyclopropylmethyl-tetrazole, 5-methyl-tetrazole, 5-hydroxymethyl-tetrazole, 5-difluoromethyl-tetrazole, 5-(2,2,2-trifluoroethyl)-tetrazole, 5-(1,1-difluoroethyl)-tetrazole, 5-cyclopropyl-triazole, 5-difluoromethyl-triazole, 5-trifluoromethyl-triazole, 5-methyl-triazole, 5-isopropyl-triazole, 5-propyl-triazole, 5-ethyl-triazole, 5-tert-butyl-triazole, 5-cyclobutyl-triazole, 5-(1,1-difluoroethyl)-triazole, 5-(2,2,2-trifluoroethyl)-triazole, 3,5-dimethyl-1,2,4-triazole, 4-methyl-piperidine, 4,4-dimethyl-piperidine, 4,4-difluoro-piperidine, 4-methyl-4-carboxamido-piperidine, 4-fluoro-piperidine, 4-trifluoromethyl-piperidine, 4-fluoromethyl-piperidine, 4-methyl-4-methoxy-piperidine, 4-methoxy-piperidine, 3-methoxy-piperidine, or 4-carboxamido-piperazine.

$R^2$ is optionally substituted aryl, optionally substituted heteroaryl, $C_1$ to $C_6$ alkyl, or $S$—$C_1$ to $C_6$ alkyl. In one embodiment, $R^2$ is optionally substituted aryl. In another embodiment, $R^2$ is optionally substituted phenyl. In a further embodiment, $R^2$ is phenyl substituted with one or more $C_1$ to $C_6$ alkyl. In yet another embodiment, $R^2$ is phenyl substituted with one $CH_3$. In still another embodiment, $R^2$ is 2-tolyl or 3-tolyl. In a further embodiment, $R^2$ is $C_1$ to $C_6$ alkyl. In another embodiment, $R^2$ is butyl. In still a further embodiment, $R^2$ is —$S$—($C_1$ to $C_6$ alkyl). In yet another embodiment, $R^2$ is $SCH_2CH_2CH_3$. In a further embodiment, $R^2$ is optionally substituted heteroaryl. In still another embodiment, $R^2$ is heteroaryl substituted with one or more halogen, cyano, $C_1$ to $C_6$ alkyl or $C_1$ to $C_6$ alkyl containing 1-3 fluorine atoms. In yet a further embodiment, $R^2$ is thiazole, thiophene, or furan. In another embodiment, $R^2$ is thiazole substituted with $C_1$ to $C_6$ alkyl. In still a further embodiment, $R^2$ is thiophene substituted with one or more of halogen, cyano, $C_1$ to $C_6$ alkyl or $C_1$ to $C_6$ alkyl containing 1-3 fluorine atoms. In yet another embodiment, $R^2$ is furan substituted with $C_1$ to $C_6$ alkyl. In a further embodiment, $R^2$ is 2-chloro-thiophene, 2-methyl-thiophene, 2-cyano-thiophene, 2-trifluoromethyl-thiophene, 5-methyl-thiazole, 2-methyl-thiazole, or 2-methyl-furan.

$R^3$ is H or $C_1$ to $C_6$ alkyl. In one embodiment, $R^3$ is H. In another embodiment, $R^3$ is $C_1$ to $C_6$ alkyl.

$R^4$ is optionally substituted heteroaryl. In one embodiment, $R^4$ is optionally substituted triazole, optionally substituted pyridine, optionally substituted pyridone, optionally substituted oxadiazole, optionally substituted pyrazine, or optionally substituted pyrimidine. In another embodiment, $R^4$ is heteroaryl optionally substituted with $C_1$ to $C_6$ alkyl, $C_3$ to $C_6$ cycloalkyl, $C_1$ to $C_6$ alkoxy, or $C_1$ to $C_6$ trifluoroalkyl. In a further embodiment, $R^4$ is pyridine substituted with one or more $C_1$ to $C_6$ alkyl, $C_3$ to $C_6$ cycloalkyl, $C_1$ to $C_6$ alkoxy, or $C_1$ to $C_6$ trifluoroalkyl. In yet another embodiment, $R^4$ is pyridine and the nitrogen atom of said pyridine is bound to an O-atom. In still a further embodiment, $R^4$ is pyrazine substituted with one or more $C_1$ to $C_6$ alkyl. In another embodiment, $R^4$ is pyrimidine substituted with one or more $C_1$ to $C_6$ alkyl or $C_1$ to $C_6$ alkoxy. In yet a further embodiment, $R^4$ is pyridone substituted with one or more $C_1$ to $C_6$ alkyl. In still another embodiment, $R^4$ is 1,2,4-triazole, 2-methyl-pyridine, 2-methoxy-pyridine, 1-oxo-pyridine, 1-oxo-2-methyl-pyridine, 1-oxo-2-trifluoromethyl-pyridine, 2-trifluoromethyl-pyridine, 2-cyclopropyl-pyridine, 1,3,4-oxadiazole, 1,2,4-oxadiazole, 3-methyl-1,2,4-oxadiazole, 2-methyl-1,3,4-oxadiazole, 2-methyl-pyrazine, 2-methyl-pyrimidine, 2-methoxy-pyrimidine, or 1-methyl-pyridone.

In one embodiment, the compound is of the structure of formula (II), wherein $R^1$, $R^2$, and $R^4$ are defined above.

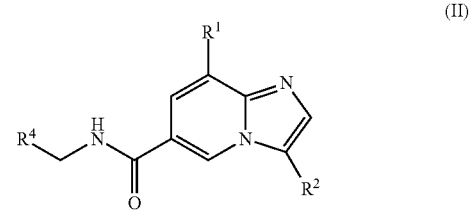

In another embodiment, the compound is of the structure of formula (III), wherein $R^1$, $R^2$, and $R^4$ are defined above.

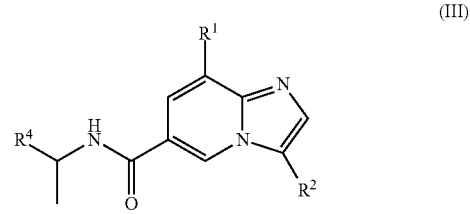

In a further embodiment, the compound is of the structure of formula (IV), wherein $R^2$ and $R^4$-$R^6$ are defined above.

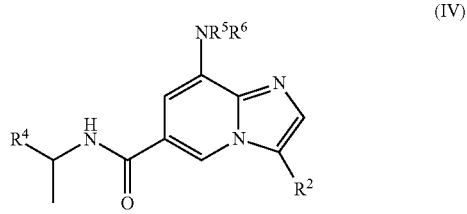

(IV)

Representative "pharmaceutically acceptable salts" include but are not limited to those of an acid or base. In one embodiment, the pharmaceutical salt is selected from among water-soluble and water-insoluble salts. The salt may be of an acid selected from, e.g., among acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, and camphorsulfonic. The salt can also be of a base selected from, e.g., sodium, potassium, calcium, and ammonium. In some embodiments, a composition of the invention may contain both a pharmaceutically acceptable salt and the free base form of a compound of the invention.

A compound of the invention may also be a prodrug of formula (I). Prodrugs of compounds of formula (I) may be prepared using various methods known to those skilled in the art. See, e.g., Rautio, Nature Reviews Drug Discovery, 7:255-270 (2008) and Ettmayer, J. Med. Chem., 47:2393-2404 (2004), which are hereby incorporated by reference. In the case of drugs containing a hydroxy moiety, acetyl and other ester analogs are contemplated for use as prodrugs. See, e.g., Beaumont, Current Drug Metabolism, 4:461-485 (2003), which is hereby incorporated by reference. In the case of drugs containing an amine moiety, prodrugs containing amides and carbamates are contemplated. See, e.g., Simplicio, Molecules, 13:519-547 (2008), which is hereby incorporated by reference. As specific examples, (alkoxycarbonyloxy)alkyl carbamates, (acyloxy)alkyl carbamates, and (oxodioxolenyl)alkyl carbamates may be utilized as effective prodrug strategies for amines. See, e.g., Li, Bioorg. Med. Chem. Lett., 7:2909-2912 (1997); Alexander, J. Med. Chem., 34:78-81 (1991); Alexander, J. Med. Chem., 31:318-322 (1988); and Alexander, J. Med. Chem., 39:480-486 (1996), all of which are incorporated by reference herein.

Some compounds described herein possess one or more chiral centers. Therefore, the disclosure of each compound includes its separate enantiomers as well as mixtures of the enantiomers. Where multiple chiral centers exist in the compounds, also provided are each possible combination of chiral centers within a compound, as well as all possible enantiomeric and diastereomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The following definitions are used in connection with the compounds described herein. In general, the number of carbon atoms present in a given group is designated "$C_x$ to $C_y$", where x and y are the lower and upper limits, respectively. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein is determined by naming from left to right the terminal portion of the functionality followed by the adjacent functionality toward the point of attachment. As used herein, "optionally substituted" means that at least 1 hydrogen atom of the optionally substituted group has been replaced.

"Alkyl" refers to a hydrocarbon chain that may be straight or branched. In one embodiment, an alkyl contains 1 to 6 (inclusive) carbon atoms. In another embodiment, an alkyl contains 1 to 5 (inclusive) carbon atoms. In a further embodiment, an alkyl contains 1 to 4 (inclusive) carbon atoms. In yet another embodiment, an alkyl contains 1 to 3 (inclusive) carbon atoms. In still a further embodiment, an alkyl contains 1 or 2 carbon atoms. Examples of alkyl groups that are hydrocarbon chains include, but are not limited to, methyl, ethyl, propyl, butyl, pentyl, and hexyl, where all isomers of these examples are contemplated.

Alkyl groups may also consist of or contain a cyclic alkyl radical, i.e., "carbocyclic ring" or "cycloalkyl". Examples of carbocyclic rings include, but are not limited to, cyclopropyl, cyclobutyl, cyclopentyl, cyclohexyl, and the like. In one embodiment, the carbocyclic ring is 3- to 6-membered. In another embodiment, the carbocyclic ring is a 3- to 5-membered ring. In a further embodiment, the carbocyclic ring is 4- to 6-membered. In still a further embodiment, the carbocyclic ring is 3- or 4-membered, i.e., cyclopropyl or cyclobutyl. Unless specifically noted, the alkyl groups are unsubstituted, i.e., they contain carbon and hydrogen atoms only. However, when the alkyl group or carbocyclic ring is substituted, it is prefaced with the term "optionally substituted" or "substituted". The optional substituents of the alkyl groups or carbocyclic rings include, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkyl-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), NHC(O)($C_1$ to $C_6$ alkyl), $NHSO_2$($C_1$ to $C_6$ alkyl), N($C_1$ to $C_6$ alkyl)$SO_2$($C_1$ to $C_6$ alkyl), $NH_2$, NH(aryl), N($C_1$ to $C_6$ alkyl)($C_1$ to $C_6$ alkyl), and NHC(O)$NH_2$.

"Alkoxy" refers to ∼O(alkyl), where the alkyl is optionally substituted and is defined above. In one embodiment, an alkoxy contains 1 to 6 (inclusive) carbon atoms or integers or ranges therebetween. In another embodiment, an alkoxy contains 1 to 5 (inclusive) carbon atoms or ranges therebetween. In a further embodiment, an alkoxy contains 1 to 4 (inclusive) carbon atoms. In still a further embodiment, an alkoxy contains 1 to 3 (inclusive) carbon atoms. In still a further embodiment, an alkoxy contains 1 or 2 carbon atoms. Examples of alkoxy include, but are not limited to, methoxy, ethoxy, propoxy, and butoxy. The alkyl radical of an alkoxy group can be unsubstituted or substituted as defined above for "alkyl".

"Aryl" refers to an aromatic hydrocarbon group containing carbon atoms. In one embodiment, the aryl contains 6 to 10 carbon atoms, i.e., 6-, 7-, 8-, 9- or 10-membered. In another embodiment, aryl is an aromatic or partly aromatic bicyclic group. In a further embodiment, the aryl is a phenyl group. In another embodiment, the aryl is naphthyl (such as α-naphthyl or β-naphthyl), 1,2,3,4-tetrahydronaphthyl, or indanyl. An aryl group can be unsubstituted or substituted with one or more groups including, without limitation, halogen, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), $NHSO_2$($C_1$ to $C_6$ alkyl), N($C_1$ to $C_6$ alkyl)$SO_2$($C_1$ to $C_6$ alkyl), $NH_2$, NH(aryl) or NHC(O)$NH_2$.

"Halogen" refers to F, Cl, Br and I.

The term "heteroatom" refers to a sulfur, nitrogen, or oxygen atom. "Heteroaryl" refers to a monocyclic aromatic 5- or 6-membered ring containing at least one ring heteroatom. In one embodiment, the heteroaryl contains 1 to 5 carbon atoms (inclusive) or integers or ranges therebetween. In another embodiment, the heteroaryl contains 2 to 5 carbon atoms (inclusive). In a further embodiment, the heteroaryl contains 3 to 5 carbon atoms (inclusive). In still a further embodiment, the heteroaryl contains 4 or 5 carbon atoms. "Heteroaryl" also refers to bicyclic aromatic ring systems wherein a heteroaryl group as just described is fused to at least one other cyclic moiety. In one embodiment, a phenyl radical is fused to a 5- or 6-membered monocyclic heteroaryl to form the bicyclic heteroaryl. In another embodiment, a cyclic alkyl is fused to a monocyclic heteroaryl to form the bicyclic heteroaryl. In a further embodiment, the bicyclic heteroaryl is a pyridine fused to a 5- or 6-membered monocyclic heteroaryl. In still a further embodiment, the heteroaryl ring has 1 or 2 nitrogen atoms in the ring. In still a further embodiment, the heteroaryl ring has 1 nitrogen atom and 1 oxygen atom. In still a further embodiment, the heteroaryl ring has 1 nitrogen atom and 1 sulfur atom. Examples of heteroaryl groups include, without limitation, furan, thiophene, indole, azaindole, oxazole, thiazole, isoxazole, isothiazole, imidazole, pyridine, pyridone, pyrazole, pyrimidine, pyrazine, pyridazine, pyrrole, oxadiazole such as 1,3,4-oxadiazole, triazole such as 1,2,4-triazole, tetrazole, benzoxazole, benzothiazole, benzofuran, benzisoxazole, benzimidazole, azabenzimidazole, indazole, quinazoline, quinoline, and isoquinoline. A heteroaryl may be unsubstituted or substituted with one or more groups including, without limitation, halogen, CN, $NO_2$, $C_1$ to $C_6$ alkyl, OH, $C_1$ to $C_6$ alkoxy, $C_3$ to $C_8$ cycloalkyl, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, $C_1$ or $C_6$ alkyl containing 1 to 3 fluorine atoms, $C_1$ to $C_6$ alkoxy containing 1 to 3 fluorine atoms, $C_3$ to $C_6$ cycloalkyl-$C_1$ to $C_6$ alkyl, $C_1$ to $C_6$ hydroxyalkyl, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), NHC(O)($C_1$ to $C_6$ alkyl), $NHSO_2$($C_1$ to $C_6$ alkyl), N($C_1$ to $C_6$ alkyl)$SO_2$($C_1$ to $C_6$ alkyl), $NH_2$, NH(aryl), N($C_1$ to $C_6$ alkyl)($C_1$ to $C_6$ alkyl) and NHC(O)$NH_2$.

"Heterocycle" refers to a monocyclic or bicyclic group in which at least 1 ring atom is a heteroatom. A heterocycle may be saturated or partially saturated. In one embodiment, the heterocycle contains 3 to 7 carbon atoms (inclusive) or integers or ranges therebetween. In another embodiment, the heterocycle contains 4 to 7 carbon atoms (inclusive). In a further embodiment, the heterocycle contains 4 to 6 carbon atoms (inclusive). In still a further embodiment, the heterocycle contains 5 or 6 carbon atoms (inclusive). Examples of heterocycles include, but are not limited to, aziridine, oxirane, thiirane, morpholine, thiomorpholine, pyrroline, pyrrolidine, azepane, dihydrofuran, tetrahydrofuran, dihydrothiophene, tetrahydrothiophene, dithiolane, piperidine, 1,2,3,6-tetrahydropyridine-1-yl, tetrahydropyran, pyran, thiane, thiine, piperazine, homopiperazine, oxazine, azecane, tetrahydroquinoline, perhydroisoquinoline, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 2,5-diazabicyclo[2.2.1]heptane-5-yl, 6-azabicyclo[3.2.1]oct-6-yl, 8-azabicyclo[3.2.1]octan-8-yl, 3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 3,4-dihydro-2H-1,4-benzoxazin-7-yl, thiazine, dithiane, and dioxane. In another embodiment, the heterocycle contains 1 or 2 nitrogen atoms. In a further embodiment, the heterocycle contains 1 or 2 nitrogen atoms and 3 to 6 carbon atoms. In still a further embodiment, the heterocycle contains 1 or 2 nitrogen atoms, 3 to 6 carbon atoms, and 1 oxygen atom. In a still a further embodiment, the heterocycle is 5- to 8-membered. In still a further embodiment, the heterocycle is 5-membered. In still a further embodiment, the heterocycle is 6-membered. In still a further embodiment, the heterocycle is 8-membered. A heterocycle may be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy-$C_1$ to $C_6$ alkoxy, $C_1$ to $C_6$ hydroxyalkyl, $C_3$ to $C_6$ cycloalkyl, $C_1$ to $C_6$ alkyl containing 1 to 3 fluorine atoms, $C_3$ to $C_6$ cycloalkyl-$C_1$ to $C_6$ alkyl, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), NHC(O)($C_1$ to $C_6$ alkyl), $NHSO_2$($C_1$ to $C_6$ alkyl), N($C_1$ to $C_6$ alkyl)$SO_2$($C_1$ to $C_6$ alkyl), $NH_2$, NH(aryl), N($C_1$ to $C_6$ alkyl)($C_1$ to $C_6$ alkyl) and NHC(O)$NH_2$.

"Alkylamino" refers to an NH or N group, the nitrogen atom of the group being attached to 1 or 2 alkyl substituents, respectively, wherein the alkyl is optionally substituted and defined above. The alkylamino is bound through the nitrogen atom of the group. In one embodiment, alkylamino refers to ⌇NH(alkyl). In another embodiment, alkylamino refers to ⌇N(alkyl)(alkyl), i.e., a "dialkylamino". In a further embodiment, alkylamino refers to ⌇N($C_1$ to $C_6$ alkyl)($C_1$ to $C_6$ alkyl). In still a further embodiment, alkylamino refers to ⌇N(alkyl)(heterocycle). In still a further embodiment, alkylamino refers to ⌇N(alkyl)(aryl). In still a further embodiment, alkylamino refers to ⌇N(alkyl)(heteroaryl). In still a further embodiment, alkylamino refers to ⌇N(alkyl)(alkenyl). When the nitrogen atom is bound to two alkyl groups, each alkyl group may be independently selected. In still a further embodiment, two alkyl groups on the nitrogen atom may be taken together with the nitrogen to which they are attached to form a 3- to 4-membered nitrogen-containing heterocycle where up to two of the carbon atoms of the heterocycle can be replaced with N(H), N($C_1$ to $C_6$ alkyl), N(aryl), N(heteroaryl), O, S(O), or $S(O)_2$. Examples of alkylamino include, but are not limited to N(CH₃)₂, N(CH₂CH₃)(CH₃), N(CH₂CH₃)₂, N(CH₂CH₂CH₃)₂, N(CH₂CH₂CH₂CH₃)₂, and N(CH(CH₃)₂)(CH₃).

"Arylamino" refers to an NH or N group, the nitrogen atom of the group being attached to 1 or 2 aryl substituents, respectively, wherein the aryl is optionally substituted and defined above. The arylamino is bound through the nitrogen atom of the group. In one embodiment, arylamino refers to ∼NH(aryl). In another embodiment, arylamino refers to ∼N(aryl)(aryl), i.e., a "diarylamino". When the nitrogen atom is bound to two aryl groups, each aryl may be independently selected.

"Alkylcarbonylamino" refers to ∼NHC(O)(alkyl) or ∼N(alkyl)C(O)(alkyl) where the alkyl groups are independently defined and independently optionally substituted as described above. Examples of alkylcarbonylamino include, but are not limited to, CH₃CONH, CH₃CH₂CONH, CH₃CH₂CH₂CONH, and CH₃CH(CH₃)CONH.

"Ester" refers to ∼C(O)O(alkyl), which is bound through the carbon atom. The alkyl group is defined and optionally substituted as described above. Examples of ester include, without limitation, C(O)OCH₃, C(O)O(CH₂CH₃), C(O)O(CH₂CH₂CH₃), and C(O)(O)(CH₂CH₂CH₂CH₃).

"Urea" refers to a group having a ∼NHC(O)NH ∼ where one of the nitrogen atoms is bound to an alkyl or heteroaryl group. The alkyl or heteroaryl groups are defined and optionally substituted as described above. Examples of urea include, without limitation, NHC(O)NHCH₃, NHC(O)NHCH₂CH₃, NHC(O)NHCH₂CH₂CH₃, and NHC(O)NHCH₂CH₂CH₂CH₃.

"Alkylaminocarbonyl" refers to ∼C(O)NH(alkyl) or ∼C(O)N(alkyl)(alkyl) where the alkyl groups are independently defined and independently optionally substituted as described above. Examples of alkylaminocarbonyl include, but are not limited to, CH₃NHCO, CH₃CH₂NHCO, CH₃CH₂CH₂NHCO, and CH₃CH(CH₃)NHCO.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively.

As used herein, the term "about" means a variability of 10% from the reference given, unless otherwise specified.

The term "regulation" or variations thereof as used herein refers to the ability of a compound of formula (I) to inhibit one or more components of a biological pathway.

As used herein, the terms "subject" and "patient" are used interchangeably and include a mammal, e.g., a human, mouse, rat, guinea pig, dog, cat, horse, cow, pig, or non-human primate, such as a monkey, chimpanzee, baboon or gorilla.

As used herein, the terms "disease", "disorder" and "condition" are used interchangeably, to indicate an abnormal state in a subject.

Unless defined otherwise in this specification, technical and scientific terms used herein have the same meaning as commonly understood by one of ordinary skill in the art and by reference to published texts, which provide one skilled in the art with a general guide to many of the terms used in the present application.

Pharmaceutical compositions described herein comprise a compound of formula (I) (which as used herein, includes compounds of formulae (II-IV) optionally with other pharmaceutically inert or inactive ingredients. In one embodiment, the pharmaceutically inert or inactive ingredient is one or more pharmaceutically acceptable carrier or excipient. Also contemplated is combining a compound of formula (I) with one or more therapeutic agents, i.e., active ingredients, as described below. In a further embodiment, a compound of formula (I) is combined with one or more inert/inactive ingredients and one or more therapeutic agents.

The pharmaceutical compositions of the invention comprise an amount of a compound of formula (I) that is effective for regulating $P2X_3$ or $P2X_{2/3}$, such as in the treatment of pain in a subject. Specifically, the dosage of the compound of formula (I) to achieve a therapeutic effect will depend on factors such as the formulation, pharmacological potency of the drug, age, weight and sex of the patient, condition being treated, severity of the patient's symptoms, specific compound of formula (I), route of delivery, and response pattern of the patient. It is also contemplated that the treatment and dosage of the compound of formula (I) may be administered in unit dosage form and that one skilled in the art would adjust the unit dosage form accordingly to reflect the relative level of activity. The decision as to the particular dosage to be employed (and the number of times to be administered per day) is within the discretion of the ordinarily-skilled physician, and may be varied by titration of the dosage to the particular circumstances to produce the therapeutic effect. Further, one of skill in the art would be able to calculate any changes in effective amounts of any one of the compounds of the compositions due to changes in the composition components or dilutions. In one embodiment, the compositions may be diluted 2-fold. In another embodiment, the compositions may be diluted 4-fold. In a further embodiment, the compositions may be diluted 8-fold.

In one embodiment, the therapeutically effective amount is about 0.0001% to about 25% w/v (i.e., weight of drug per mL of formulation). In another embodiment, the therapeutically effective amount is less than about 20% w/v, about 15% w/v, about 10% w/v, about 5% w/v, or about 1% w/v. In another embodiment, the therapeutically effective amount is about 0.0001% to about 10% w/v. In a further embodiment, the therapeutically effective amount is about 0.005 to about 5% w/v. In still a further embodiment, the therapeutically effective amount is about 0.01 to about 5% w/v. In still a further embodiment, the therapeutically effective amount is about 0.01% w/v, about 0.05% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 2% w/v, about 3% w/v, about 4% w/v, or about 5% w/v. In one embodiment, the therapeutically effective amount of the compound of formula (I) is about 0.2% w/v. In another embodiment, the therapeutically effective amount is about 0.5% w/v.

The therapeutically effect amount of the compound of formula (I) may, therefore, be about 1 mg to about 1000 mg per dose based on a 70 kg mammalian, for example human, subject. In another embodiment, the therapeutically effective amount is about 2 mg to about 250 mg per dose. In a further embodiment, the therapeutically effective amount is about 5 mg to about 100 mg. In yet a further embodiment, the therapeutically effective amount is about 25 mg to 50 mg, about 20 mg, about 15 mg, about 10 mg, about 5 mg, about 1 mg, about 0.1 mg, about 0.01 mg, about 0.001 mg.

The therapeutically effective amounts may be provided on regular schedule, i.e., on a daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every 2 weeks, about every 3 weeks, about every month, about every 2 months, about every 3 months and about every 6 months. The number and frequency of dosages corresponding to a completed course of therapy will be determined according to the judgment of a health-care practitioner. The therapeutically effective amounts described herein refer to total amounts administered for a given time period; that is, if more than one compound of formula (I) is administered, the therapeutically effective amounts correspond to the total amount administered.

The compound of formula (I) may be administered by any route, taking into consideration the specific condition for which it has been selected. The compounds of formula (I) may be delivered orally, by injection, inhalation (including orally, intranasally and intratracheally), ocularly, transdermally (via simple passive diffusion formulations or via facilitated delivery using, for example, iontophoresis, microporation with microneedles, radio-frequency ablation or the like), intravascularly, cutaneously, subcutaneously, intramuscularly, sublingually, intracranially, epidurally, rectally, intravesically, and vaginally, among others.

In one embodiment, the compound of formula (I) may be administered by injection, including microinjection, transdermally or topically. In one embodiment, the amount of the compound of formula (I) is about 0.05% w/w to about 10% w/w of the preparation depending on the route of administration. In one embodiment, the compound of formula (I) is present in a concentration of about 0.1% w/w to about 3% w/w. These compositions may also contain stabilizing agents, antibacterial agents, buffers and may be manufactured in different dosage unit ampoules or bottles. When for ocular use, the amount of the compound of formula (I) can be about 0.05% w/w to about 2.5% w/w. Compositions for injection or infusion may be prepared as an aqueous suspension or solution.

When used for dermal anesthesia, the amount of the compound of formula (I) can be about 0.1% w/w to about 10% w/w. When used for non-ocular, topical (e.g., oral, nasal, rectal, urethral, vaginal) administration the amount of the compound of formula (I) can be about 0.5% w/w to about 5% w/w. When used as in an injection, the amount of the compound of formula (I) can be about 0.25% w/w to about 3% w/w for injections. When used for infusions (e.g., for epidural, spinal or regional anesthesia), the amount of the compound of formula (I) can be about 0.1% w/w to about 3% w/w.

In one embodiment, the compound of formula (I) may be administered topically to the eye, e.g., as solutions, suspensions or ointments. Examples of ophthalmically compatible carriers which may be used include, without limitation, an aqueous solution, such as saline solution, oil solution or ointments containing ophthalmically compatible preservatives, surfactants, buffers, and viscosity regulators. These compositions may also contain stabilizing agents, antibacterial agents, and may be manufactured in different dosage units, suitable for ocular administration. Drug inserts, either soluble or insoluble, may also be used.

In another embodiment, the compound of formula (I) may be administered by injection. Solutions for injection or infusion may be prepared as aqueous solutions. In one embodiment, the compound of formula (I) is present in a concentration of about 0.1% w/w to about 3% w/w. These solutions may also contain stabilizing agents, antibacterial agents, buffers and may be manufactured in different dosage unit ampoules or bottles.

In a further embodiment, the compound of formula (I) may be administered rectally. Dosage units for rectal administration may be prepared in the form of ointments or suppositories, which contain the compound of formula (I) in a mixture with a neutral fat base, or they may be prepared in the form of gelatin-rectal capsules that contain the compound of formula (I) in a mixture with, e.g., a vegetable oil or paraffin oil. Ointments, suppositories or creams containing at least one compound of formula (I) are useful for the treatment of hemorrhoids.

In still another embodiment, the compound of formula (I) may be administered transdermally. A variety of transdermal delivery systems are known. For use in these systems, a compound of formula (I) may be admixed with a variety of excipients which may include, e.g., pH adjusters, preservatives, and/or penetration enhancers in order to form a solution, ointment, cream, lotion, or gel. Such a composition may form a constituent of a transdermal delivery system ("patch" etc.).

A transdermal delivery system may be selected which permits or assists a compound of the invention in passing through the dermal layer and to the targeted area, such as muscular tissues or a perineural space. Such systems may include formulation with skin penetration enhancers. Examples of skin penetration enhancers include physical enhancers (ultrasound, iontophoresis, electroporation, magnetophoresis, microneedle), vesicles, particulate systems (liposome, niosome, transfersome, microemulsion, solid lipid nanoparticle), and chemical enhancers (sulfoxides, azones, glycols, alkanols, terpenes, etc.). Further examples of chemical enhancers include, e.g., propylene glycol, polyethylene glycol, isopropanol, ethanol, oleic acid, N-methylpyrrolidone, which increase the permeability of the skin to the compounds, and permit the compounds to penetrate through the skin to deeper tissues. See, Sagie & Kohane, "Prolonged Sensory-Selective Nerve Blockade", PNAS, 2010(8): 3740-3745, 2010, which is herein incorporated by reference, for additional examples of chemical enhancers.

As a further embodiment, the compound of formula (I) may be instilled via direct instillation into the bladder and/or urothelium. In one example, a pharmaceutical composition containing a compound of formula (I) and one or more carriers or excipients is formulated for instillation. For example, the compound of formula (I) may be instilled as a solution. In a further example, the compound instilled may be placed into said bladder or urothelium as an extended-release formulation. A variety of extended-release formulations may be utilized for this purpose and include, without limitation, solution, suspension, gel or other solid dosage form containing reservoirs, a drug coated material, a drug impregnated material, a liposomal-drug formulation, among others.

The pharmaceutical compositions containing a compound of formula (I) may be formulated neat or with one or more pharmaceutical carriers and/or excipients for administration. The amount of the pharmaceutical carrier(s) is determined by the solubility and chemical nature of the compound of formula (I), chosen route of administration and standard pharmacological practice. The pharmaceutical carrier(s)

may be solid or liquid and may incorporate both solid and liquid carriers/matrices. A variety of suitable liquid carriers is known and may be readily selected by one of skill in the art. Such carriers may include, e.g., dimethylsulfoxide (DMSO), saline, buffered saline, cyclodextrin, hydroxypropylcyclodextrin (HPβCD), n-dodecyl-β-D-maltoside (DDM) and mixtures thereof. Similarly, a variety of solid (rigid or flexible) carriers and excipients are known to those of skill in the art. Such carriers may also be designed so as to undergo a state transition when injected into the bladder (e.g., liquid to gel, liquid to solid, gel to solid); such materials are known to those skilled in the art. Such carriers may also comprise a membrane, for example comprising a thermoelastic polymer, which defines a reservoir containing a solid or liquid composition. Such carriers may also comprise a thermoelastic polymer matrix, in which a composition which contains a compound of formula (I) is embedded.

The compounds of formula (I) can also be administered together with other-membrane stabilizers (local anesthetics), for example to form eutectic mixtures.

Although the compound of formula (I) may be administered alone, it may also be administered in the presence of one or more pharmaceutical carriers that are physiologically compatible. The carriers may be in dry or liquid form and must be pharmaceutically acceptable. Liquid pharmaceutical compositions may be sterile solutions or suspensions. When liquid carriers are utilized, they may be sterile liquids. Liquid carriers may be utilized in preparing solutions, suspensions, emulsions, syrups and elixirs. In one embodiment, the compound of formula (I) is dissolved a liquid carrier. In another embodiment, the compound of formula (I) is suspended in a liquid carrier. One of skill in the art of formulations would be able to select a suitable liquid carrier, depending on the route of administration. The compound of formula (I) may alternatively be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, a solid carrier may also act as a flavoring agent, lubricant, solubilizer, suspending agent, filler, glidant, compression aid, binder, disintegrant, or encapsulating material. In one embodiment, a solid carrier acts as a lubricant, solubilizer, suspending agent, binder, disintegrant, or encapsulating material. In another embodiment, the carrier comprises a thermoelastic polymer defining a reservoir containing at a minimum, at least one compound of formula (I) as a solid or liquid composition. In a further embodiment, such carriers comprise a thermoelastic polymer matrix, in which a composition described herein is embedded.

The composition may also be sub-divided to contain appropriate quantities of the compound of formula (I). For example, the unit dosage can be packaged compositions, e.g., packeted powders, vials, ampoules, prefilled syringes or sachets containing liquids.

In one embodiment, compositions described herein optionally contain one or more carriers and one or more excipients, and one or more compounds of formula (I). Examples of suitable excipients include without limitation, surfactants, adjuvants, antioxidants, binders, buffers, coatings, coloring agents, compression aids, diluents, disintegrants, emulsifiers (e.g., polyoxyethylene fatty acid esters), emollients, encapsulating materials, fillers, flavoring agents, glidants, granulating agents, lubricants, metal chelators, osmo-regulators, pH adjustors (e.g., sodium hydroxide), preservatives, solubilizers, sorbents, stabilizing agents, sweeteners (such as saccharin), surfactants, suspending agents, syrups, thickening agents (e.g., carboxypolymethylene or hydroxypropylmethylcellulose), penetration enhancers (e.g., hydroxypolyethoxydodecane, DMSO, DMAC, DDM, etc.) or viscosity regulators (such as polymers to increase viscosity). See, for example, the excipients described in the "Handbook of Pharmaceutical Excipients", 5$^{th}$ Edition, Eds.: Rowe, Sheskey, and Owen, APhA Publications (Washington, D.C.), Dec. 14, 2005, which is incorporated herein by reference.

In one embodiment, the compositions may be utilized as inhalants. For this route of administration, compositions may be prepared as fluid unit doses using a compound of formula (I) and a vehicle for delivery by an atomizing spray pump or by dry powder for insufflation.

In another embodiment, the compositions may be utilized as aerosols, i.e., oral or intranasal. For this route of administration, the compositions are formulated for use in a pressurized aerosol container together with a gaseous or liquefied propellant, e.g., dichlorodifluoromethane, carbon dioxide, nitrogen, propane, and the like. Also provided is the delivery of a metered dose in one or more actuations.

In another embodiment, the compositions may be administered by a modified-release delivery device. "Modified-release" as used herein refers to delivery of a compound of formula (I) which is controlled, for example over a period of at least about 8 hours (e.g., extended delivery) to at least about 12 hours (e.g., sustained delivery). Such devices may also permit immediate release (e.g., therapeutic levels achieved in under about 1 hour, or in less than about 2 hours). Those of skill in the art know suitable modified-release delivery devices. For use in such modified-release delivery devices, the compound of formula (I) is formulated as described herein.

Suitable modified release delivery devices include drug-eluting implants. Such implants can comprise a thermoelastic polymer matrix, such as a silicon or ethylene vinyl acetate matrix, wherein one or more compounds of formula (I), optionally with one or more excipients, is embedded. See, e.g., U.S. Pat. No. 7,736,665 and US Patent Publication No. US-2011/0280922, the disclosures of which are herein incorporated by reference. Other drug-eluting implants can comprise an "osmotic pump" or other mechanism by which a solution comprising one or more compounds of formula (I) (optionally with one or more excipients) contained within the device is forced out, for example through the implant walls or through one or more apertures, by osmotic pressure which builds within the device once it is implanted into a subject. See, e.g., U.S. Pat. Nos. 5,035,891 and 6,464,688, the disclosures of which are herein incorporated by reference. Still other drug-eluting implants can comprise a hydrogel such as a polymethacrylate-based polymer (e.g., U.S. Pat. Nos. 5,292,515 and 5,266,325, the disclosures of which are herein incorporated by reference), or a thermoelastic polymer, such as a polyurethane (e.g., U.S. Pat. Nos. 7,858, 110 and 7,842,303, the disclosures of which are herein incorporated by reference), which define a reservoir containing a solid or liquid composition comprising one or more compounds of formula (I) optionally with one or more excipients. Still other drug-eluting implants can comprise a bio-degradable or bio-erodable polymer and at least one or more compounds of formula (I), optionally with one or more excipients. See, e.g., U.S. Pat. Nos. 4,906,474 and 5,633, 002, the disclosures of which are herein incorporated by reference.

Modified release of the compounds of formula (I) may also be achieved by injecting a composition comprising one or more of these compounds into the bladder tissue (e.g., into the urothelium or muscularis propria) with a device that can be employed via an endoscope inserted into the bladder or percutaneously. For example, one or more compounds of formula (I) can be injected into the bladder tissue via a needle, or a needleless device as described in US Patent Publication No. US-2011/0046600, the disclosure of which is incorporated by reference. A suitable needleless injection device includes the JetTouch™ platform (American Medical Systems; Minnetonka, Minn.). The injected compounds can form a depot, and in certain embodiments, the one or more compounds of formula (I) can be encapsulated in a biodegradable or bio-erodable polymer, for example as described in U.S. Pat. Nos. 5,480,656 and 6,036,976, the disclosures of which are incorporated by reference.

Modified release of the compounds of formula (I) may also be achieved by instilling a composition comprising one or more compounds of formula (I) and a material which solidifies or gels, for example once instilled into the bladder or upon contact with the bladder urothelium, to coat at least a portion of the bladder wall. The one or more compounds of formula (I) can then elute from the solidified or gelled material. See, e.g., U.S. Pat. Nos. 6,894,071; 5,575,815 and 6,039,967, the disclosures of which are incorporated by reference.

In still a further embodiment, the compositions may be administered transdermally, i.e., via the use of a drug-eluting patch. In one embodiment, the patch is an "iontophoretic" transdermal patch in which one or more medication(s) is delivered using a simple or more sophisticated, e.g., microprocessor-controlled, electrical current using, for example, an on-board battery. In still a further embodiment, the patch is a "microneedle" transdermal patch which contains microneedles coated with or containing (in dissolvable or non-dissolvable form) a pharmaceutical composition of the invention. See, e.g., U.S. Pat. Nos. 7,798,987 and 7,537,795, the disclosures of which are herein incorporated by reference. The microneedles can themselves be dissolvable or non-dissolvable; see, for example, the "microneedle" technology described in Sullivan, "Dissolving Polymer Microneedle Patches for Influenza Vaccination", Nature Medicine, 16:915-920 (Jul. 18, 2010 online publication) and Lee, "Dissolving Microneedle Patch for Transdermal Delivery of Human Growth Hormone", Small, 7(4):531-539 (Jan. 4, 2011 online publication), which are herein incorporated by reference. Other suitable transdermal delivery systems include the radio-frequency ablations systems described in Sintov, "Radiofrequency-Driven Skin Microchanneling as a New Way for Electrically Assisted Transdermal Delivery of Hydrophilic Drugs", Controlled Release 89: 311-320 (2003), and U.S. Pat. No. 7,558,625, the disclosures of which are herein incorporated by reference.

Further examples of transdermal patches useful for administration of the compounds of formula (I) include those described in U.S. Pat. Nos. 5,411,738 and 5,827,528 and Prausnitz and Langer, "Transdermal drug delivery", Nature Biotechnology, 26(11):1261-1268, November 2006, which are herein incorporated by reference. In one embodiment, a patch is applied via a suitable adhesive on the skin, where it remains in place for at least one hour. In a further embodiment, the patch remains in place for about 1 hour and is replaced weekly, for a total of about 2 or about 3 hours wear time. In another embodiment, the patch remains in place for about 2 hours. In a further embodiment, the patch remains in place for about 3 hours. In still another embodiment, the patch remains in place for about 4 hours. In yet another embodiment, the patch remains in place for longer or shorter periods of time.

Also contemplated is the administration of the compounds of formula (I) with other medication(s) or therapeutic agent(s). In one embodiment, the compounds of formula (I) are combined with other medications or therapeutic agents in a single composition. In other embodiments, the compounds of formula (I) may be administered in one or more separate formulations from other compounds of formula (I), or other medications or therapeutic agents as described below.

In one embodiment, the compounds of the invention may be utilized for regulating $P2X_3$ or $P2X_{2/3}$ (such as treating pain) when combined with a TRPV1 receptor activator. The term "TRPV1 receptor activator" as used herein refers to any agent or stimulus that activates TRPV1 receptors on nociceptors or puriceptors and allows for entry of at least one inhibitor of voltage-gated ion (e.g., sodium or calcium) channels. In one embodiment, the TRPV1 receptor activator includes, but is not limited to, capsaicin, dihydrocapsaicin and nordihydrocapsaicin, lidocaine, articaine, procaine, tetracaine, mepivicaine, bupivicaine, eugenol, camphor, clotrimazole, arvanil (N-arachidonoylvanillamine), anandamide, 2-aminoethoxydiphenyl borate (2APB), AM404, resiniferatoxin, phorbol 12-phenylacetate 13-acetate 20-homovanillate (PPAHV), olvanil (NE 19550), OLDA (N-oleoyldopamine), N-arachidonyldop amine (NADA), 6'-iodoresiniferatoxin (6'-IRTX), Cl 8 N-acylethanolamines, lipoxygenase derivatives (such as 12-hydroperoxyeicosatetraenoic acid), inhibitor cysteine knot (ICK) peptides (vanillotoxins), MSKI 95 (N-[2-(3,4-dimethylbenzyl)-3-(pivaloyloxy)propyl]-2-[4-(2-aminoethoxy)-3-methoxyphenyl] acetamide), JYL79 (N-[2-(3,4-dimethylbenzyl)-3-(pivaloyloxy)propyl]-N'-(4-hydroxy-3-methoxybenzyl) thiourea), hydroxy-α-sanshool, 2-aminoethoxydiphenyl borate, 10-shogaol, oleylgingerol, oleylshogaol, SU200 (N-(4-tert-butylbenzyl)-N'-(4-hydroxy-3-methoxybenzyl)thiourea) nonivamide, and fatty acyl amides of tetrahydroisoquinolines. In another embodiment, the TRPV1 receptor activator is lidocaine, aprindine, benzocaine, butacaine, cocaine, dibucaine, encainide, mexiletine, oxetacaine (oxethazaine), prilocaine, proparacaine, procainamide, n-acetyl-procainamide, chloroprocaine (nesacaine, nescaine), dyclonine, etidocaine, levobupivacaine, ropivacaine, cyclomethycaine, dimethocaine (larocaine), propoxycaine, trimecaine, and sympocaine. In a further embodiment, the TRPV1 receptor activator is lidocaine. In another embodiment, the TRPV1 activator may be a detergent or a surfactant, examples of which may be found in commonly-used hygiene products such as soaps and shampoos (e.g., sodium lauryl sulfate). See, Lilja, "Surfactant-Induced TRPV1 activity—A Novel Mechanism for Eye Irritation?" Technological Sciences, 99(1):174-180, 2007, which is incorporated herein by reference. In another embodiment, the TRPV1 receptor activator is heat or inflammation (which is known to activate TRPV1 receptors).

In one embodiment, the therapeutically effective amount of the TRPV1 receptor activator is about 0.0001% to about 10% w/v. One of skill in the art would readily understand that the recited therapeutically effective amount is based on the free base of the TRPV1 receptor activator. By using this information and skill in the art, one would be able to determine the amount of the corresponding TRPV1 receptor activator salt for use in the compositions and methods described herein. In another embodiment, the therapeutically effective amount is less than about 10% w/v, about 9% w/v, about 8% w/v, about 7% w/v, about 6% w/v, about 5% w/v, about 4% w/v, about 3% w/v, about 2% w/v, or about 1% w/v. In another embodiment, the therapeutically effective amount is about 0.1% to about 5% w/v. In a further embodiment, the therapeutically effective amount is about 0.5 to about 3% w/v. In yet another embodiment, the therapeutically effective amount is about 0.5 to about 2% w/v. In another embodiment, the therapeutically effective amount of a TRPV1 receptor activator is about 2% w/v. In another embodiment, the therapeutically effective amount is about 1% w/v. In a further embodiment, the therapeutically effective amount is about 0.5% w/v.

The therapeutically effect amount of the TRPV1 receptor activator may, therefore, be about 0.001 mg to about 100 mg per dose based on a 70 kg mammalian subject. In another embodiment, the therapeutically effective amount is about 0.1 mg to about 25 mg per dose. In a further embodiment, the therapeutically effective amount is about 1 mg to about 5 mg. In yet a further embodiment, the therapeutically effective amount is about 0.1 mg, about 0.5 mg, about 1 mg, about 2 mg, about 3 mg, about 4 mg, about 5 mg, about 6 mg, about 7 mg, or about 8 mg.

Provided herein also is a composition containing a compound of formula (I) and lidocaine. In one embodiment, the composition contains about 0.01% to about 1% w/v of a compound of formula (I) and about 0.1% to about 5% w/v of lidocaine. In another embodiment, the composition contains about 0.1% to about 0.7% w/v of a compound of formula (I) and about 1% to about 3% w/v of lidocaine. In a further embodiment, the composition contains about 0.2% to about 0.5% w/v of a compound of formula (I) and about 1% to about 3% w/v of lidocaine. In yet another embodiment, the composition contains about 0.2% to about 0.5% w/v of a compound of formula (I) and about 2% w/v of lidocaine. In still another embodiment, the composition contains about 0.2% w/v of a compound of formula (I) and about 2% w/v of lidocaine. In another embodiment, the composition contains about 0.5% w/v of a compound of formula (I) and about 2% w/v of lidocaine. As discussed above, these compositions may be further diluted. In one embodiment, these compositions may be diluted 2-fold. In another embodiment, these compositions may be diluted 4-fold.

Also contemplated for use in the pharmaceutical combinations and methods described below are inhibitors of voltage-gated ion channels. In one embodiment, the voltage-gated ion channels are sodium or calcium ion channels. In a further embodiment, the voltage-gated sodium channel inhibitor includes, without limitation, QX-314, N-methyl-procaine (QX-222), N-octyl-guanidine, 9-aminoacridine, and pancuronium. In another embodiment, the inhibitor of voltage-gated calcium channels includes, but is not limited to, D-890 (quaternary methoxyverapamil) and CERM 1 1888 (quaternary bepridil). In a further embodiment, voltage-gated ion channel inhibitors such as riluzole, mexilitine, phenytoin, carbamazepine, procaine, tocainide, prilocaine, diisopyramide, bencyclane, quinidine, bretylium, lifarizine, lamotrigine, flunarizine, articaine, bupivicaine, mepivicaine, fluspirilene, orphenadrine, phenbenzamine, bepridil, pimozide, penfluridol, fluspirilene, propiverine, disopyramide, methadone, tolterodine, tridihexethyl salts, tripelennamine, mepyramine, brompheniramine, chlorpheniramine, dexchlorpheniramine, carbinoxamine, levomethadyl acetate, gallopamil, verapamil, devapamil, tiapamil, emopamil, dyclonine, pramoxine, lamotrigine, mibefradil, gabapentin, amiloride, diltiazem, nifedipine, nimodipine, nitrendipine, cocaine, mexiletine, propafenone, quinidine, oxethazaine, articaine, riluzole, bencyclane, lifarizine, and strychnine may be combined with the compound of formula (I).

Membrane permeable inhibitors of voltage-gated ion channels may also be utilized in combination with the compound of formula (I) in the compositions, combinations, or methods described herein. In one embodiment, the membrane permeable inhibitor of voltage-gated ion channels includes, but is not limited to, cocaine, carbamazepine, disopyramide, lamotrigine, procainamide, phenytoin, oxcarbazepine, topiramate, zonisamide, tetracaine, ethyl aminobenzoate, prilocaine, disopyramide phosphate, flecainide acetate, mexiletine, propafenone, quinidine gluconate, quinidine polygalacturonate, chloroprocaine, dibucaine, dyclonine, mepivacaine, pramoxine, procaine, tetracaine, oxethazaine, propitocaine, levobupivacaine, bupivacaine, lidocaine, moricizine, tocainide, proparacaine, ropivacaine, quinidine sulfate, encainide, ropivacaine, etidocaine, moricizine, quinidine, encainide, flecainide, tocainide, fosphenytoin, chloroprocaine, dyclonine, L-(−)-1-butyl-2',6'-pipecoloxylidide, and pramoxine.

Additionally, one or more agents may be used to treat pain, i.e., analgesics, may be used in conjunction with a combination of the invention in the methods, compositions, and kits described herein. Such agents include, but are not limited to, non-steroidal anti-inflammatory drugs (NSAIDs), opioids, tricyclic antidepressants, amine transporter inhibitors, and anticonvulsants (such as gabapentinoids).

The compound of formula (I) may be administered together with a vasoconstrictor, e.g., epinephrine or vasopressin, when utilized in injectable solutions.

The compound of formula (I) may be combined with glucose or dextrose when utilized for infusion or as a regional analgesic or anti-pruritic.

Further, the compound of formula (I) may be combined with thickening agents to form a jelly, or may also contain penetration enhancers, for use in topical or dermal applications such as for urogenital topical procedures.

Sprays for topical anesthesia of the mouth and oropharynx may contain the compound of formula (I), saccharin and/or alcohol.

The compound of formula (I) may also be formulated as an ointment for administration to accessible mucous membranes.

Also provided herein are regimens, kits or packages of pharmaceutical formulations comprising the compounds of formula (I) or compositions described herein. The kits may be organized to indicate a single formulation or combination of formulations to be taken at a designated time or times.

The kit may further comprise packaging or a container with the compound of formula (I) formulated for the delivery route. Suitably, the kit contains instructions on dosing and an insert regarding the compound of formula (I). Optionally, the kit may further contain instructions for monitoring local or circulating levels of product and materials for performing such assays including, e.g., reagents, well plates, containers, markers or labels, and the like. Such kits are readily packaged in a manner suitable for treatment of an indication. For example, the kit may also contain instructions for use of a patch, spray pump or other delivery device. Other suitable components to include in such kits will be readily apparent to one of skill in the art, taking into consideration the indication and the delivery route and may contain lubricants, antiseptic solutions and local anesthetic agents to facilitate the placement of the delivery device.

The compounds of formula (I) or compositions described herein can be a single dose or for continuous or periodic discontinuous administration. For continuous administration, a package or kit can include the compound of formula (I) in each dosage unit, e.g., solution, lotion, tablet, pill, drug-eluting unit/patch or other unit described above or utilized in drug delivery, and optionally instructions for administering the doses less-than-daily, daily, weekly, or monthly, for a predetermined length of time or as prescribed. When the compound of formula (I) is to be delivered periodically in a discontinuous fashion, a package or kit can include placebos during periods when the compound of formula (I) is not delivered. When varying concentrations of a composition, of the components of the composition, or the relative ratios of the compounds of formula (I) or agents within a composition over time, a package or kit may contain a sequence of dosage units which provide the variability.

A number of packages or kits are known in the art for dispensing pharmaceutical agents for periodic oral use. In one embodiment, the package has indicators for each period. In another embodiment, the package is a foil or blister package, labeled ampoule, vial or bottle.

The packaging means of a kit may itself be geared for administration, such as an inhaler, syringe, pipette, eye dropper, catheter, cytoscope, trocar, cannula, pressure ejection device, or other such apparatus, from which the formulation may be applied to an affected area of the body, such as the lungs, injected into a subject, delivered to bladder tissue or even applied to and mixed with the other components of the kit.

One or more components of these kits also may be provided in dried or lyophilized forms. When reagents or components are provided as a dried form, reconstitution generally is by the addition of a suitable solvent. It is envisioned that the solvent also may be provided in another package.

The kits may include a means for containing the vials or other suitable packaging means in close confinement for commercial sale such as, e.g., injection or blow-molded plastic containers into which the vials are retained. Irrespective of the number or type of packages and as discussed above, the kits also may include, or be packaged with a separate instrument for assisting with the injection/administration or placement of the composition within the body of an animal. Such an instrument may be an inhaler, syringe, pipette, forceps, measuring spoon, eye dropper, catheter, cytoscope, trocar, cannula, pressure-delivery device or any such medically approved delivery means.

In one embodiment, a kit is provided and comprises a compound of formula (I). The compound of formula (I) may be in the presence or absence of one or more of the carriers or excipients described above. The kit may optionally contain instructions for administering the compound of formula (I) to a subject having pain.

In a further embodiment, a kit is provided and comprises a compound of formula (I) in a second dosage unit, and one or more of the carriers or excipients described above in a third dosage unit. The kit may optionally contain instructions for administering the compound of formula (I) to a subject having pain.

The compound of formula (I) may also be administered prior to, concurrently with, or subsequent to administration of additional therapeutic agents or non-medication related therapies. In one embodiment, the compounds of formula (I) may be administered in conjunction with nerve stimulation, e.g., transcutaneous electrical nerve stimulation (TENS) or sacral nerve stimulation.

The compounds described herein are useful in regulating or modulating conditions which are associated with the $P2X_3$ and/or $P2X_{2/3}$ pathway. The term "regulation," "modulation" or variations thereof as used herein are used interchangeably and refer to the ability of a compound of formula (I) to inhibit or reduce the activity of one or more components of a biological pathway. In one embodiment, "regulation" refers to inhibition of $P2X_3$ activity. In another embodiment, "regulation" refers to inhibition of $P2X_{2/3}$ activity. In a further embodiment, regulation refers to dual inhibition of $P2X_3$ and $P2X_{2/3}$ activity.

Accordingly, the methods, compositions, and kits of the invention can be used to treat pain resulting from a number of conditions. The term "pain" as used herein includes all types of pain. In one embodiment, the pain may be acute or chronic. In another embodiment, the pain may be nociceptive, dysfunctional, idiopathic, neuropathic, somatic, central, visceral, inflammatory, and/or procedural. For example, the pain may be from a migraine, back pain, neck pain, gynecological pain, pre-labor or labor pain, orthopedic pain, post-stroke pain, post-surgical or procedural pain, post herpetic neuralgia, sickle cell crises, interstitial cystitis, urological pain (such as urethritis), dental pain, headache, pain from a wound or from a medical procedure such as surgery (such as bunionectomy or hip, knee or other joint replacement), suturing, setting a fracture, biopsy, and the like. Pain may also occur in patients with cancer, which may be due to multiple causes, such as inflammation, nerve compression, and mechanical forces resulting from tissue distension as a consequence of invasion by a tumor and tumor metastasis into bone or other tissues. In one embodiment, the cancer is bone cancer.

In one embodiment, the pain is neuropathic pain, such as post-herpetic neuralgia. In another embodiment, the pain is inflammatory pain. In a further embodiment, the pain is nociceptive pain. In still another embodiment, the pain is procedural pain. In yet a further embodiment, the pain is caused by esophageal cancer, colitis, cystitis, irritable bowel syndrome, colitis or idiopathic neuropathy. In still another embodiment, the pain is caused by airway, bladder or visceral organ dysfunction.

"Somatic pain" includes pain from bone, joint, muscle, skin, or connective tissue.

"Central pain" includes pain arising as a consequence of brain trauma, stroke, or spinal cord injury.

"Visceral pain" includes pain from visceral organs, such as the respiratory or gastrointestinal tract and pancreas, the urinary tract and reproductive organs. In one embodiment, visceral pain results from tumor involvement of the organ capsule. In another embodiment, visceral pain results from obstruction of hollow viscus. In a further embodiment, visceral pain results from inflammation as in cystitis or reflux esophagitis.

"Idiopathic pain" refers to pain which has no underlying cause or refers to pain caused by condition which remains undiagnosed.

"Dysfunctional pain" refers to pain which occurs in the absence of a noxious stimulus, tissue damage or a lesion to the nervous system. In one embodiment, dysfunctional pain results from rheumatologic conditions such as arthritis and fibromyalgia, tension type headache, irritable bowel disorders and erythermalgia.

"Nociceptive pain" includes pain caused by noxious stimuli that threaten to or actually injure body tissues. In one embodiment, nociceptive pain results from a cut, bruise, bone fracture, crush injury, burn, trauma, surgery, labor, sprain, bump, injection, dental procedure, skin biopsy, or obstruction. In another embodiment, nociceptive pain is located in the skin, musculoskeletal system, or internal organs.

"Neuropathic pain" is pain due to abnormal processing of sensory input by the peripheral or central nervous system consequent on a lesion to these systems. In one embodiment, neuropathic pain is chronic and non-malignant. In one embodiment, neuropathic pain is due to trauma, surgery, herniation of an intervertebral disk, spinal cord injury, diabetes, infection with herpes zoster (shingles), HIV/AIDS, late-stage cancer, amputation (such as mastectomy), carpal tunnel syndrome, chronic alcohol use, exposure to radiation, and as an unintended side-effect of neurotoxic treatment agents, such as certain anti-HIV and chemotherapeutic drugs. In another embodiment, neuropathic pain is may be described as "burning," "electric," "tingling," or "shooting".

The phrase "inflammatory pain" includes pain resulting from inflammation caused by any number of factors. In one embodiment, inflammatory pain occurs due to tissue damage or inflammation. In another embodiment, inflammatory pain is due to injury (including joints, muscle, and tendons injuries), surgical procedures, infection, and/or arthritis.

"Procedural pain" includes refers to pain arising from a medical procedure. The medical procedure may include any type of medical, dental or surgical procedure. In one embodiment, the procedural pain is postoperative. In another embodiment, the pain is associated with an injection, draining an abscess, surgery, dermatological, dental procedure, ophthalmic procedure, arthroscopy and use of other medical instrumentation, and/or cosmetic surgery.

A "migraine" is a headache due to activation of sensory fibers innervating the meninges of the brain.

The term "treat", "treating", or any variation thereof is meant to include therapy utilized to remedy a health problem or condition in a patient or subject. In one embodiment, the health problem or condition may be eliminated permanently or for a short period of time. In another embodiment, the severity of the health problem or condition, or of one or more symptoms characteristic of the health problem or condition, may be lessened permanently, or for a short period of time. The effectiveness of a treatment of pain can be determined using any standard pain index, such as those described herein, or can be determined based on the patient's subjective pain. A patient is considered "treated" if there is a reported reduction in pain or a reduced reaction to stimuli that should cause pain.

In order to measure the efficacy of any of the methods, compositions, or kits described herein, a measurement index may be used. Indices that are useful for the measurement of pain associated with musculoskeletal, immunoinflammatory and neuropathic disorders include a visual analog scale (VAS), a Likert scale, categorical pain scales, descriptors, the Lequesne index, the WOMAC index, and the AUSCAN index, each of which is well known in the art. Such indices may be used to measure pain, function, stiffness, or other variables.

Indices that are useful of the measurement of pain associated with interstitial cystitis include the interstitial cystitis symptom index (ICSI), the interstitial cystitis problem index (ICPI), the pain-urgency-frequency score (PUF), the Wisconsin Symptom Instrument (UWI) and a visual analog scale (VAS) such as the Likert scale and other categorical pain scales.

A visual analog scale (VAS) provides a measure of a one-dimensional quantity. A VAS generally utilizes a representation of distance, such as a picture of a line with hash marks drawn at regular distance intervals, e.g., ten 1-cm intervals. For example, a patient can be asked to rank a sensation of pain by choosing the spot on the line that best corresponds to the sensation of pain, where one end of the line corresponds to "no pain" (score of 0 cm) and the other end of the line corresponds to "unbearable pain". This procedure provides a simple and rapid approach to obtaining quantitative information about how the patient is experiencing pain. VAS scales and their use are described, e.g., in U.S. Pat. Nos. 6,709,406 and 6,432,937, the relevant disclosures of which are herein incorporated by reference.

A Likert scale similarly provides a measure of a one-dimensional quantity. Generally, a Likert scale has discrete integer values ranging from a low value, e.g., 0, meaning no pain, to a high value, e.g., 7, meaning extreme pain. A patient experiencing pain is asked to choose a number between the low value and the high value to represent the degree of pain experienced. Likert scales and their use are described, e.g., in U.S. Pat. Nos. 6,623,040 and 6,766,319, the relevant disclosures of which are herein incorporated by reference.

The Lequesne index and the Western Ontario and McMaster Universities (WOMAC) osteoarthritis (OA) index assess pain, function, and stiffness in the knee and hip of OA patients using self-administered questionnaires. Both knee and hip are encompassed by the WOMAC, whereas there is one Lequesne questionnaire for the knee and a separate one for the hip. These questionnaires are useful because they contain more information content in comparison with VAS or Likert scale. Both the WOMAC index and the Lequesne index questionnaires have been extensively validated in OA, including in surgical settings, e.g., knee and hip arthroplasty. Their metric characteristics do not differ significantly.

The AUSCAN (Australian-Canadian hand arthritis) index employs a valid, reliable, and responsive patient self-reported questionnaire. In one instance, this questionnaire contains 15 questions within three dimensions (Pain, 5 questions; Stiffness, 1 question; and Physical function, 9 questions). An AUSCAN index may utilize, e.g., a Likert or a VAS scale.

The O'Leary-Sant score and IC Problem Index are self-administered indices for measuring lower urinary tract symptoms.

The Pain-Urgency-Frequency symptom scale is balanced assessment of urinary dysfunction, pelvic pain and symptoms associated with sexual intercourse and frequently used in conjunction with intravesical potassium chloride administration.

The UWI utilizes seven IC-related questions about frequency, urgency, noctuira and pain.

Other suitable indices that are useful for the measurement of pain include the Pain Descriptor Scale (PDS), the Verbal Descriptor Scales (VDS), the Numeric Pain Intensity Scale (NPIS), the Neuropathic Pain Scale (NPS), the Neuropathic Pain Symptom Inventory (NPSI), the Present Pain Inventory (PPI), the Geriatric Pain Measure (GPM), the McGill Pain Questionnaire (MPQ), mean pain intensity (Descriptor Differential Scale), numeric pain scale (NPS) global evaluation score (GES) the Short-Form McGill Pain Questionnaire, the Minnesota Multiphasic Personality Inventory, the Pain Profile and Multidimensional Pain Inventory, the Child Heath Questionnaire, and the Child Assessment Questionnaire.

In one embodiment, the treatment methods described herein include administering a compound of formula (I) to a patient. Additional, optional agents, such as those described above for use in the combination, may be administered to the patient prior to, concurrently with, or subsequent to the compound of formula (I).

A variety of in vivo assays and animal models are useful for assessing the ability of compounds to inhibit pain via internal sodium channel inhibition. These models may or may not involve opening (activation) of TRPV1 channels via inducing pain through physical, mechanical, or chemical, e.g., capsaicin, means. Examples of suitable models include, e.g., those described in Binshtok, Anesthesiology, July 2009, 111(1):127-137; Reis, Anesthesiology, July 2009, 111(1):122-126; Gerner, Anesthesiology, November 2008, 109(5):872-878; and Binshtok, Nature, October 2007, 449: 607-610, the use of isolated bladder detrusor muscle preparations (Witte, Naunyn-Schmeideberg's Arch. Pharmacol. 2011, 384:555-563), measurement of voiding frequency and volume in freely moving animals (Clouse, 2012, Urology 79:1410e1-1410e6), measurement of bladder urodynamics using cystometry in anesthetized animals (Shimizu, 2000, British Journal of Pharmacology 131:610-616), which are incorporated by reference herein. However, for a variety of reasons which will be readily apparent to those of ordinary skill in the art, one may provide in vitro assays which allow for the identification of compounds with the properties. Described herein are several such in vitro assays.

In one embodiment, a modified FLIPR® (Fluorometric Imaging Plate Reader) based assay system was developed which is capable of discriminating between non-specific versus hTRPV1-mediated entry of test compounds. Advantageously, the assay system utilizes heat activated opening of hTRPV1 channels followed by an assessment of internal sodium channel block. The assay allows a permanently charged compound to selectively enter through opened hTRPV1 channels and that compound's potency in inhibiting sodium channels from the cytoplasm side of the same cell can be assessed and quantified.

The modified FLIPR® assay utilizes cells which functionally express hTRPV1. As used herein, the term "functionally express" includes those cells which express the human TRPV1 protein and which respond to stimuli which naturally open this channel, including, e.g., thermal (heat) or chemical (capsaicin, lidocaine, among others) means described herein. Suitable assays may include the calcium or membrane potential assays described herein, e.g., Example 49. However, other functional assays are known in the art, e.g., voltage-clamp electrophysiology such as used by Binshtok, Nature 449(4) 607-610, 2007.

A suitable cell may be selected for expression of TRPV1 in cis or in trans and constructed using known techniques. In one embodiment, a neuroblastoma cell line such as N1E115 [CRL-2263] or ND7/23 [ECACC catalog code: 92090903] is selected for expression of the hTRPV1. However, another neuroblastoma cell line may be selected, e.g., such as IMR-32 [CRL-127]; Neuro-2a [CRL-131]; NB41A3 [CRL-147]; B104-1-1 [CRL-1887]; SK-N-AS [CRL-2137]; SK-N-F1 [CRL-2142]; SK-N-DZ [CRL-2149]; SH-SY5Y [CRL-2266]; BE(2)-M17 [CRL-2267]; BE(2)-C [CRL-2268]; MC-IXC [CRL-2270]; SK—N-BE(2) (CRL-2271); CHP-212 (CRL-2273]; B35 [CRL-2754], which are available from the American Type Culture Collection, Manassas, Va. (US). Still other cell lines may be selected.

For a generation description of how the cells are produced, see generally, e.g., Sambrook, Molecular Cloning: A Laboratory Manual, Cold Spring Harbor Press, Cold Spring Harbor, N.Y. (US) 2001. In one embodiment, a stable cell line may be prepared using the techniques in Sambrook, using wild-type (wt) or recombinant hTRPV1 coding sequences. For example, preparation of one such cell line is described in detail herein (see Example 32). Preparation of another cell line is described in International Patent Publication N. WO 2007/0066068; the Lipofectamine® method may be employed for transfection of TRPV1 and hTRPV1 into Human Embryonic Kidney cells (HEK293) according to the manufacturers protocol (Gibco). To create a permanently expressing cell line, wt-TRPV1 transfected HEK cells can be subcloned in geneticin (0.6 mg/mL) containing medium (DMEM containing 10% FCS, 100 U/mL penicillin, 100 g/mL streptomycin, and 250 ng/mL amphotericin B) and propagated for two weeks to allow selection. To obtain a TRPV1 permanently expressing single cell line, transfected cells can be plated in 96 well plates (1 cell per well) and colonies grown from single cells were subsequently tested for capsaicin responsiveness by measuring increases in intracellular calcium. The final clones selected, are taken through three further rounds of single cell cloning to ensure the cell lines are derived from a single cell. Variations on this methodology will be readily apparent to one of skill in the art. In another embodiment, cells may be selected from a stable cell line to express the hTRPV1, in trans, e.g., from a viral vector or another suitable genetic element.

The following examples are illustrative only and are not intended to limit the present invention.

EXAMPLES

Unless otherwise stated, all the raw materials are purchased from commercially available common suppliers. $^1$H-NMR spectra were recorded using trimethylsilane (TMS) as the internal reference for $CDCl_3$ dissolved compounds. For DMSO-$d_6$ and $CD_3OD$ dissolved compounds the instrument was calibrated at δ 2.5 and 3.3 ppm respectively. The chemical shift values are quoted in δ (parts per million).

For LCMS analysis LCMS/MS API 2000 (Applied Biosystem) instrument was used. The columns included:
Column U: YMC, 4.6×50 mm, 5μ
Column V: Zorbax® C18 column, 4.6×50 mm, 5μ
Column W: Zorbax® Extend C18 column, 4.6×50 mm, 5μ
Column X: Gemini® NX C18 column, 4.6×50 mm, 5μ
Column Y: Xbridge® C18 column, 4.6×50 mm, 5μ
Column Z: Reprosil® column, 4.6×50 mm, 5μ
The eluent (solvent) typically included (acidic or basic buffer as aqueous phase):
A channel: (i) 0.05% formic acid in water;
(ii) 10 mM ammonium acetate in water; or
(iii) 0.05% TFA in water.
B channel: acetonitrile (organic phase).
The detector was UV measured at dual wavelengths: 220 and 260 nm.
The LCMS gradients were one of the following:
1. LCMS reaction monitoring and final compound analysis method (for general polarity compounds)
Gradient condition: 5 min run time
Time Programs: P1:10 mM ammonium acetate in water/acetonitrile
Q1: 0.05% TFA in water/acetonitrile,
R1: 0.05% formic acid in water/acetonitrile.
The gradient varied acetonitrile from 10% to 90% to 10%. Flow rate: 1.2 mL/min.
2. LCMS reaction monitoring and final compound analysis method in 12 min run (for close eluting compounds):
Gradient condition: 12 min run time
Time Programs: P2: 10 mM ammonium acetate in water/acetonitrile
Q2: 0.05% TFA in water/acetonitrile
R2: 0.05% formic acid in water/acetonitrile
The gradient varied acetonitrile from 5% to 90% to 5%
Flow rate: 1.0 mL/min.
3. LCMS after method development in HPLC—gradient conditions are as per HPLC.
Mass spectral data was obtained using the following:
Ionization technique: ESI (Electron Spray Ionization) using API (Atmospheric pressure Ionization) source Declustering Potential: 10-70 V depending on the ionization of compound
Mass range: 100-800 amu
Scan type: Q1
Polarity: +/−ve
Ion Source: Turbo spray
Ion spray voltage: +5500 for +ve mode and −4500 for −ve mode
Mass Source temperature: 200° C.

Preparation of Intermediates—few of the intermediates were used for the synthesis of the compounds which were synthesized by following sixteen (16) routes which are listed as examples below.

Preparation 1: 1-Pyrazin-2-yl-ethylamine

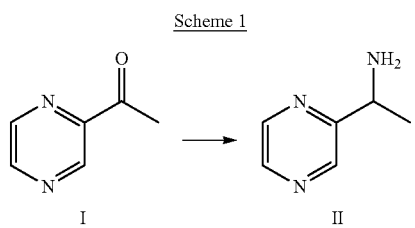

To a stirred solution of compound I (2 g; 16.4 mmol; 1 eq) in methanol (20 mL) were added ammonium acetate (12.6 g; 164 mmol; 10 eq) and sodium cyanoborohydride (1 g; 16.4 mmol; 1 eq) and the resulting mixture was stirred at 23° C. for 17 h. The mixture was quenched with water (50 mL) and the organic components were extracted with ethyl acetate (2×200 mL). The combined organic layers were washed with water and brine, dried over anhydrous sodium sulfate, filtered and the solvents were removed in vacuo to afford crude compound, which was purified by silica gel (230-400 mesh) column chromatography, eluting with 10% MeOH/CH$_2$Cl$_2$, to afford the title compound (0.8 g, 40%). $^1$H NMR (CDCl$_3$) δ 8.60 (s, 1H), 8.49 (m, 1H), 8.43 (d, 1H, J=2 Hz), 4.20 (m, 1H), 1.45 (d, 3H, J=7 Hz).

Preparation 2: 4-Aminomethyl-1-methyl-1H-pyridin-2-one

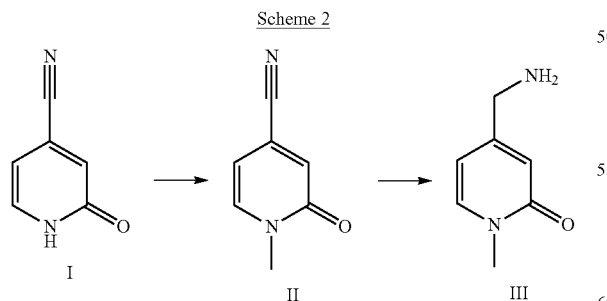

Step 1: 4-Cyano-1-methyl-1H-pyridin-2-one

To a stirred solution of compound I (0.25 g; 2.08 mmol; 1 eq) in DMF (5 mL) was added sodium hydride (0.12 g; 3.12 mmol; 1.5 eq) and the resulting mixture was stirred for 10 min at 0° C. To the mixture was then added methyl iodide (0.4 mL; 6.25 mmol; 3 eq) and the resulting mixture was stirred at 23° C. for 2 h. The mixture was diluted with water (50 mL) and the organic components were extracted with ethyl acetate (2×200 mL). The combined organic layers were washed with water and brine, dried over anhydrous sodium sulfate, filtered and the solvents were removed in vacuo to obtain the title compound (0.18 g, 67%). $^1$H NMR (DMSO-d$_6$) δ 7.93 (d, 1H, J=7 Hz), 7.00 (s, 1H), 6.52 (dd, 1H, J=2, 7 Hz), 3.45 (s, 3H).

Step 2: 4-Aminomethyl-1-methyl-1H-pyridin-2-one

To a stirred solution of compound II (1.67 g; 11.9 mmol; 1 eq) in methanol (80 mL) was added concentrated HCl (1 mL) followed by 10% Pd/C (1.6 g) and the resulting mixture was stirred under hydrogen atmosphere at a pressure of 50 psi for 4 h in a Parr autoclave. The mixture was filtered through a Celite® bed, washed with methanol and solvent of the filtrate was removed in vacuo to obtain the title compound (2 g, 92%). $^1$H NMR (DMSO-d$_6$) δ 8.55 (brs, 1H), 7.72 (d, 1H, J=7 Hz), 6.46 (s, 1H), 6.31 (dd, 1H, J=2, 7 Hz), 3.86 (m, 2H), 3.40 (s, 3H).

Preparation 3: 6-Methyl-1-oxypyridin-3-yl)methylamine hydrochloride

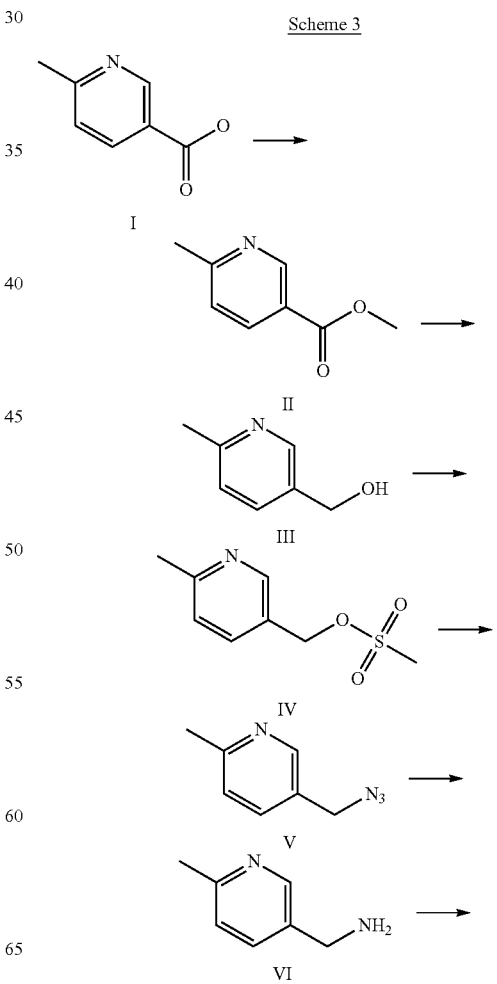

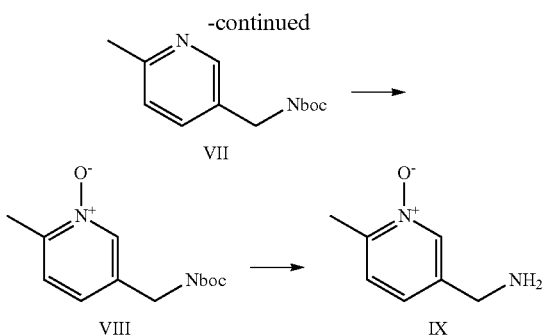

Step 1: 6-Methyl-nicotinic acid methyl ester

To a stirred solution of compound I (40 g; 290 mmol; 1 eq) in methanol (0.75 L) was added sulfuric acid (40 mL) and the resulting mixture was heated at reflux for 17 h. The mixture was then evaporated to dryness and the pH was adjusted to 7 using saturated ice-cold aqueous NaHCO$_3$ solution and solid NaHCO$_3$. The organic components were extracted from the aqueous layer with ethyl acetate (3×500 mL) and the combined organic layers were washed with brine, dried over anhydrous sodium sulfate, filtered and the solvent was removed in vacuo to afford the title compound (33 g, 75%) as an off-white solid. $^1$H NMR (CDCl$_3$) δ 9.06 (s, 1H), 8.13 (dd, 1H, J=2, 8 Hz), 7.20 (d, 1H, J=8 Hz), 3.89 (s, 3H), 2.58 (s, 3H). LCMS: m/z=152.4 [M+H]$^+$, RT=2.36 minutes, (Program P1, Column W).

Step 2: (6-Methyl-pyridin-3-yl)methanol

To a stirred solution of compound II (21 g; 140 mmol; 1 eq) in dry THF (150 mL) was added 1M LiAlH$_4$ solution in THF (210 mL; 210 mmol; 1.5 eq) dropwise at −5° C. and after completion of the addition it was stirred at 23° C. for 2 h. The mixture was cooled to −10° C. and quenched with sodium sulfate decahydrate and ethyl acetate until effervescence ceased. The mixture was filtered through a Celite® pad and the filtrate was evaporated to dryness to afford the title compound (17 g, 100%). $^1$H NMR (DMSO-d$_6$) δ 8.37 (s, 1H), 7.59 (dd, 1H, J=2, 8 Hz), 7.19 (d, 1H, J=8 Hz), 5.22 (t, 1H, J=6 Hz), 4.47 (d, 2H, J=6 Hz), 2.45 (s, 3H).

Step 3: Methanesulfonic acid (6-methyl-pyridin-3-yl)methyl ester

To a stirred solution of compound III (25 g; 200 mmol; 1 eq) in CH$_2$Cl$_2$ (0.5 L) were added TEA (42.5 mL; 300 mmol; 1.5 eq) and methane sulfonyl chloride (23.5 mL; 300 mmol; 1.5 eq) dropwise and the resulting mixture was stirred at 23° C. for 1 h. The mixture was diluted with water (100 mL) and the organic components were extracted with CH$_2$Cl$_2$ (2×200 mL). The combined organic layers were washed with water and brine, dried over anhydrous sodium sulfate, filtered, and the solvents were removed in vacuo to afford the title compound (41 g, 100%).

Step 4: 3-Azidomethyl-6-methylpyridine

To a stirred solution of compound IV (43 g; 0.21 mol; 1 eq) in dry DMF (150 mL) was added sodium azide (139 g; 2.13 mol; 10 eq) and the resulting mixture was stirred at 23° C. for 17 h. The mixture was quenched with water (500 mL) and the organic components were extracted with ethyl acetate (2×200 mL). The combined organic layers were washed with water and brine, dried over anhydrous sodium sulfate, filtered, and then concentrated in vacuo to obtain compound (31.6 g, 100%) as crude material.

Step 5: (6-Methyl-pyridin-3-yl)methylamine

To a stirred solution of compound V (8 g; 50 mmol; 1 eq) in THF (250 mL) and water (5.7 mL) was added triphenyl phosphine (28 g; 100 mmol; 2 eq), and the resulting mixture was heated at reflux for 4 h. The mixture was evaporated to dryness to obtain a crude material. The crude product was purified by column chromatography, eluting with 10% MeOH/CH$_2$Cl$_2$, to afford the title compound (3 g, 46%). $^1$H NMR (DMSO-d$_6$) δ 8.36 (s, 1H), 7.61 (dd, 1H, J=2, 8 Hz), 7.16 (d, 1H, J=8 Hz), 3.67 (s, 2H), 2.49 (s, 3H). LCMS: m/z=123.0 [M+H]$^+$, RT=0.45 minutes, (Program R1, Column X).

Step 6: N-(6-Methyl-pyridin-3-yl)methyl)carbamic acid tert-butyl ester

To a stirred solution of compound VI (0.75 g; 6 mmol; 1 eq) in dry CH$_2$Cl$_2$ (10 mL) were added TEA (2.59 mL; 18 mmol; 3 eq), boc anhydride (1.55 mL; 6 mmol; 1.1 eq) and the resulting mixture was stirred at 23° C. for 17 h. The mixture was diluted with water (50 mL) and the organic components were extracted with dichloromethane (2×100 mL). The combined organic layers were washed with water and brine, dried over anhydrous sodium sulfate, filtered, and concentrated in vacuo to obtain the title compound (1.36 g, 100%). $^1$H NMR (CDCl$_3$) δ 8.39 (s, 1H), 7.51 (d, J=8 Hz, 1H), 7.10 (d, J=8 Hz, 1H), 4.84 (brs, 1H), 4.27 (d, J=4 Hz, 2H), 2.52 (s, 3H), 1.44 (s, 9H); LCMS: m/z=222.8 [M+H]$^+$, RT=2.69 minutes, (Program P1, Column W).

Step 7: N-(6-Methyl-1-oxy-pyridin-3-ylmethyl)carbamic acid tert-butyl ester

To a stirred solution of compound VII (1.36 g; 6 mmol; 1 eq) in chloroform (30 mL) were added meta chloroperbenzoic acid (1.32 g; 7 mmol; 1.25 eq) and 2,6-ditertiary butyl-4-methyl phenol (6 mg; 0.3 mmol; 0.05 eq) and the resulting mixture was heated at reflux for 2 days. The mixture was diluted with water (50 mL) and the organic components were extracted with dichloromethane (2×100 mL). The combined organic layers were washed with water and brine, dried over anhydrous sodium sulfate, filtered, and concentrated in vacuo to obtain the title compound (1.1 g, 76%). $^1$H NMR (CDCl$_3$) δ 8.21 (s, 1H), 7.19 (d, 1H, J=8 Hz), 7.11 (d, 1H, J=8 Hz), 5.00 (brs, 1H), 4.24 (d, 2H, J=5 Hz), 2.48 (s, 3H), 1.47 (s, 9H). LCMS: m/z=239.0 [M+H]$^+$, RT=2.06 minutes, (Program P1, Column W).

Step 8: (6-Methyl-1-oxy-pyridin-3-yl)methylamine hydrochloride

To a stirred solution of compound VIII (1.1 g; 4 mmol; 1 eq) in 1,4-dioxane (5 mL) was added 4M HCl in 1,4-dioxane (20 mL) and the resulting mixture was stirred at 23° C. for 4 h. The solvents were removed in vacuo to afford the title compound (0.71 g, 89%). $^1$H NMR (DMSO-d$_6$) δ 8.50 (m, 3H), 7.57 (d, 1H, J=8 Hz), 7.48 (d, 1H, J=8 Hz), 4.02 (q, 2H, J=11 Hz), 2.38 (s, 3H). LCMS: m/z=139.0 [M+H]$^+$, RT=0.45 minutes, (Program P1, Column W).

The following amines were also prepared using the above mentioned procedure:

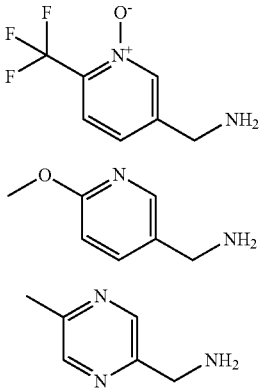

A
B
C

Preparation 4:
(2-Methoxypyrimidin-5-yl)methylamine hydrochloride

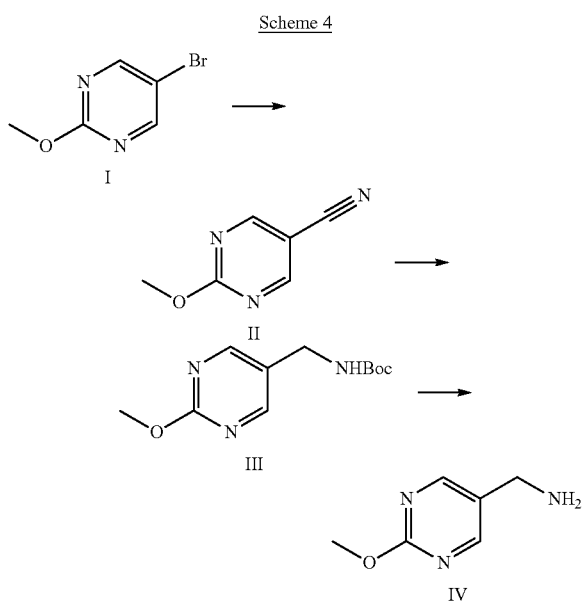

Scheme 4

I
II
III
IV

Step 1: 5-Cyano-2-methoxypyrimidine

To a stirred DMF (80 mL) solution of compound I (5 g; 26 mmol; 1 eq) in a reaction tube was added zinc cyanide (5 g; 53 mmol; 2 eq) and the resulting mixture was degassed with argon for 5 min. To the mixture was then added Pd(PPh$_3$)$_4$ (5 g; 5.20 mmol; 0.2 eq), and the resulting mixture was degassed with argon for another 5 min. The reaction tube was sealed and heated at 115° C. for 3 h. The mixture was filtered through a Celite® pad and the filtrate was washed with saturated aqueous NaHCO$_3$ solution, followed by brine. The organic layer was then dried over anhydrous Na$_2$SO$_4$ and evaporated to dryness to obtain a crude material. The crude product was purified by silica gel (100-200 mesh) column chromatography, eluting with 50% EtOAc/hexanes to obtain the title compound (3.5 g, 100%). $^1$H NMR (DMSO-d$_6$) δ 9.11 (s, 2H), 4.00 (s, 3H). LCMS: m/z=136.0 [M+H]$^+$, RT=1.74 minutes, (Program P1, Column V).

Step 2:
N-((2-Methoxy-pyrimidin-5-yl)methyl)carbamic acid tert-butyl ester

To a stirred solution of compound II (4.5 g; 33.3 mmol; 1 eq) in methanol (230 mL) were added nickel chloride hexahydrate (3.15 g; 13.3 mmol; 0.4 eq) and boc anhydride (14.4 g; 66.66 mmol; 2 eq) at 0° C. To the mixture was then added powdered NaBH$_4$ (8.7 g; 233 mmol; 7 eq) in portions and stirred at 23° C. for 17 h. The mixture was evaporated to dryness, diluted with water and the organic components were extracted with ethyl acetate (2×100 mL). The combined organic layers were washed with brine, dried over anhydrous sodium sulfate, filtered, and the solvents were removed in vacuo to obtain a dry residue which was purified by silica gel (230-400 mesh) column chromatography using 2-5% methanol/dichloromethane as the eluent to afford the title compound (3.8 g, 48%). $^1$H NMR (DMSO-d$_6$) δ 8.46 (s, 2H), 4.06 (d, 2H, J=6 Hz), 3.88 (s, 3H), 1.36 (s, 9H). LCMS: m/z=240.0 [M+H]$^+$, RT=2.67 minutes, (Program P1, Column W).

Step 3: 2-Methoxypyrimidin-5-yl)methylamine hydrochloride

To a stirred solution of compound III (4 g; 28.98 mmol; 1 eq) in 1,4-dioxane (20 mL) was added 4M HCl in 1,4-dioxane (30 mL) and the mixture was stirred at 23° C. for 4 h. The solvent was removed in vacuo to afford the title compound (2.8 g, 95%). $^1$H NMR (DMSO-d$_6$) δ 8.73 (s, 2H), 4.03 (m, 2H), 3.89 (s, 3H). LCMS: m/z=140.0 [M+H]$^+$, RT=0.59 minutes, (Program P1, Column V).

Preparation 5:
(2-Cyclopropylpyridin-5-yl)methylamine hydrochloride

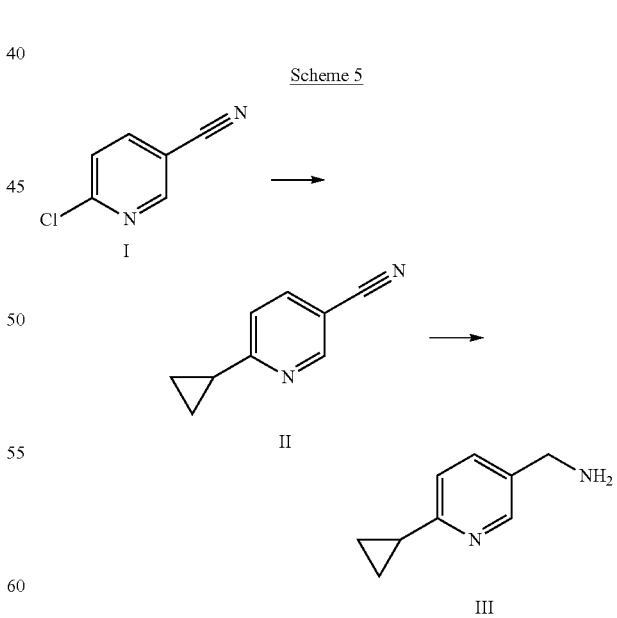

Scheme 5

I
II
III

Step 1: 2-Cyclopropyl-5-cyanopyridine

To a stirred solution of compound I (0.5 g; 3.62 mmol; 1 eq) in toluene (20 mL) and water (1 mL) in a reaction tube, was added cyclopropyl boronic acid (0.46 g; 5.43 mmol; 1.5 eq) and the resulting mixture was degassed with argon for 5 min. To the mixture was then added K₃PO₄ (2.7 g; 12.7 mmol; 3.5 eq), Pd(OAc)₂ (0.04 g; 0.18 mmol; 0.05 eq), tricyclohexyl phosphine (0.10 g; 0.36 mmol; 0.1 eq), and the resulting mixture was degassed with argon for another 5 min, then the reaction tube was sealed and heated at 110° C. for 3 h. The mixture was filtered through a Celite® pad and the filtrate was washed with saturated aqueous NaHCO₃ solution, followed by brine. The organic layer was then dried over anhydrous Na₂SO₄ and evaporated to dryness to obtain the crude material product. The crude material was purified by silica gel (100-200 mesh) column chromatography, eluting with 5-30% EtOAc/hexanes to obtain the title compound (0.28 g, 56%). $^1$H NMR (CDCl₃) δ 8.67 (s, 1H), 7.75 (dd, 1H, J=2, 8 Hz), 7.23 (m, 1H), 2.06 (m, 1H), 1.09 (m, 4H).

Step 2: (2-Cyclopropylpyridin-5-yl)methylamine hydrochloride

To a stirred solution of compound II (1.5 g; 11.11 mmol; 1 eq) in methanol (80 mL) was added concentrated HCl (1 mL) followed by 10% Pd/C (1.6 g) and stirred under a hydrogen atmosphere at a pressure of 50 psi for 4 h in a Parr autoclave. The mixture was filtered through a Celite® pad, washed with methanol, and solvent from the filtrate was removed in vacuo to afford the title compound (1.2 g, 78%). $^1$H NMR (DMSO-d₆) δ 8.33 (s, 1H), 7.64 (dd, 1H, J=2, 8 Hz), 7.27 (d, 1H, J=8 Hz), 1.89 (m, 1H), 0.92 (m, 4H).

Preparation 6: 1-(2-Methyl-pyrimidin-5-yl)-ethylamine

Scheme 6

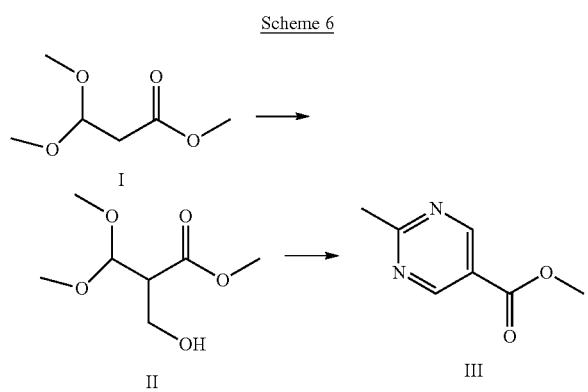

Step 1: 3,3-Dimethoxy-2-methoxycarbonyl-1-propen-1-ol sodium salt

To a stirred solution of compound I (50 g; 337 mmol; 1 eq) in 1,2-dimethoxy ethane (0.2 L) was added methyl formate (50 mL; 809 mmol; 2.4 eq) and the mixture was cooled to −5° C. To the mixture was added sodium hydride (60% in mineral oil, 17.5 g; 438 mmol; 1.3 eq) in portions and the resulting mixture was stirred at 50° C. until effervescence had ceased. The mixture was then allowed to stir at 23° C. for 17 h. The mixture was filtered and the solid residue was collected, washed with ether and dried under reduced pressure to afford the title compound (63 g, 100%) as an off-white solid. $^1$H NMR (CD₃OD) δ 8.88 (s, 1H), 8.54 (s, 1H), 5.30 (s, 1H), 3.51 (s, 3H), 3.30 (s, 6H).

Step 2: 2-Methylpyrimidine-5-carboxylic acid methyl ester

To a stirred solution of compound II (60 g; 340 mmol; 1 eq) in dry DMF (1L) was added acetamidine hydrochloride (38.6 g; 409 mmol; 1.2 eq) and the resulting mixture was heated at 100° C. for 3 h. The mixture was quenched with water (500 mL) and the organic components were extracted with ethyl acetate (2×200 mL). The combined organic layers were washed with water and brine, dried over anhydrous sodium sulfate, filtered and concentrated in vacuo to obtain the title compound (27 g, 53%). $^1$H NMR (CDCl₃) δ 9.13 (s, 2H), 3.93 (s, 3H), 2.77 (s, 3H).

The following amine was synthesized from compound III following the procedure of preparation 3, steps 2-5.

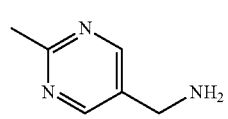

D

Preparation 7: (S)-1-(4H-[1,2,4]-Triazol-3-yl)ethylamine hydrochloride

Scheme 7

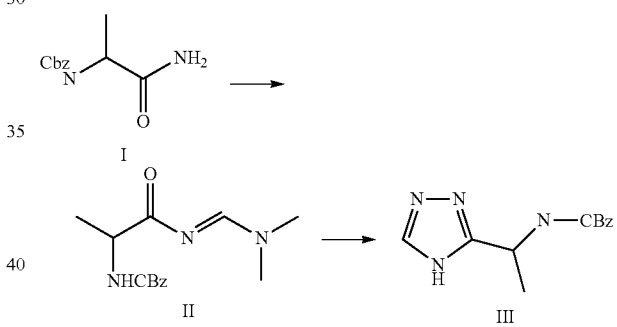

Step 1: (S)-(E)-Benzyl (1-(((dimethylamino)methylene)amino)-1-oxopropan-2-yl)carbamate To (S)-benzyl (1-amino-1-oxopropan-2-yl)carbamate I (20 g, 90 mmol) was added DMF-DMA (100 mL) and the resulting mixture was heated at 40° C. for 40 min. The mixture was diluted with ethyl acetate and washed with water and brine. The organic layer was dried over sodium sulphate, filtered and concentrated under reduced pressure to provide compound II (crude).

Step 2: [(S)-1-(4H-[1,2,4]-Triazol-3-yl)ethyl]carbamic acid benzyl ester

To a stirred solution of compound II (crude) in dry DMF (109 mL) was added hydrazine (1M solution in THF) (135 mL, 135 mmol) and the resulting mixture was heated at 100° C. for 1.5 h. The mixture was diluted with ethyl acetate and washed with water and brine. The organic layer was dried over anhydrous sodium sulfate, filtered and concentrated under reduced pressure to obtain the crude product. The crude product was purified by silica gel chromatography, eluting with 15-20% acetone/CH₂Cl₂, to obtain compound III as a white solid (5 g, 41%, 2 steps). $^1$H NMR (DMSO-d₆)

δ 13.7 (s, 1H), 8.43 (s, 1H), 7.83 (s, 1H), 7.35-7.30 (m, 5H), 5.01-4.98 (m, 2H), 4.80 (brs, 1H), 1.40 (s, 3H). LCMS: m/z=246.8 [M+H]$^+$, RT=2.51 min (Program P1, Column V). Chiral SFC: 99.07% (210 nm), RT 12.54 min (Mobile phase: A: ACN, B: MeOH)

Step 3: (S)-1-(4H-[1,2,4]-Triazol-3-yl)ethylamine hydrochloride

To a stirred solution of compound III (1 g; 4.06 mmol; 1 eq) in HCl (4M in 1,4-dioxane, 20 mL) was added 10% Pd/C (1 g) and the resulting mixture was stirred under a hydrogen atmosphere at a pressure of 60 psi for 16 h. The mixture was filtered through a Celite® pad and the filtrate was evaporated to dryness to obtain compound IV (0.6 g, 100%). $^1$H NMR (DMSO-d$_6$) δ 8.71 (brs, 3H), 8.65 (s, 1H), 4.48 (m, 1H), 1.55 (d, 3H, J=6 Hz,). LCMS: m/z=113.2 [M+H]$^+$, RT=0.47 minutes, (Program P1, Column W). Chiral SFC: 99.07% (210 nm), RT 12.54 min (Mobile phase: A: ACN, B: MeOH).

Preparation 8: (S)-2-Methyl-1-(4H-[1,2,4]triazol-3-yl)-propylamine

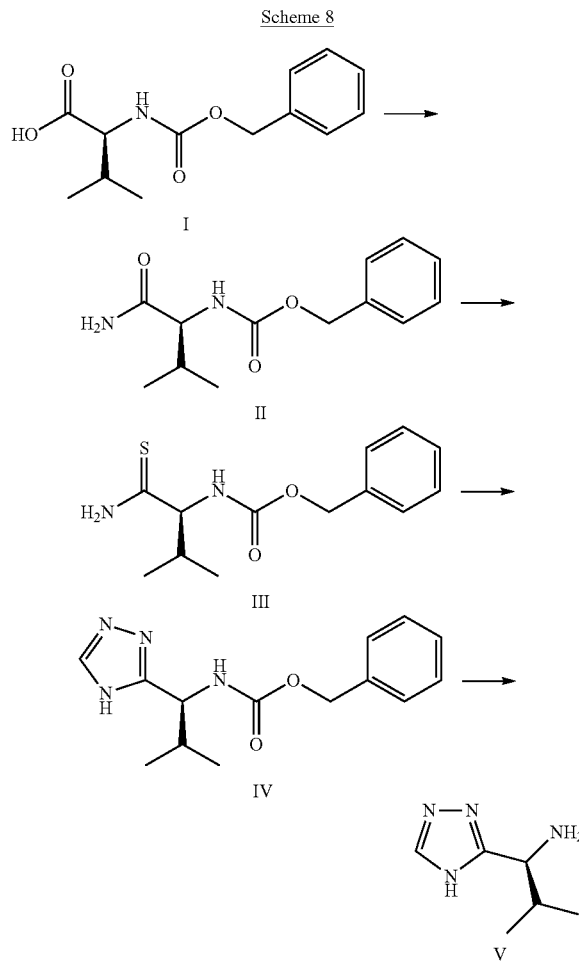

Scheme 8

Step 1: ((S)-1-Carbamoyl-2-methyl-propyl)-carbamic acid benzyl ester

To a stirred solution of compound I (10 g, 39.84 mmol, 1 eq) in DMF (100 mL) was added DIPEA (19.7 mL, 119.5 mmol, 3 eq) and HATU (18.17 g, 47.8 mmol, 1.2 eq) at 0° C. and the resulting mixture was stirred for 15 min. To the mixture was added ammonium chloride (10.7 g, 199.2 mmol, 5 eq) and the resulting mixture was allowed to stir at 23° C. for another 16 h. The mixture was poured into ice cold water (500 mL), the organic components were extracted with EtOAc (3×500 mL) and the combined organic layers were washed with aqueous ammonium chloride solution and brine. The organic layer was dried over anhydrous sodium sulfate, filtered and concentrated to dryness. The crude product was recrystallized from ethanol to obtain the title compound (9.8 g, 98%) as an off-white solid. $^1$H NMR (400 MHz, DMSO-d$_6$) δ 7.35 (m, 6H), 7.12 (d, 1H, J=9 Hz), 7.01 (s, 1H), 5.03 (s, 2H), 3.80 (t, 1H, J=8 Hz), 1.95 (m, 1H), 0.85 (m, 6H). LCMS: m/z=251.2 [M+H]$^+$, RT=2.81 minutes, (Program P1, Column Y).

Step 2: ((S)-2-Methyl-1-thiocarbamoyl-propyl)-carbamic acid benzyl ester

To a stirred solution of compound II (5.5 g, 22 mmol, 1 eq) in dry CH$_2$Cl$_2$ (100 mL) at 23° C. was added Lawesson's reagent (5.5 g, 13.2 mmol, 0.7 eq) and the mixture was heated at reflux for 2-3 h. The mixture was cooled to room temperature and concentrated in vacuo to obtain a crude material which was purified by gravity column chromatography using silica gel (100-200 mesh), eluting with 1.5% MeOH/CH$_2$Cl$_2$ to obtain the title compound (1.8 g, 31%) as an off-white solid. $^1$H NMR (400 MHz, DMSO-d$_6$) δ 9.63 (s, 1H), 9.21 (s, 1H), 7.32 (m, 5H), 7.13 (d, 1H, J=9 Hz), 5.03 (s, 2H), 4.03 (m, 1H), 2.06 (m, 1H), 0.95 (m, 6H). LCMS: m/z=267.2 [M+H]$^+$, RT=3.10 minutes, (Program P1, Column Y).

Step 3: [(S)-2-Methyl-1-(4H-[1,2,4]triazol-3-yl)-propyl]-carbamic acid benzyl ester To a stirred solution of compound III (1.8 g; 6.7 mmol; 1 eq) in ethanol (80 mL) was added formic acid hydrazide (2 g; 33 mmol; 5 eq), mercury (II) chloride (2.38 g; 8.7 mmol; 1.3 eq) and the mixture was degassed with argon for 15 min, then stirred at 23° C. for 17 h. The mixture was then filtered through the Celite® reagent and the filtrate was evaporated to dryness. The residue was diluted with EtOAc (200 mL) and washed with 20% aq. sodium carbonate solution. The organic layer was then dried over anhydrous sodium sulfate, filtered and concentrated under reduced pressure to provide a crude compound. The crude material was dissolved in ethanol (100 mL) and heated at reflux for 17 h. The mixture was concentrated in vacuo to provide a crude compound which was purified by silica gel (100-200 mesh) gravity column chromatography eluting with 3% MeOH/CH$_2$Cl$_2$ to obtain the title compound (1.4 g, 74%) as a white solid. $^1$H NMR (400 MHz, DMSO-d$_6$) δ 13.76 (brs, 1H), 8.44 (s, 1H), 7.51 (m, 1H), 7.34 (m, 5H), 5.03 (m, 2H), 4.51 (m, 1H), 2.12 (m, 1H), 0.90 (m, 3H), 0.79 (m, 3H).

Step 4: (S)-2-Methyl-1-(4H-[1,2,4]triazol-3-yl)-propylamine

To a stirred solution of compound IV (0.5 g; 1.84 mmol; 1 eq) in EtOH, degassed with argon, was added 10% Pd/C (1.5 g) and HCl in dioxane (4.0 M solution, 10 mL) and the resulting mixture was stirred at 23° C. under a hydrogen atmosphere of 50 psi pressure in a Parr shaker for 10 h. The mixture was filtered through the Celite® reagent and the filtrate was evaporated to dryness to afford the title compound (0.23 g, 90%) as an off white solid. $^1$H NMR (400 MHz, DMSO-$d_6$) δ 8.10 (brs, 3H), 7.86 (s, 1H), 7.56 (s, 1H), 3.52 (m, 1H), 2.10 (m, 1H), 0.94 (m, 6H).

Preparation 9: (R)-1-(3-Methyl-[1,2,4]oxadiazol-5-yl)-ethylamine hydrochloride salt Scheme 9

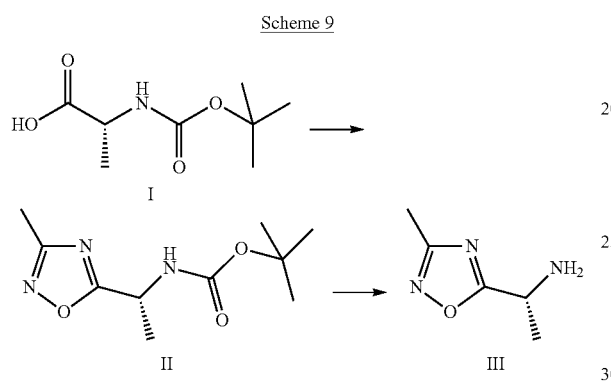

Step 1: [(R)-1-(3-Methyl-[1,2,4]oxadiazol-5-yl)-ethyl]-carbamic acid tert-butyl ester To a stirred solution of compound I (3 g, 15.9 mmol, 1 eq) in DMF (15 mL) were added TEA (6.7 mL, 47.6 mmol, 3 eq), N-hydroxy acetamidine hydrochloride (1.5 g, 20.6 mmol, 1.3 eq) and T3P (50% in ethyl acetate, 7 mL, 23.8 mmol, 1.5 eq) at 23° C. and the resulting mixture was heated at 110° C. for 3 h. The mixture was cooled to room temperature and quenched with water. The organic components were extracted with ethyl acetate (2×200 mL) and the combined extracts were washed with brine. The organic layer was dried over anhydrous sodium sulfate, filtered and concentrated in vacuo to dryness. The crude product was purified by silica gel (100-200 mesh) gravity column chromatography eluting with 10-50% EtOAc/hexane to obtain the title compound (3 g, 83%) as sticky liquid. $^1$H NMR (400 MHz, CDCl$_3$) δ 5.06 (m, 1H), 2.38 (s, 3H), 1.43 (s, 9H).

Step 2: (R)-1-(3-Methyl-[1,2,4]oxadiazol-5-yl)-ethylamine hydrochloride salt

To a stirred solution of compound II (3 g; 13.2 mmol; 1 eq) in 1,4-dioxane (15 mL) at 0° C. was added 4 M HCl in 1,4-dioxane (53 mL) dropwise over a period of 30 min and the resulting mixture was stirred at 23° C. for 24 h. The mixture was concentrated in vacuo to obtain the title compound (2.1 g, 100%) as an off white solid. $^1$H NMR (400 MHz, DMSO-$d_6$) δ 9.02 (brs, 3H), 4.86 (q, 1H, J=7 Hz), 2.39 (s, 3H), 1.60 (d, 3H, J=7 Hz). The analytical chiral HPLC chromatogram showed that the compound was not chirally pure.

Preparation 10: (R)-1-(5-Methyl-[1,3,4]oxadiazol-2-yl)-ethylamine trifluoro acetic acid salt Scheme 10

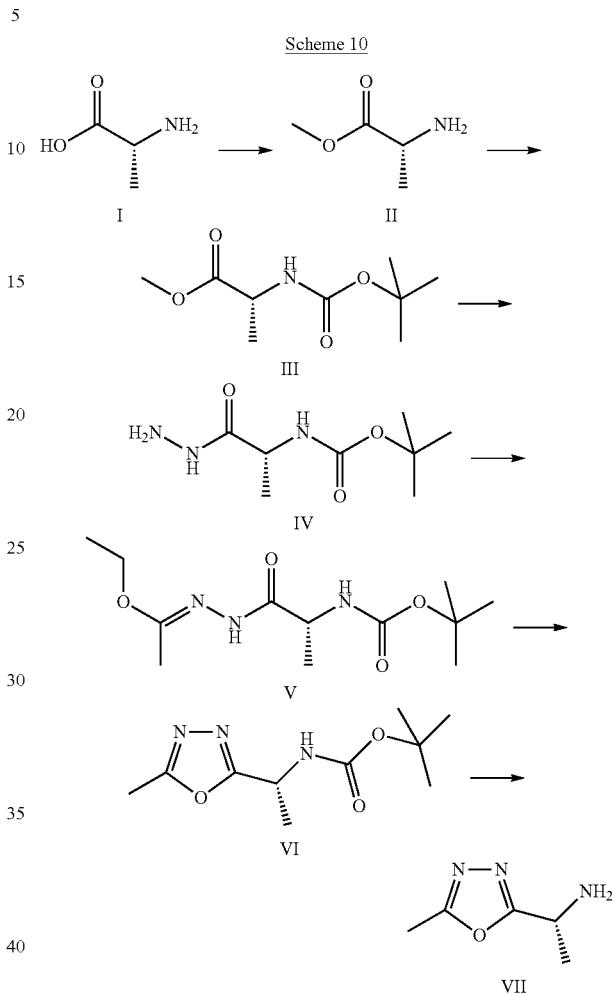

Step 1: (R)-2-Amino-propionic acid methyl ester

To a stirred solution of compound I (10 g, 112.24 mmol, 1 eq) in methanol (160 mL) was added thionyl chloride (16.3 mL, 224.5 mmol, 2 eq) at 0° C. and the resulting mixture was stirred at 23° C. for 10 h. The mixture was concentrated under reduced pressure and diluted with ice cold sodium bicarbonate solution (300 mL). The organic components were extracted with EtOAc (3×300 mL) and the combined extracts were washed with brine. The organic phase was dried over anhydrous sodium sulfate, filtered and concentrated in vacuo to obtain the crude title compound (17.9 g, 15.6 g, 100%) as a semi solid material. $^1$H NMR (400 MHz, DMSO-$d_6$) δ 8.56 (brs, 3H), 4.05 (m, 1H), 3.73 (s, 3H), 1.41 (d, 3H, J=7 Hz).

Step 2: (R)-2-tert-Butoxycarbonylamino-propionic acid methyl ester

To a stirred solution of compound II (16.0 g, 114.7 mmol, 1 eq) in CH$_2$Cl$_2$ (60 mL) was added TEA (48.1 mL, 344.1 mmol, 3 eq) and BOC-anhydride (30 g 137.6 mmol, 1.2 eq) at 0° C. and the resulting mixture was stirred at 23° C. for 16 h. The mixture was poured into ice cold water (500 mL), extracted with EtOAc (2×300 mL) and the combined extracts were washed with brine. The organic layer was dried over anhydrous sodium sulfate, filtered and concentrated to dryness to obtain crude title compound (20.0 g 72%) as an off white solid. $^1$H NMR (400 MHz, DMSO-$d_6$) δ 7.25 (d, 1H, J=7 Hz), 3.99 (m, 1H), 3.30 (s, 3H), 1.37 (m, 9H), 1.22 (d, 3H, J=7 Hz).

Step 3: ((R)-1-Hydrazinocarbonyl-ethyl)-carbamic acid tert-butyl ester

To a stirred solution of compound III (10 g; 41.84 mmol; 1 eq) in THF (30 mL) in a reaction tube was added hydrazine hydrate (6.08 mL; 125.52 mmol; 3 eq). The reaction tube was sealed and heated at 110° C. for 10 h. The mixture was concentrated in vacuo to obtain crude title compound (11 g, 100%) as an off white solid. $^1$H NMR (400 MHz, DMSO-$d_6$) δ 8.98 (brs, 1H), 7.10 (brs, 1H), 6.82 (d, 1H, J=7 Hz), 6.48 (brs, 1H), 4.11 (m, 1H), 1.30 (m, 9H), 1.10 (m, 3H).

Step 4: {(R)-1-[1-Ethoxy-eth-(E)-ylidene-hydrazinocarbonyl]-ethyl}-carbamic acid tert-butyl ester A solution of compound IV (2.5 g; 9.16 mmol; 1 eq) in triethyl orthoacetate (10.4 mL; 55 mmol; 6 eq) was heated at reflux for 2-3 h. The mixture was poured into ice cold water (100 mL) and the organic components were extracted with EtOAc (2×100 mL) and the combined extracts were washed with brine. The organic layer was dried over anhydrous sodium sulfate, filtered and concentrated in vacuo to obtain the crude title compound (3.6 g, 100%) as a brown solid.

Step 5: [(R)-1-(5-Methyl-[1,3,4]oxadiazol-2-yl)-ethyl]-carbamic acid tert-butyl ester A solution of compound V (3.5 g, 12.8 mmol, 1 eq) in acetic acid (7.3 mL, 128 mmol, 10 eq) was heated at 60° C. under stirring for 5 h. The mixture was concentrated in vacuo to remove the acetic acid and the residue was neutralized with ice cold sodium bicarbonate solution. The organic components were extracted with EtOAc (2×200 mL) and the combined extracts were washed with brine. The organic layer was dried over anhydrous sodium sulfate, filtered and concentrated in vacuo, to obtain the title compound (0.65 g, 23%) as a brown solid. $^1$H NMR (400 MHz, DMSO-$d_6$) δ 7.56 (d, 1H, J=8 Hz), 4.82 (m, 1H), 2.46 (s, 3H), 4.40 (m, 12H).

Step 6: (R)-1-(5-Methyl-[1,3,4]oxadiazol-2-yl)-ethylamine trifluoro acetic acid salt To a solution of compound VI (0.5 g, 2.2 mmol, 1 eq) in $CH_2Cl_2$ (10 mL) was added trifluoroacetic acid (0.4 mL, 4.4 mmol, 2 eq) and the resulting mixture was stirred at 23° C. for 18 h. The mixture was concentrated under reduced pressure to remove the trifluoroacetic acid and the residue was washed with hexane to obtain the title compound (0.28 g, 100%) as a brown solid. $^1$H NMR (400 MHz, DMSO-$d_6$) δ 8.72 (brs, 3H), 4.18 (m, 1H), 2.54 (s, 3H), 1.56 (d, 3H, J=7 Hz).

Preparation 11: 2-[4-(4,4,5,5-Tetramethyl-[1,3,2]dioxaborolan-2-yl)-pyrazol-1-yl]-acetamide

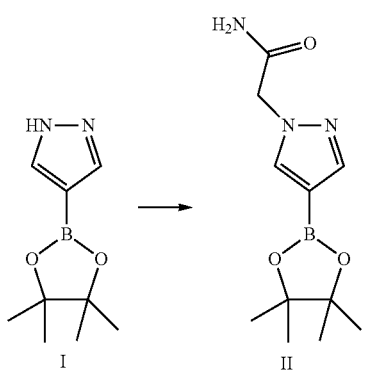

Scheme 11

To a solution of compound I (5 g, 25.7 mmol; 1 eq) in acetonitrile in a reaction tube (150 mL) was added bromo acetamide (5.68 g, 41.2 mmol; 1.6 eq) and cesium carbonate (33.5 g, 102 mmol; 4 eq), and the reaction tube was sealed and heated at 90° C. for 3 h. The mixture was cooled to room temperature and filtered through a Celite® pad and the filtrate was concentrated in vacuo to obtain the title compound (4.2 g, 65%), as a crude product which was directly used in next step without further purification. $^1$H NMR (400 MHz, DMSO-$d_6$) δ 7.67 (d, 1H, J=2 Hz), 7.57 (m, 1H), 7.48 (brs, 1H), 7.42 (s, 1H), 4.76 (s, 2H), 0.89 (s, 12H)

Preparation 12: 5,5,5-Trifluoro-3-oxo-pentanoic acid methyl ester synthesis

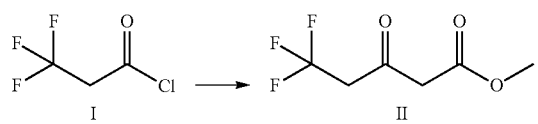

Scheme 12

To a stirred solution of Meldrum's acid (5 g, 34.7 mmol; 1 eq) in dry $CH_2Cl_2$ (5 mL) was added pyridine (3.07 mL; 38.2 mmol; 1.1 eq) at 0° C. followed by 3,3,3-trifluoropropionyl chloride I (5.5 g; 38.2 mmol; 1.1 eq) and the resulting mixture was allowed to stir at 0° C. for 1 h. The temperature of the reaction was then increased to 23° C. and stirring was continued for another 2 h. The mixture was concentrated under reduced pressure to remove volatiles and the resulting paste-like material was dissolved in methanol and heated at 80° C. for 5 h. The mixture was cooled to room temperature, concentrated under reduced pressure and diluted with aqueous ammonium chloride solution. The organic components were extracted with EtOAc, washed with 1N HCl solution, and brine. The organic layer was dried over anhydrous sodium sulfate, filtered and concentrated to dryness to obtain the title compound (3.1 g, 50%), as a crude product which was directly used in next step without purification. $^1$H NMR (DMSO-$d_6$) δ 3.87 (m, 2H), 3.70 (s, 3H), 3.64 (s, 3H).

Preparation 13: 4,4-Difluoro-3-oxo-pentanoic acid methyl ester

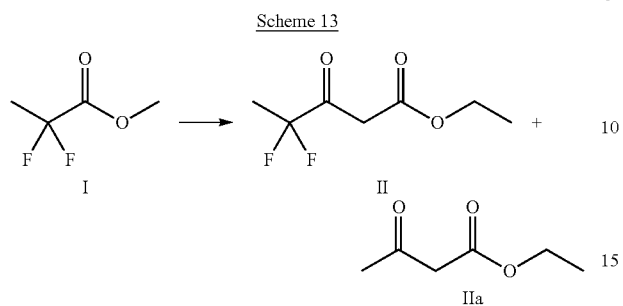

Scheme 13

To a stirred solution of diisopropyl amine in dry THF (150 mL) was added n-butyllithium (2.3 M in hexane, 161 mL; 370.9 mmol; 2 eq) at −78° C. and the resulting mixture was allowed to stir at 0° C. for 40 min. The mixture was cooled to −78° C., ethyl acetate in dry THF was added drop wise and stirring was continued at −78° C. for 1 h. To the mixture, compound I (23 g; 185.4 mmol; 1 eq) in dry THF was added slowly and the resulting mixture was stirred for another 1 h at −78° C. The mixture was allowed to stir at 23° C. for 16 h. The mixture was quenched with aqueous ammonium chloride solution (200 mL) and the organic components were extracted with EtOAc (2×700 mL). The combined organic layers were washed with 1N HCl solution, brine and dried over anhydrous sodium sulfate, then filtered. The filtrate was then concentrated under reduced pressure to obtain the title compound (23 g, 75%) as a crude material which was directly used for the next step without any purification. $^1$H NMR (DMSO-d$_6$) δ 4.21 (m, 4H), 3.93 (s, 4H), 2.17 (s, 2H), 1.77 (t, 3H), 1.187 (m, 6H).

Preparation 14: Tributyl-(5-methyl-thiophen-2-yl)stannane

Scheme 14

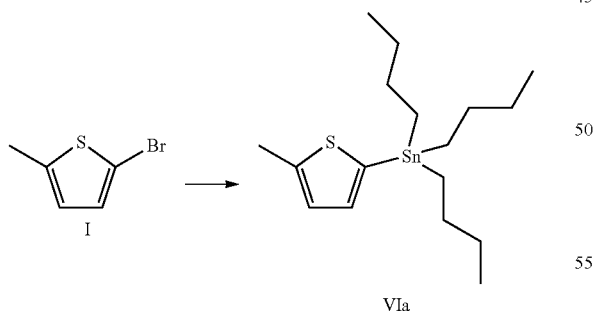

To a stirred solution of 2-bromo-5-methyl thiophene I (6 g, 33.9 mmol, 1 eq) in dry THF (60 mL) cooled to −78° C., was added n-BuLi (14.7 mL, 2.3 M in THF, 1 eq) and the resulting mixture was stirred for 45 min at −78° C. To the mixture was added tributyltin chloride (11 g, 33.9 mmol, 1 eq) and the resulting mixture was allowed to stir at −78° C. for another 1 h. The mixture was then diluted with saturated aqueous ammonium chloride solution, and the organic components were extracted with CH$_2$Cl$_2$ (2×50 mL). The combined organic layers were washed with water and brine, dried over anhydrous sodium sulfate, filtered and concentrated to dryness to obtain crude tributyl-(5-methyl-thiophen-2-yl)stannane (13.1 g) which was directly used in subsequent reactions without any purification. $^1$H NMR (CDCl$_3$) δ 6.95 (d, 1H, J=3 Hz), 6.87 (d, 1H, J=2 Hz), 2.53 (s, 3H), 1.54 (m, 6H), 1.30 (m, 6H), 1.06 (m, 6H), 0.88 (m, 9H).

Following the same protocol, the below compounds were also prepared.

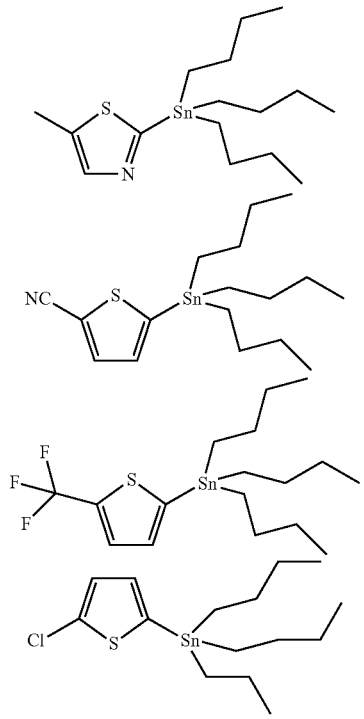

Preparation 15: Tributyl-(5-methyl-furan-2-yl)-stannane

Scheme 15

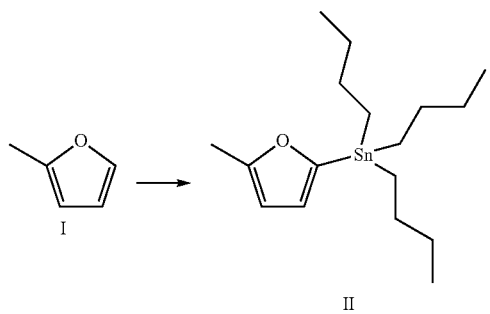

To a stirred solution of 2-methylfuran I (3 g, 36.5 mmol, 1 eq) in dry THF (20 mL) cooled to −78° C. was added n-butyllithium (15.9 mL, 2.3 M in THF, 1 eq) and the resulting mixture was stirred for 1 h at 0° C. The mixture was then cooled to −78° C. and tributyltin chloride was added (11.9 g, 36.5 mmol, 1 eq) and the resulting mixture was allowed to stir at 23° C. for 18 h. The mixture was then diluted with saturated aqueous ammonium chloride solution, and the organic components were extracted with ethyl acetate (2×50 mL). The combined organic layers were washed with water, brine, dried over anhydrous sodium sulfate, filtered and concentrated to dryness to obtain the title compound as a crude product (4.5 g) which was directly used for the next reaction without any purification $^1$H NMR (400 MHz, CDCl$_3$) δ 6.43 (d, 1H, J=3 Hz), 5.97 (d, 1H, J=3 Hz), 2.32 (s, 3H), 1.70-1.40-1.28 (m, 6H), 1.32 (m, 12H), 0.91 (m, 9H).

Preparation 16: 8-(Cyclopropyl-propionyl-amino)-imidazo[1,2-a]pyridine-6-carboxylic acid ethyl ester

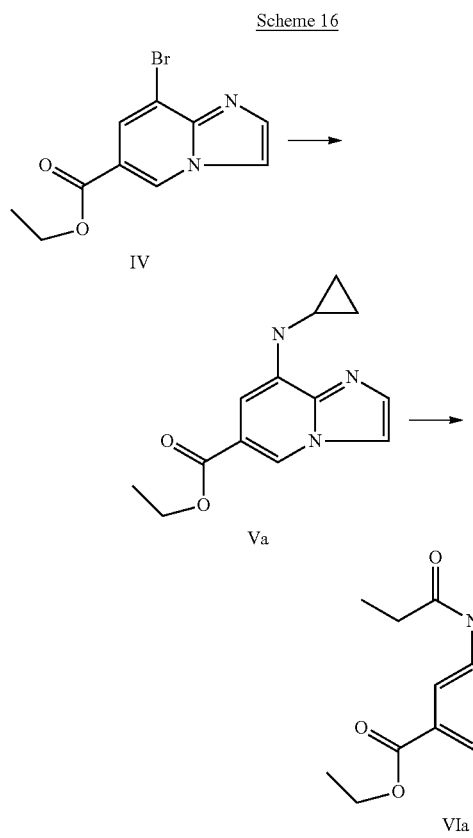

Following the experimental procedure described for Example 8, compound IV was prepared. Compound VIa was converted to Example 188 using the general procedure described in Example 20.

Step 3a: 8-Cyclopropylamino-imidazo[1,2-a]pyridine-6-carboxylic acid ethyl ester To a stirred toluene solution of compound IV (1.5 g; 5.57 mmol; 1 eq) in a reaction tube was added cyclopropyl amine (0.47 g; 8.36 mmol; 1.5 eq) and the resulting mixture was degassed with argon for 5 min, followed by addition of Cs$_2$CO$_3$ (2.72 g; 8.36 mmol; 1.5 eq), Pd$_2$(dba)$_3$ (0.25 g; 0.28 mmol; 0.05 eq) and xantphos (0.32 g; 0.56 mmol; 0.1 eq). The mixture was then degassed again with argon for 5 min and then the reaction tube was sealed and heated to 110° C. for 2 h. The mixture was filtered through a Celite® pad and the filtrate was washed with saturated aqueous NaHCO$_3$ solution, followed by brine. The organic layer was then dried over anhydrous Na$_2$SO$_4$, filtered and evaporated to dryness to obtain a crude material. The crude product was purified by silica gel (100-200 mesh) column chromatography, eluting with 20% EtOAc/hexanes to obtain the title compound (0.31 g, 23%) as a light brown solid. $^1$H NMR (400 MHz, CDCl$_3$) δ 8.35 (s, 1H), 7.54 (s, 1H), 7.50 (s, 1H), 6.95 (s, 1H), 5.51 (s, 1H), 4.39 (q, 2H, J=7 Hz), 2.59 (m, 1H), 1.40 (t, 3H, J=7 Hz), 0.83 (m, 2H), 0.64 (m, 2H). LCMS: m/z=246.2 [M+], RT=3.13 minutes, (Program P1, Column V).

Step 4a: 8-(Cyclopropyl-propionyl-amino)-imidazo[1,2-a]pyridine-6-carboxylic acid ethyl ester To a solution of compound Va (1 g, 4.08 mmol, 1 eq) in dry THF (50 mL) were added pyridine (0.67 mL, 8.16 mmol, 2 eq) and propionyl chloride (0.73 mL, 8.16 mmol, 2 eq) and the resulting mixture was heated at reflux with stirring under an argon atmosphere for 17 h. The mixture was cooled to room temperature and quenched with saturated aqueous sodium bicarbonate solution (100 mL) and the organic components were extracted with ethyl acetate (2×200 mL). The combined organic layers were washed with brine (100 mL), dried over anhydrous sodium sulfate, filtered and the filtrate was concentrated under reduced pressure to provide a crude compound. The crude product was purified by Combiflash™ chromatography eluting with 5% methanol/dichloromethane to obtain the title compound (0.83 g, 68%) as a grey solid. $^1$H NMR (400 MHz, CDCl$_3$) δ 8.87 (s, 1H), 7.69 (s, 2H), 7.47 (s, 1H), 4.40 (q, 2H, J=7 Hz), 3.35 (m, 1H), 2.47 (m, 2H), 1.40 (t, 3H, J=7 Hz), 1.12 (t, 3H, J=7 Hz), 0.81 (m, 2H), 0.63 (m, 2H). LCMS: m/z=302.2 [M+], RT=2.75 minutes, (Program P1, Column W).

Example 1: (S)—N-(1-(4H-1,2,4-Triazol-3-yl)ethyl)-8-(5-ethyl-1,3,4-oxadiazol-2-yl)-3-(5-methyl-thiophen-2-yl)imidazo[1,2-a]pyridine-6-carboxamide

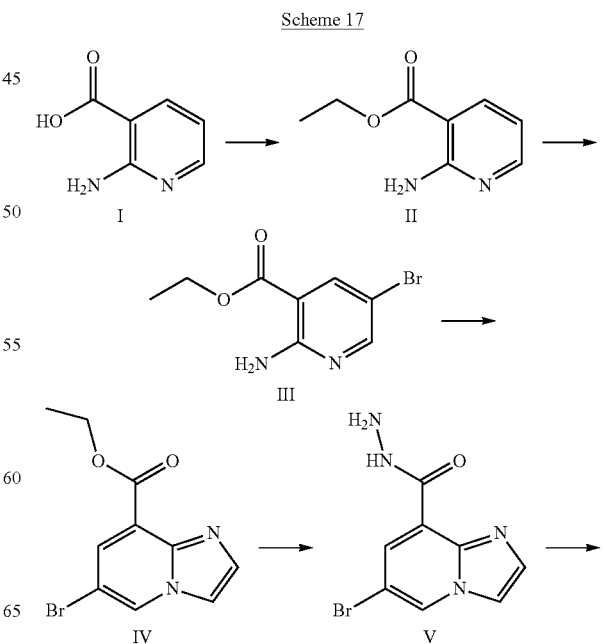

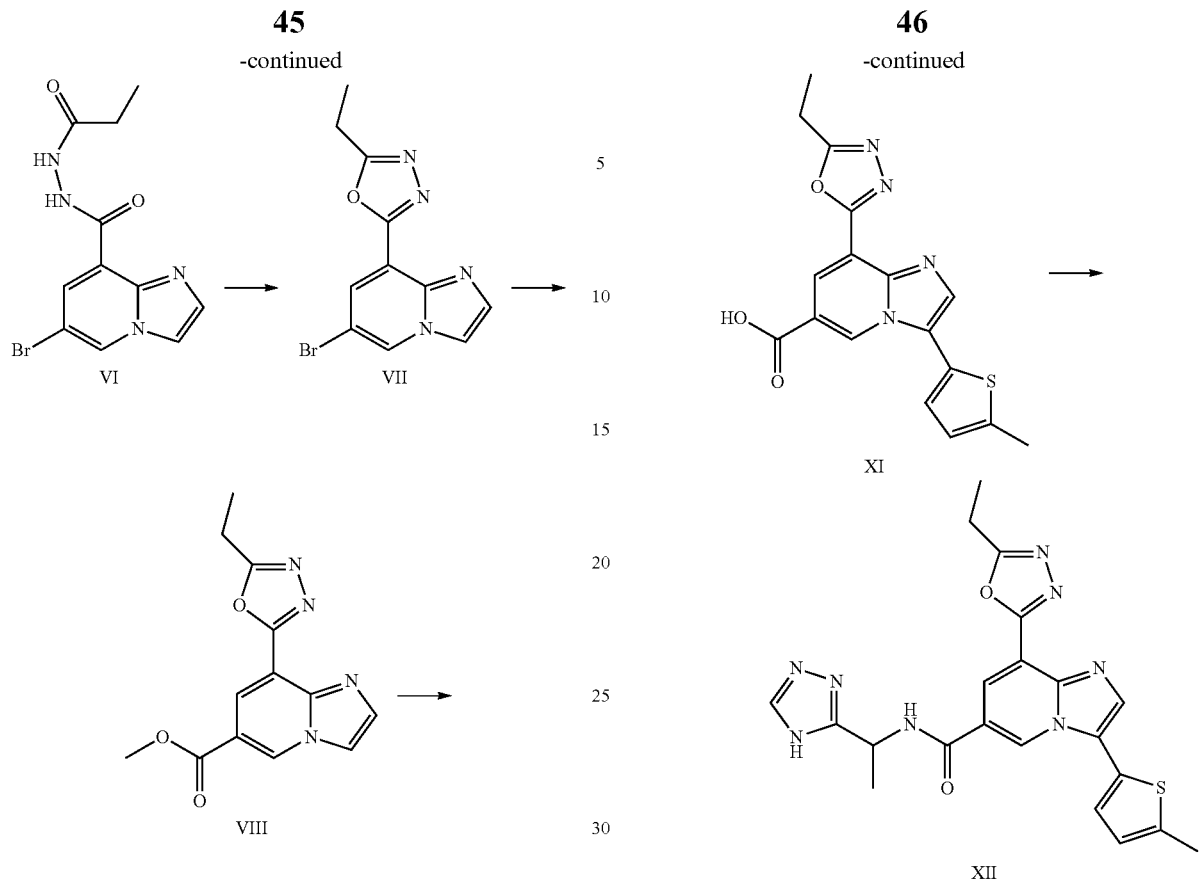

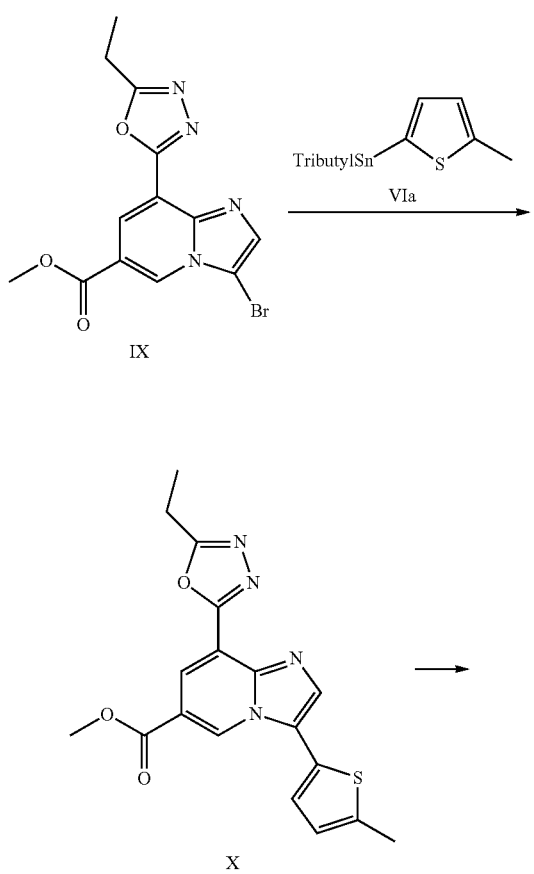

Step 1: 2-Aminonicotinic acid ethyl ester

To a stirred solution of compound I (10 g; 72 mmol; 1 eq) in ethanol (150 mL) was added thionyl chloride (15.7 mL; 217 mmol; 3 eq) dropwise at 60° C. and the resulting mixture was heated at reflux for 17 h. The mixture was evaporated to dryness and pH was adjusted to 7 by adding ice-cold saturated aqueous NaHCO$_3$ solution and solid NaHCO$_3$. The organic components were extracted from the aqueous layer with ethyl acetate (3×500 mL), and the combined organic layers were washed with brine solution, dried over anhydrous sodium sulfate, filtered and the solvent was removed in vacuo to afford the title compound (8 g, 66%) as an off-white solid. $^1$H NMR (DMSO-d$_6$) δ 8.20 (m, 1H), 8.05 (m, 1H), 7.13 (s, 2H), 6.62 (m, 1H), 4.28 (q, 2H, J=7 Hz), 1.30 (t, 3H, J=7 Hz).

Step 2: 2-Amino-5-bromonicotinic acid ethyl ester

To a stirred solution of compound II (15 g; 90.36 mmol; 1 eq) in dry THF (150 mL) was added NBS (16 g; 90.36 mmol; 1 eq) in portions at 0° C. and the resulting mixture was stirred at 23° C. for 18 h. The mixture was poured into ice-cold saturated aqueous NaHCO$_3$ solution and the organic components were extracted with ethyl acetate (3×200 mL). The combined organic layers were then washed with brine solution, dried over anhydrous sodium sulfate, filtered and evaporated to dryness to afford the title compound (22 g, 100%) as an off white solid. $^1$H NMR (DMSO-d$_6$) δ 8.29 (d, 1H, J=3 Hz), 8.12 (d, 1H, J=2 Hz), 7.31 (s, 2H), 4.29 (q, 2H, J=7 Hz), 1.30 (t, 3H, J=7 Hz). LCMS: m/z=245.0 [M+], 247.0 [M+2], RT=3.34 minutes, (Program P1, Column W).

Step 3: 6-Bromo-imidazo[1,2-a]pyridine-8-carboxylic acid ethyl ester

To a stirred solution of compound III (22 g; 90 mmol; 1 eq) in ethanol (500 mL) was added sodium bicarbonate (13 g; 179 mmol; 2 eq) and chloroacetaldehyde solution (~50% aqueous solution, 60 mL; 449 mmol; 5 eq) drop wise and the mixture was heated at reflux for 8 h. The mixture was then evaporated to dryness and the pH was adjusted to 7 using ice-cold saturated aqueous $NaHCO_3$ solution and solid $NaHCO_3$. The organic components were extracted from the aqueous layer with ethyl acetate (3×700 mL) and the combined organic layers were washed with brine, dried over anhydrous sodium sulfate, filtered and the solvents were removed in vacuo to obtain a dry residue which was purified by silica gel (230-400 mesh) column chromatography using 10-50% ethyl acetate/hexanes to afford the title compound (14.5 g, 60%) as a brown solid. $^1$H NMR (DMSO-$d_6$) δ 9.16 (s, 1H), 8.02 (s, 1H), 7.84 (s, 1H), 7.70 (s, 1H), 4.38 (q, 2H, J=7 Hz), 1.30 (t, 3H, J=7 Hz). LCMS: m/z=268.8 [M+], 270.8 [M+2], RT=2.77 minutes, (Program P1, Column Y).

Step 4: 6-Bromo-imidazo[1,2-a]pyridine-8-carboxylic acid hydrazide

To a stirred solution of compound IV (5 g; 18.6 mmol; 1 eq) in ethanol (50 mL) was added hydrazine hydrate (9.3 g; 186 mmol; 10 eq) and the resulting mixture was heated at reflux for 5 h. The mixture was cooled, filtered and the solid residue was washed with hexane and dried under reduced pressure to obtain the title compound (4.5 g, 95%) as white solid. $^1$H NMR (DMSO-$d_6$) δ 10.91 (s, 1H), 9.13 (d, 1H, J=2 Hz), 8.07 (s, 1H), 7.96 (d, 1H, J=2 Hz), 7.74 (s, 1H) 4.86 (s, 2H).

Step 5: 6-Bromo-imidazo[1,2-a]pyridine-8-carboxylic acid N'-propionyl-hydrazide To a stirred solution of compound V (4.5 g; 17.6 mmol; 1 eq) in dry $CH_2Cl_2$ (50 mL) at 0° C. were added TEA (7.6 mL; 52.9 mmol; 3 eq) and propionyl chloride dropwise and the resulting mixture was allowed to stir at 23° C. for 2 h. The mixture was poured into saturated ice-cold aqueous $NaHCO_3$ solution and the organic components were extracted with ethyl acetate (3×250 mL). The combined organic layers were washed with brine, dried over anhydrous sodium sulfate, filtered and the solvents were removed in vacuo to obtain a dry residue which was purified by silica gel (230-400 mesh) column chromatography using 0-5% methanol/dichloromethane as eluent to afford the title compound (1.2 g, 23%) as an off white solid. $^1$H NMR (DMSO-$d_6$) δ 11.97 (d, 1H, J=4 Hz), 10.73 (d, 1H, J=4 Hz), 9.19 (d, 1H, J=2 Hz), 8.10 (s, 1H), 8.01 (d, 1H, J=2 Hz), 7.77 (s, 1H), 2.27 (q, 2H, J=8 Hz), 1.07 (t, 3H, J=8 Hz). LCMS: m/z=311.0 [M+], 313.0 [M+2], RT=2.29 minutes, (Program P1, Column W).

Step 6: 6-Bromo-8-(5-ethyl-[1,3,4]oxadiazol-2-yl)-imidazo[1,2-a]pyridine

A stirred solution of compound VI (1.2 g; 3.8 mmol; 1 eq) in dry $POCl_3$ (20 mL) was heated at reflux for 2 h. The mixture was evaporated to dryness and diluted with saturated aqueous $NaHCO_3$ solution. The organic components were extracted with ethyl acetate (3×100 mL) and the combined extracts were washed with brine, dried over anhydrous sodium sulfate, filtered and concentrated in vacuo to obtain a dry residue. The crude material was purified by silica gel (230-400 mesh) column chromatography using 0-5% methanol/dichloromethane as the eluent to obtain the title compound (0.6 g, 53%) as a light brown solid. $^1$H NMR (DMSO-$d_6$) δ 9.18 (s, 1H), 8.09 (s, 1H), 7.99 (s, 1H), 7.76 (s, 1H), 3.32 (s, 3H), 3.02 (q, 2H), 1.36 (t, 3H). LCMS: m/z=293.0 [M+], 295.0 [M+2], RT=2.46 minutes, (Program P1, Column W).

Step 7: 8-(5-Ethyl-[1,3,4]oxadiazol-2-yl)-imidazo[1,2-a]pyridine-6-carboxylic acid methyl ester To a solution of compound VII (0.6 g; 2.1 mmol; 1 eq) in methanol (20 mL) was added diisopropylethyl amine (1.05 mL; 6.0 mmol; 3 eq), and the resulting solution was degassed with argon for 5 min, followed by an addition of $PdCl_2$(dppf) (0.16 g; 0.21 mmol; 0.1 eq). The mixture was then degassed again with argon for 5 min, and heated to 90° C. for 16 h in an autoclave at a pressure of 50 psi under carbon monoxide atmosphere. The mixture was filtered through a Celite® pad and the filtrate was washed with saturated aqueous $NaHCO_3$ solution, followed by brine. The organic layer was dried over anhydrous $Na_2SO_4$ and finally evaporated to dryness to obtain a crude material. The crude product was purified by silica gel (100-200 mesh) column chromatography, eluting with 0-10% methanol/dichloromethane as the eluent to obtain the title compound (0.3 g, 55%) as a light brown solid. LCMS: m/z=272.8 $[M+H]^+$, RT=2.46 minutes, (Program P1, Column Y).

Step 8: 3-Bromo-8-(5-ethyl-[1,3,4]oxadiazol-2-yl)-imidazo[1,2-a]pyridine-6-carboxylic acid methyl ester To a stirred solution of compound VIII (0.32 g; 1.17 mmol; 1 eq) in dry THF (15 mL) was added NBS (0.12 g; 0.71 mmol; 0.6 eq) in portions at 0° C. and the mixture was stirred for 30 min. The mixture was poured into ice-cold saturated aqueous $NaHCO_3$ solution and the organic components were extracted with ethyl acetate (3×50 mL). The organic layer was then washed with brine, dried over anhydrous sodium sulfate, filtered and evaporated to dryness to obtain a crude material. The crude product was purified by silica gel (100-200 mesh) column chromatography, eluting with 0-5% methanol/dichloromethane to obtain the title compound (0.21 g, 51%) as a brown solid. $^1$H NMR (DMSO-$d_6$) δ 8.94 (s, 1H), 8.36 (s, 1H), 8.04 (s, 1H), 3.97 (s, 3H), 3.03 (q, 2H, J=8 Hz), 1.36 (t, 3H). LCMS: m/z=350.8 [M+], 352.8 [M+2], RT=2.70 minutes, (Program P1, Column Y).

Step 9: 8-(5-Ethyl-[1,3,4]oxadiazol-2-yl)-3-(5-methyl-thiophen-2-yl)-imidazo[1,2-a]pyridine-6-carboxylic acid methyl ester To a stirred solution of compound IX (0.21 g; 0.6 mmol; 1 eq) in dry toluene in a reaction tube was added compound VIa (0.27 g; 0.72 mmol; 1.2 eq) and the resulting mixture was degassed with argon for 5 min. To the mixture was then added $Pd(PPh_3)_4$ (0.06 g; 0.06 mmol; 0.1 eq) and the mixture was degassed further with argon for 5 min. The reaction tube was sealed and heated at 115° C. with stirring for 4 h. The mixture was filtered through a Celite® ad and the filtrate was washed with saturated aqueous $NaHCO_3$ solution, followed by brine. The organic layer was dried over anhydrous $Na_2SO_4$ and the solvent was evaporated to dryness to obtain a crude material. The crude product was purified by silica gel (230-400 mesh) column chromatography eluting with 0-5% methanol/dichloromethane to obtain the title compound (0.22 g, 100%) which was used for the next step without further purification. LCMS: m/z=368.8 [M+H]⁺, RT=3.07 minutes, (Program P1, Column Y).

Step 10: 8-(5-Ethyl-[1,3,4]oxadiazol-2-yl)-3-(5-methyl-thiophen-2-yl)-imidazo[1,2-a]pyridine-6-carboxylic acid To a solution of compound X (0.26 g, 0.7 mmol, 1 eq) in THF:methanol:H₂O (12 mL, 3:2:1) was added an aqueous solution (1 mL) of lithium hydroxide monohydrate (0.09 g, 2.12 mmol, 3 eq) at 0° C. and the resulting mixture was stirred at 23° C. for 3 h. The solvent of the mixture was removed under reduced pressure, the residue was diluted with water, and acidified with 1N HCl to adjust the pH to 3. The precipitated solid was filtered and the residue was dried under vacuum to afford the title compound (0.12 g, 48%). ¹H NMR (DMSO-d₆) δ 9.08 (s, 1H), 8.37 (s, 1H), 7.94 (s, 1H), 7.36 (d, 1H, J=4 Hz), 7.03 (m, 1H), 3.03 (q, 2H, J=8 Hz), 2.56 (s, 3H), 1.36 (t, 3H, J=8 Hz). LCMS: m/z=355.0 [M+H]⁺, RT=2.06 minutes, (Program P1, Column V).

Step 11: (S)—N-(1-(4H-1,2,4-Triazol-3-yl)ethyl)-8-(5-ethyl-1,3,4-oxadiazol-2-yl)-3-(5-methylthiophen-2-yl)imidazo[1,2-a]pyridine-6-carboxamide To a stirred solution of compound XI (80 mg, 0.22 mmol, 1 eq) in DMF (5 mL) was added DIPEA (0.12 mL, 0.7 mmol, 3 eq) and HATU (0.10 g, 0.3 mmol, 1.2 eq) at 0° C. and the resulting mixture was allowed to stir for 15 min. To the mixture was added (S)-1-(4H-[1,2,4]triazol-3-yl)-ethyl-amine hydrochloride (0.101 g, 0.7 mmol, 3 eq) and the resulting mixture was stirred at 23° C. for another 16 h. From the mixture, solvent was removed in vacuo and the residue was diluted with EtOAc and washed with saturated aqueous sodium bicarbonate solution, aqueous ammonium chloride solution and brine. The organic phase was dried over anhydrous sodium sulfate, filtered and concentrated to dryness. The crude product was finally purified by silica gel (230-400 mesh) column chromatography eluting with 0-5% methanol/CH₂Cl₂ to obtain the title compound (4 mg, 4%) as off white solid. ¹H NMR (DMSO-d₆) δ 13.86 (s, 1H), 9.39 (s, 1H), 9.19 (s, 1H), 8.53 (s, 1H), 7.65 (s, 1H), 7.75 (m, 1H), 7.43 (d, 1H, J=4 Hz), 7.04 (d, 1H, J=3 Hz), 5.36 (m, 1H), 3.05 (q, 2H, J=8 Hz), 2.55 (s, 3H), 1.56 (d, 3H, J=7 Hz), 1.38 (t, 3H, J=8 Hz). LCMS: m/z=449.2 [M+H]⁺, RT=2.76 minutes, (Program P1, Column V).

Example 2: 8-(2,5-Dimethyl-1H-imidazol-1-yl)-N-((6-methylpyridin-3-yl)methyl)-3-(5-methylthiophen-2-yl)imidazo[1,2-a]pyridine-6-carboxamide Scheme 18

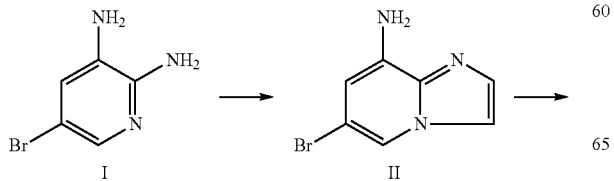

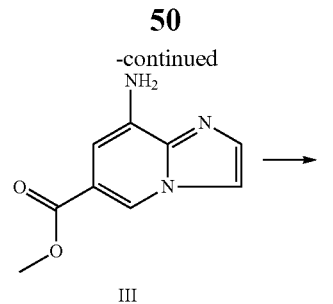

III

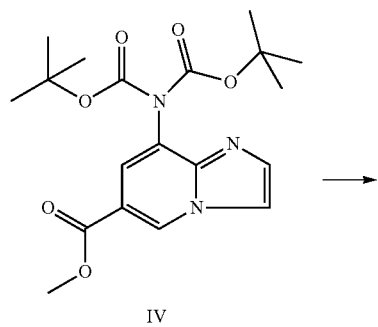

IV

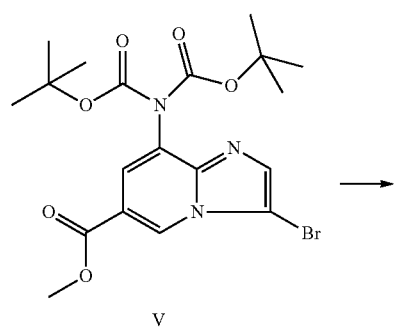

V

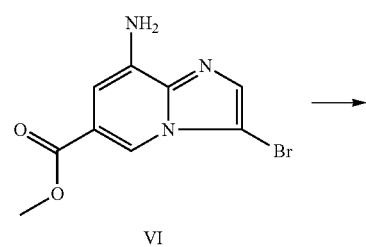

VI

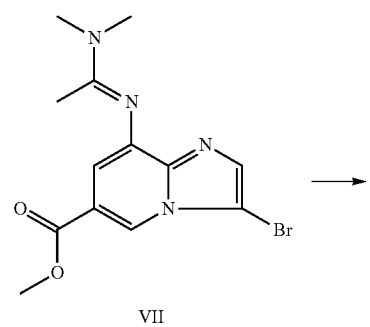

VII

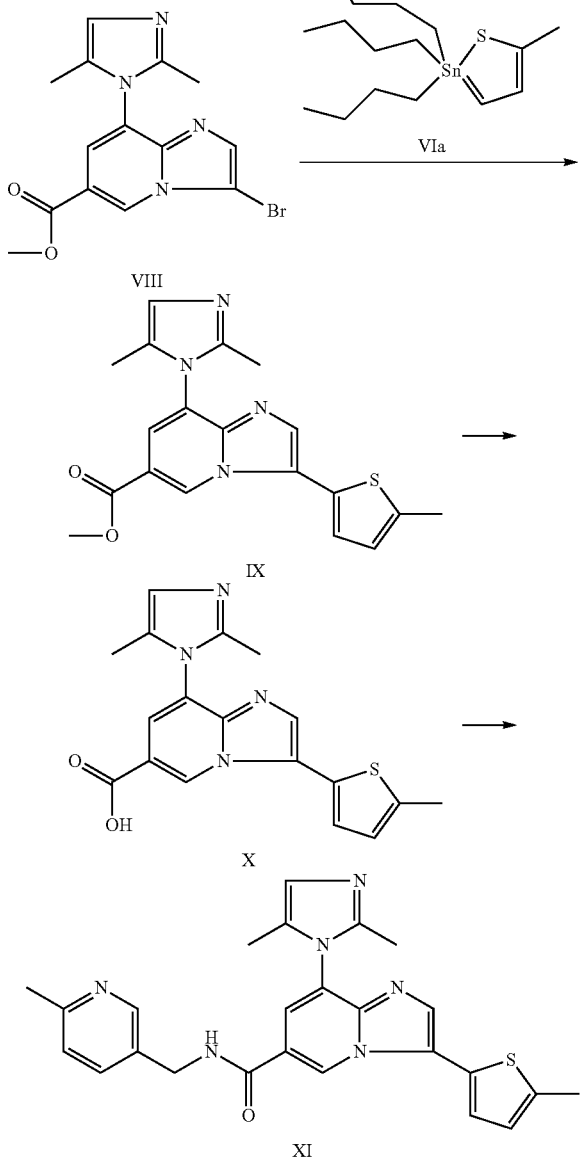

Step 1: 6-Bromoimidazo-[1,2-a]pyridin-8-ylamine

To a stirred solution of compound I (50 g; 0.26 mol; 1 eq) in ethanol (2 L) was added sodium bicarbonate (46 g; 0.53 mol; 2 eq) and chloroacetaldehyde solution (~50% aqueous solution, 86 mL; 0.66 mol; 2.5 eq) drop wise and the resulting mixture was heated at reflux for 17 h. The mixture was then evaporated to dryness and the pH was adjusted to 7 using ice-cold saturated aqueous $NaHCO_3$ solution and solid $NaHCO_3$. The organic components were extracted from the aqueous layer with ethyl acetate (3×1000 mL) and the combined organic layers were washed with brine, dried over anhydrous sodium sulfate, filtered and the solvent was removed in vacuo to obtain a dry residue which was purified by silica gel (230-400 mesh) column chromatography using 10-50% ethyl acetate/hexanes as the eluent to afford the title compound (40 g, 71%) as a brown solid. $^1$H NMR (DMSO-$d_6$) δ 8.04 (s, 1H), 7.77 (s, 1H), 7.44 (s, 1H), 6.31 (s, 1H), 5.99 (s, 2H). LCMS: m/z=212.0 [M+], 214.0 [M+2], RT=2.55 minutes, (Program P1, Column V).

Step 2: 8-Amino-imidazo[1,2-a]pyridine-6-carboxylic acid methyl ester

To a solution of compound II (10 g; 47 mmol; 1 eq) in methanol (200 mL) was added diisopropylethyl amine (41 mL; 236 mmol; 5 eq) and the resulting mixture was degassed with argon for 5 min. To the mixture was added $PdCl_2$(dppf) (4 g; 4.72 mmol; 0.1 eq) and the resulting solution was degassed with argon for another 5 min and then heated in an autoclave at 90° C. at 50 psi carbon monoxide pressure for 16 h. The mixture was filtered through a Celite® pad and the filtrate was washed with saturated aqueous $NaHCO_3$ solution, followed by brine. The organic layer was then dried over anhydrous $Na_2SO_4$ and evaporated to dryness to obtain a crude material. The crude product was purified by silica gel (100-200 mesh) column chromatography, eluting with 0-10% methanol/dichloromethane as the eluent to obtain the title compound (5 g, 55%) as a light brown solid. $^1$H NMR (DMSO-$d_6$) δ 8.57 (s, 1H), 7.97 (s, 1H), 7.5135 (s, 1H), 6.67 (s, 1H), 5.86 (s, 2H), 3.84 (s, 3H). LCMS: m/z=191.8 [M+H]$^+$, RT=2.03 minutes, (Program P1, Column V).

Step 3: 8-[bis-(tert-Butoxycarbonyl)amino]-imidazo[1,2-a]pyridine-6-carboxylic acid methyl ester To a stirred solution of compound III (3 g; 15.6 mmol; 1 eq) in dry THF (200 mL) at 0° C. were added TEA (6.52 mL; 46 mmol; 3 eq), boc anhydride (4.32 mL, 18.8 mmol; 1.2 eq) dropwise and a catalytic amount of DMAP, and the resulting mixture was heated at reflux for 17 h. The mixture was diluted with water (300 mL) and the organic components were extracted with ethyl acetate (3×200 mL). The combined organic layers were washed with brine, dried over anhydrous sodium sulfate, filtered and the solvents were removed in vacuo to obtain dry residue which was purified by silica gel (230-400 mesh) column chromatography using 10-50% ethyl acetate/hexanes as the eluent to afford the title compound (2.9 g, 49%) as a solid. $^1$H NMR (DMSO-$d_6$) δ 9.36 (s, 1H), 8.15 (s, 1H), 7.67 (s, 1H), 7.50 (s, 1H), 3.89 (s, 3H), 1.33 (s, 18H). LCMS: m/z=391.8 [M+H]$^+$, RT=3.18 minutes, (Program P1, Column Y).

Step 4: 3-Bromo-8-[bis-(tert-Butoxycarbonyl)amino]-imidazo[1,2-a]pyridine-6-carboxylic acid methyl ester To a stirred solution of compound IV (2.88 g; 7.3 mmol; 1 eq) in dry THF (80 mL) was added NBS (1.31 g; 7.3 mmol; 1 eq) in portions at 0° C. and the resulting mixture was stirred for 30 min at 0° C. The temperature of the mixture was then slowly raised to 23° C. and the mixture was stirred for 2 h. The mixture was poured into ice-cold saturated aqueous $NaHCO_3$ solution and the organic components were extracted with ethyl acetate (3×50 mL). The combined organic layers were then washed with brine, dried over anhydrous sodium sulfate, filtered and concentrated in vacuo to obtain a dry residue which was purified by silica gel (230-400 mesh) column chromatography using 10-50% ethyl acetate/hexanes as the eluent to afford the title compound (3.46 g, 100%) as a solid. $^1$H NMR (DMSO-$d_6$) δ 8.79 (s, 1H), 7.88 (s, 1H), 7.68 (s, 1H), 3.93 (s, 3H), 1.34 (s, 18H). LCMS: m/z=469.8 [M+], 471.8 [M+2], RT=3.54 minutes, (Program P1, Column Y).

Step 5: 8-Amino-3-bromo-imidazo[1,2-a]pyridine-6-carboxylic acid methyl ester To a stirring solution of compound V (3.5 g; 7.4 mmol; 1 eq) in methanol (50 mL) at 0° C. was added 4M methanolic HCl (100 mL) dropwise over a period of 30 min and the resulting mixture was stirred at 23° C. for 24 h. The mixture was poured into ice-cold saturated aqueous NaHCO$_3$ solution and the organic components were extracted with ethyl acetate (3×500 mL). The combined organic layers were washed with brine, dried over anhydrous sodium sulfate, filtered and concentrated in vacuo to obtain the title compound (2 g, 100%) as solid. LCMS: m/z=269.8 [M+], 271.8 [M+2], RT=2.91 minutes, (Program P1, Column Y).

Step 6: 3-Bromo-8-[1-dimethylamino-ethylideneamino]-imidazo[1,2-a]pyridine-6-carboxylic acid methyl ester A stirring solution of compound VI (0.42 g; 2.19 mmol; 1 eq) in dimethyl acetamide dimethyl acetal (1.5 mL) was heated at reflux for 1 h. The mixture was evaporated to dryness to afford the title compound (0.74 g, 100%). LCMS: m/z=339.0 [M+], 341.0 [M+2], RT=2.69 minutes, (Program P1, Column W).

Step 7: 3-Bromo-8-(2, 5-dimethyl-imidazol-1-yl)-imidazo-[1,2-a]pyridine-6-carboxylic acid methyl ester To compound VII (0.73 g; 2.15 mmol; 1 eq) was added aqueous HCl dropwise at 0° C., followed by propargyl amine (1.18 g; 21.53 mmol; 10 eq) and the resulting mixture was stirred at 0° C. for 30 min. The temperature was then raised to 100° C. and stirred for another 3 h. The mixture was cooled to room temperature and diluted with ice-cold saturated aqueous NaHCO$_3$ solution and the organic components were extracted with ethyl acetate (3×50 mL). The combined organic layers were then washed with brine, dried over anhydrous sodium sulfate, filtered and concentrated to dryness. The crude product was purified by silica gel (230-400 mesh) column chromatography eluting with 0-5% methanol/CH$_2$Cl$_2$ to obtain the title compound (0.38 g, 51%) as a brown solid. $^1$H NMR (CDCl$_3$) δ 8.99 (s, 1H), 7.72 (s, 2H), 6.82 (s, 1H), 4.01 (s, 3H), 2.20 (s, 3H), 2.00 (s, 3H). LCMS: m/z=349.0 [M+], 351.0 [M+2], RT=2.79 minutes, (Program P1, Column Y).

Step 8: 8-(2,5-Dimethyl-imidazol-1-yl)-3-(5-methyl-thiophen-2-yl)-imidazo[1,2-a]pyridine-6-carboxylic acid methyl ester To a stirred dry toluene solution of compound (0.38 g; 1.08 mmol; 1 eq) in a reaction tube was added compound VIa (0.63 g; 1.63 mmol; 1.5 eq) and the resulting mixture was degassed with argon for 5 min. To the mixture was added Pd(PPh$_3$)$_4$ (0.12 g; 0.1 mmol; 0.1 eq) and degassing with argon was repeated for an additional 5 min. The reaction tube was sealed and heated at 115° C. for 4 h. The mixture was filtered through a Celite® pad and the filtrate was washed with saturated aqueous NaHCO$_3$ solution, followed by brine. The organic layer was then dried over anhydrous Na$_2$SO$_4$, filtered and the solvents were removed in vacuo to obtain a crude material. The crude product was purified by silica gel (230-400 mesh) column chromatography eluting with 0-5% methanol/CH$_2$Cl$_2$ to obtain the title compound (0.18 g, 46%) as a light brown solid. $^1$H NMR (DMSO-d$_6$) δ 9.09 (s, 1H), 7.89 (s, 1H), 7.74 (s, 1H), 7.43 (d, 1H, J=3 Hz), 7.04 (d, 1H, J=3 Hz), 6.71 (s, 1H), 3.91 (s, 3H), 2.56 (s, 3H), 2.10 (s, 3H), 1.96 (s, 3H). LCMS: m/z=366.8 [M+H]$^+$, RT=3.04 minutes, (Program P1, Column W).

Step 9: 8-(2,5-Dimethyl-imidazol-1-yl)-3-(5-methyl-thiophen-2-yl)-imidazo[1,2-a]pyridine-6-carboxylic acid To a solution of compound IX (0.18 g, 0.5 mmol, 1 eq) in THF:methanol:H$_2$O (15 mL, 3:2:1) at 0° C. was added a solution of lithium hydroxide monohydrate (0.062 g, 1.5 mmol, 3 eq) in water (1 mL) and the resulting mixture was stirred at 23° C. for 3 h. The solvent was removed under reduced pressure and the residue was diluted with water and acidified with 1N HCl to adjust the pH to 3. The precipitated solid was collected by filtration and dried under vacuum to afford the title compound (0.15 g, 88%). $^1$H NMR (DMSO-d$_6$) δ 9.83 (s, 1H), 9.09 (s, 1H), 7.89 (s, 1H), 7.74 (s, 1H), 7.43 (d, 1H, J=3 Hz), 7.04 (d, 1H, J=3 Hz), 6.71 (s, 1H), 2.50 (s, 3H), 2.10 (s, 3H), 1.96 (s, 3H). LCMS: m/z=353.0 [M+H]$^+$, RT=2.03 minutes, (Program P1, Column Y).

Step 10: 8-(2,5-Dimethyl-1H-imidazol-1-yl)-N-((6-methylpyridin-3-yl)methyl)-3-(5-methylthiophen-2-yl)imidazo[1,2-a]pyridine-6-carboxamide To a stirred solution of compound X (0.07 g, 0.2 mmol, 1 eq) in CH$_2$Cl$_2$ (5 mL) were added DIPEA (0.1 mL, 0.6 mmol, 3 eq) and HATU (0.092 g, 0.24 mmol, 1.2 eq) at 0° C. and the resulting mixture was stirred for 15 min. To the mixture was added C-(6-methyl-pyridin-3-yl)-methylamine (0.048 g, 0.30 mmol, 1.5 eq) and the resulting mixture was allowed to stir at 23° C. for another 16 h. From the mixture, solvent was removed in vacuo and the residue was diluted with EtOAc, washed with saturated aqueous sodium bicarbonate solution, aqueous ammonium chloride solution and brine. The organic layer was dried over anhydrous sodium sulfate, filtered and concentrated to dryness. The crude product was purified by silica gel (230-400 mesh) column chromatography eluting with 0-5% methanol/CH$_2$Cl$_2$ to obtain the title compound (0.01 g, 11%) as an off-white solid. $^1$H NMR (DMSO-d$_6$) δ 9.30 (t, 1H, J=6 Hz), 9.11 (s, 1H), 8.44 (s, 1H), 7.85 (d, 2H, J=8 Hz), 7.64 (dd, 1H, J=2, 8 Hz), 7.43 (d, 1H, J=3 Hz), 7.21 (d, 1H, J=8 Hz), 7.03 (d, 1H, J=3 Hz), 6.71 (s, 1H), 4.48 (d, 2H, J=6 Hz), 2.55 (s, 3H), 2.42 (s, 3H), 2.11 (s, 3H), 1.97 (s, 3H). LCMS: m/z=457.2 [M+H]$^+$, RT=2.96 minutes, (Program P1, Column Y).

Example 3: (S)—N-(1-(4H-1,2,4-Triazol-3-yl)ethyl)-8-(3,5-dimethyl-4H-1,2,4-triazol-4-yl)-3-(5-methylthiophen-2-yl)imidazo[1,2-a]pyridine-6-carboxamide Scheme 19

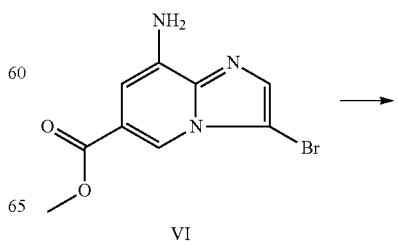

VI

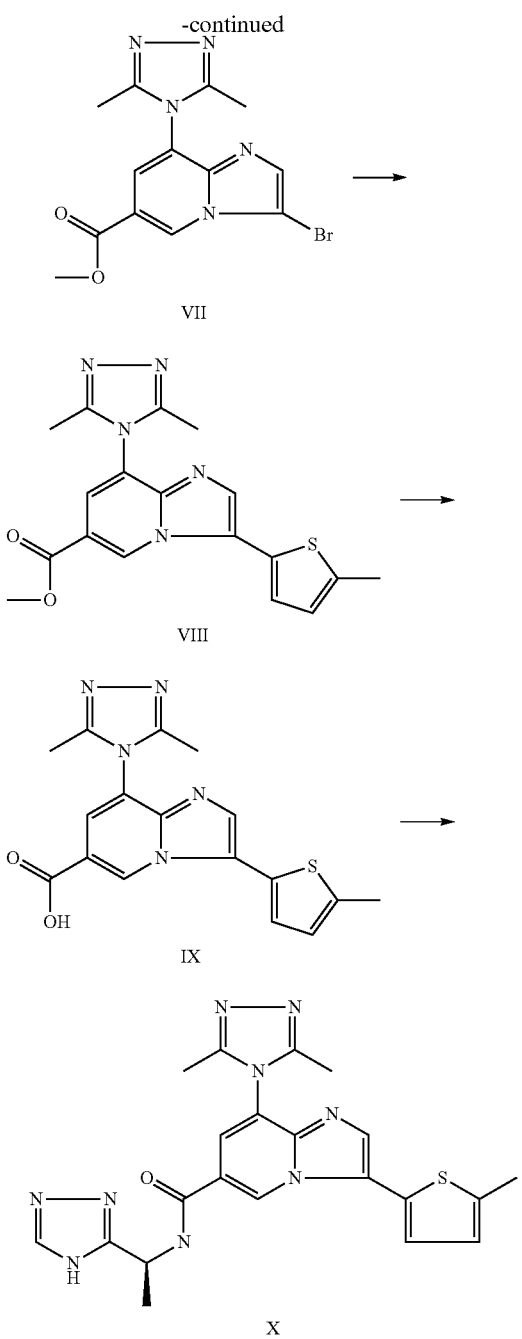

Following the experimental procedure described for Example 2, compound VI was prepared.

Step 6: 3-Bromo-8-(3,5-dimethyl-[1,2,4]triazol-4-yl)-imidazo[1,2-a]pyridine-6-carboxylic acid methyl ester A solution of compound VI (0.6 g; 2.22 mmol; 1 eq) in dimethyl acetamide dimethyl acetal (6 mL) was heated at reflux under stirring for 1 h. The mixture was evaporated to dryness and after cooling the residue to 0° C., HCl (1 mL) was added drop wise, followed by acetic acid hydrazide (0.98 g; 13.33 mmol; 6 eq) and the resulting mixture was stirred at 0° C. for 30 min. The temperature was then raised to 130° C. and stirring was continued for another 2 h. The mixture was cooled to room temperature and diluted with ice-cold saturated aqueous NaHCO$_3$ solution and the organic components were extracted with ethyl acetate (3×50 mL). The combined organic layers were then washed with brine, dried over anhydrous sodium sulfate and concentrated to dryness. The crude product was purified by silica gel (230-400 mesh) column chromatography, eluting with 0-5% methanol/CH$_2$Cl$_2$, to obtain the title compound (0.34 g, 44%) as a brown solid. $^1$H NMR (DMSO-d$_6$) δ 8.90 (s, 1H), 8.03 (s, 1H), 7.94 (s, 1H), 3.94 (s, 3H), 2.14 (s, 6H). LCMS: m/z=350.0 [M+], 352.0 [M+2], RT=2.42 minutes, (Program P1, Column Y).

Step 7: 8-(3,5-Dimethyl-[1,2,4]triazol-4-yl)-3-(5-methyl-thiophen-2-yl)-imidazo[1,2-a]pyridine-6-carboxylic acid methyl ester To a stirred dry DMF solution of compound VII (0.34 g; 0.97 mmol; 1 eq) in a reaction tube was added compound VIa (0.57 g; 1.46 mmol; 1.5 eq) and the resulting mixture was degassed with Argon for 5 min. To the mixture was added Pd(PPh$_3$)$_4$ (0.12 g; 0.09 mmol; 0.1 eq) and degassing with Argon was repeated for about 5 min, then the reaction tube was sealed and heated at 130° C. for 4 h. The mixture was quenched with ice cold water and the organic components were extracted with EtOAc. The organic layer was washed with saturated aqueous sodium bicarbonate solution, aqueous ammonium chloride solution and brine. The organic layer was dried over anhydrous sodium sulfate, filtered and concentrated to dryness. The crude product was purified by silica gel (100-200 mesh) column chromatography, eluting with 0-5% Methanol/CH$_2$Cl$_2$, to obtain the title compound (0.29 g, 80%) as an off white solid. LCMS: m/z=368.0 [M+H]$^+$, RT=2.97 minutes, (Program P1, Column Y).

Step 8: 8-(3,5-Dimethyl-[1,2,4]triazol-4-yl)-3-(5-methyl-thiophen-2-yl)-imidazo[1,2-a]pyridine-6-carboxylic acid To a solution of compound VIII (0.29 g, 0.79 mmol, 1 eq) in THF:methanol:H$_2$O (15 mL, 3:2:1) at 0° C. was added a solution of lithium hydroxide monohydrate (0.1 g, 2.37 mmol, 3 eq) in water (1 mL) and the resulting mixture was stirred at 23° C. for 30 min. The solvent was removed under reduced pressure and the residue was diluted with water and acidified with 1N HCl to adjust the pH to 3 and organic components were extracted with EtOAc. The organic layer was dried over anhydrous sodium sulfate, filtered, and concentrated to dryness to afford the title compound (0.28 g, 99%) as an off white solid. $^1$H NMR (DMSO-d$_6$) δ 9.11 (s, 1H), 8.01 (s, 1H), 7.91 (s, 1H), 7.41 (d, 1H, J=4 Hz), 7.03 (m, 1H), 2.25 (s, 6H). LCMS: m/z=354.2 [M+H]$^+$, RT=2.08 minutes, (Program P1, Column Y).

Step 9: (S)—N-(1-(4H-1,2,4-Triazol-3-yl)ethyl)-8-(3,5-dimethyl-4H-1,2,4-triazol-4-yl)-3-(5-methylthiophen-2-yl)imidazo[1,2-a]pyridine-6-carboxamide To a stirred solution of compound IX (0.3 g, 0.85 mmol, 1 eq) in DMF (50 mL) were added TEA (0.8 mL, 4.25 mmol, 5 eq), T3P (0.4 mL, 1.30 mmol, 1.5 eq) and (S)-1-(4H-[1,2,4]triazol-3-yl)-ethylamine hydrochloride (0.15 g, 1.30 mmol, 1.5 eq) at 23° C., then the resulting mixture was heated at 130° C. for 4 h. The mixture was quenched with ice cold water and the organic components were extracted with EtOAc. The organic layer was washed with saturated aqueous sodium bicarbonate solution, aqueous ammonium chloride solution and brine. The organic layer was dried over anhydrous sodium sulfate, filtered, and concentrated to dryness. The crude product was initially purified by silica gel (100-200 mesh) column chromatography eluting with 0-10% methanol/$CH_2Cl_2$ and purified by preparative TLC to obtain the title compound (0.015 g, 4%) as an off white solid. $^1$H NMR (DMSO-$d_6$) δ 13.86 (d, 1H, J=2.4 Hz), 9.16 (m, 2H), 8.48 (s, 1H), 8.04 (s, 1H), 7.86 (s, 1H), 7.43 (s, 1H), 7.04 (s, 1H), 5.33 (m, 1H), 2.55 (s, 3H), 2.20 (s, 6H), 1.55 (m, 3H). LCMS: m/z=448.2 [M+H]$^+$, RT=2.45 minutes, (Program P1, Column Y).

Example 4: (S)—N-(1-(4H-1,2,4-Triazol-3-yl)ethyl)-8-(5-(difluoromethyl)-1H-1,2,3-triazol-1-yl)-3-(5-methylthiophen-2-yl)imidazo[1,2-a]pyridine-6-carboxamide

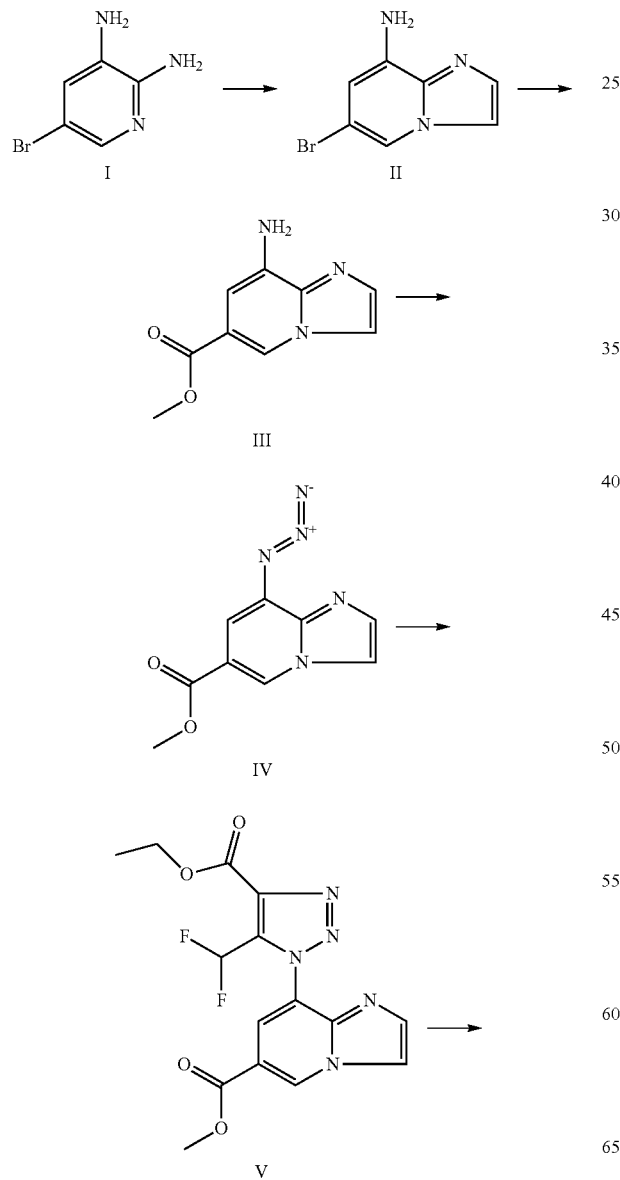
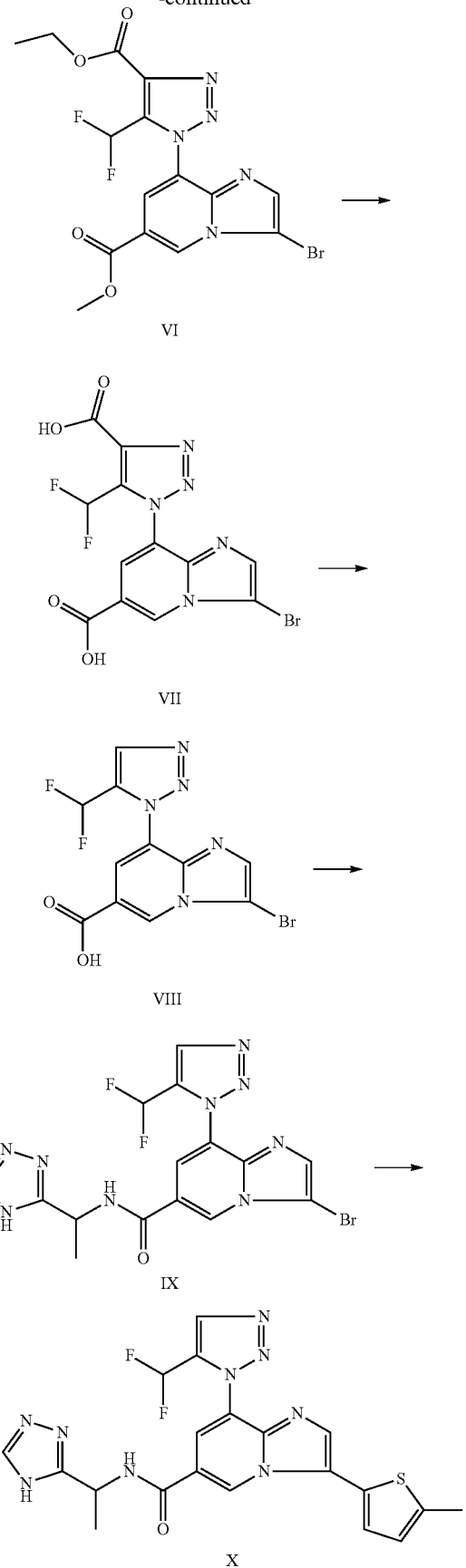

Step 1: 6-Bromo-imidazo[1,2-a]pyridin-8-ylamine

To a stirred solution of compound I (50 g; 0.26 mol; 1 eq) in ethanol (2 L) was added sodium bicarbonate (46 g; 0.53 mol; 2 eq) and chloroacetaldehyde solution (~50% aqueous solution, 86 mL; 0.66 mol; 2.5 eq) dropwise and the resulting mixture was heated at reflux for 17 h. The mixture was evaporated to dryness and the pH was adjusted to 7 using ice-cold saturated aqueous $NaHCO_3$ solution and solid $NaHCO_3$. The organic components were extracted from the aqueous layer with ethyl acetate (3×1000 mL) and the combined organic layers were washed with brine, dried over anhydrous sodium sulfate, filtered and the solvents were removed in vacuo to obtain a dry residue which was purified by silica gel (230-400 mesh) column chromatography using 10-50% ethyl acetate/hexanes as the eluent to afford the title compound (40 g, 71%) as a brown solid. $^1H$ NMR (DMSO-$d_6$) δ 8.04 (s, 1H), 7.77 (s, 1H), 7.44 (s, 1H), 6.31 (s, 1H), 5.99 (s, 2H). LCMS: m/z=212.0 [M+], 214.0 [M+2], RT=2.55 minutes, (Program P1, Column V).

Step 2: 8-Amino-imidazo[1,2-a]pyridine-6-carboxylic acid methyl ester

To a solution of compound II (10 g; 47.2 mmol; 1 eq) in methanol (200 mL) was added diisopropylethyl amine (41 mL; 236 mmol; 5 eq) and the resulting solution was degassed with argon for 5 min. To the mixture was added $PdCl_2(dppf)$ (4 g; 4.72 mmol; 0.1 eq) and the resulting solution was degassed with argon for another 5 min. The solution was then heated in an autoclave at 90° C. at 50 psi carbon monoxide pressure for 16 h. The mixture was filtered through a Celite® pad and the filtrate was washed with saturated aqueous $NaHCO_3$ solution, followed by brine. The organic layer was then dried over anhydrous $Na_2SO_4$, filtered and evaporated to dryness to obtain a crude material. The crude product was purified by silica gel (100-200 mesh) column chromatography, eluting with 0-10% methanol/dichloromethane as the eluent to obtain the title compound (5 g, 55%) as light brown solid. $^1H$ NMR (DMSO-$d_6$) δ 8.57 (s, 1H), 7.97 (s, 1H), 7.51 (s, 1H), 6.67 (s, 1H), 5.86 (s, 2H), 3.84 (s, 3H). LCMS: m/z=191.8 [M+H]$^+$, RT=2.03 minutes, (Program P1, Column V).

Step 3: 8-Azido-imidazo[1,2-a]pyridine-6-carboxylic acid methyl ester

To a stirred solution of compound III (10 g; 52.36 mmol; 1 eq) in dry THF (600 mL) were added tertiarybutylnitrite (32 mL; 230 mmol; 4.4 eq) dropwise and trimethylsilylazide (16 mL, 115 mmol, 2.2 eq) at 0° C., and the resulting mixture was stirred at 23° C. for 17 h. The mixture was evaporated to dryness to obtain a crude material which was purified by silica gel (100-200 mesh) column chromatography, eluting with 0-50% ethylacetate/hexanes as the eluent to obtain the title compound (9 g, 80%) as light brown solid. $^1H$ NMR (DMSO-$d_6$) δ 9.17 (s, 1H), 8.19 (s, 1H), 7.71 (s, 1H), 7.11 (s, 1H), 3.87 (s, 3H). LCMS: m/z=218.2 [M+H]$^+$, RT=2.69 minutes, (Program P1, Column V).

Step 4: 8-(5-Difluoromethyl-4-ethoxycarbonyl-[1,2,3]triazol-1-yl)-imidazo[1,2-a]pyridine-6-carboxylic acid methyl ester To a stirred solution of DBU (25 mL; 166 mmol; 1.2 eq) in dry DMF:THF (1 L; 1:1) was added 4,4-difluoro-3-oxobutyric acid ethyl ester (22 mL; 207 mmol; 1.5 eq) slowly and the resulting mixture was stirred at 23° C. for 30 min. The mixture was then cooled to 0° C. and compound IV (30 g; 138.2 mmol; 1 eq) in DMF:THF solution was added dropwise and the mixture was allowed to stir at 23° C. for 17 h. The mixture was diluted with water (1 L) and the organic components were extracted with ethyl acetate (3×700 mL). The combined organic layers were washed with brine, dried over anhydrous sodium sulfate, filtered and the solvents were removed in vacuo to obtain a dry residue which was chromatographically purified by silica gel (230-400 mesh) column chromatography using 10-50% ethyl acetate/hexanes as the eluent to afford the title compound (32 g, 65%) as solid. $^1H$ NMR (DMSO-$d_6$) δ 9.65 (s, 1H), 8.33 (s, 1H), 8.10 (s, 1H), 7.74 (s, 1H), 7.46 (m, 1H), 4.43 (q, J=7 Hz, 2H), 3.96 (s, 3H), 1.36 (t, J=7 Hz, 3H). LCMS: m/z=365.8 [M+H]$^+$, RT=2.97 minutes, (Program P1, Column Y).

Step 5: 3-Bromo-8-(5-difluoromethyl-4-ethoxycarbonyl-[1,2,3]triazol-1-yl)-imidazo[1,2-a]pyridine-6-carboxylic acid methyl ester To a stirred solution of compound V (10 g; 27.4 mmol; 1 eq) in dry THF (150 mL) at 0° C. was added NBS (7.4 g; 41.1 mmol; 1.5 eq) in portions and the resulting mixture was stirred at 0° C. for 30 min. The mixture was poured into ice-cold saturated aqueous $NaHCO_3$ solution and the organic components were extracted with ethyl acetate (3×500 mL). The organic layer was then washed with brine, dried over anhydrous sodium sulfate and the solvents were removed in vacuo to obtain a dry residue which was chromatographically purified by silica gel (230-400 mesh) gravity column using 10-50% ethyl acetate/hexanes as the eluent to afford the title compound (10 g, 82%) as a solid. $^1H$ NMR (DMSO-$d_6$) δ 9.00 (s, 1H), 8.27 (s, 1H), 7.96 (s, 1H), 7.44 (m, 1H), 4.43 (q, 2H, J=5 Hz), 3.96 (s, 3H), 1.35 (t, 3H, J=7 Hz). LCMS: m/z=443.8 [M+], 445.8 [M+2], RT=3.20 minutes, (Program P1, Column Y).

Step 6: 3-Bromo-8-(4-carboxy-5-difluoromethyl-[1,2,3]triazol-1-yl)-imidazo[1,2-a]pyridine-6-carboxylic acid To a solution of compound VI (7 g, 15.8 mmol, 1 eq) in THF:methanol:$H_2O$ (115 mL, 3:2:1) at 0° C. was added a solution of lithium hydroxide monohydrate (2 g, 47.3 mmol, 3 eq) in water (5 mL) and the resulting mixture was stirred at 23° C. for 3 h. The solvent was removed under reduced pressure and the residue was diluted with water and acidified with 1N HCl to adjust the pH to 3. The precipitated solid was collected by filtration and dried under vacuum to afford the title compound (5 g, 80%). $^1H$ NMR (DMSO-$d_6$) δ 14.01 (s, 2H), 8.97 (s, 1H), 8.19 (s, 1H), 7.93 (s, 1H), 7.46 (m, 1H). LCMS: m/z=402.0 [M+], 403.8 [M+2], RT=0.84 minutes, (Program P1, Column Y).

Step 7: 3-Bromo-8-(5-difluoromethyl-[1,2,3]triazol-1-yl)-imidazo[1,2-a]pyridine-6-carboxylic acid Compound VII (5 g; 12.4 mmol; 1 eq) was heated at 200° C. for 1 h to obtain the title compound (3.5 g; 80%). $^1H$ NMR (DMSO-$d_6$) δ 14.01 (s, 1H), 8.96 (s, 1H), 8.43 (s, 1H), 8.15 (s, 1H), 7.94 (s, 1H), 7.38 (m, 1H). LCMS: m/z=357.8 [M+], 359.8 [M+2], RT=1.71 minutes, (Program P1, Column Y).

Step 8: 3-Bromo-8-(5-difluoromethyl-[1,2,3]triazol-1-yl)-imidazo[1,2-a]pyridine-6-carboxylic acid [(S)-1-(4H-[1,2,4]triazol-3-yl)-ethyl]-amide To a stirred solution of compound VIII (2 g, 5.6 mmol, 1 eq) in DMF (20 mL) were added DIPEA (3 mL, 16.8 mmol, 3 eq) and HATU (3.2 g, 8.40 mmol, 1.5 eq) at 0° C. and the resulting mixture was stirred for 15 min. To the mixture was added (S)-1-(4H-[1,2,4]triazol-3-yl)-ethylamine hydrochloride (0.94 g, 8.40 mmol, 1.2 eq) and the resulting mixture was allowed to stir at 23° C. for another 16 h. From the mixture, solvent was removed in vacuo and the residue was diluted with EtOAc. The organic layer was washed with saturated aqueous sodium bicarbonate solution, aqueous ammonium chloride solution and brine. The organic layer was dried over anhydrous sodium sulfate, filtered and concentrated to dryness. The crude product was purified by silica gel (230-400 mesh) column chromatography eluting with 0-5% methanol/$CH_2Cl_2$ to obtain the title compound (1 g, 49%) as brown solid. $^1$H NMR (DMSO-$d_6$) δ 13.94 (d, 1H), 9.48 (dd, 1H, J=8 Hz), 9.36 (d, 1H), 8.45 (d, 2H), 8.29 (d, 1H, J=12 Hz), 7.93 (m, 1H), 7.52 (m, 1H), 5.35 (q, 1H, J=8 Hz), 1.55 (d, 3H, J=7 Hz). LCMS: m/z=452.2 [M+], 454.2 [M+2], RT=2.40 minutes, (Program P1, Column Y).

Step 9: (S)—N-(1-(4H-1,2,4-Triazol-3-yl)ethyl)-8-(5-(difluoromethyl)-1H-1,2,3-triazol-1-yl)-3-(5-methylthiophen-2-yl)imidazo[1,2-a]pyridine-6-carboxamide To a stirred, dry DMF solution of compound IX (0.7 g; 1.55 mmol; 1 eq) in a reaction tube was added compound VIa (0.9 g; 2.32 mmol; 1.5 eq) and the resulting mixture was degassed with argon for 5 min. To the mixture was added Pd(PPh$_3$)$_4$ (0.2 g; 0.15 mmol; 0.1 eq) and degassing with argon was repeated for about 5 min. The reaction tube was sealed and heated at 115° C. for 4 h. The mixture was filtered through a Celite® pad and the filtrate was washed with saturated aqueous NaHCO$_3$ solution, followed by brine. The organic layer was then dried over anhydrous Na$_2$SO$_4$, filtered and solvent was removed in vacuo to obtain a crude material. The crude product was purified by silica gel (230-400 mesh) column chromatography eluting with 0-5% methanol/$CH_2Cl_2$ to obtain the title compound (0.29 g, 40%) as light brown solid. $^1$H NMR (DMSO-$d_6$) δ 13.56 (s, 1H), 9.20 (s, 1H), 9.00 (d, 1H), 8.32 (s, 1H), 8.23 (s, 1H), 7.85 (s, 1H), 7.41 (m, 3H), 7.03 (s, 1H), 5.37 (q, 1H), 2.50 (s, 3H), 1.60 (s, 3H). LCMS: m/z=470.2 [M+H]$^+$, RT=2.87 minutes, (Program P1, Column Y).

Example 5: 8-(5-(Difluoromethyl)-1H-1,2,3-triazol-1-yl)-3-(5-methyl-1,3,4-thiadiazol-2-yl)-N-((6-methylpyridin-3-yl)methyl)imidazo[1,2-a]pyridine-6-carboxamide Scheme 21

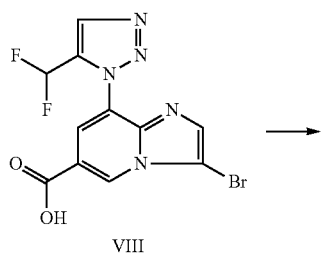

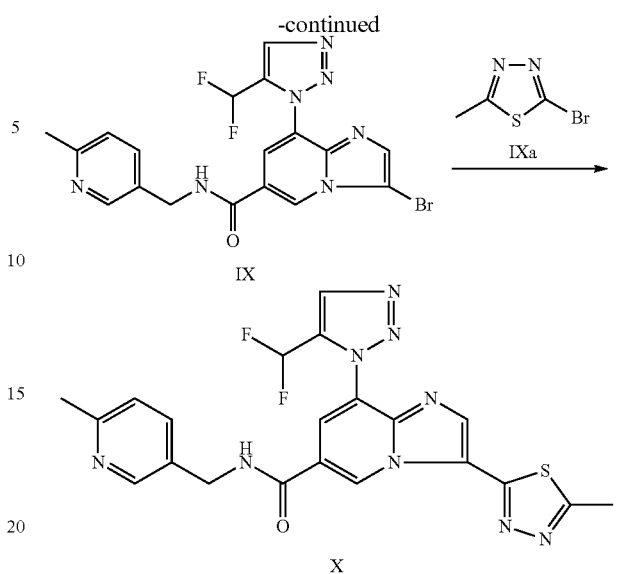

Following the experimental procedure described for Example 4, compound VIII was prepared.

Step 8: 3-Bromo-8-(5-difluoromethyl-[1,2,3]triazol-1-yl)-imidazo[1,2-a]pyridine-6-carboxylic acid (6-methyl-pyridin-3-ylmethyl)-amide To a stirred solution of compound VIII (1 g, 2.8 mmol, 1 eq) in DMF (10 mL) were added DIPEA (5 mL, 26 mmol, 8 eq) and HATU (1.6 g, 4.20 mmol, 1.5 eq) at 23° C. and the resulting mixture was stirred for 15 min. To the mixture was added C-(6-methyl-pyridin-3-yl)-methylamine (520 mg, 4.20 mmol, 1.5 eq) and the resulting mixture was allowed to stir at 23° C. for another 16 h. The mixture was quenched with ice cold water (100 mL) and the organic components were extracted with EtOAc (2×400 mL). The organic layer was washed with saturated aqueous sodium bicarbonate solution, aqueous ammonium chloride solution and brine. The organic layer was dried over anhydrous sodium sulfate, filtered and concentrated to dryness. The crude residue was purified by silica gel (100-200 mesh) column chromatography eluting with 0-4% methanol/$CH_2Cl_2$ to obtain the title compound (0.73 g, 57%) as a brown solid. $^1$H NMR (DMSO-$d_6$) δ 9.51 (t, 1H, J=6 Hz), 9.11 (s, 1H), 8.46 (m, 2H), 8.23 (s, 1H), 7.93 (s, 1H), 7.65 (dd, 1H, J=8, 2 Hz), 7.39 (t, 1H, J=54 Hz), 7.23 (d, 1H, J=8 Hz), 4.52 (d, 2H, J=5.6 Hz), 2.44 (s, 3H). LCMS: m/z=462.0 [M+], 464.2 [M+2], RT=2.80 minutes, (Program P1, Column Y).

Step 9: 8-(5-(Difluoromethyl)-1H-1,2,3-triazol-1-yl)-3-(5-methyl-1,3,4-thiadiazol-2-yl)-N-((6-methyl-pyridin-3-yl)methyl)imidazo[1,2-a]pyridine-6-carboxamide To a stirred, dry DMF solution of compound IX (50 mg; 0.11 mmol; 1 eq) in a reaction tube were added 2-bromo-5-methyl-[1,3,4]thiadiazole (20 mg; 0.11 mmol; 1 eq), hexamethylditin (50 mg; 0.16 mmol; 1.5 eq), and the resulting mixture was degassed with argon for 5 min. To the mixture was added Pd(PPh$_3$)$_4$ (10 mg; 0.01 mmol; 0.1 eq) and degassing with argon was repeated for about 5 min, and the reaction tube was sealed then heated at 130° C. for 2 h. The mixture was quenched with ice cold water (50 mL) and the organic components were extracted with EtOAc (2×150 mL). The combined organic layers were washed with saturated aqueous sodium bicarbonate solution, aqueous ammonium chloride solution and brine. The organic layer was dried over anhydrous sodium sulfate, filtered and concentrated to dryness. The crude product was initially purified by silica gel (100-200 mesh) column chromatography eluting with 0-2% methanol/CH$_2$Cl$_2$ and further purified using preparative TLC to obtain the title compound (20 mg, 13%) as off white solid. $^1$H NMR (DMSO-d$_6$) δ 10.27 (s, 1H), 9.47 (t, 1H, J=6 Hz), 8.53 (s, 1H), 8.49 (s, 1H), 8.45 (m, 2H), 7.66 (dd, 1H, J=8, 2 Hz), 7.41 (t, 1H, J=53 Hz), 7.23 (d, 1H, J=8 Hz), 4.53 (d, 2H, J=6 Hz), 2.84 (s, 3H), 2.44 (s, 3H). LCMS: m/z=482.2 [M+H]$^+$, RT=2.94 minutes, (Program P1, Column Y).

Example 6: 8-(5-Ethyl-1H-pyrazol-1-yl)-N-((6-methylpyridin-3-yl)methyl)-3-(5-methylthiophen-2-yl)imidazo[1,2-a]pyridine-6-carboxamide

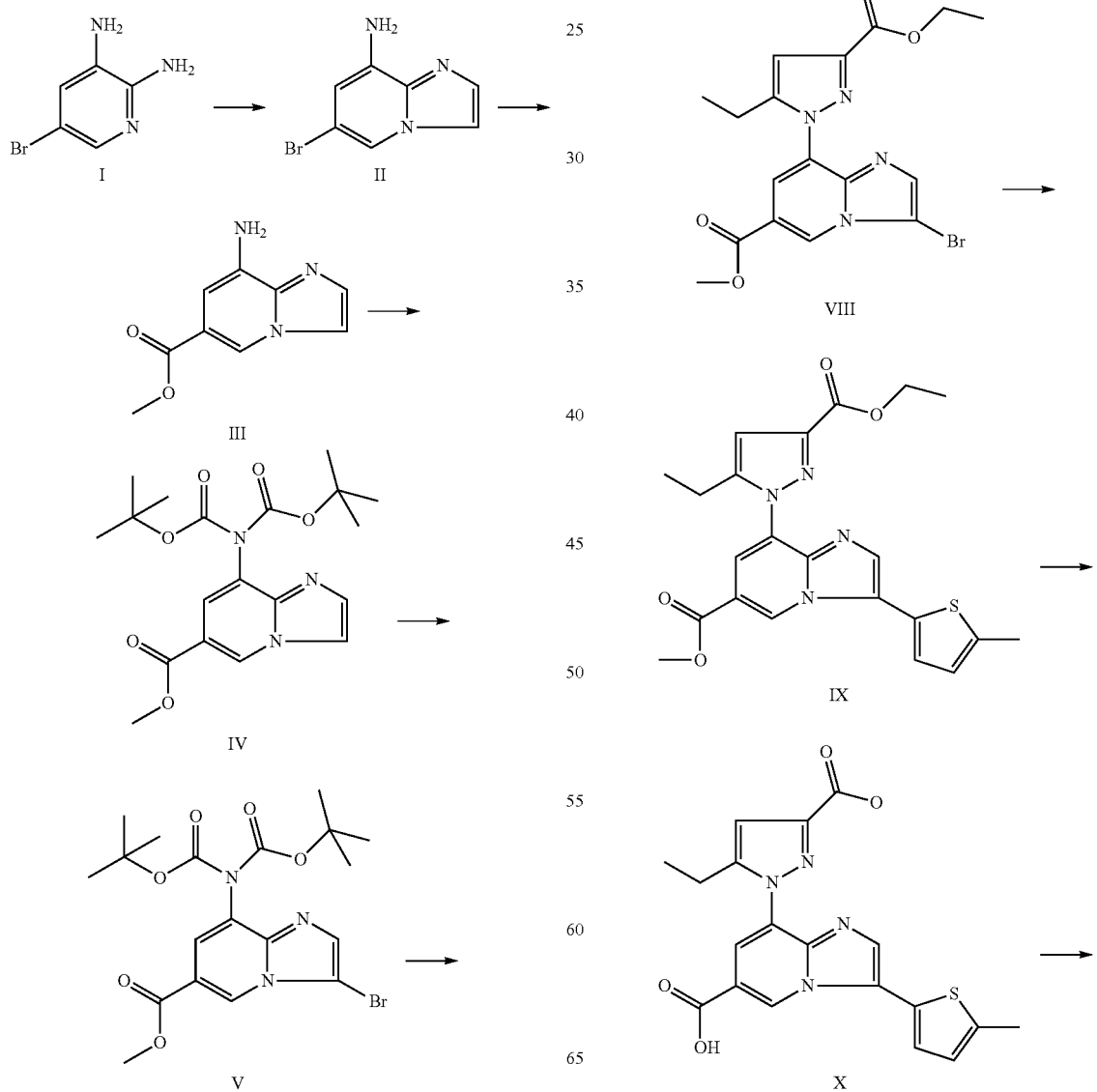

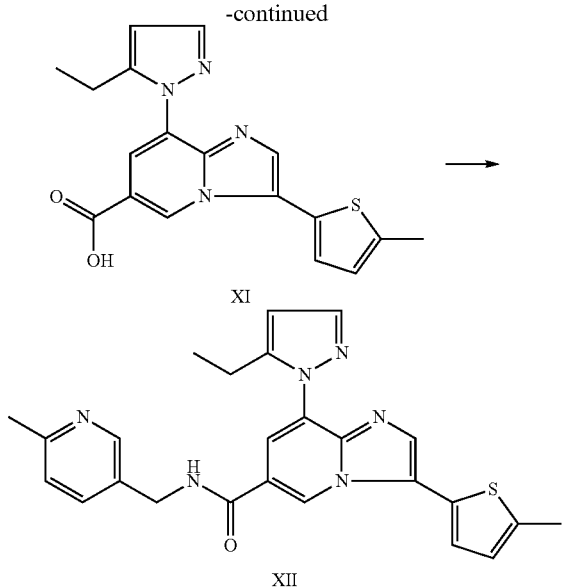

Step 1: 6-Bromo-imidazo[1,2-a]pyridin-8-ylamine

To a stirred solution of compound I (50 g; 0.26 mol; 1 eq) in ethanol (2 L) were added sodium bicarbonate (46 g; 0.53 mol; 2 eq) and chloroacetaldehyde solution (~50% aqueous solution, 86 mL; 0.66 mol; 2.5 eq) drop wise and the resulting mixture was heated at reflux for 17 h. The mixture was then evaporated to dryness and the pH was adjusted to 7 using ice-cold saturated aqueous NaHCO₃ solution and solid NaHCO₃. The organic components were extracted from the aqueous layer with ethyl acetate (3×1000 mL) and the combined organic layers were washed with brine, dried over anhydrous sodium sulfate and the solvents were removed in vacuo to obtain a dry residue which was purified by silica gel (230-400 mesh) column chromatography using 10-50% ethyl acetate/hexanes as the eluent to afford the title compound (40 g, 71%) as a brown solid. $^1$H NMR (DMSO-d₆) δ 8.04 (s, 1H), 7.77 (s, 1H), 7.44 (s, 1H), 6.31 (s, 1H), 5.99 (s, 2H). LCMS: m/z=212.0 [M+], 214.0 [M+2], RT=2.55 minutes, (Program P1, Column V).

Step 2: 8-Amino-imidazo[1,2-a]pyridine-6-carboxylic acid methyl ester

To a solution of compound II (10 g; 47.2 mmol; 1 eq) in methanol (200 mL) was added diisopropylethyl amine (41 mL; 236 mmol; 5 eq) and the resulting mixture was degassed with argon for 5 min. To the mixture was added PdCl₂(dppf) (4 g; 4.7 mmol; 0.1 eq) and the resulting mixture was degassed with argon for another 5 minutes and then heated in an autoclave at 90° C. at 50 psi carbon monoxide pressure for 16 h. The mixture was filtered through a Celite® pad and the filtrate was washed with saturated aqueous NaHCO₃ solution, followed by brine. The organic layer was then dried over anhydrous Na₂SO₄, filtered and evaporated to dryness to obtain a crude material. The crude product was purified by silica gel (100-200 mesh) column chromatography, eluting with 0-10% methanol/dichloromethane as the eluent to obtain the title compound (5 g, 55%) as light brown solid. $^1$H NMR (DMSO-d₆) δ 8.57 (s, 1H), 7.97 (s, 1H), 7.5135 (s, 1H), 6.67 (s, 1H), 5.86 (s, 2H), 3.84 (s, 3H). LCMS: m/z=191.8 [M+H]⁺, RT=2.03 minutes, (Program P1, Column V).

Step 3: 8-[bis-(tert-Butoxycarbonyl)amino]-imidazo[1,2-a]pyridine-6-carboxylic acid methyl ester To a stirred solution of compound III (3 g; 15.6 mmol; 1 eq) in dry THF (200 mL) at 0° C. were added TEA (6.52 mL; 46 mmol; 3 eq), boc anhydride (4.32 mL; 18.8 mmol; 1.2 eq) dropwise and a catalytic amount of DMAP, and the resulting mixture was heated at reflux for 17 h. The mixture was diluted with water (300 mL) and the organic components were extracted with ethyl acetate (3×200 mL). The combined organic layers were washed with brine, dried over anhydrous sodium sulfate, filtered and the solvents were removed in vacuo to obtain a dry residue which was purified by silica gel (230-400 mesh) column chromatography using 10-50% ethyl acetate/hexanes as the eluent to afford the title compound (2.9 g, 49%) as solid. $^1$H NMR (DMSO-d₆) δ 9.36 (s, 1H), 8.15 (s, 1H), 7.67 (s, 1H), 7.50 (s, 1H), 3.89 (s, 3H), 1.33 (s, 18H). LCMS: m/z=391.8 [M+H]⁺, RT=3.18 minutes, (Program P1, Column Y).

Step 4: 3-Bromo-8-[bis-(tert-Butoxycarbonyl)amino]-imidazo[1,2-a]pyridine-6-carboxylic acid methyl ester To a stirred solution of compound IV (2.88 g; 7.3 mmol; 1 eq) in dry THF (80 mL) was added NBS (1.31 g; 7.3 mmol; 1 eq) in portions at 0° C. and the resulting mixture was stirred for 30 min at 0° C. The temperature of the mixture was then slowly raised to 23° C. and the mixture was stirred for 2 h. The mixture was poured into ice-cold saturated aqueous NaHCO₃ solution and the organic components were extracted with ethyl acetate (3×50 mL). The combined organic layers were then washed with brine, dried over anhydrous sodium sulfate and concentrated in vacuo to obtain a dry residue which was purified by silica gel (230-400 mesh) column chromatography using 10-50% ethyl acetate/hexanes as the eluent to afford the title compound (3.46 g, 100%) as a solid. $^1$H NMR (DMSO-d₆) δ 8.79 (s, 1H), 7.88 (s, 1H), 7.68 (s, 1H), 3.93 (s, 3H), 1.34 (s, 18H). LCMS: m/z=469.8 [M+], 471.8 [M+2], RT=3.54 minutes, (Program P1, Column Y).

Step 5: 8-Amino-3-bromo-imidazo[1,2-a]pyridine-6-carboxylic acid methyl ester

To a stirring solution of compound V (3.5 g; 7.4 mmol; 1 eq) in methanol (50 mL) at 0° C. was added 4M methanolic HCl (100 mL) dropwise over a period of 30 min and the resulting solution was stirred at 23° C. for 24 h. The mixture was poured into ice-cold saturated aqueous NaHCO₃ solution and the organic components were extracted with ethyl acetate (3×500 mL). The combined organic layers were washed with brine, dried over anhydrous sodium sulfate and concentrated in vacuo to obtain the title compound (2 g, 100%) as a solid. LCMS: m/z=269.8 [M+], 271.8 [M+2], RT=2.91 minutes, (Program P1, Column Y).

Step 6: 3-Bromo-8-hydrazino-imidazo[1,2-a]pyridine-6-carboxylic acid methyl ester To a stirred, cooled (−10° C.) solution of compound VI (0.7 g; 2.5 mmol; 1 eq) in concentrated HCl (7 mL) was added an aqueous solution of sodium nitrite (0.35 g; 5.1 mmol; 2 eq) and the resulting mixture was stirred at −10° C. for 1 h. Tin chloride dehydrate (1.69 g; 7.51 mmol; 3 eq) was then added and the resulting mixture was allowed to stir at 23° C. for 1 h. The mixture was treated with ice-cold saturated aqueous NaHCO₃ solution and solid NaHCO₃ to adjust the pH to 7. The aqueous phase was extracted with ethyl acetate (3×500 mL) and the combined organic layers were washed with brine, dried over anhydrous sodium sulfate, filtered and concentrated in vacuo to obtain a dry residue which was purified by silica gel (230-400 mesh) column chromatography using 10-50% ethyl acetate/hexanes as the eluent to afford the title compound (0.3 g, 43%) as an off white solid. LCMS: m/z=285.0 [M+], 286.8 [M+2], RT=2.69 minutes, (Program P1, Column Y).

Step 7: 3-Bromo-8-(3-ethoxycarbonyl-5-ethyl-pyrazol-1-yl)-imidazo[1,2-a]pyridine-6-carboxylic acid methyl ester To a stirred solution of compound VII (0.3 g; 1 mmol; 1 eq) in ethanol was added 2-[1-dimethylamino-methylidene]-3-oxo-pentanoic acid ethyl ester (0.41 g; 2.1 mmol; 2 eq) and the resulting mixture was heated at reflux for 4 h. The mixture was cooled to room temperature, ice-cold saturated aqueous NaHCO$_3$ solution was added and the organic components were extracted with ethyl acetate (3×50 mL). The combined organic layers were then washed with brine, dried over anhydrous sodium sulfate and concentrated to dryness. The crude product was purified by silica gel (230-400 mesh) column chromatography eluting with 0-5% methanol/CH$_2$Cl$_2$ to obtain the title compound (0.32 g, 73%). LCMS: m/z=421.0 [M+], 423.0 [M+2], RT=3.30 minutes, (Program P1, Column Y).

Step 8: 8-(3-Ethoxycarbonyl-5-ethyl-pyrazol-1-yl)-3-(5-methyl-thiophen-2-yl)-imidazo[1,2-]pyridine-6-carboxylic acid methyl ester To a stirred dry DMF solution of compound VIII (0.4 g; 0.91 mmol; 1 eq) in a reaction tube was added compound VIa (0.53 g; 1.3 mmol; 1.5 eq) and the resulting mixture was degassed with argon for 5 min. To the mixture was added Pd(PPh$_3$)$_4$ (0.1 g; 0.09 mmol; 0.1 eq) and degassing with argon was repeated for about 5 min. The reaction tube was sealed and heated at 115° C. for 4 h. The mixture was filtered through a Celite® pad and the filtrate was washed with saturated aqueous NaHCO$_3$ solution, followed by brine. The organic layer was then dried over anhydrous Na$_2$SO$_4$, filtered and solvents were removed in vacuo to obtain a crude material. The crude product was purified by silica gel (230-400 mesh) column chromatography eluting with 0-50% ethyl acetate/hexane to obtain the title compound (0.25 g, 61%). $^1$H NMR (DMSO-d$_6$) δ 9.12 (s, 1H), 8.09 (s, 1H), 7.90 (s, 1H), 7.85 (s, 1H), 7.43 (d, 1H, J=3 Hz), 7.05 (d, 1H), 4.37 (q, 2H, J=7 Hz), 4.28 (q, 2H, J=7 Hz), 2.82 (q, 2H, J=1 Hz), 2.56 (s, 3H), 1.30 (m, 6H), 1.00 (t, 3H, J=7 Hz). LCMS: m/z=439.0 [M+H]$^+$, RT=3.56 minutes, (Program P1, Column Y).

Step 9: 8-(3-Carboxy-5-ethyl-pyrazol-1-yl)-3-(5-methyl-thiophen-2-yl)-imidazo[1,2-a]pyridine-6-carboxylic acid To a solution of compound IX (0.25 g, 0.5 mmol, 1 eq) in THF:methanol:H$_2$O (15 mL, 3:2:1) at 0° C. was added a solution of lithium hydroxide monohydrate (46 mg, 1.1 mmol, 3 eq) in water (1 mL) and the resulting mixture was stirred at 23° C. for 3 h. The solvents were removed under reduced pressure and the residue was diluted with water and acidified with 1N HCl to adjust the pH to 3. The precipitated solid was collected by filtration and dried under vacuum to afford the title compound (0.2 g, 87%). $^1$H NMR (DMSO-d$_6$) δ 9.11 (s, 1H), 8.04 (s, 1H), 7.89 (s, 1H), 7.80 (s, 1H), 7.42 (d, 1H, J=3 Hz), 7.03 (d, 1H, J=3 Hz), 2.87 (q, 2H, J=7 Hz), 2.56 (s, 3H), 0.88 (t, 3H, J=7 Hz). LCMS: m/z=397.0 [M+H]$^+$, RT=1.57 minutes, (Program P1, Column Y).

Step 10: 8-(5-Ethyl-pyrazol-1-yl)-3-(5-methyl-thiophen-2-yl)-imidazo[1,2-a]pyridine-6-carboxylic acid Compound X (0.17 g; 0.42 mmol; 1 eq) was heated at 200° C. for 1 h to obtain the title compound (0.13 g; 86%).

Step 11: 8-(5-Ethyl-1H-pyrazol-1-yl)-N-((6-methyl-pyridin-3-yl)methyl)-3-(5-methylthiophen-2-yl)imidazo[1,2-a]pyridine-6-carboxamide To a stirred solution of compound XI (0.15 g, 0.42 mmol, 1 eq) in CH$_2$Cl$_2$: DMF (1:5, 20 mL) were added DIPEA (0.22 mL, 1.2 mmol, 3 eq) and HATU (0.2 g, 0.54 mmol, 1.3 eq) and the resulting mixture was stirred at 0° C. for 15 min. To the mixture was added C-(6-methyl-pyridin-3-yl)-methylamine (0.13 g, 0.85 mmol, 2 eq) and the resulting mixture allowed to stir at 23° C. for another 16 h. From the mixture, solvent was removed in vacuo, the residue was diluted with EtOAc and washed with saturated aqueous sodium bicarbonate solution, aqueous ammonium chloride solution and brine. The organic layer was dried over anhydrous sodium sulfate, filtered and concentrated to dryness. The crude product was purified by silica gel (230-400 mesh) column chromatography eluting with 0-10% methanol/CH$_2$Cl$_2$ to obtain the title compound (30 mg, 16%) as an off white solid. $^1$H NMR (DMSO-d$_6$) δ 9.37 (t, 1H, J=6 Hz), 9.10 (d, 1H, J=1 Hz), 8.42 (d, 1H, J=2 Hz), 7.90 (d, 1H, J=1 Hz), 7.84 (s, 1H), 7.68 (d, 1H, J=1 Hz), 7.63 (dd, 1H, J=2, 8 Hz), 7.43 (d, 1H, J=4 Hz), 7.22 (d, 1H, J=8 Hz), 7.03 (d, 1H, J=3 Hz), 6.35 (s, 1H), 4.48 (d, 2H, J=6 Hz), 2.62 (q, 2H, J=8 Hz), 2.55 (s, 3H), 2.50 (s, 3H), 1.11 (t, 3H, J=8 Hz). LCMS: m/z=457.0 [M+H]$^+$, RT=3.21 minutes, (Program P1, Column Y).

Example 7: (S)—N-(1-(4H-1,2,4-Triazol-3-yl)ethyl)-3-(5-methylthiophen-2-yl)-8-(phenylamino)imidazo[1,2-a]pyridine-6-carboxamide Scheme 23

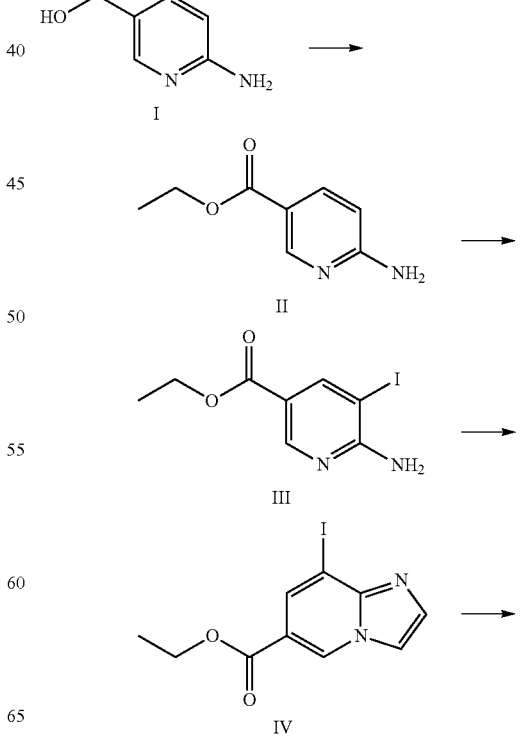

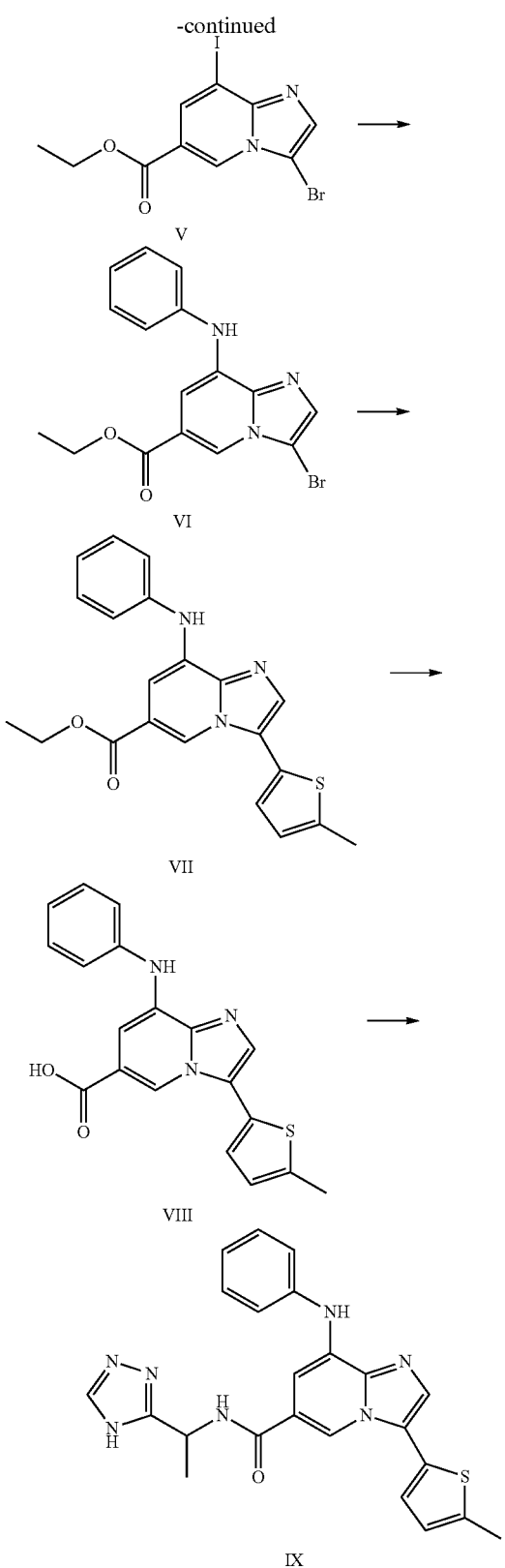

Step 1: 6-Amino-nicotinic acid ethyl ester

To a stirred solution of compound I (150 g; 108.5 mmol; 1 eq) in ethanol (1.5 L) was added thionyl chloride (236 mL; 325 mmol; 3 eq) dropwise at 60° C. and the resulting mixture was heated at reflux for 17 h. The mixture was evaporated to dryness and the pH was adjusted to 7, using ice-cold saturated aqueous NaHCO$_3$ solution and solid NaHCO$_3$. The organic components were extracted from the aqueous phase with ethyl acetate (3×500 mL), and the combined organic layers were washed with brine, dried over anhydrous sodium sulfate and the solvent was removed in vacuo to afford the title compound (152 g, 84%) as an off-white solid. $^1$H NMR (CDCl$_3$) δ 8.71 (s, 1H), 7.99 (d, 1H, J=12 Hz), 6.45 (d, 1H, J=8 Hz), 4.95 (s, 2H), 4.31 (q, 2H, J=8 Hz); 1.35 (t, 3H, J=8 Hz). LCMS: m/z=167.3 [M+H]$^+$, RT=2.32 minutes, (Program P1, Column Y).

Step 2: 6-Amino-5-iodo-nicotinic acid ethyl ester

To a stirred solution of iodine (55 g, 219 mmol, 1.4 eq) in ethanol (1 L) was added silver sulfate (48.7 g, 312 mmol, 2 eq) and after 5 min, compound II (26 g; 156.4 mmol; 1 eq) was added and the resulting mixture was stirred at 23° C. for 24 h. The mixture was evaporated to dryness and diluted with 20% aqueous sodium thiosulfate solution. The organic components were extracted from the aqueous phase with ethyl acetate (3×1000 mL) and the combined organic layers were washed with brine, dried over anhydrous sodium sulfate and the solvents were removed in vacuo to afford the title compound (45 g, 100%) as a brown solid.

Step 3: 8-Iodo-imidazo[1,2-a]pyridine-6-carboxylic acid ethyl ester

To a stirred solution of compound III (45 g; 154 mmol; 1 eq) in ethanol (2 L) were added sodium bicarbonate (25.9 g; 308 mmol; 2 eq) and chloroacetaldehyde solution (~50% aqueous solution, 121 mL; 770 mmol; 5 eq) dropwise and the resulting mixture was heated at reflux for 18 h. The mixture was then evaporated to dryness and the pH was adjusted to 7 using ice-cold saturated aqueous NaHCO$_3$ solution and solid NaHCO$_3$. The organic components were extracted from the aqueous phase with ethyl acetate (3×500 mL) and the combined organic layers were washed with brine, dried over anhydrous sodium sulfate and the solvents were removed in vacuo to obtain a dry residue which was purified by silica gel (230-400 mesh) column chromatography using 10-50% ethyl acetate/hexanes as the eluent to afford the title compound (40 g, 83%) as a brown solid. $^1$H NMR (DMSO-d$_6$) δ 9.34 (s, 1H), 8.27 (s, 1H), 8.05 (s, 1H), 7.71 (s, 1H), 4.35 (q, 2H, J=7 Hz), 1.34 (t, 3H, J=7 Hz). LCMS: m/z=317.0 [M+H]$^+$, RT=2.96 minutes, (Program P1, Column Y).

Step 4: 3-Bromo-8-iodo-imidazo[1,2-a]pyridine-6-carboxylic acid ethyl ester

To a stirred solution of compound IV (30 g; 95 mmol; 1 eq) in dry THF (200 mL) at 0° C. was added NBS (16.8 g; 94.9 mmol; 1 eq) in portions and the resulting mixture was stirred at 23° C. for 1 h. The mixture was poured into ice-cold saturated NaHCO$_3$ aqueous solution and the organic components were extracted with ethyl acetate (3×500 mL). The combined organic layers then washed with brine, dried over anhydrous sodium sulfate, filtered and the solvents were removed in vacuo to obtain a dry residue. The crude material was purified by silica gel (230-400 mesh) column chromatography using 10-50% ethyl acetate/hexanes as the eluent to afford the compound (38 g, 100%) as a brown solid. $^1$H NMR (DMSO-d$_6$) δ 8.75 (s, 1H), 8.16 (s, 1H), 7.93 (s, 1H), 4.39 (q, 2H, J=7 Hz), 1.36 (t, 3H, J=7 Hz). LCMS: m/z=395.0 [M+], 397.0 [M+2], RT=3.35 minutes, (Program P1, Column Y).

Step 5: 3-Bromo-8-phenylamino-imidazo[1,2-a]pyridine-6-carboxylic acid ethyl ester To a stirred 1,4-dioxane solution of compound V (1 g; 2.55 mmol; 1 eq) in a reaction tube were added aniline (280 mg; 3.03 mmol; 1.2 eq) and the resulting mixture was degassed with argon for 5 min, followed by an addition of $K_2CO_3$ (1.05 g; 7.59 mmol; 3 eq), $Pd(OAc)_2$ (57 mg; 0.25 mmol; 0.1 eq), xantphos (0.46 g; 0.51 mmol; 0.2 eq). The mixture was then degassed again with argon for 5 min, the reaction tube was sealed and heated at 110° C. for 5 h. The mixture was filtered through a Celite® pad and the filtrate was washed with saturated aqueous $NaHCO_3$ solution, followed by brine. The organic layer was then dried over anhydrous $Na_2SO_4$ and evaporated to dryness to obtain a crude material. The crude product was purified by silica gel (100-200 mesh) column chromatography, eluting with 5-30% EtOAc/hexanes to obtain the title compound (1.5 g, 82%). LCMS: m/z=360.2 [M+], 362.0 [M+2], RT=3.84 minutes, (Program P1, Column W).

Step 6: 3-(5-Methyl-thiophen-2-yl)-8-phenylamino-imidazo[1,2-a]pyridine-6-carboxylic acid ethyl ester To a stirred dry toluene solution of compound VI (0.75 g; 2.1 mmol; 1 eq) in a reaction tube was added compound VIa (0.96 g; 2.5 mmol; 1.2 eq) and the resulting mixture was degassed with argon for 5 min. To the mixture was added $Pd(PPh_3)_4$ (0.24 g; 0.21 mmol; 0.1 eq) and the resulting mixture was degassed with argon for an additional 5 min. The reaction tube was sealed and heated at 115° C. for 4 h. The mixture was filtered through a Celite® pad and the filtrate was washed with saturated aqueous $NaHCO_3$ solution, followed by brine, and the organic layer was dried over anhydrous $Na_2SO_4$, filtered and evaporated to dryness to obtain a crude material. The crude product was purified by silica gel (230-400 mesh) column chromatography eluting with 50% EtOAc/hexanes to obtain the title compound (0.48 g, 61%) as a light brown solid. $^1H$ NMR ($CDCl_3$) δ 8.63 (s, 1H), 7.63 (s, 1H), 7.42 (m, 1H), 7.38 (d, 2H, J=7 Hz), 7.34 (d, 2H, J=8 Hz), 7.20 (m, 1H), 6.86 (m, 1H), 6.68 (d, 2H, J=8 Hz), 4.38 (q, 2H, J=7 Hz), 2.57 (s, 3H) 1.37 (t, 3H, J=7 Hz). LCMS: m/z=378.2 $[M+H]^+$, RT=4.20 minutes, (Program P1, Column W).

Step 7: 3-(5-Methyl-thiophen-2-yl)-8-phenylamino-imidazo[1,2-a]pyridine-6-carboxylic acid To a solution of compound VII (0.48 g, 1.27 mmol, 1 eq) in THF:methanol:$H_2O$ (12 mL, 3:2:1) at 0° C. was added a solution of lithium hydroxide monohydrate (0.161 g, 3.81 mmol, 3 eq) in water (1 mL) and the resulting mixture was stirred at 23° C. for 3 h. The solvent was removed under reduced pressure and the residue was diluted with water, acidified with 1N HCl to adjust the pH to 3. The precipitated solid was collected by filtration and dried under vacuum to afford the title compound (0.38 g, 86%). $^1H$ NMR (DMSO-$d_6$) δ 8.44 (s, 1H), 8.26 (s, 1H), 7.69 (s, 1H), 7.41 (m, 1H), 7.35 (m, 4H), 7.23 (d, 1H, J=4 Hz), 6.98 (m, 2H), 2.54 (s, 3H). LCMS: m/z=350.0 $[M+H]^+$, RT=2.71 minutes, (Program P1, Column W).

Step 8: (S)—N-(1-(4H-1,2,4-Triazol-3-yl)ethyl)-3-(5-methylthiophen-2-yl)-8-(phenylamino)imidazo[1,2-a]pyridine-6-carboxamide To a stirred solution of compound VIII (0.38 g, 1.1 mmol, 1 eq) in DMF (10 mL) were added DIPEA (0.6 mL, 3.3 mmol, 3 eq) and HATU (0.49 g, 1.3 mmol, 1.2 eq) at 0° C. and the resulting mixture was allowed to stir for 15 min. To the mixture was added (S)-1-(4H-[1,2,4]triazol-3-yl)-ethylamine hydrochloride (0.48 g, 3.3 mmol, 3 eq) and the resulting mixture was allowed to stir at 23° C. for another 16 h. From the mixture, solvent was removed in vacuo and the residue was diluted with EtOAc and then washed with saturated aqueous sodium bicarbonate solution, aqueous ammonium chloride solution and brine. The organic phase was dried over anhydrous sodium sulfate, filtered and concentrated to dryness. The crude product was purified by silica gel (230-400 mesh) column chromatography eluting with 0-5% methanol/$CH_2Cl_2$ to obtain the title compound (0.18 g, 38%) as brown solid. $^1H$ NMR (DMSO-$d_6$) δ 13.78 (m, 1H), 9.14-9.00 (m, 1H), 8.50 (m, 3H), 7.86 (s, 1H), 7.40 (d, 1H, J=6 Hz), 7.35 (m, 6H), 7.01 (m, 2H), 5.29 (m, 1H), 2.54 (s, 3H), 1.53 (m, 3H). LCMS: m/z=444.0 $[M+H]^+$, RT=3.00 minutes, (Program P1, Column Y).

Example 8: (S)—N-(1-(4H-1,2,4-Triazol-3-yl)ethyl)-8-(1-methyl-1H-pyrazol-4-yl)-3-(5-methylthiophen-2-yl)imidazo[1,2-a]pyridine-6-carboxamide

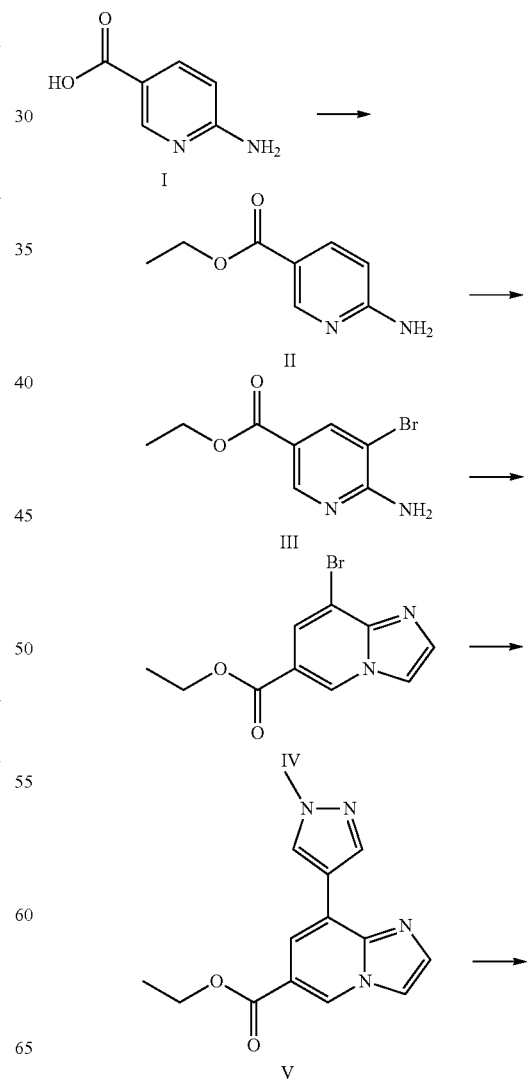

Scheme 24

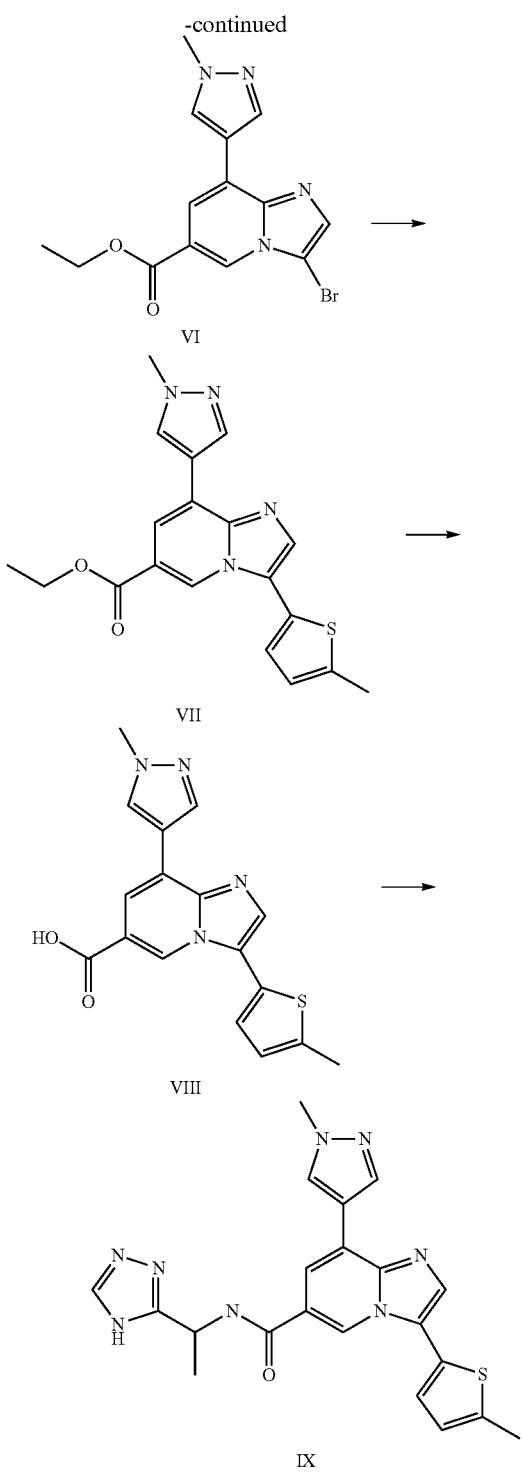

Step 1: 6-Amino-nicotinic acid ethyl ester

To a stirred solution of compound I (150 g; 108.5 mmol; 1 eq) in ethanol (1.5 L) at 60° C., was added thionyl chloride (236 mL; 325 mmol; 3 eq) dropwise and the resulting mixture was heated at reflux for 17 h. The mixture was evaporated to dryness and the pH was adjusted to 7 using ice-cold saturated aqueous NaHCO₃ solution and solid NaHCO₃. The organic components were extracted from the aqueous phase with ethyl acetate (5×1000 mL) and the organic layer was washed with brine, dried over anhydrous sodium sulfate, filtered and the solvent was removed in vacuo to afford the title compound (152 g, 84%) as an off-white solid. ¹H NMR (CDCl₃) δ 8.71 (s, 1H), 7.99 (d, 1H, J=12 Hz), 6.45 (d, 1H, J=8 Hz), 4.95 (s, 2H), 4.31 (q, 2H, J=8 Hz), 1.35 (t, 3H, J=8 Hz). LCMS: m/z=167.3 [M+H]+, RT=2.32 minutes, (Program P1, Column Y).

Step 2: 6-Amino-5-bromo-nicotinic acid ethyl ester

To a stirred solution of compound II (50 g; 30.1 mmol; 1 eq) in dry THF (500 mL) at 0° C. was added NBS (53.6 g; 30.1 mmol; 1 eq) in portions and the resulting mixture was stirred at 23° C. for 17 h. The mixture was poured into ice-cold saturated aqueous NaHCO₃ solution and the organic components were extracted with ethyl acetate (3×1000 mL). The combined organic layers were then washed with brine, dried over anhydrous sodium sulfate and evaporated to dryness to afford the title compound (71 g, 96%) as an off white solid. ¹H NMR (DMSO-d₆) δ 8.49 (s, 1H), 8.07 (s, 1H), 7.15 (s, 2H), 4.22 (q, 2H, J=8 Hz), 1.30 (t, 3H, J=8 Hz). LCMS: m/z=245 [M+], 247 [M+2], RT=2.97 minutes, (Program P1, Column W).

Step 3: 8-Bromo-imidazo[1,2-a]pyridine-6-carboxylic acid ethyl ester

To a stirred solution of compound III (80 g; 32.6 mmol; 1 eq) in ethanol (1 L) were added sodium bicarbonate (54.83 g; 65.2 mmol; 2 eq) and chloroacetaldehyde solution (~50% aqueous solution, 212 mL; 163.2 mmol; 5 eq) dropwise and the resulting mixture was heated at reflux for 17 h. The mixture was then evaporated to dryness and the pH was adjusted to 7 using ice-cold saturated aqueous NaHCO₃ solution and solid NaHCO₃. The organic components were extracted from the aqueous phase with ethyl acetate (3×500 mL) and the organic layer was washed with brine, dried over anhydrous sodium sulfate, filtered and the solvent was removed in vacuo to obtain a dry residue which was purified by silica gel (230-400 mesh) column chromatography using 10-50% ethyl acetate/hexanes as the eluent to afford the title compound (55 g, 63%) as a brown solid. ¹H NMR (DMSO-d₆) δ 9.33 (s, 1H), 8.24 (s, 1H), 7.84 (s, 1H), 7.73 (s, 1H), 4.34 (q, 2H, J=8 Hz), 1.34 (t, 3H, J=8 Hz). LCMS: m/z=268.8 [M+], 270.8 [M+2], RT=2.90 minutes, (Program P1, Column W).

Step 4: 8-(1-Methyl-1H-pyrazol-4-yl)-imidazo[1,2-a]pyridine-6-carboxylic acid ethyl ester To a stirred solution of compound IV (1 g; 3.73 mmol; 1 eq) in toluene:ethanol (20 mL; 7:3) in a reaction tube was added 1-methyl-4-(4,4,5,5-tetramethyl-[1,3,2]dioxaborolan-2-yl)-1H-pyrazole (0.93 g; 4.47 mmol; 1.2 eq) and the resulting solution was degassed with argon for 5 min, followed by addition of Cs₂CO₃ (3.03 g; 9.32 mmol; 2.5 eq), Pd(PPh₃)₄ (0.43 g; 0.37 mmol; 0.1 eq). The mixture was then degassed again with argon for 5 min, the reaction tube was then sealed and heated at 115° C. for 3 h. The mixture was filtered through a Celite® pad and the filtrate was washed with saturated aqueous NaHCO₃ solution, followed by brine. The organic layer was then dried over anhydrous Na₂SO₄, filtered and evaporated to dryness to obtain a crude material. The crude product was purified by silica gel (100-200 mesh) column chromatography, eluting with 50% EtOAc/hexanes to obtain compound the title compound (1.2 g, 60%). ¹H NMR (CDCl₃) δ 8.79 (s, 1H), 8.62 (s, 1H), 8.12 (s, 1H), 7.90 (s, 1H), 7.69 (s, 1H), 7.66 (s, 1H), 4.40 (q, 2H, J=7 Hz), 3.98 (s, 3H), 1.40 (t, 3H, J=7 Hz). LCMS: m/z=271.0 [M+H]+, RT=2.83 minutes, (Program P1, Column W).

Step 5: 3-Bromo-8-(1-methyl-1H-pyrazol-4-yl)-imidazo[1,2-a]pyridine-6-carboxylic acid ethyl ester To a stirred solution of compound V (0.8 g; 2.90 mmol; 1 eq) in dry THF (20 mL) at 0° C. was added NBS (520 mg; 2.9 mmol; 1 eq) in portions and the resulting mixture was stirred at 0° C. for 30 min. The mixture was poured into ice-cold saturated aqueous NaHCO$_3$ solution and the organic components were extracted with ethyl acetate (3×50 mL). The combined organic layers were then washed with brine, dried over anhydrous sodium sulfate and evaporated to dryness to afford the title compound (0.5 g, 50%) as an off white solid. $^1$H NMR (DMSO-d$_6$) δ 8.75 (s, 1H), 8.64 (s, 1H), 8.36 (s, 1H), 7.97 (s, 1H), 7.93 (s, 1H), 4.40 (q, 2H, J=7 Hz), 3.94 (s, 3H), 1.38 (t, 3H, J=7 Hz). LCMS: m/z=349.0 [M+], 351.0 [M+2], RT=3.28 minutes, (Program P1, Column Y).

Step 6: 8-(1-Methyl-1H-pyrazol-4-yl)-3-(5-methyl-thiophen-2-yl)-imidazo[1,2-a]pyridine-6-carboxylic acid ethyl ester To a stirred solution of compound VI (0.5 g; 1.49 mmol; 1 eq) in dry toluene in a reaction tube was added compound VIa (0.63 g; 1.64 mmol; 1.1 eq) and the resulting mixture was degassed with argon for 5 min. To the mixture was added Pd(PPh$_3$)$_4$ (0.17 g; 0.14 mmol; 0.1 eq) and the resulting mixture was degassed with argon again for about 5 min. The reaction tube was then sealed and heated at 115° C. for 4 h. The mixture was filtered through a Celite® pad and the filtrate was washed with saturated aqueous NaHCO$_3$ solution, followed by brine. The organic layer was then dried over anhydrous Na$_2$SO$_4$, filtered and solvents were removed in vacuo to obtain a crude material. The crude product was purified by silica gel (230-400 mesh) column chromatography eluting with 50% EtOAc/hexanes to obtain the title compound (0.32 g, 63%). $^1$H NMR (DMSO-d$_6$) δ 8.87 (s, 1H), 8.78 (s, 1H), 8.37 (s, 1H), 7.94 (s, 1H), 7.90 (s, 1H), 7.34 (d, 1H, J=4 Hz), 7.02 (d, 1H, J=3 Hz), 4.38 (q, 2H, J=7 Hz), 3.95 (s, 3H), 2.56 (s, 3H), 1.35 (t, 3H, J=7 Hz). LCMS: m/z=367.0 [M+H]$^+$, RT=3.58 minutes, (Program P1, Column Y).

Step 7: 8-(1-Methyl-1H-pyrazol-4-yl)-3-(5-methyl-thiophen-2-yl)-imidazo[1,2-a]pyridine-6-carboxylic acid To a solution of compound VII (0.25 g, 0.68 mmol, 1 eq) in THF:methanol:H$_2$O (12 mL, 3:2:1) at 0° C. was added a solution of lithium hydroxide monohydrate (57 mg, 1.30 mmol, 2 eq) in water (1 mL) and the resulting mixture was stirred at 23° C. for 3 h. The solvent was removed under reduced pressure and the residue was diluted with water and acidified with 1N HCl to adjust the pH to 3. The precipitated solid was collected by filtration and dried in vacuo to afford the title compound (0.2 g, 100%). $^1$H NMR (DMSO-d$_6$) δ 8.87 (s, 1H), 8.77 (s, 1H), 8.35 (s, 1H), 7.96 (s, 1H), 7.91 (s, 1H), 7.34 (d, 1H, J=4 Hz), 7.01 (d, 1H, J=3 Hz), 3.94 (s, 3H), 2.56 (s, 3H). LCMS: m/z=339.0 [M+H]$^+$, RT=2.43 minutes, (Program P1, Column W).

Step 8: (S)—N-(1-(4H-1,2,4-Triazol-3-yl)ethyl)-8-(1-methyl-1H-pyrazol-4-yl)-3-(5-methylthiophen-2-yl)imidazo[1,2-a]pyridine-6-carboxamide To a stirred solution of compound VIII (0.2 g, 0.59 mmol, 1 eq) in DMF (10 mL) were added DIPEA (0.3 mL, 1.70 mmol, 3 eq) and HATU (0.26 g, 0.71 mmol, 1.2 eq) at 0° C. and the resulting mixture was allowed to stir for 15 min at 23° C. To the mixture was added (S)-1-(4H-[1,2,4]triazol-3-yl)-ethylamine hydrochloride (0.10 g, 0.71 mmol, 1.2 eq) and the resulting mixture was stirred at 23° C. for another 16 h. From the mixture, solvent was removed in vacuo, the residue was diluted with EtOAc and washed with saturated aqueous sodium bicarbonate solution, aqueous ammonium chloride solution and brine. The organic phase was dried over anhydrous sodium sulfate, filtered and concentrated to dryness. The crude product was purified by silica gel (230-400 mesh) column chromatography eluting with 0-5% methanol/CH$_2$Cl$_2$ to obtain the title compound (0.07 g, 30%) as a brown solid. $^1$H NMR (DMSO-d$_6$) δ 13.85 (m, 1H), 9.20 (m, 1H), 8.87 (d, 1H, J=16 Hz), 8.75 (s, 1H), 8.49 (s, 1H), 8.34 (s, 1H), 8.16 (d, 1H, J=8 Hz), 7.86 (m, 1H), 7.37 (s, 1H), 7.01 (s, 1H), 5.35 (m, 1H), 3.96 (s, 3H), 2.54 (s, 3H), 1.58 (m, 3H). LCMS: m/z=433.2 [M+H]$^+$, RT=2.78 minutes, (Program P1, Column V).

Example 9: (S)—N-(1-(4H-1,2,4-Triazol-3-yl)ethyl)-3-butyl-8-(4-methylpiperidin-1-yl)imidazo[1,2-a]pyridine-6-carboxamide

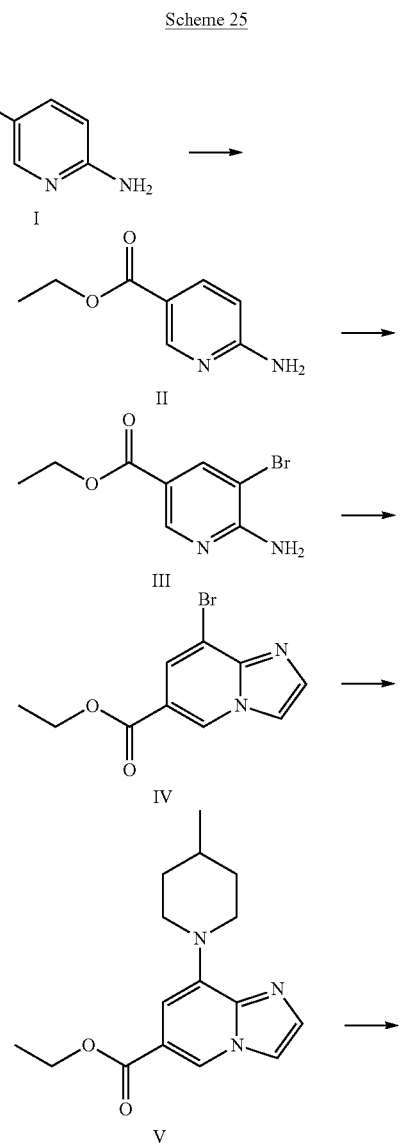

Scheme 25

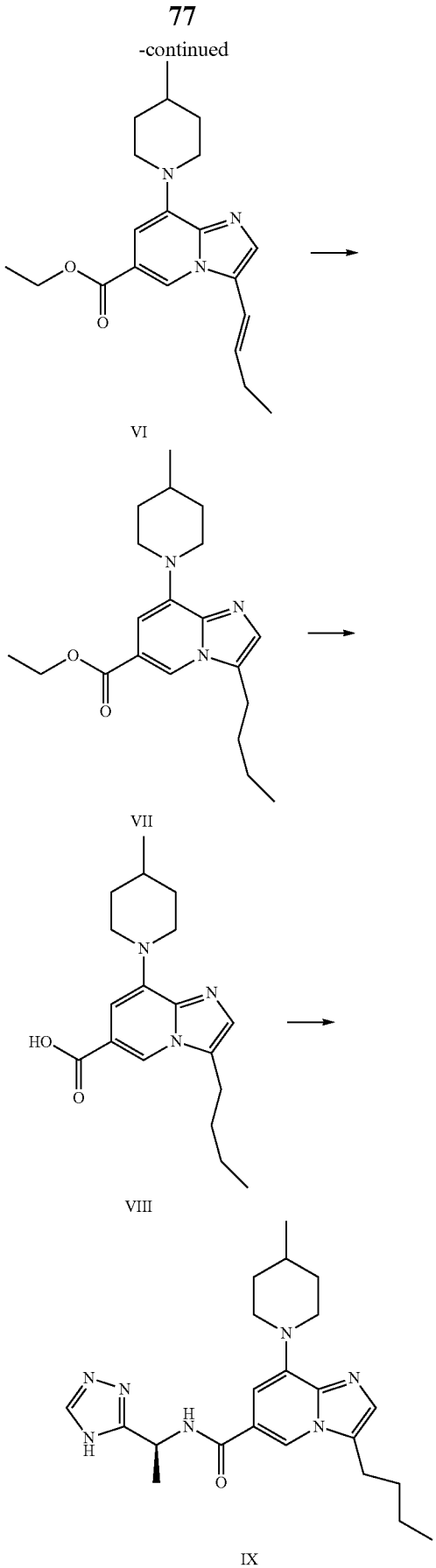

Step 1: 6-Amino-nicotinic acid ethyl ester

To a stirred solution of compound I (150 g; 1.08 mol; 1 eq) in ethanol (1.5 L) was added thionyl chloride (236 mL; 3.25 mol; 3 eq) dropwise at 60° C. and the resulting mixture was heated at reflux for 17 h. The mixture was evaporated to dryness and the pH of the residue was adjusted to 7 using ice-cold saturated aqueous NaHCO$_3$ solution and solid NaHCO$_3$. The organic components were extracted from the aqueous phase with ethyl acetate (5×1000 mL), and the combined organic layers were washed with brine solution, dried over anhydrous sodium sulfate, filtered and the solvent was removed in vacuo to afford the title compound (152 g, 84%) as an off-white solid. $^1$H NMR (CDCl$_3$) δ 8.71 (s, 1H), 7.99 (d, 1H, J=8 Hz), 6.45 (d, 1H, J=8 Hz), 4.95 (s, 2H), 4.31 (q, 2H, J=8 Hz); 1.35 (t, 3H, J=8 Hz). LCMS: m/z=167.3 [M+H]$^+$, RT=2.32 minutes, (Program P1, Column Y).

Step 2: 6-Amino-5-bromo-nicotinic acid ethyl ester

To a stirred solution of compound II (50 g; 301 mmol; 1 eq) in dry THF (500 mL) at 0° C. was added NBS (53.6 g; 301 mmol; 1 eq) in portions and the mixture was stirred at 23° C. for 17 h. The mixture was poured into ice-cold saturated aqueous NaHCO$_3$ solution and the organic components were extracted from the aqueous phase with ethyl acetate (3×1000 mL). The organic layer was then washed with brine, dried over anhydrous sodium sulfate, filtered and evaporated to dryness to afford the title compound (71 g, 96%) as an off white solid. $^1$H NMR (DMSO-d$_6$) δ 8.49 (s, 1H), 8.07 (s, 1H), 7.15 (s, 2H), 4.22 (q, 2H, J=8 Hz), 1.30 (t, J=8 Hz, 3H). LCMS: m/z=245 [M+], 247 [M+2], RT=2.97 minutes, (Program P1, Column W).

Step 3: 8-Bromo-imidazo[1,2-a]pyridine-6-carboxylic acid ethyl ester

To a stirred solution of compound III (80 g; 326 mmol; 1 eq) in ethanol (1 L) was added sodium bicarbonate (54.8 g; 652 mmol; 2 eq) and chloroacetaldehyde solution (~50% aqueous solution, 212 mL; 1.63 mol; 5 eq) dropwise and the mixture was heated at reflux for 17 h. The mixture was then evaporated to dryness and the pH was adjusted to 7 using saturated ice-cold aqueous NaHCO$_3$ solution and solid NaHCO$_3$. The organic components were extracted from the aqueous phase with ethyl acetate (3×1000 mL) and the combined organic layers were washed with brine, dried over anhydrous sodium sulfate, filtered and the solvent was removed in vacuo to obtain a dry residue which was purified by silica gel (230-400 mesh) column chromatography using 10-50% ethyl acetate/hexanes to afford the title compound (55 g, 63%) as a brown solid. $^1$H NMR (DMSO-d$_6$) δ 9.33 (s, 1H), 8.24 (s, 1H), 7.84 (s, 1H), 7.73 (s, 1H), 4.34 (q, 2H, J=8 Hz), 1.34 (t, 3H, J=12 Hz). LCMS: m/z=268.8 [M+], 270.8 [M+2], RT=2.90 minutes, (Program P1, Column W).

Step 4: 8-(4-Methyl-piperidin-1-yl)-imidazo[1,2-a]pyridine-6-carboxylic acid ethyl ester To a stirred 1,4-dioxane solution of compound IV (1 g; 3.71 mmol; 1 eq) in a reaction tube was added 4-methyl piperidine (0.73 g; 7.43 mmol; 2 eq) and the resulting mixture was degassed with argon for 5 min, followed by an addition of Cs$_2$CO$_3$ (1.81 g; 5.56 mmol; 1.5 eq), Pd$_2$(dba)$_3$ (0.16 g; 0.018 mmol; 0.05 eq), and xantphos (0.21 g; 0.37 mmol; 0.1 eq). The mixture was then degassed again with argon for 5 min, then the reaction tube was sealed and heated at 115° C. for 5 h. The mixture was filtered through a Celite® pad and the filtrate was washed with saturated aqueous NaHCO$_3$ solution, followed by brine. The organic layer was then dried over anhydrous Na$_2$SO$_4$ and evaporated to dryness to obtain a crude material. The crude product was purified by silica gel (100-200 mesh) column chromatography, eluting with 50% EtOAc/hexanes to obtain the title compound (0.25 g, 23%) as light brown solid. $^1$H NMR (DMSO-d$_6$) δ 8.84 (s, 1H), 8.03 (s, 1H), 7.55 (s, 1H), 6.75 (s, 1H), 4.31 (m, 4H), 2.73 (q, 2H, J=8 Hz), 1.73 (d, 2H, J=12 Hz), 1.56 (m, 1H), 1.3 (m, 5H), 0.9 (t, 3H, J=4 Hz). LCMS: m/z=288 [M+H]$^+$, RT=3.56 minutes, (Program P1, Column W).

Step 5: 3-((E)-But-1-enyl)-8-(4-methyl-piperidin-1-yl)-imidazo[1,2-a]pyridine-6-carboxylic acid ethyl ester To a stirred solution of compound V (0.15 g; 0.52 mmol; 1 eq) in acetic acid (2 mL) were added sodium acetate (0.17 g; 2 mmol; 4 eq) and butaraldehyde (0.46 mL; 5.22 mmol; 10 eq) in a sealed tube and the mixture was heated at 150° C. for 4 h. The mixture was poured into ice-cold saturated aqueous NaHCO$_3$ solution and the organic components were extracted with ethyl acetate (3×50 mL). The combined organic layers were washed with brine, dried over anhydrous sodium sulfate, filtered and evaporated to dryness to obtain a crude material. The crude product was purified by silica gel (230-400 mesh) column chromatography eluting with 50% EtOAc/hexanes to obtain the title compound (0.12 g, 70%). $^1$H NMR (DMSO-d$_6$) δ 8.60 (s, 1H), 7.75 (s, 1H), 6.90-6.70 (m, 2H), 6.45-6.20 (m, 1H), 4.40-4.38 (m, 4H), 2.73 (t, 2H, J=10 Hz), 2.31-2.24 (m, 2H), 1.75 (m, 2H), 1.56-1.48 (m, 3H), 1.12 (t, 3H, J=4 Hz), 0.97-0.95 (m, 3H), 0.81-0.79 (m, 3H). LCMS: m/z=343.2 [M+H]$^+$, RT=2.44 minutes, (Program P1, Column Y).

Step 6: 3-Butyl-8-(4-methyl-piperidin-1-yl)-imidazo[1,2-a]pyridine-6-carboxylic acid ethyl ester To a stirred solution of compound VI (0.12 g; 0.36 mmol; 1 eq) in dry methanol was added 10% Pd/C (40 mg) and the resulting mixture was stirred under hydrogen atmosphere for 2 h. The mixture was filtered through a Celite® pad and the filtrate was evaporated to dryness to obtain the title compound (0.115 g, 92%). $^1$H NMR (DMSO-d$_6$) δ 8.36 (s, 1H), 7.36 (s, 1H), 6.77 (s, 1H), 4.40-4.25 (m, 4H), 2.88 (t, 2H, J=8 Hz), 2.75 (t, 2H, J=10 Hz), 1.75-1.64 (m, 4H), 1.56 (m, 2H), 1.45-1.38 (m, 3H), 1.32 (t, 3H, J=4 Hz), 0.97-0.95 (m, 3H), 0.81-0.79 (m, 3H). LCMS: m/z=344.6 [M+H]$^+$, RT=2.55 minutes, (Program P1, Column Y).

Step 7: 3-Butyl-8-(4-methyl-piperidin-1-yl)-imidazo[1,2-a]pyridine-6-carboxylic acid To a solution of compound VII (0.11 g, 0.32 mmol, 1 eq) in THF:methanol:H$_2$O (9 mL, 3:2:1) at 0° C. was added a solution of lithium hydroxide monohydrate (45 mg, 0.96 mmol, 3 eq) in water (0.5 mL) and the resulting mixture was stirred at 23° C. for 3 h. The solvent was removed under reduced pressure and the residue was diluted with water and acidified with 1N HCl to adjust the pH to 3. The organic components were extracted from the aqueous phase with ethyl acetate (3×50 mL). The combined organic layers were washed with brine, dried over anhydrous sodium sulfate, filtered and evaporated to dryness to obtain the title compound (0.07 g, 70%). $^1$H NMR (DMSO-d$_6$) δ 8.53 (s, 1H), 7.66 (s, 1H), 7.12 (s, 1H), 3.93 (m, 2H), 2.93 (t, 2H, J=15 Hz), 2.75 (t, 2H, J=12 Hz), 1.80-1.74 (m, 4H), 1.60 (m, 1H), 1.45-1.32 (m, 4H), 0.97-0.90 (m, 6H). LCMS: m/z=316.2 [M+H]$^+$, RT=2.60 minutes, (Program P1, Column Y).

Step 8: (S)—N-(1-(4H-1,2,4-Triazol-3-yl)ethyl)-3-butyl-8-(4-methylpiperidin-1-yl)imidazo[1,2-a]pyridine-6-carboxamide To a stirred solution of compound VIII (40 mg, 0.12 mmol, 1 eq) in CH$_2$Cl$_2$ (10 mL) were added DIPEA (0.06 mL, 0.38 mmol, 3 eq) and HATU (58 mg, 0.15 mmol, 1.2 eq) at 0° C. and the resulting mixture was allowed to stir for 15 min. To the mixture was added (S)-1-(4H-[1,2,4]triazol-3-yl)-ethylamine hydrochloride (0.022 g, 0.15 mmol, 1.2 eq) and the resulting mixture was stirred at 23° C. for another 16 h. From the mixture, solvent was removed in vacuo, the residue was diluted with EtOAc and washed with aqueous saturated sodium bicarbonate solution, aqueous ammonium chloride solution and brine. The organic phase was separated, dried over anhydrous sodium sulfate, filtered and concentrated to dryness. The crude product was purified by silica gel (230-400 mesh) column chromatography eluting with 0-5% methanol/CH$_2$Cl$_2$ to obtain the title compound (0.015 g, 30%) as off white solid. $^1$H NMR (DMSO-d$_6$) δ 13.83 (m, 1H), 8.86 (m, 1H), 8.44 (m, 2H), 7.87 (s, 1H), 7.34 (m, 1H), 6.86 (s, 1H), 5.34 (m, 1H), 4.32 (m, 2H), 2.85 (t, 2H, J=7 Hz), 2.71 (t, 2H, J=11 Hz), 1.73 (m, 4H), 1.55 (m, 4H), 1.44-1.32 (m, 4H), 0.97-0.90 (m, 6H). LCMS: m/z=409.6 [M+H]$^+$, RT=2.60 minutes, (Program R1, Column Y).

Example 10: (S)—N-(1-(4H-1,2,4-Triazol-3-yl)ethyl)-8-(4-methylpiperidin-1-yl)-3-(propylthio)imidazo[1,2-a]pyridine-6-carboxamide

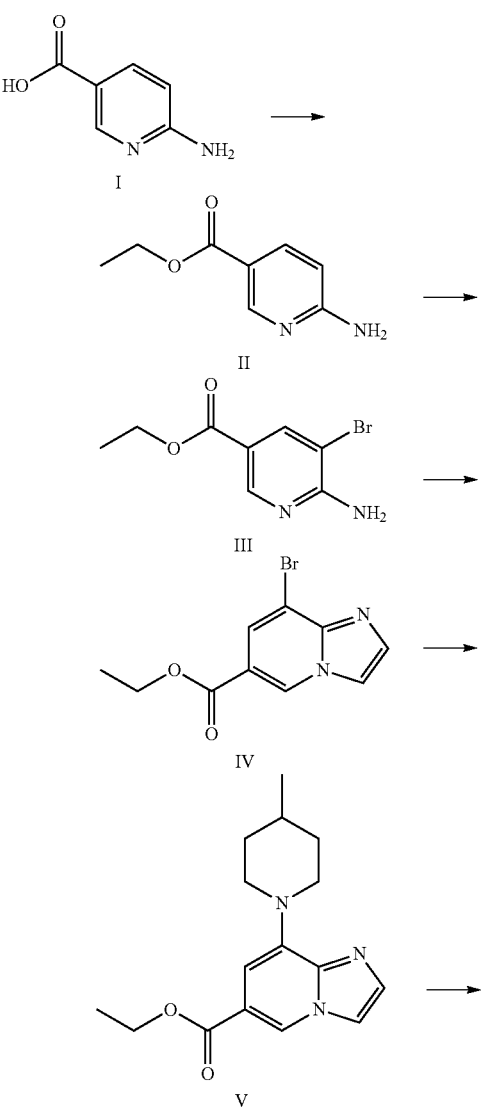

Scheme 26

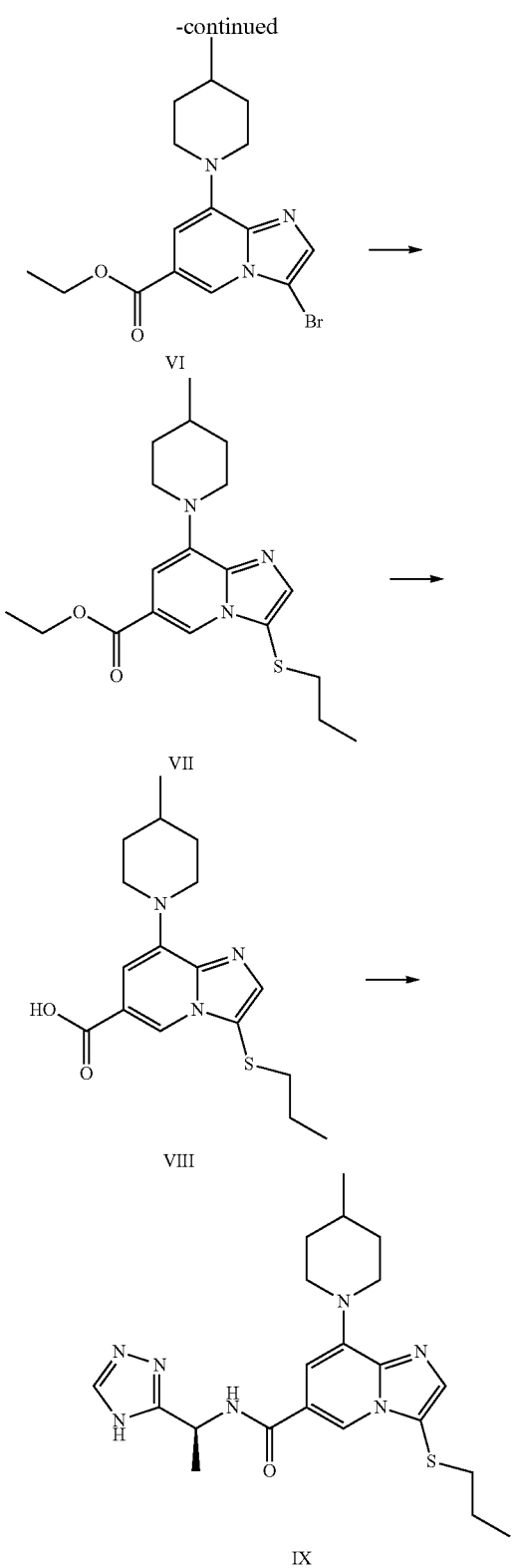

Step 1: 6-Amino-nicotinic acid ethyl ester

To a stirred solution of compound I (150 g, 1.08 mol; 1 eq) in ethanol (1.5 L) was added thionyl chloride (236 mL; 3.25 mol; 3 eq) dropwise at 60° C. and the resulting mixture was heated at reflux for 17 h. The mixture was then evaporated to dryness and the pH of the residue was adjusted to 7 using ice-cold saturated aqueous NaHCO$_3$ solution and solid NaHCO$_3$. The organic components were extracted from the aqueous phase with ethyl acetate (5×1000 mL) and the combined organic layers were washed with brine solution, dried over anhydrous sodium sulfate, filtered and the solvent was removed in vacuo to afford the title compound (152 g, 84%) as an off-white solid. $^1$H NMR (CDCl$_3$) δ 8.71 (s, 1H), 7.99 (d, 1H, J=12 Hz), 6.45 (d, 1H, J=8 Hz), 4.95 (s, 2H), 4.31 (q, 2H, J=8 Hz), 1.35 (t, 3H, J=8 Hz). LCMS: m/z=167.3 [M+H]$^+$, RT=2.32 minutes, (Program P1, Column Y).

Step 2: 6-Amino-5-bromo-nicotinic acid ethyl ester

To a stirred solution of compound II (50 g; 301 mmol; 1 eq) in dry THF (500 mL) at 0° C. was added NBS (53.6 g; 301 mmol; 1 eq) in portions, and the mixture was stirred at 23° C. for 17 h. The mixture was poured into ice-cold saturated aqueous NaHCO$_3$ solution and extracted with ethyl acetate (3×1000 mL). The combined organics were then washed with brine solution, dried over anhydrous sodium sulfate, filtered and evaporated to dryness to afford the title compound (71 g, 96%) as an off white solid. $^1$H NMR (DMSO-d$_6$) δ 8.49 (s, 1H), 8.07 (s, 1H), 7.15 (s, 2H), 4.22 (q, 2H, J=8 Hz), 1.30 (t, 3H, J=8 Hz). LCMS: m/z=245 [M+], 247 [M+2], RT=2.97 minutes, (Program P1, Column W).

Step 3: 8-Bromo-imidazo[1,2-a]pyridine-6-carboxylic acid ethyl ester

To a stirred solution of compound III (80 g; 326 mmol; 1 eq) and sodium bicarbonate (54.83 g; 652 mmol; 2 eq) in ethanol (1 L) was added chloroacetaldehyde solution (~50% aqueous solution, 212 mL; 1.6 mol; 5 eq) dropwise and the resulting mixture was heated at reflux for 17 h. The mixture was then evaporated to dryness and the pH was adjusted to 7 using ice-cold saturated aqueous NaHCO$_3$ solution and solid NaHCO$_3$. The organic components were extracted from the aqueous phase with ethyl acetate (3×1000 mL) and the combined organic layers were washed with brine, dried over anhydrous sodium sulfate, filtered and the solvents were removed in vacuo to obtain a dry residue which was purified by silica gel (230-400 mesh) column chromatography using 10-50% ethyl acetate/hexanes as the eluent to afford the title compound (55 g, 63%) as a brown solid. $^1$H NMR (DMSO-d$_6$) δ 9.33 (s, 1H), 8.24 (s, 1H), 7.84 (s, 1H), 7.73 (s, 1H), 4.34 (q, 2H, J=8 Hz), 1.34 (t, 3H, J=12 Hz). LCMS: m/z=268.8 [M+], 270.8 [M+2], RT=2.90 minutes, (Program P1, Column W).

Step 4: 8-(4-Methyl-piperidin-1-yl)-imidazo[1,2-a]pyridine-6-carboxylic acid ethyl ester To a stirred 1,4-dioxane solution of compound IV (1 g; 3.71 mmol; 1 eq) in a reaction tube was added 4-methyl piperidine (0.73 g; 7.43 mmol; 2 eq) and the resulting mixture was degassed with argon for 5 min. To the mixture were then added Cs$_2$CO$_3$ (1.81 g; 5.56 mmol; 1.5 eq), Pd$_2$(dba)$_3$ (0.16 g; 0.018 mmol; 0.05 eq), xantphos (0.21 g; 0.37 mmol; 0.1 eq) and the resulting mixture was degassed with argon for another 5 min and the reaction tube was sealed. The mixture was then heated to 115° C. and stirred for 5 h. The mixture was filtered through a Celite® pad and the filtrate was washed with saturated aqueous NaHCO$_3$ solution, followed by brine. The organic layer was then dried over anhydrous Na$_2$SO$_4$ and evaporated to dryness to obtain a crude material. The crude product was purified by silica gel (100-200 mesh) column chromatography, eluting with 50% EtOAc/hexanes to obtain the title compound (0.25 g, 23%) as light brown solid. $^1$H NMR (DMSO-d$_6$) δ 8.84 (s, 1H), 8.03 (s, 1H), 7.55 (s, 1H), 6.75 (s, 1H), 4.31 (m, 4H), 2.73 (q, 2H, J=8 Hz), 1.73 (d, 2H, J=12 Hz), 1.56 (m, 1H), 1.3 (m, 5H), 0.9 (t, 3H, J=4 Hz). LCMS: m/z=288 [M+H]$^+$, RT=3.56 minutes, (Program P1, Column W).

Step 5: 3-Bromo-8-(4-methyl-piperidin-1-yl)-imidazo[1,2-a]pyridine-6-carboxylic acid ethyl ester To a stirred solution of compound V (1.6 g; 5.5 mmol; 1 eq) in dry THF (30 mL) at 0° C. was added NBS (0.99 g; 5.5 mmol; 1 eq) in portions and the resulting mixture was stirred at 0° C. for 30 min. The mixture was poured into ice-cold saturated aqueous NaHCO$_3$ solution and the organic components were extracted with ethyl acetate (3×500 mL). The combined organic layers were then washed with brine, dried over anhydrous sodium sulfate, filtered and evaporated to dryness to afford the title compound (1.7 g, 83%) as an off white solid. $^1$H NMR (DMSO-d$_6$) δ 8.34 (s, 1H), 7.75 (s, 1H), 6.87 (s, 1H), 4.35 (m, 4H), 2.79 (q, 2H, J=12 Hz), 1.73 (d, 2H, J=12 Hz), 1.58 (s, 1H), 1.3 (m, 5H), 0.95 (t, 3H, J=4 Hz). LCMS: m/z=366.2 [M+], 368.2 [M+2], RT=2.51 minutes, (Program P1, Column W).

Step 6: 8-(4-Methyl-piperidin-1-yl)-3-propylsulfanyl-imidazo[1,2-a]pyridine-6-carboxylic acid ethyl ester To a stirred 1,4-dioxane solution of compound VI (0.15 g; 0.40 mmol; 1 eq) in a reaction tube was added propanethiol (73 mg; 0.81 mmol; 2 eq) and the mixture was degassed with argon for 5 min. To the mixture were then added Cs$_2$CO$_3$ (195 mg; 0.6 mmol; 1.5 eq), Pd$_2$(dba)$_3$ (18 mg; 0.02 mmol; 0.05 eq), xantphos (23 mg; 0.04 mmol; 0.1 eq), the resulting mixture was degassed with argon for another 5 min and the reaction tube was sealed. The mixture was then heated to 115° C. and stirred for 5 h. The mixture was filtered through a Celite® pad and the filtrate was washed with saturated aqueous NaHCO$_3$ solution, followed by brine. The organic layer was then dried over anhydrous Na$_2$SO$_4$, filtered and evaporated to dryness to obtain a crude material. The crude product was purified by silica gel (100-200 mesh) column chromatography, eluting with 50% EtOAc/hexanes to obtain the title compound (0.14 g, 91%). $^1$H NMR (DMSO-d$_6$) δ 8.63 (s, 1H), 7.80 (s, 1H), 6.89 (s, 1H), 4.37 (q, 2H, J=4 Hz), 4.33 (m, 2H), 2.78 (t, 2H, J=12 Hz), 2.69 (m, 2H), 1.76 (m, 2H), 1.60 (m, 1H), 1.42-1.39 (m, 7H), 0.96 (d, 3H, J=6 Hz), 0.83 (t, 3H, J=7 Hz). LCMS: m/z=375.8 [M+H]$^+$, RT=2.97 minutes, (Program P1, Column W).

Step 7: 8-(4-Methyl-piperidin-1-yl)-3-propylsulfanyl-imidazo[1,2-a]pyridine-6-carboxylic acid To a solution of compound VII (150 mg, 0.41 mmol, 1 eq) in THF:methanol:H$_2$O (12 mL, 3:2:1) at 0° C. was added a solution of lithium hydroxide monohydrate (34 mg, 0.83 mmol, 2 eq) in water (0.5 mL) and the resulting mixture was stirred at 23° C. for 3 h. The solvent was removed under reduced pressure and the residue was diluted with water and acidified with 1N HCl to adjust the pH to 3. The solid precipitate was collected by filtration and dried under vacuum to afford the title compound (0.11 g, 79%). $^1$H NMR (DMSO-d$_6$) δ 13.30 (s, 1H), 8.63 (s, 1H), 7.79 (s, 1H), 6.91 (s, 1H), 4.27 (d, 2H, J=12 Hz), 2.77 (t, 2H, J=8 Hz), 2.66 (t, 2H, J=8 Hz), 1.73 (d, 2H, J=12 Hz), 1.58 (m, 1H), 1.40-1.47 (m, 2H), 1.35-1.27 (m, 2H), 0.95-0.91 (m, 6H). LCMS: m/z=334 [M+H]$^+$, RT=2.64 minutes, (Program P1, Column W).

Step 8: (S)—N-(1-(4H-1,2,4-Triazol-3-yl)ethyl)-8-(4-methylpiperidin-1-yl)-3-(propylthio)imidazo[1,2-a]pyridine-6-carboxamide To a stirred solution of compound VIII (0.05 g, 0.14 mmol, 1 eq) in CH$_2$Cl$_2$ (10 mL) was added DIPEA (0.075 mL, 0.42 mmol, 3 eq) and HATU (0.069 g, 0.18 mmol, 1.3 eq) at 0° C. and the resulting mixture was allowed to stir for 15 min. To the mixture was added (S)-1-(4H-[1,2,4]triazol-3-yl)-ethylamine hydrochloride (0.025 g, 0.17 mmol, 1.2 eq) and the resulting mixture was allowed to stir at 23° C. for another 16 h. From the mixture, solvent was removed in vacuo, diluted with EtOAc and washed with saturated aqueous sodium bicarbonate solution, aqueous ammonium chloride solution and brine. The organic layer was dried over anhydrous sodium sulfate, filtered and concentrated to dryness to obtain a crude product. The crude material was purified by silica gel (230-400 mesh) column chromatography eluting with 0-5% methanol/CH$_2$Cl$_2$ to obtain the title compound (0.015 g, 23%). $^1$H NMR (CDCl$_3$) δ 11.79 (s, 1H), 8.52 (s, 1H), 8.04 (s, 1H), 7.72 (s, 1H), 6.85 (s, 1H), 6.70 (s, 1H), 5.46 (q, 1H, J=8 Hz), 4.19 (d, 2H, J=12 Hz), 2.79 (t, 2H, J=12 Hz), 2.56 (t, 2H, J=8 Hz), 1.78 (d, 4H, J=4 Hz), 1.53-1.46 (m, 5H), 1.0-0.93 (m, 6H). LCMS: m/z=428.4 [M+H]$^+$, RT=3.15 minutes, (Program P1, Column W).

Example 11: (S)—N-(1-(4H-1,2,4-Triazol-3-yl) ethyl)-8-(4-methylpiperidin-1-yl)-3-(5-methylthiophen-2-yl)imidazo[1,2-a]pyridine-6-carboxamide Scheme 27

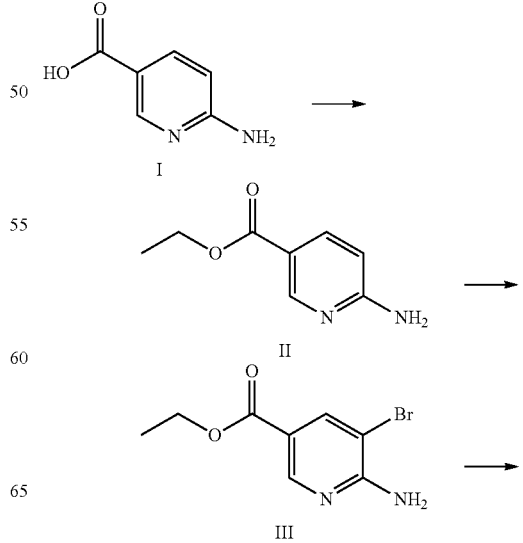

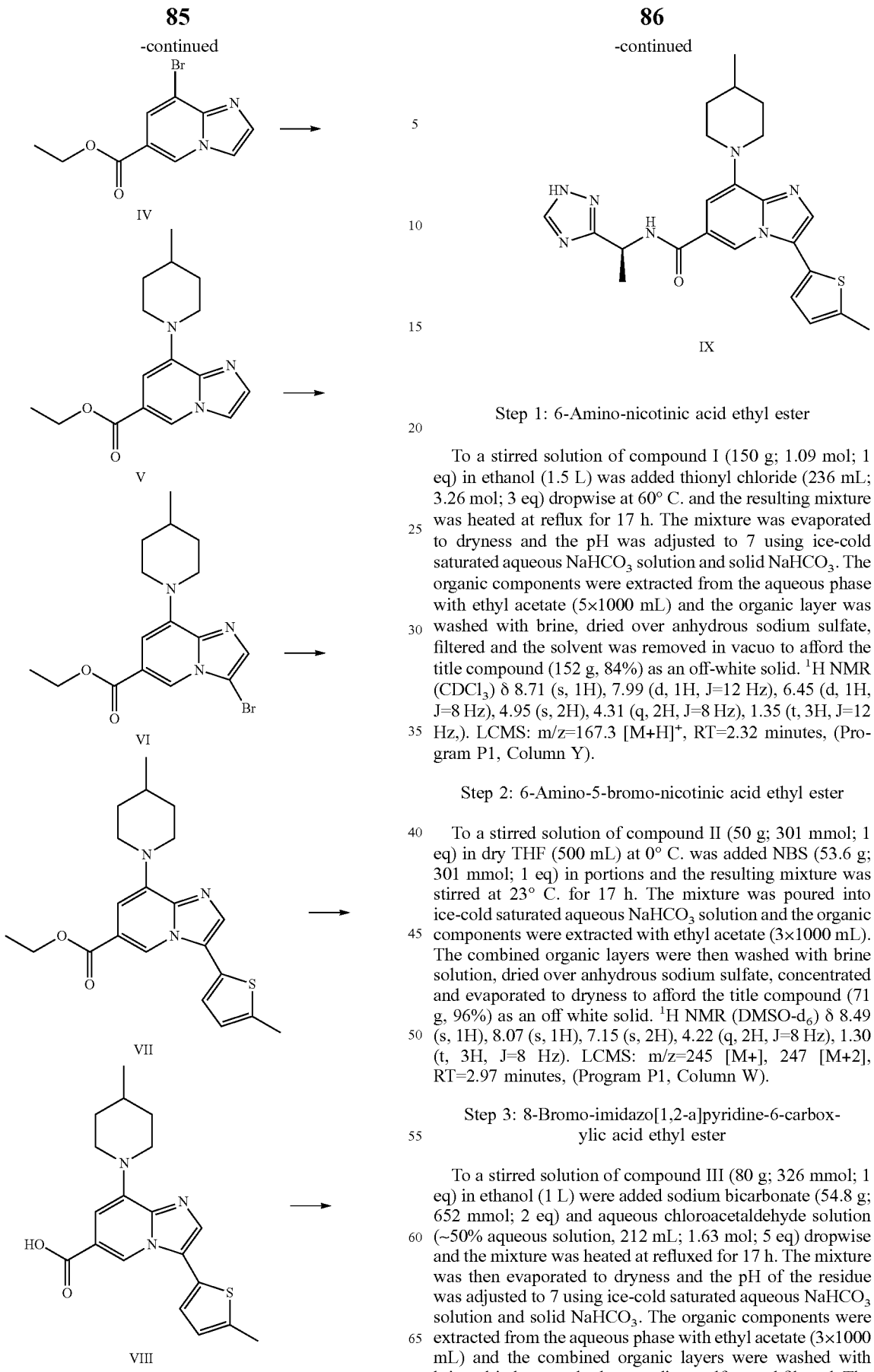

Step 1: 6-Amino-nicotinic acid ethyl ester

To a stirred solution of compound I (150 g; 1.09 mol; 1 eq) in ethanol (1.5 L) was added thionyl chloride (236 mL; 3.26 mol; 3 eq) dropwise at 60° C. and the resulting mixture was heated at reflux for 17 h. The mixture was evaporated to dryness and the pH was adjusted to 7 using ice-cold saturated aqueous NaHCO₃ solution and solid NaHCO₃. The organic components were extracted from the aqueous phase with ethyl acetate (5×1000 mL) and the organic layer was washed with brine, dried over anhydrous sodium sulfate, filtered and the solvent was removed in vacuo to afford the title compound (152 g, 84%) as an off-white solid. $^1$H NMR (CDCl₃) δ 8.71 (s, 1H), 7.99 (d, 1H, J=12 Hz), 6.45 (d, 1H, J=8 Hz), 4.95 (s, 2H), 4.31 (q, 2H, J=8 Hz), 1.35 (t, 3H, J=12 Hz,). LCMS: m/z=167.3 [M+H]⁺, RT=2.32 minutes, (Program P1, Column Y).

Step 2: 6-Amino-5-bromo-nicotinic acid ethyl ester

To a stirred solution of compound II (50 g; 301 mmol; 1 eq) in dry THF (500 mL) at 0° C. was added NBS (53.6 g; 301 mmol; 1 eq) in portions and the resulting mixture was stirred at 23° C. for 17 h. The mixture was poured into ice-cold saturated aqueous NaHCO₃ solution and the organic components were extracted with ethyl acetate (3×1000 mL). The combined organic layers were then washed with brine solution, dried over anhydrous sodium sulfate, concentrated and evaporated to dryness to afford the title compound (71 g, 96%) as an off white solid. $^1$H NMR (DMSO-d₆) δ 8.49 (s, 1H), 8.07 (s, 1H), 7.15 (s, 2H), 4.22 (q, 2H, J=8 Hz), 1.30 (t, 3H, J=8 Hz). LCMS: m/z=245 [M+], 247 [M+2], RT=2.97 minutes, (Program P1, Column W).

Step 3: 8-Bromo-imidazo[1,2-a]pyridine-6-carboxylic acid ethyl ester

To a stirred solution of compound III (80 g; 326 mmol; 1 eq) in ethanol (1 L) were added sodium bicarbonate (54.8 g; 652 mmol; 2 eq) and aqueous chloroacetaldehyde solution (~50% aqueous solution, 212 mL; 1.63 mol; 5 eq) dropwise and the mixture was heated at refluxed for 17 h. The mixture was then evaporated to dryness and the pH of the residue was adjusted to 7 using ice-cold saturated aqueous NaHCO₃ solution and solid NaHCO₃. The organic components were extracted from the aqueous phase with ethyl acetate (3×1000 mL) and the combined organic layers were washed with brine, dried over anhydrous sodium sulfate and filtered. The filtrate was concentrated in vacuo to obtain a dry residue which was purified by silica gel (230-400 mesh) column chromatography using 10-50% ethyl acetate/hexanes as the eluent to afford the title compound (55 g, 63%) as a brown solid. $^1$H NMR (DMSO-d$_6$) δ 9.33 (s, 1H), 8.24 (s, 1H), 7.84 (s, 1H), 7.73 (s, 1H), 4.34 (q, 2H, J=8 Hz), 1.34 (t, 3H, J=8 Hz). LCMS: m/z=268.8 [M+], 270.8 [M+2], RT=2.90 minutes, (Program P1, Column W).

Step 4: 8-(4-Methyl-piperidin-1-yl)-imidazo[1,2-a]pyridine-6-carboxylic acid ethyl ester To a stirred 1,4-dioxane solution of compound IV (1 g; 3.71 mmol; 1 eq) in a reaction tube was added 4-methyl piperidine (0.73 g; 7.43 mmol; 2 eq) and the resulting mixture was degassed with argon for 5 min, followed by addition of Cs$_2$CO$_3$ (1.81 g; 5.56 mmol; 1.5 eq), Pd$_2$(dba)$_3$ (0.16 g; 0.018 mmol; 0.05 eq) and xantphos (0.21 g; 0.37 mmol; 0.1 eq). The mixture was then degassed again with argon for 5 min, the reaction tube was sealed and heated at 115° C. for 5 h. The mixture was filtered through a Celite® pad and the filtrate was washed with saturated aqueous NaHCO$_3$ solution, followed by brine. The organic layer was then dried over anhydrous Na$_2$SO$_4$, filtered and evaporated to dryness to obtain a crude material. The crude product was purified by silica gel (100-200 mesh) column chromatography, eluting with 50% EtOAc/hexanes to obtain the title compound (0.25 g, 23%) as a light brown solid. $^1$H NMR (DMSO-d$_6$) δ 8.84 (s, 1H), 8.03 (s, 1H), 7.55 (s, 1H), 6.75 (s, 1H), 4.31 (m, 4H), 2.73 (q, 2H, J=8 Hz), 1.73 (d, 2H, J=12 Hz), 1.56 (m, 1H), 1.3 (m, 5H), 0.9 (t, 3H, J=4 Hz). LCMS: m/z=288 [M+H]$^+$, RT=3.56 minutes, (Program P1, Column W).

Step 5: 3-Bromo-8-(4-methyl-piperidin-1-yl)-imidazo[1,2-a]pyridine-6-carboxylic acid ethyl ester To a stirred solution of compound (1.6 g; 5.5 mmol; 1 eq) in dry THF (30 mL) at 0° C. was added NBS (0.99 g; 5.5 mmol; 1 eq) in portions, and the resulting mixture was stirred at 0° C. for 30 min. The mixture was poured into ice-cold saturated aqueous NaHCO$_3$ solution and the organic components were extracted with ethyl acetate (3×500 mL). The combined organic layers were then washed with brine solution, dried over anhydrous sodium sulfate, filtered and evaporated to dryness to afford the title compound (1.7 g, 83%) as an off white solid. $^1$H NMR (DMSO-d$_6$) δ 8.34 (s, 1H), 7.75 (s, 1H), 6.87 (s, 1H), 4.35 (m, 4H), 2.79 (q, 2H, J=12 Hz), 1.73 (d, 2H, J=12 Hz), 1.58 (s, 1H), 1.3 (m, 5H), 0.95 (t, 3H, J=4 Hz). LCMS: m/z=366.2 [M+], 368.2 [M+2], RT=2.51 minutes, (Program P1, Column W).

Step 6: 8-(4-Methyl-piperidin-1-yl)-3-(5-methyl-thiophen-2-yl)-imidazo[1,2-a]pyridine-6-carboxylic acid ethyl ester To a stirred solution of compound VI (1 g; 2.7 mmol; 1 eq) in dry toluene in a reaction tube was added compound VIa (1.58 g; 4 mmol; 1.5 eq) and the resulting mixture was degassed with argon for 5 min. Pd(PPh$_3$)$_4$ (0.31 g; 0.27 mmol; 0.1 eq) was added to the mixture and the resulting mixture was degassed again with argon for 5 min. The reaction tube was sealed and the mixture was heated at 115° C. with stirring for 4 h. The mixture was then filtered through a Celite® pad and the filtrate was washed with saturated aqueous NaHCO$_3$ solution, followed by brine. The organic layer was then dried over anhydrous Na$_2$SO$_4$, filtered and evaporated to dryness to obtain a crude material. The crude product was purified by silica gel (230-400 mesh) column chromatography eluting with 50% EtOAc/hexanes to obtain the title compound (0.8 g, 80%) as light brown solid. $^1$H NMR (DMSO-d$_6$) δ 8.57 (s, 1H), 7.72 (s, 1H), 7.27 (d, 1H, J=4 Hz), 6.98 (d, 1H, J=2 Hz), 6.85 (s, 1H), 4.3 (m, 4H), 2.79 (q, 2H, J=12 Hz), 2.53 (s, 3H), 1.75 (d, 2H, J=8 Hz), 1.58 (s, 1H), 1.32 (m, 5H), 0.96 (d, 3H). LCMS: m/z=384 [M+H]$^+$, RT=4.50 minutes, (Program P1, Column Y).

Step 7: 8-(4-Methyl-piperidin-1-yl)-3-(5-methyl-thiophen-2-yl)-imidazo[1,2-a]pyridine-6-carboxylic acid To a solution of compound VII (0.8 g, 2.08 mmol, 1 eq) in THF:methanol:H$_2$O (12 mL, 3:2:1) at 0° C. was added a solution of lithium hydroxide monohydrate (0.175 g, 4.1 mmol, 2 eq) in water (1 mL) and the resulting mixture was stirred at 23° C. for 3 h. The solvents were removed under reduced pressure and the residue was diluted with water and acidified with 1N HCl to adjust the pH to 3. The precipitated solid was collected by filtration and dried under vacuum to afford the title compound (0.74 g, 100%). $^1$H NMR (DMSO-d$_6$) δ 8.55 (s, 1H), 7.68 (s, 1H), 7.23 (d, 1H, J=3 Hz), 6.97 (d, 1H, J=2 Hz), 6.94 (s, 1H), 4.27 (d, 2H, J=12 Hz), 2.76 (m, 2H), 2.52 (s, 3H), 1.74 (d, 2H, J=8 Hz), 1.67 (m, 1H), 1.37 (m, 2H); 0.96 (m, 3H). LCMS: m/z=356.3 [M+H]$^+$, RT=2.69 minutes, (Program P1, Column Y).

Step 8: (S)—N-(1-(4H-1,2,4-Triazol-3-yl)ethyl)-8-(4-methylpiperidin-1-yl)-3-(5-methylthiophen-2-yl)imidazo[1,2-a]pyridine-6-carboxamide To a stirred solution of compound VIII (0.2 g, 0.56 mmol, 1 eq) in DMF (10 mL) were added DIPEA (0.3 mL, 1.6 mmol, 3 eq) and HATU (0.27 g, 0.72 mmol, 1.3 eq) at 0° C. and the resulting mixture was allowed to stir for 15 min. To the mixture was added (S)-1-(4H-[1,2,4]triazol-3-yl)-ethylamine hydrochloride (0.1 g, 0.67 mmol, 1.2 eq) and the resulting mixture was allowed to stir at 23° C. for another 16 h. From the mixture, solvent was removed in vacuo, the residue was diluted with EtOAc and washed with saturated aqueous sodium bicarbonate solution, aqueous ammonium chloride solution and brine. The organic layer was dried over anhydrous sodium sulfate, filtered and concentrated to dryness. The crude product was purified by silica gel (230-400 mesh) column chromatography eluting with 0-5% methanol/CH$_2$Cl$_2$ to obtain the title compound (0.12 g, 48%) as brown solid. $^1$H NMR (CDCl$_3$) δ 8.46 (s, 1H), 8.00 (s, 1H), 7.62 (s, 1H), 7.04 (d, 1H, J=2 Hz), 6.82 (m, 2H), 6.61 (s, 1H), 5.42 (m, 1H), 4.15 (m, 2H), 2.77 (t, 2H, J=12 Hz), 2.48 (s, 3H), 1.75 (m, 5H), 1.52 (m, 3H), 0.99 (d, 3H, J=8 Hz). LCMS: m/z=450.0 [M+H]$^+$, RT=3.20 minutes, (Program P1, Column W).

Example 12: (S)—N-(1-(4H-1,2,4-Triazol-3-yl)ethyl)-8-(4-carbamoyl-4-methylpiperidin-1-yl)-3-(5-methylthiophen-2-yl)imidazo[1,2-a]pyridine-6-carboxamide
Scheme 28
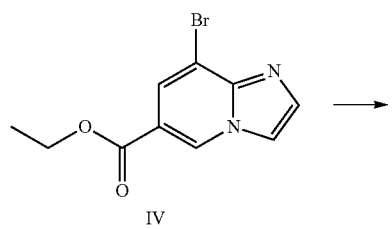
IV
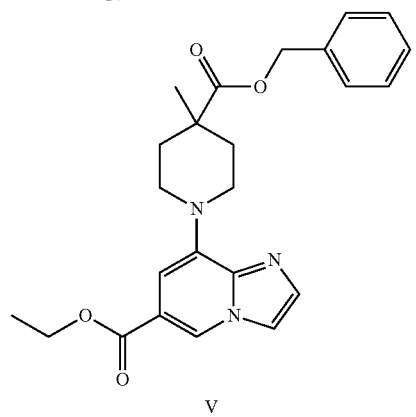
V
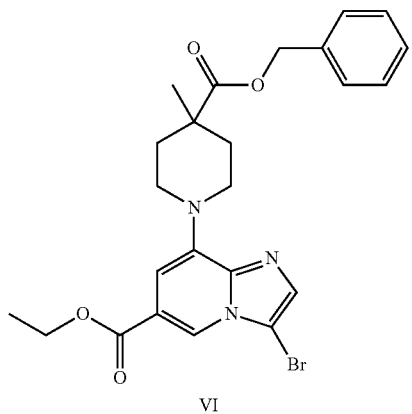
VI
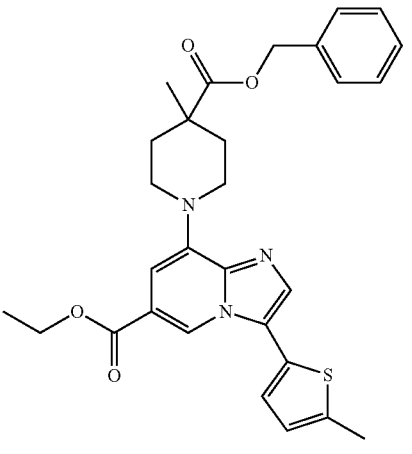
VII
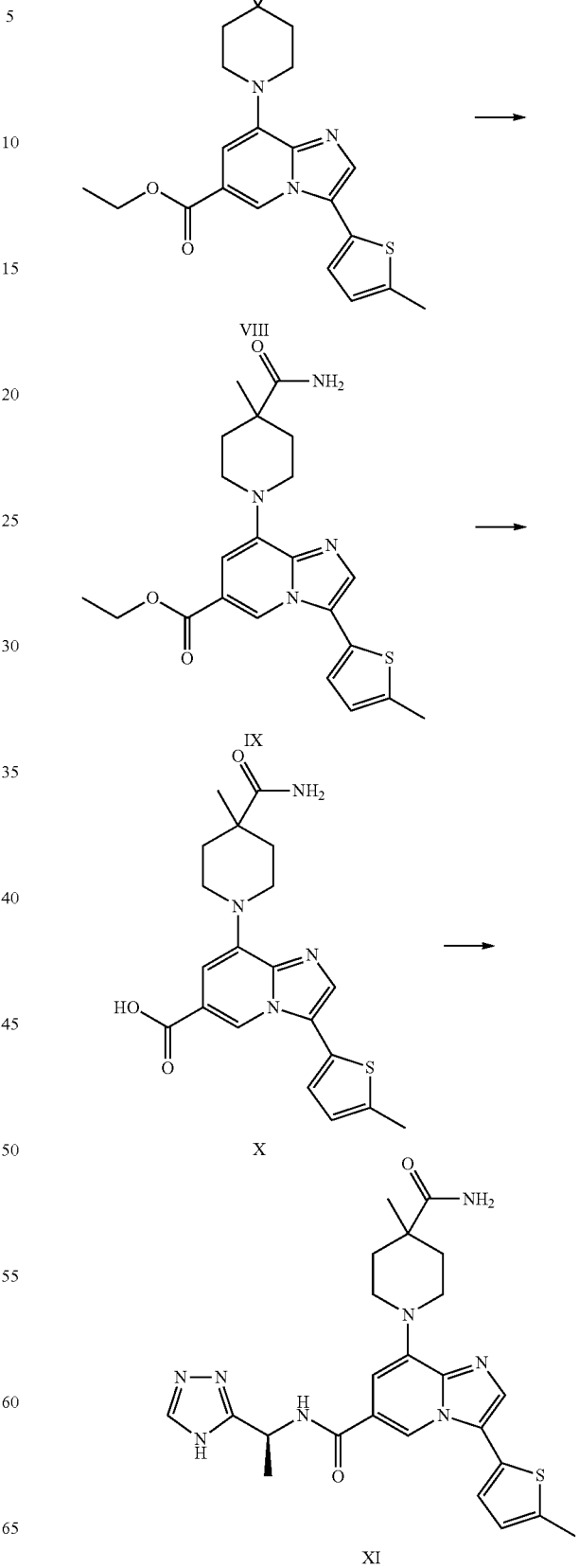

Following the experimental procedure described for Example 11, compound IV was prepared.

Step 4: 8-(4-Benzyloxycarbonyl-4-methyl-piperidin-1-yl)-imidazo[1,2-a]pyridine-6-carboxylic acid ethyl ester To a stirred 1,4-dioxane (40 mL) solution of compound IV (1 g; 3.71 mmol; 1 eq) in a reaction tube was added 4-methyl-piperidine-4-carboxylic acid benzyl ester (1.5 g; 5.6 mmol; 1.5 eq) and the resulting mixture was degassed with argon for 5 min, followed by an addition of $Cs_2CO_3$ (3.63 g; 11.15 mmol; 3 eq), $Pd_2(dba)_3$ (0.17 g; 0.019 mmol; 0.05 eq) and xantphos (0.21 g; 0.37 mmol; 0.1 eq). The mixture was then degassed again with argon for 5 min, the tube was sealed and heated at 130° C. for 5 h. The mixture was filtered through a Celite® pad, the filtrate was diluted with water (200 mL), and the organic components were extracted with ethyl acetate (200 mL). The organic layer was washed with saturated aqueous $NaHCO_3$ solution, brine and dried over anhydrous $Na_2SO_4$ then filtered. The filtrate was then concentrated under reduced pressure to obtain a crude material which was purified by Combiflash™ chromatography, eluting with 50% EtOAc/hexanes to obtain the title compound (0.33 g, 23%) as a light brown solid. $^1$H NMR ($CDCl_3$) δ 8.52 (s, 1H), 7.59 (s, 1H), 7.55 (s, 1H), 7.33 (m, 5H), 6.91 (s, 1H), 5.16 (s, 2H), 4.37 (q, 2H, J=7 Hz), 3.92 (m, 2H), 3.06 (t, 2H, J=10 Hz), 2.34 (d, 2H, J=14 Hz), 1.77 (m, 2H), 1.39 (t, 3H, J=7 Hz), 1.29 (s, 3H). LCMS: m/z=422.2 [M+H]$^+$, RT=3.77 minutes, (Program P1, Column W).

Step 5: 8-(4-Benzyloxycarbonyl-4-methyl-piperidin-1-yl)-3-bromo-imidazo[1,2-a]pyridine-6-carboxylic acid ethyl ester To a stirred solution of compound V (1 g; 2.37 mmol; 1 eq) in dry THF (20 mL) at 0° C. was added NBS (0.29 g; 1.66 mmol; 0.7 eq) in portions, and the resulting mixture was stirred at 0° C. for 5 min. The mixture was poured into ice-cold saturated aqueous $NaHCO_3$ solution and the organic components were extracted with ethyl acetate (3×100 mL). The combined organic layers were then washed with brine solution, dried over anhydrous sodium sulfate, filtered and evaporated to dryness to afford the title compound (0.67 g, 56%) as an off white solid. $^1$H NMR ($CDCl_3$) δ 8.48 (s, 1H), 7.57 (s, 1H), 7.33 (m, 5H), 6.99 (s, 1H), 5.16 (s, 2H), 4.40 (q, 2H, J=7 Hz), 3.90 (m, 2H), 3.06 (t, 2H, J=11 Hz), 2.34 (d, 2H, J=13 Hz), 1.77 (m, 2H), 1.41 (t, 3H, J=7 Hz), 1.29 (s, 3H). LCMS: m/z=500.2 [M+], 502.4 [M+2], RT=4.06 minutes, (Program P1, Column V).

Step 6: 8-(4-Benzyloxycarbonyl-4-methyl-piperidin-1-yl)-3-(5-methyl-thiophen-2-yl)-imidazo[1,2-a]pyridine-6-carboxylic acid ethyl ester To a stirred solution of compound VI (0.67 g; 1.34 mmol; 1 eq) in dry DMF (5 mL) in a reaction tube was added compound VIa (0.66 g; 1.60 mmol; 1.2 eq) and the resulting mixture was degassed with argon for 5 min. $Pd(PPh_3)_4$ (0.15 g; 0.13 mmol; 0.1 eq) was then added to the mixture and degassed again with argon for 5 min. The reaction tube was sealed and the mixture was heated at 140° C. with stirring for 4 h. The mixture was filtered through a Celite® pad and the filtrate was diluted with ethyl acetate (200 mL) and water (200 mL). The organic layer was washed with water (200 mL) and brine, then dried over anhydrous $Na_2SO_4$ and filtered. The filtrate was evaporated under vacuum to obtain a crude material which was purified by Combiflash® chromatography, eluting with 50% EtOAc/hexanes to obtain the title compound (0.65 g, 94%) as a light brown solid. $^1$H NMR ($CDCl_3$) δ 8.71 (s, 1H), 7.63 (s, 1H), 7.34 (m, 5H), 7.06 (d, 1H, J=4 Hz), 6.96 (s, 1H), 6.84 (d, 1H, J=4 Hz), 5.17 (s, 2H), 4.38 (q, 2H, J=7 Hz), 3.92 (m, 2H), 3.07 (t, 2H, J=10 Hz), 2.55 (s, 3H), 2.35 (d, 2H, J=14 Hz), 1.77 (m, 2H), 1.38 (t, 3H, J=7 Hz), 1.30 (s, 3H). LCMS: m/z=518.4 [M+H]$^+$, RT=4.31 minutes, (Program P1, Column V).

Step 7: 8-(4-Carboxy-4-methyl-piperidin-1-yl)-3-(5-methyl-thiophen-2-yl)-imidazo[1,2-a]pyridine-6-carboxylic acid ethyl ester To a stirred solution of compound VII (0.65 g; 1.25 mmol; 1 eq) in dry methanol was added 10% Pd/C (650 mg) and the resulting mixture was stirred under hydrogen atmosphere at a pressure for 15 h. The mixture was filtered through a Celite® pad and the filtrate was concentrated to dryness to obtain the title compound (0.45 g, 85%). $^1$H NMR (DMSO-$d_6$) δ 8.58 (s, 1H), 7.74 (s, 1H), 7.28 (d, 1H, J=3 Hz), 7.00 (m, 1H), 6.87 (s, 1H), 4.32 (q, 2H, J=7 Hz), 4.15 (m, 1H), 3.92 (m, 2H), 2.87 (t, 2H, J=7 Hz), 2.54 (s, 3H), 2.33 (m, 2H), 1.70 (m, 2H), 1.37 (m, 3H), 1.30 (s, 3H). LCMS: m/z=428.2 [M+H]$^+$, RT=2.96 minutes, (Program P1, Column W).

Step 8: 8-(4-Carbamoyl-4-methyl-piperidin-1-yl)-3-(5-methyl-thiophen-2-yl)-imidazo[1,2-a]pyridine-6-carboxylic acid ethyl ester To a stirred solution of compound VIII (0.45 g, 1.05 mmol, 1 eq) in DMF (5 mL) were added DIPEA (0.54 mL, 3.16 mmol, 3 eq) and HATU (0.48 g, 1.26 mmol, 1.2 eq) at 0° C. and the resulting mixture was stirred for 15 min. To the mixture was added ammonium chloride (0.17 g, 3.16 mmol, 3 eq) and the resulting mixture was allowed to stir at 23° C. for another 18 h. The mixture was quenched with water and the organic components were extracted with ethyl acetate (3×100 mL) and washed with brine. The combined organic layers were dried over anhydrous sodium sulfate, filtered and concentrated to dryness to obtain a crude material which was purified by Combiflash™ chromatography, eluting with 0-5% methanol/$CH_2Cl_2$, to obtain the title compound (0.28 g, 63%) as a brown solid. $^1$H NMR (DMSO-$d_6$) δ 8.57 (s, 1H), 7.73 (s, 1H), 7.28 (d, 1H, J=4 Hz), 7.24 (m, 1H), 7.00 (m, 1H), 6.91 (brs, 1H), 6.85 (s, 1H), 4.33 (q, J=11 Hz, 2H), 3.87 (m, 2H), 3.20 (t, J=10 Hz, 2H), 2.54 (s, 3H), 2.14 (m, 2H), 1.55 (m, 2H), 1.31 (m, 3H), 1.16 (s, 3H). LCMS: m/z=427.2 [M+H]$^+$, RT=3.27 minutes, (Program P1, Column V).

Step 9: 8-(4-Carbamoyl-4-methyl-piperidin-1-yl)-3-(5-methyl-thiophen-2-yl)-imidazo[1,2-a]pyridine-6-carboxylic acid To a solution of compound IX (0.28 g, 0.9 mmol, 1 eq) in THF:methanol:$H_2O$ (14 mL, 5:1:1) at 0° C. was added a solution of lithium hydroxide monohydrate (0.108 g, 2.6 mmol, 3 eq) in water (1 mL) and the resulting mixture was stirred at 23° C. for 2 h. The organic solvent was removed under reduced pressure and the residue was diluted with water and acidified with 6N HCl to adjust the pH to 3. The precipitated solid was collected by filtration and the solid was dried under vacuum to afford the title compound (0.20 g, 76%). $^1$H NMR (DMSO-d$_6$) δ 8.52 (s, 1H), 7.66 (s, 1H), 7.22 (m, 2H), 6.90 (m, 3H), 3.77 (m, 2H), 3.18 (m, 2H), 2.53 (s, 3H), 2.15 (m, 2H), 1.55 (m, 2H), 1.16 (s, 3H). LCMS: m/z=399.0 [M+H]$^+$, RT=2.08 minutes, (Program P1, Column W).

Step 10: (S)—N-(1-(4H-1,2,4-Triazol-3-yl)ethyl)-8-(4-carbamoyl-4-methylpiperidin-1-yl)-3-(5-methyl-thiophen-2-yl)imidazo[1,2-a]pyridine-6-carboxamide To a stirred solution of compound X (0.1 g, 0.25 mmol, 1 eq) in DMF (5 mL) were added TEA (2 mL, 0.4 mmol, 3 eq), a DMF (2 mL) solution of (S)-1-(4H-[1,2,4]triazol-3-yl)-ethylamine hydrochloride (0.06 g, 0.4 mmol, 1.5 eq) and T3P (0.2 mL, 0.4 mmol, 1.5 eq) at 23° C. and the resulting mixture was stirred for 16 h. The mixture was quenched with water and the organic components were extracted with 10% methanol/dichloromethane (2×200 mL). The combined organic layers were washed with brine, dried over anhydrous sodium sulfate, filtered and concentrated to dryness. The crude residue was purified by silica gel (100-200 mesh) column chromatography eluting with 0-10% methanol/CH$_2$Cl$_2$ (at 8% compound started) to obtain the title compound (0.012 g, 10%) as an off white solid. $^1$H NMR (DMSO-d$_6$—80° C.) δ 13.61 (brs, 1H), 8.77 (s, 1H), 8.54 (s, 1H), 8.14 (brs, 1H), 7.64 (s, 1H), 7.26 (s, 1H), 6.96 (s, 2H), 6.78 (brs, 2H), 5.34 (m, 1H), 3.86 (m, 2H), 3.36 (m, 2H), 2.54 (s, 3H), 2.17 (m, 2H), 1.63 (m, 2H), 1.57 (m, 3H), 1.21 (s, 3H). LCMS: m/z=493.4 [M+H]$^+$, RT=2.60 minutes, (Program P1, Column V).

Example 13: 8-(4-Carbamoylpiperazin-1-yl)-N-((6-methylpyridin-3-yl)methyl)-3-(5-methylthiophen-2-yl)imidazo[1,2-a]pyridine-6-carboxamide Scheme 29

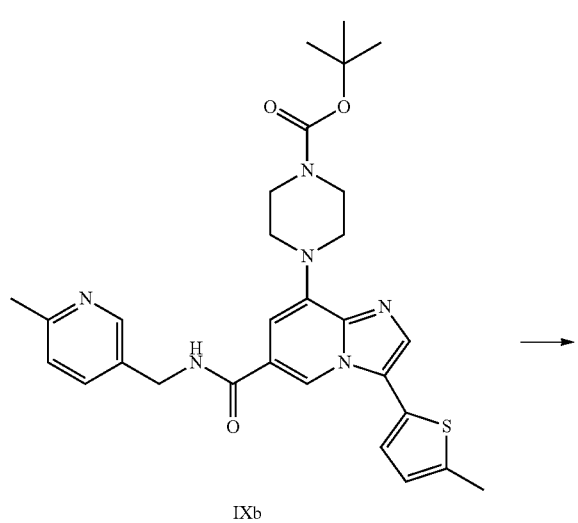

IXb

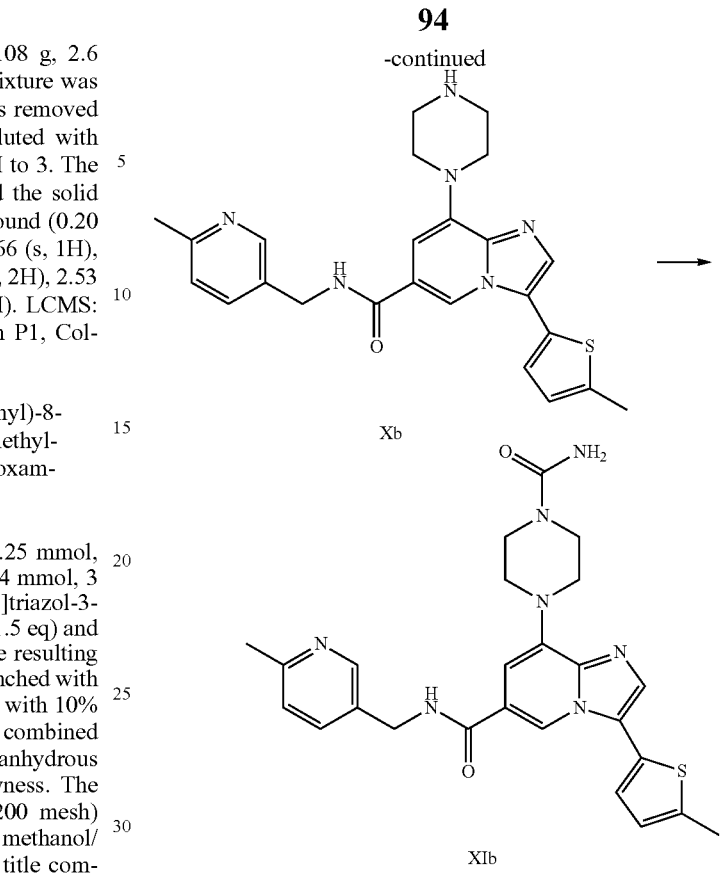

Xb

XIb

Compound IXb was synthesized in a similar way as compound IX was prepared in scheme 28, replacing 4-methyl piperidine with N-BOC piperazine in step-4 and the triazole amine analog with the pyridine amine analog in step 8. Step-A and Step-B were subsequently carried out to synthesize compound XIb.

Step A: 3-(5-Methyl-thiophen-2-yl)-8-piperazin-1-yl-imidazo[1,2-a]pyridine-6-carboxylic acid [(S)-1-(1H-[1,2,4]triazol-3-yl)-ethyl]-amide To the solution of IXb (240 mg, 0.44 mmol, 1 eq) in CH$_2$Cl$_2$ (8 mL) was added TFA (0.33 mL, 4.4 mmol, 10 eq) and the resulting mixture was stirred at 23° C. for 16 h. The mixture was concentrated in vacuo to remove TFA and diluted with water. Aqueous NaHCO$_3$ was added and the organic components were extracted with 5% MeOH/CH$_2$Cl$_2$. The organic layer was dried over anhydrous Na$_2$SO$_4$, filtered and concentrated under reduced pressure to obtain the title compound (140 mg, 72%) as an off white solid. $^1$H NMR (DMSO-d$_6$) δ 9.24 (t, 1H, J=5 Hz), 8.60 (s, 1H), 8.42 (s, 1H), 7.69 (s, 1H), 7.62-7.60 (m, 1H), 7.30 (d, 1H, J=3 Hz), 7.21-7.20 (m, 1H), 6.99-6.97 (m, 2H), 4.45 (d, 2H, J=5 Hz), 3.57 (s, 4H), 3.02 (s, 4H), 2.53 (s, 3H), 2.43 (s, 3H). LCMS: m/z=447.3 [M+H]$^+$, RT=2.54 minutes, (Program P1, Column V).

Step B: 8-(4-Carbamoylpiperazin-1-yl)-N-((6-methylpyridin-3-yl)methyl)-3-(5-methylthiophen-2-yl)imidazo[1,2-a]pyridine-6-carboxamide To the solution of Xb (80 mg, 0.18 mmol, 1 eq) in THF (5 mL) was added TMS-isocyanate (0.05 ml, 0.36 mmol, 2 eq) at 23° C. and the resulting mixture was stirred for 4 h. The mixture was then diluted with aqueous NaHCO₃ and the organic components were extracted with 15% MeOH/CH₂Cl₂, dried over anhydrous sodium sulfate, filtered and concentrated under reduced pressure. The crude residue was purified by flash Combiflash™ chromatography using 100-200 mesh silica gel eluting with 17% MeOH/CH₂Cl₂ to obtain the title compound (14 mg, 16%) as an off white solid. $^1$H NMR (DMSO-d$_6$) δ 9.20 (t, 1H, J=6 Hz), 8.60 (s, 1H), 8.42 (s, 1H), 7.70 (s, 1H), 7.62-7.60 (m, 1H), 7.30 (d, 1H, J=3 Hz), 7.22-7.20 (m, 1H), 6.98 (m, 2H), 4.46 (d, 2H, J=6 Hz), 3.51 (s, 8H), 2.53 (s, 3H), 2.43 (s, 3H). LCMS: m/z=490.2 [M+H]$^+$, RT=2.65 minutes, (Program P1, Column W).

Example 14: (S)—N-(1-(1,3,4-Oxadiazol-2-yl)ethyl)-8-(5-(difluoromethyl)-1H-1,2,3-triazol-1-yl)-3-(5-methylthiophen-2-yl)imidazo[1,2-a]pyridine-6-carboxamide

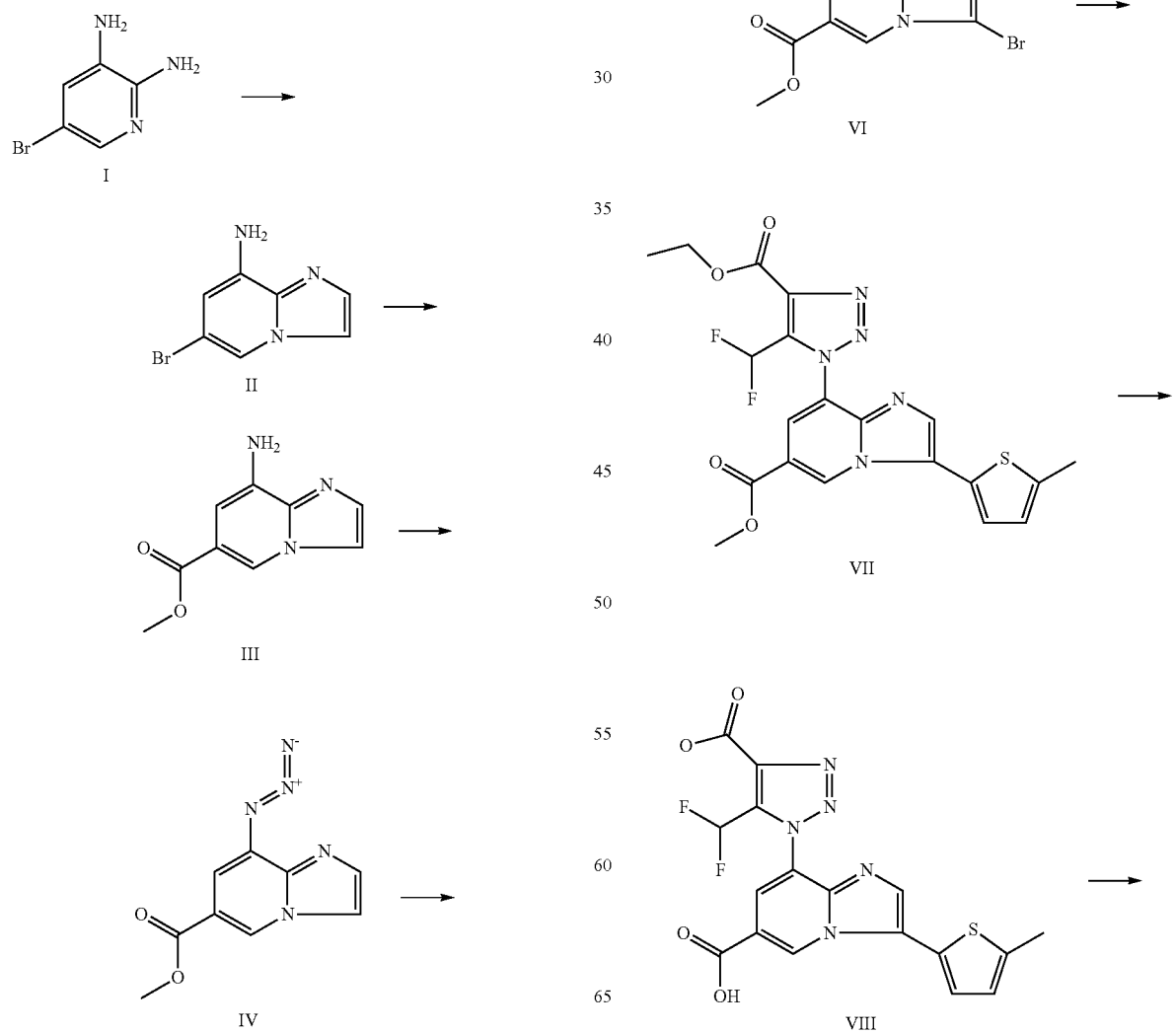

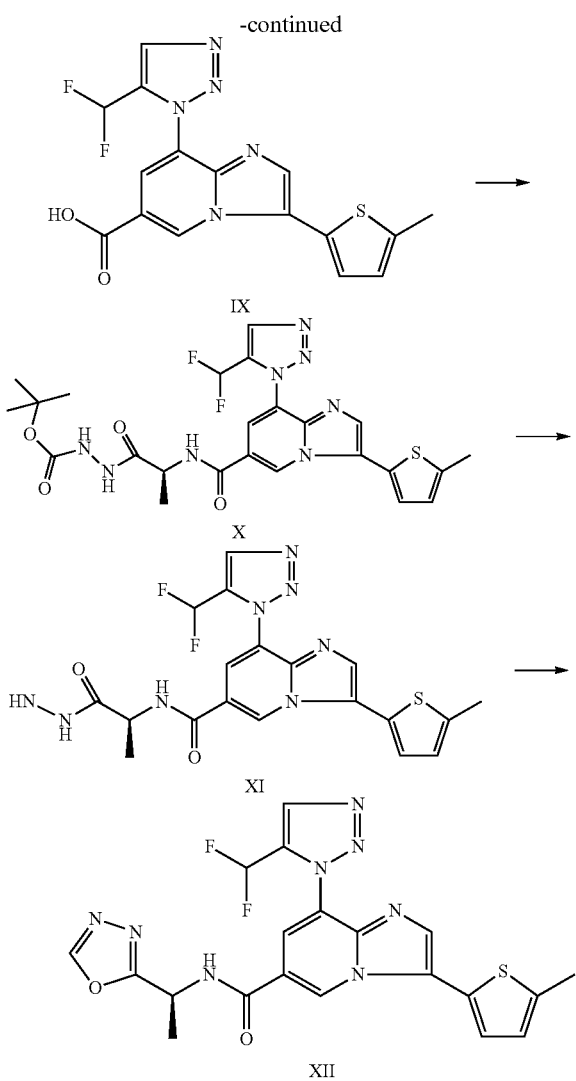

Step 1: 6-Bromo-imidazo[1,2-a]pyridin-8-ylamine

To a stirred solution of compound I (50 g; 0.26 mol; 1 eq) in ethanol (2 L) were added sodium bicarbonate (46 g; 0.53 mol; 2 eq) and chloroacetaldehyde solution (~50% aqueous solution, 86 mL; 0.66 mol; 2.5 eq) dropwise and the resulting mixture was heated at reflux for 17 h. The mixture was evaporated to dryness and the pH was adjusted to 7 using ice-cold saturated aqueous NaHCO$_3$ solution and solid NaHCO$_3$. The organic components were extracted from the aqueous phase with ethyl acetate (3×1000 mL) and the combined organic layers were washed with brine, dried over anhydrous sodium sulfate and the solvents were removed in vacuo to obtain a dry residue which was purified by silica gel (230-400 mesh) column chromatography using 10-50% ethyl acetate/hexanes as the eluent to afford the title compound (40 g, 71%) as a brown solid. $^1$H NMR (DMSO-d$_6$) δ 8.04 (s, 1H), 7.77 (s, 1H), 7.44 (s, 1H), 6.31 (s, 1H), 5.99 (s, 2H). LCMS: m/z=212.0 [M+], 214.0 [M+2], RT=2.55 minutes, (Program P1, Column V).

Step 2: 8-Amino-imidazo[1,2-a]pyridine-6-carboxylic acid methyl ester

To a solution of compound II (10 g; 47.20 mmol; 1 eq) in methanol (200 mL) was added diisopropylethyl amine (41 mL; 236 mmol; 5 eq) and the resulting mixture was degassed with argon for 5 min. To the mixture was added PdCl$_2$(dppf) (4 g; 4.72 mmol; 0.1 eq) and the resulting mixture was degassed with argon for another 5 min and then heated in an autoclave at 90° C. at 50 psi carbon monoxide pressure for 16 h. The mixture was filtered through a Celite® pad and the filtrate was washed with saturated aqueous NaHCO$_3$ solution, followed by brine. The organic layer was then dried over anhydrous Na$_2$SO$_4$, filtered and evaporated to dryness to obtain a crude material. The crude product was purified by silica gel (100-200 mesh) column chromatography, eluting with 0-10% methanol/dichloromethane as the eluent to obtain the title compound (5 g, 55%) as light brown solid. $^1$H NMR (DMSO-d$_6$) δ 8.57 (s, 1H), 7.97 (s, 1H), 7.51 (s, 1H), 6.67 (s, 1H), 5.86 (s, 2H), 3.84 (s, 3H). LCMS: m/z=191.8 [M+H]$^+$, RT=2.03 minutes, (Program P1, Column V).

Step 3: 8-Azido-imidazo[1,2-a]pyridine-6-carboxylic acid methyl ester

To a stirred solution of compound III (10 g; 52.36 mmol; 1 eq) in dry THF (600 mL) were added tertiarybutylnitrite (32 mL; 230 mmol; 4.4 eq) dropwise and trimethylsilylazide (16 mL, 115 mmol, 2.20 eq) at 0° C., and the resulting mixture was stirred at 23° C. for 17 h. The mixture was evaporated to dryness to obtain a crude material which was purified by silica gel (100-200 mesh) column chromatography, eluting with 0-50% ethylacetate/hexanes as eluent to obtain the title compound (9 g, 80%) as light brown solid. $^1$H NMR (DMSO-d$_6$) δ 9.17 (s, 1H), 8.19 (s, 1H), 7.71 (s, 1H), 7.11 (s, 1H), 3.87 (s, 3H). LCMS: m/z=218.2 [M+H]$^+$, RT=2.69 minutes, (Program P1, Column V).

Step 4: 8-(5-Difluoromethyl-4-ethoxycarbonyl-[1,2,3]triazol-1-yl)-imidazo[1,2-a]pyridine-6-carboxylic acid methyl ester To a stirred solution of DBU (25 mL; 166 mmol; 1.2 eq) in dry DMF:THF (1000 mL; 1:1) was added 4,4-difluoro-3-oxo-butyric acid ethyl ester (22 mL; 207.3 mmol; 1.5 eq) slowly at 23° C. and the mixture was stirred for 30 min. The mixture was then cooled to 0° C. and a DMF:THF (200 ml, 1:1) solution of compound IV (30 g; 138.2 mmol; 1 eq) was added dropwise and the resulting mixture was allowed to stir at 23° C. for 17 h. The mixture was diluted with water (1000 mL) and the organic components were extracted with ethyl acetate (3×500 mL). The combined organic layers were washed with brine, dried over anhydrous sodium sulfate, filtered and the solvent was removed in vacuo to obtain a dry residue which was purified by silica gel (230-400 mesh) column chromatography using 10-50% ethyl acetate/hexanes as the eluent to afford the title compound (32 g, 65%) as a solid. $^1$H NMR (DMSO-d$_6$) δ 9.65 (s, 1H), 8.33 (s, 1H), 8.10 (s, 1H), 7.74 (s, 1H), 7.46 (m, 1H), 4.43 (q, 2H, J=7 Hz), 3.96 (s, 3H), 1.36 (t, 3H, J=7 Hz). LCMS: m/z=365.8 [M+H]$^+$, RT=2.97 minutes, (Program P1, Column Y).

Step 5: 3-Bromo-8-(5-difluoromethyl-4-ethoxycarbonyl-[1,2,3]triazol-1-yl)-imidazo[1,2-a]pyridine-6-carboxylic acid methyl ester To a stirred solution of compound V (10 g; 27.4 mmol; 1 eq) in dry THF (150 mL) at 0° C. was added NBS (7.4 g; 41.1 mmol; 1.5 eq) in portions and the resulting mixture was stirred at 0° C. for 30 min. The mixture was poured into ice-cold saturated aqueous NaHCO$_3$ solution and the organic components were extracted with ethyl acetate (3×500 mL). The combined organic layers were then washed with brine, dried over anhydrous sodium sulfate and the solvents were removed in vacuo to obtain a dry residue which was chromatographically purified by silica gel (230-400 mesh) gravity column using 10-50% ethyl acetate/hexane as the eluent to afford the title compound (10 g, 82%) as a solid. $^1$H NMR (DMSO-d$_6$) δ 9.00 (s, 1H), 8.27 (s, 1H), 7.96 (s, 1H), 7.44 (m, 1H), 4.43 (q, 2H, J=7 Hz), 3.96 (s, 3H), 1.35 (t, 3H, J=7 Hz). LCMS: m/z=443.8 [M+], 445.8 [M+2], RT=3.20 minutes, (Program P1, Column Y).

Step 6: 8-(5-Difluoromethyl-4-ethoxycarbonyl-[1,2,3]triazol-1-yl)-3-(5-methyl-thiophen-2-yl)-imidazo[1,2-a]pyridine-6-carboxylic acid methyl ester To a stirred dry DMF solution of compound VI (0.5 g; 1.13 mmol; 1 eq) in a reaction tube was added compound VIa (0.7 g; 1.70 mmol; 1.5 eq) and the resulting mixture was degassed with argon for 5 min. To the mixture was added Pd(PPh$_3$)$_4$ (0.13 g; 0.11 mmol; 0.1 eq) and degassing with argon was repeated for about 5 min. The reaction tube was sealed and heated at 115° C. for 4 h. The mixture was filtered through a Celite® pad and the filtrate was washed with saturated aqueous NaHCO$_3$ solution, followed by brine. The organic layer was then dried over anhydrous Na$_2$SO$_4$, filtered and solvents were removed in vacuo to obtain a crude material. The crude product was purified by silica gel (230-400 mesh) column chromatography eluting with 0-5% methanol/CH$_2$Cl$_2$ to obtain the title compound (0.25 g, 50%) as a light brown solid. $^1$H NMR (DMSO-d$_6$) δ 9.18 (s, 1H), 8.21 (s, 1H), 7.93 (s, 1H), 7.47 (m, 2H), 7.05 (s, 1H), 4.44 (q, 2H, J=7 Hz), 3.93 (s, 3H), 2.56 (s, 3H), 1.37 (t, 3H, J=7 Hz). LCMS: m/z=461.8 [M+H]$^+$, RT=3.56 minutes, (Program P1, Column Y).

Step 7: 8-(4-Carboxy-5-difluoromethyl-[1,2,3]triazol-1-yl)-3-(5-methyl-thiophen-2-yl)-imidazo[1,2-a]pyridine-6-carboxylic acid To a solution of compound VII (0.5 g, 1.10 mmol, 1 eq) in THF:methanol:H$_2$O (55 mL, 3:2:1) at 0° C. was added a solution of lithium hydroxide monohydrate (0.14 g, 3.25 mmol, 3 eq) in water (5 mL) and the resulting mixture was stirred at 23° C. for 3 h. The solvents were removed under reduced pressure and the residue was diluted with water and acidified with 1N HCl to adjust the pH to 3. The precipitated solid was collected by filtration and dried under vacuum to afford the title compound (0.35 g, 70%)).

Step 8: 8-(5-Difluoromethyl-[1,2,3]triazol-1-yl)-3-(5-methyl-thiophen-2-yl)-imidazo[1,2-a]pyridine-6-carboxylic acid Compound VIII (0.35 g; 0.83 mmol; 1 eq) was heated at 200° C. for 1 h to obtain the title compound (0.31 g, 95%).

Step 9: N'—((S)-2-{[8-(5-Difluoromethyl-[1,2,3]triazol-1-yl)-3-(5-methyl-thiophen-2-yl)-imidazo[1,2-a]pyridine-6-carbonyl]-amino}-propionyl)-hydrazine carboxylic acid tert-butyl ester To a stirred solution of compound IX (0.31 g, 0.83 mmol, 1 eq) in DMF (30 mL) were added DIPEA (0.5 mL, 2.50 mmol, 3 eq) and HATU (0.47 g, 1.24 mmol, 1.5 eq) at 0° C. and the resulting mixture was stirred for 15 min. To the mixture was added (S)-1-(4H-[1,2,4]triazol-3-yl)-ethylamine hydrochloride (0.25 g, 1.24 mmol, 1.5 eq) and the resulting mixture was allowed to stir at 23° C. for another 16 h. From the mixture, solvent was removed in vacuo and the residue was diluted with EtOAc. The organic layer was washed with saturated aqueous sodium bicarbonate solution, aqueous ammonium chloride solution and brine. The organic layer was dried over anhydrous sodium sulfate, filtered and concentrated to dryness. The crude product was purified by silica gel (230-400 mesh) column chromatography eluting with 0-5% methanol/CH$_2$Cl$_2$ to obtain the title compound (0.3 g, 65%) as a brown solid. $^1$H NMR (DMSO-d$_6$) δ 9.76 (s, 1H), 9.21 (s, 1H), 9.07 (d, 1H, J=7 Hz), 8.78 (s, 1H), 8.46 (s, 1H), 8.28 (s, 1H), 7.90 (s, 1H), 7.47 (m, 2H), 7.06 (s, 1H), 4.57 (m, 1H), 2.56 (s, 3H), 1.37 (m, 12H). LCMS: m/z=561.2 [M+H]$^+$, RT=3.20 minutes, (Program P1, Column Y).

Step 10: 8-(5-Difluoromethyl-[1,2,3]triazol-1-yl)-3-(5-methyl-thiophen-2-yl)-imidazo[1,2-a]pyridine-6-carboxylic acid ((S)-1-hydrazinocarbonyl-ethyl)-amide To a stirring solution of compound X (0.3 g; 0.53 mmol; 1 eq) in 1,4-dioxane (20 mL) at 0° C. was added 4 M HCl in 1,4-dioxane (10 mL) dropwise over a period of 30 min and the resulting mixture was stirred at 23° C. for 24 h. The volatiles were evaporated in vacuo to obtain the title compound (0.2 g, 80%) as a solid. $^1$H NMR (DMSO-d$_6$) δ 11.26 (s, 1H), 10.40 (brs, 3H), 9.26 (d, 1H, J=6 Hz), 9.22 (s, 1H), 8.47 (s, 1H), 8.29 (s, 1H), 7.93 (s, 1H), 7.47 (m, 2H), 7.06 (s, 1H), 4.57 (m, 1H), 2.56 (s, 3H), 1.43 (d, 3H, J=7 Hz). LCMS: m/z=461.4 [M+H]$^+$, RT=2.80 minutes, (Program P1, Column Y).

Step 11: (S)—N-(1-(1,3,4-Oxadiazol-2-yl)ethyl)-8-(5-(difluoromethyl)-1H-1,2,3-triazol-1-yl)-3-(5-methylthiophen-2-yl)imidazo[1,2-a]pyridine-6-carboxamide To a stirring solution of compound XI (0.18 g; 0.40 mmol; 1 eq) in acetic acid (16 mL) at 0° C. was added triethyl orthoformate (0.5 mL, 2.40 mmol, 6 eq) dropwise and the resulting mixture was heated at reflux for 2 h. The mixture was poured into ice-cold saturated aqueous NaHCO$_3$ solution and the organic components were extracted with ethyl acetate (3×50 mL). The combined organic layers were then washed with brine, dried over anhydrous sodium sulfate and concentrated in vacuo to obtain a dry residue which was purified by silica gel (230-400 mesh) column chromatography using 0-5% methanol/dichloromethane as the eluent to afford the title compound (0.11 g, 60%) as a solid. $^1$H NMR (DMSO-d$_6$) δ 9.50 (d, 1H, J=7 Hz), 9.20 (s, 1H), 8.46 (s, 1H), 8.25 (s, 1H), 7.91 (s, 1H), 7.45 (m, 3H), 7.05 (d, 1H, J=1 Hz), 5.48 (m, 1H), 2.56 (s, 3H), 1.64 (d, 3H, J=7 Hz). LCMS: m/z=471.0 [M+H]$^+$, RT=3.08 minutes, (Program P1, Column Y).

101

Example 15: (S)—N-(1-(4H-1,2,4-Triazol-3-yl)ethyl)-8-(4-methylpiperidin-1-yl)-3-(o-tolyl)imidazo[1,2-a]pyridine-6-carboxamide

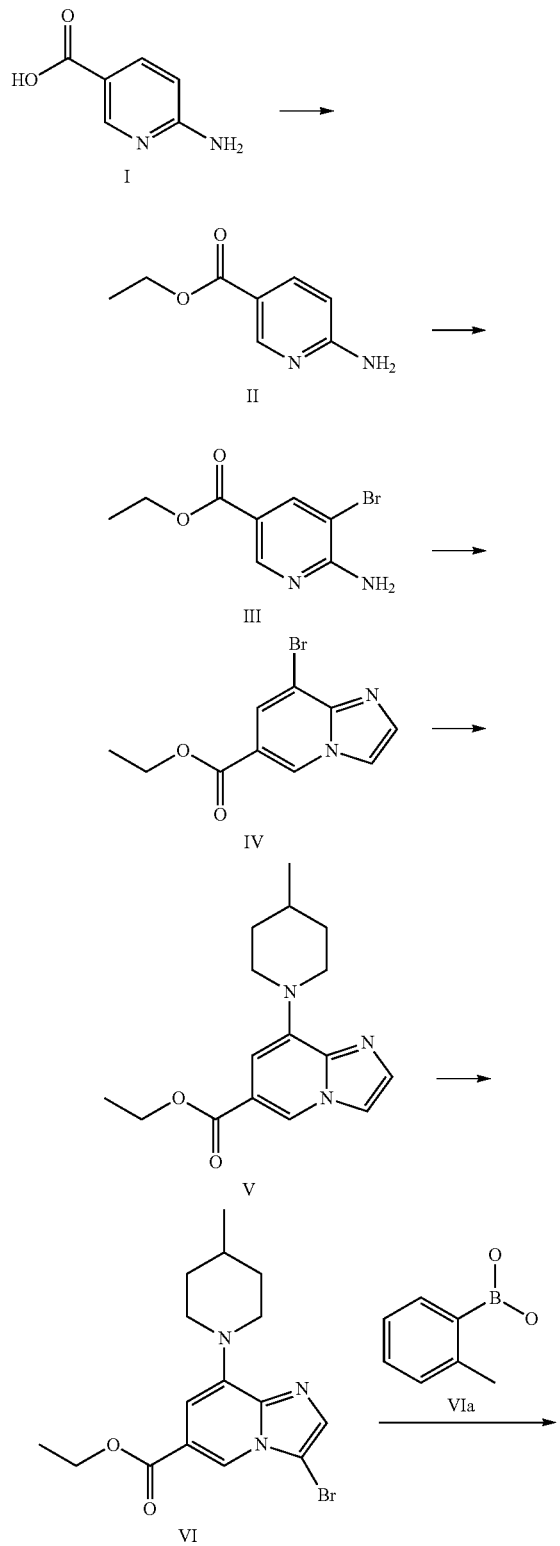

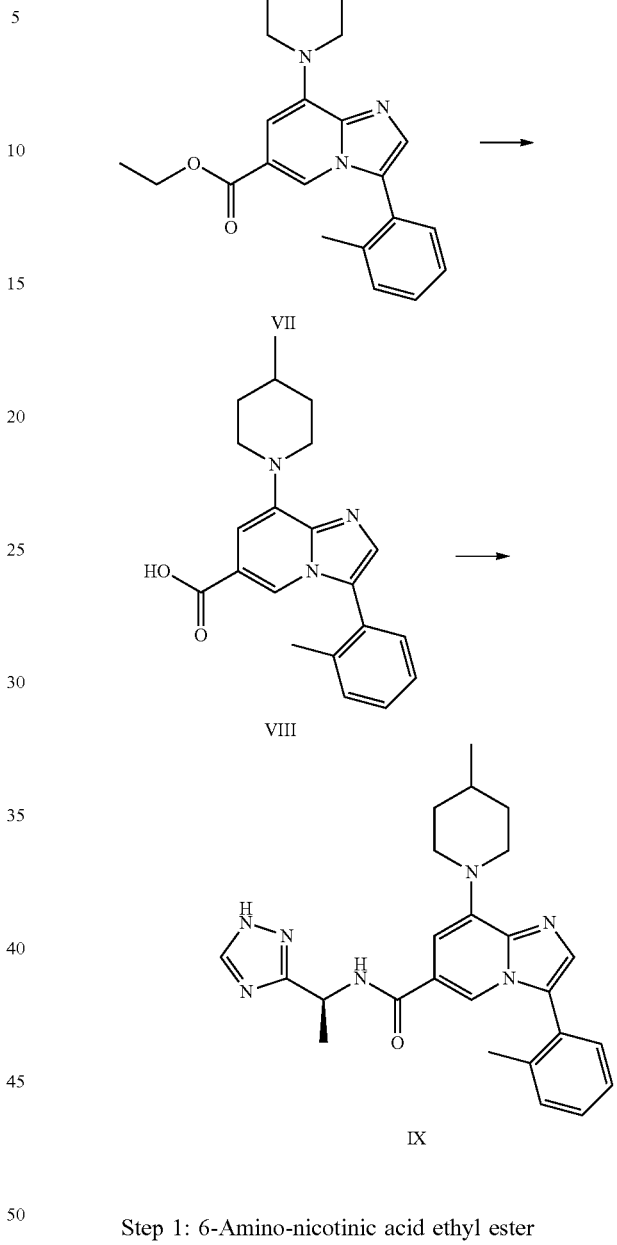

-continued

Step 1: 6-Amino-nicotinic acid ethyl ester

To a stirred solution of compound I (150 g; 1.09 mol; 1 eq) in ethanol (1.5 L) was added thionyl chloride (236 mL; 3.26 mol; 3 eq) dropwise at 60° C. and the resulting mixture was heated at reflux for 17 h. The mixture was evaporated to dryness and the pH was adjusted to 7 using ice-cold saturated aqueous $NaHCO_3$ solution and solid $NaHCO_3$. The organic components were extracted from the aqueous phase with ethyl acetate (5×1000 mL) and the combined organic layers were washed with brine, dried over anhydrous sodium sulfate, filtered and the solvent was removed in vacuo to afford the title compound (152 g, 84%) as an off-white solid. $^1$H NMR (CDCl$_3$) δ 8.71 (s, 1H), 7.99 (d, 1H, J=12 Hz), 6.45 (d, 1H, J=8 Hz), 4.95 (s, 2H), 4.31 (q, 2H, J=8 Hz); 1.35 (t, 3H, J=8 Hz). LCMS: m/z=167.3 [M+H]$^+$, RT=2.32 minutes, (Program P1, Column Y).

Step 2: 6-Amino-5-bromo-nicotinic acid ethyl ester

To a stirred solution of compound II (50 g; 301 mmol; 1 eq) in dry THF (500 mL) at 0° C. was added NBS (53.6 g; 301 mmol; 1 eq) in portions and the resulting mixture was stirred at 23° C. for 17 h. The mixture was poured into ice-cold saturated aqueous NaHCO$_3$ solution and the organic components were extracted with ethyl acetate (3×1000 mL). The combined organic layers were then washed with brine solution, dried over anhydrous sodium sulfate and evaporated to dryness to afford compound (71 g, 96%) as an off white solid. $^1$H NMR (DMSO-d$_6$) δ 8.49 (s, 1H), 8.07 (s, 1H), 7.15 (s, 2H), 4.22 (q, 2H, J=8 Hz), 1.30 (t, 3H, J=8 Hz). LCMS: m/z=245 [M+], 247 [M+2], RT=2.97 minutes, (Program P1, Column W).

Step 3: 8-Bromo-imidazo[1,2-a]pyridine-6-carboxylic acid ethyl ester

To a stirred solution of compound III (80 g; 326 mmol; 1 eq) in ethanol (1 L) were added sodium bicarbonate (54.8 g; 652 mmol; 2 eq) and aqueous chloroacetaldehyde solution (~50% aqueous solution, 212 mL; 1.63 mol; 5 eq) dropwise and the mixture was heated at reflux for 17 h. The mixture was then evaporated to dryness and the pH was adjusted to 7 using ice-cold saturated aqueous NaHCO$_3$ solution and solid NaHCO$_3$. The organic components were extracted from the aqueous phase with ethyl acetate (3×1000 mL) and the combined organic layers were washed with brine, dried over anhydrous sodium sulfate. The solvent from the organic layer was removed in vacuo to obtain a dry residue which was purified by silica gel (230-400 mesh) column chromatography using 10-50% ethyl acetate/hexanes as the eluent to afford the title compound (55 g, 63%) as a brown solid. $^1$H NMR (DMSO-d$_6$) δ 9.33 (s, 1H), 8.24 (s, 1H), 7.84 (s, 1H), 7.73 (s, 1H), 4.34 (q, 2H, J=8 Hz), 1.34 (t, 3H, J=8 Hz). LCMS: m/z=268.8 [M+], 270.8 [M+2], RT=2.90 minutes, (Program P1, Column W).

Step 4: 8-(4-Methyl-piperidin-1-yl)-imidazo[1,2-a]pyridine-6-carboxylic acid ethyl ester To a stirred 1,4-dioxane solution of compound IV (1 g; 3.71 mmol; 1 eq) in a reaction tube was added 4-methyl piperidine (0.73 g; 7.43 mmol; 2 eq) and the resulting mixture was degassed with argon for 5 min, followed by an addition of Cs$_2$CO$_3$ (1.81 g; 5.56 mmol; 1.5 eq), Pd$_2$(dba)$_3$ (0.16 g; 0.018 mmol; 0.05 eq) and xantphos (0.21 g; 0.37 mmol; 0.1 eq). The mixture was then degassed again with argon for 5 min, and the reaction tube was sealed and heated at 115° C. for 5 h. The mixture was filtered through a Celite® pad and the filtrate was washed with saturated aqueous NaHCO$_3$ solution, followed by brine. The organic layer was then collected and dried over anhydrous Na$_2$SO$_4$, filtered and evaporated to dryness to obtain a crude material. The crude product was purified by silica gel (100-200 mesh) column chromatography, eluting with 50% EtOAc/hexanes to obtain the title compound (0.25 g, 23%) as a light brown solid. $^1$H NMR (DMSO-d$_6$) δ 8.84 (s, 1H), 8.03 (s, 1H), 7.55 (s, 1H), 6.75 (s, 1H), 4.31 (m, 4H), 2.73 (q, 2H, J=8 Hz), 1.73 (d, 2H, J=12 Hz), 1.56 (m, 1H), 1.3 (m, 5H), 0.9 (t, 3H, J=4 Hz). LCMS: m/z=288 [M+H]$^+$, RT=3.56 minutes, (Program P1, Column W).

Step 5: 3-Bromo-8-(4-methyl-piperidin-1-yl)-imidazo[1,2-a]pyridine-6-carboxylic acid ethyl ester To a stirred solution of compound V (1.6 g; 5.5 mmol; 1 eq) in dry THF (30 mL) at 0° C. was added NBS (0.99 g; 5.5 mmol; 1 eq) in portions, and the resulting mixture was stirred at 0° C. for 30 min. The mixture was poured into ice-cold saturated aqueous NaHCO$_3$ solution and the organic components were extracted with ethyl acetate (3×500 mL). The combined organic layers were then washed with brine solution, dried over anhydrous sodium sulfate and evaporated to dryness to afford the title compound (1.7 g, 83%) as an off white solid. $^1$H NMR (DMSO-d$_6$) δ 8.34 (s, 1H), 7.75 (s, 1H), 6.87 (s, 1H), 4.35 (m, 4H), 2.79 (q, 2H, J=12 Hz), 1.73 (d, 2H, J=12 Hz), 1.58 (s, 1H), 1.3 (m, 5H), 0.95 (t, 3H, J=4 Hz). LCMS: m/z=366.2 [M+], 368.2 [M+2], RT=2.51 minutes, (Program P1, Column W).

Step 6: 8-(4-Methyl-piperidin-1-yl)-3-o-tolyl-imidazo[1,2-a]pyridine-6-carboxylic acid ethyl ester To a stirred solution of compound VI (0.6 g; 1.63 mmol; 1 eq) in dry toluene:ethanol (7:3, 20 mL) was added compound VIa (0.33 g; 2.45 mmol; 1.5 eq) and the resulting mixture was degassed with argon for 5 min. To the mixture was then added Pd(PPh$_3$)$_4$ (0.18 g; 0.16 mmol; 0.1 eq), the resulting mixture was degassed with argon for another 5 min, then heated at 115° C. with stirring for 4 h. The mixture was filtered through a Celite® pad and the filtrate was washed with saturated aqueous NaHCO$_3$ solution, followed by brine. The organic layer was then dried over anhydrous Na$_2$SO$_4$, filtered and evaporated to dryness to obtain a crude material. The crude product was purified by silica gel (230-400 mesh) column chromatography eluting with 50% EtOAc/hexanes to obtain the title compound (0.3 g, 55%) as light brown solid. $^1$H NMR (DMSO-d$_6$) δ 7.93 (s, 1H), 7.65 (s, 1H), 7.47 (d, 2H, J=3 Hz), 7.40 (d, 2H, J=3 Hz), 6.83 (s, 1H), 4.36 (d, 2H, J=12 Hz), 4.28 (q, 2H, J=7 Hz), 2.81 (t, 2H, J=11 Hz), 2.10 (s, 3H), 1.77 (d, 2H, J=12 Hz), 1.60 (m, 1H), 1.36 (m, 2H), 1.25 (t, 3H, J=7 Hz), 0.98 (d, 3H, J=6 Hz). LCMS: m/z=378.4 [M+H]$^+$, RT=4.11 minutes, (Program P1, Column Y).

Step 7: 8-(4-Methyl-piperidin-1-yl)-3-o-tolyl-imidazo[1,2-a]pyridine-6-carboxylic acid To a solution of compound VII (0.34 g, 0.90 mmol, 1 eq) in THF:methanol:H$_2$O (12 mL, 3:2:1) at 0° C. was added a solution of lithium hydroxide monohydrate (0.75 g, 1.80 mmol, 2 eq) in water (1 mL) and the resulting mixture was stirred at 23° C. for 3 h. The solvent was removed under reduced pressure and the residue was diluted with water and then acidified with 1N HCl to adjust the pH to 3. The precipitated solid was collected by filtration and dried in vacuo to obtain the title compound (0.28 g, 88%). $^1$H NMR (DMSO-d$_6$) δ 8.15 (s, 1H), 8.02 (s, 1H), 7.55-7.37 (m, 4H), 7.34 (s, 1H), 3.83 (d, 2H, J=11 Hz), 2.86 (t, 2H, J=11 Hz), 2.18 (s, 3H), 1.78 (d, 2H, J=12 Hz), 1.62 (m, 1H), 1.48 (m, 2H), 1.00 (d, 3H, J=6 Hz). LCMS: m/z=350.0 [M+H]$^+$, RT=2.80 minutes, (Program P1, Column Y).

Step 8: (S)—N-(1-(4H-1,2,4-Triazol-3-yl)ethyl)-8-(4-methylpiperidin-1-yl)-3-(o-tolyl)imidazo[1,2-a]pyridine-6-carboxamide To a stirred solution of compound VIII (0.05 g, 0.14 mmol, 1 eq) in CH$_2$Cl$_2$ (10 mL) were added DIPEA (0.07 mL, 0.42 mmol, 3 eq) and HATU (0.06 g, 0.18 mmol, 1.3 eq) at 0° C. and the resulting mixture was allowed to stir for 15 min. To the mixture was added (S)-1-(4H-[1,2,4]triazol-3-yl)-ethylamine hydrochloride (0.02 g, 0.17 mmol, 1.2 eq) and the resulting mixture was allowed to stir at 23° C. for another 16 h. From the mixture, solvent was removed in vacuo, the residue was diluted with EtOAc and washed with saturated aqueous sodium bicarbonate solution, aqueous ammonium chloride solution and brine. The organic layer was dried over anhydrous sodium sulfate, filtered and concentrated to dryness. The crude product was purified by silica gel (230-400 mesh) column chromatography eluting with 0-5% methanol/$CH_2Cl_2$ to obtain the title compound (0.02 g, 40%) as a brown solid. $^1$H NMR (DMSO-$d_6$) (100° C.) δ 13.78 (brs, 1H), 8.54 (s, 1H), 7.93 (s, 1H), 7.53-7.37 (s, 1H), 7.37 (m, 4H), 6.92 (s, 1H), 5.30 (m, 1H), 4.42 (d, 2H, J=12 Hz), 2.88 (t, 2H, J=11 Hz), 1.81 (s, 3H), 1.79 (d, 2H, J=12 Hz), 1.55 (m, 1H), 1.43 (d, 3H, J=12 Hz), 1.39 (m, 2H), 1.02 (d, 3H, J=5 Hz). LCMS: m/z=444.4 [M+H]$^+$, RT=3.03 minutes, (Program P1, Column V).

Example 16: 8-(5-Cyclopropyl-1H-tetrazol-1-yl)-N-((6-methylpyridin-3-yl)methyl)-3-(5-methylthiophen-2-yl)imidazo[1,2-a]pyridine-6-carboxamide

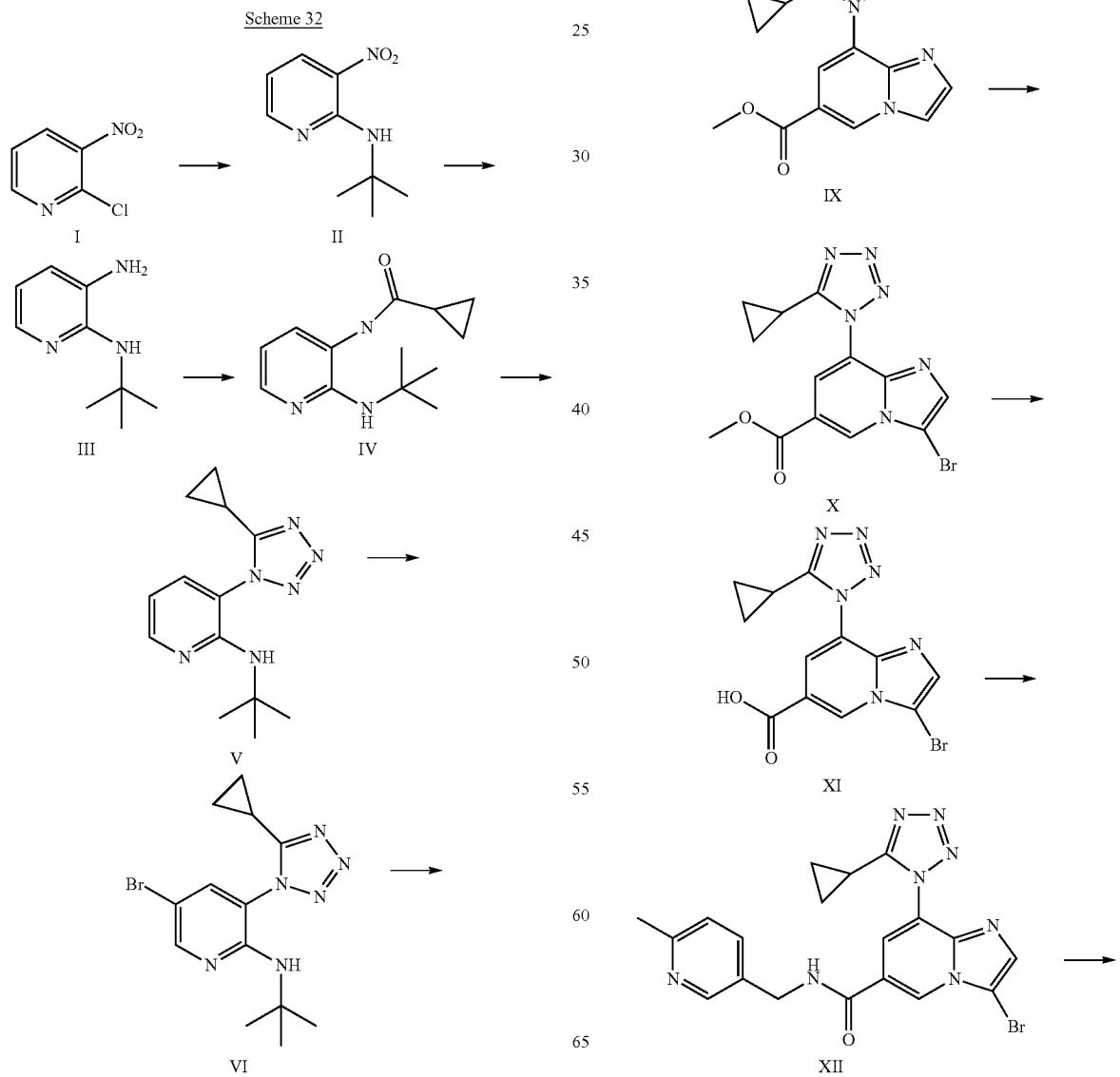

-continued

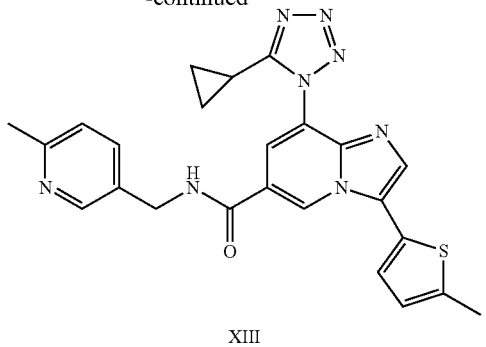

XIII

Step 1: tert-Butyl-(3-nitro-pyridin-2-yl)-amine

To a solution of compound I (20 g, 127 mmol, 1 eq) in N-methyl-2-pyrrolidine (100 mL, 1.04 mol, 8.2 eq) was added tert-butyl amine (100 mL, 950 mmol, 7.5 eq) and the resulting mixture was stirred at 60° C. for 5 h. The mixture was poured into ice-cold 1N aqueous HCl solution (500 mL) and the organic components were extracted with ethyl acetate (3×300 mL). The combined organic layers were washed with saturated aqueous sodium bicarbonate solution (400 mL) and brine (2×300 mL), dried over anhydrous sodium sulfate, filtered and concentrated under reduced pressure to provide crude compound. The crude product was purified by silica gel (100-200 mesh) column chromatography using 2% ethyl acetate/hexanes to obtain the title compound (18 g, 73%) as yellow viscous liquid. $^1$H NMR (400 MHz, DMSO-$d_6$) δ 8.48 (dd, 1H, J=1, 4 Hz), 8.41 (dd, 1H, J=2, 8 Hz), 8.20 (brs, 1H), 6.76 (dd, 1H, J=4, 8 Hz), 1.51 (s, 9H).

Step 2: 2-tert-Butylamino-3-aminopyridine

To a solution of compound II (18 g, 92.3 mmol, 1 eq) in ethanol (300 mL), degassed with argon, was added 10% Pd/C (12 g) and the resulting mixture was degassed with argon for another 15 min. The reaction vessel was attached to Parr shaker and stirred at 50 psi under hydrogen atmosphere for 16 h. The mixture was filtered through a Celite® pad and the filtrate was concentrated in vacuo to obtain the title compound (13 g, 85%) as deep brown solid. $^1$H NMR (400 MHz, DMSO-$d_6$) δ 7.36 (dd, 1H, J=1, 5 Hz), 6.65 (dd, 1H, J=2, 7 Hz), 6.29 (dd, 1H, J=5, 7 Hz), 4.80 (s, 1H), 4.66 (s, 2H), 1.41 (s, 9H). LCMS: m/z=166.4 [M+H], RT=0.79 minutes; (Program R1, Column Y).

Step 3: Cyclopropanecarboxylic acid (2-tert-butylamino-pyridin-3-yl)-amide

To a solution of compound III (7 g, 42.4 mmol, 1 eq) in THF (300 mL) at 0° C. was added DIPEA (22.2 mL, 127.2 mmol, 3 eq) dropwise and the resulting mixture was stirred for 10 min. Cyclopropane carbonyl chloride (3.9 mL, 42.4 mmol, 1 eq) was then added dropwise and the resulting mixture was stirred at 0° C. for 1.5 h. The mixture was diluted with ice-water (200 mL) and the organic components were extracted with ethyl acetate (3×100 mL). The combined organic layers were washed with brine (150 mL), dried over anhydrous sodium sulfate, filtered and concentrated under reduced pressure to provide crude compound. The crude material was purified by silica gel (100-200 mesh) column chromatography using 20% ethyl acetate/hexanes to obtain the title compound (8 g, 81%) as a brown solid. $^1$H NMR (400 MHz, DMSO-$d_6$) δ 9.50 (s, 1H), 7.85 (d, 1H, J=4 Hz), 7.46 (d, 1H, J=7 Hz), 6.50 (dd, 1H, J=5, 8 Hz), 5.22 (s, 1H), 1.89-1.76 (m, 1H), 1.42 (s, 9H), 0.85-0.75 (m, 4H). LCMS: m/z=234.2 [M+H], RT=3.09 minutes; (Program P1, Column Y).

Step 4: tert-Butyl-[3-(5-cyclopropyl-tetrazol-1-yl)-pyridin-2-yl]-amine

To a stirred solution of compound IV (8.0 g, 34.3 mmol, 1 eq) in acetonitrile (240 mL) was added sodium azide (44 g, 686 mmol, 20 eq) at 0° C. Silicon tetrachloride (12 mL, 103 mmol, 3 eq) was added to the mixture at 0° C. After the completion of the addition, the mixture was stirred at 90° C. for 9 h. The mixture was poured into ice cold water and solid NaHCO$_3$ was added in portions to adjust the pH to 8. The resulting mixture was then filtered through a Celite® plug and the filtrate was collected. The organic components were extracted with ethyl acetate (500 mL) and washed with brine (300 mL). The organic layer was dried over anhydrous sodium sulfate and concentrated in vacuo to provide crude compound. The crude material was purified by silica gel (100-200 mesh) column chromatography using 10% ethyl acetate/hexanes to obtain crude title compound (8 g) as brown sticky solid. LCMS: m/z=259.2 [M+H], RT=3.52 minutes; (Program P1, Column Y).

Step 5: [5-Bromo-3-(5-cyclopropyl-tetrazol-1-yl)-pyridin-2-yl]-tert-butyl-amine To a stirred solution of compound V (8 g, 31 mmol, 1 eq) in THF (300 mL) was added N-bromosuccinimide (5 g, 27.9 mmol, 0.9 eq) in small portions at 0° C. After completion of the addition, the mixture was stirred at 23° C. for 2 h. The mixture was then concentrated in vacuo and the residue was diluted with aqueous sodium bicarbonate solution (200 mL) to adjust the pH to 8. The organic components were extracted with ethyl acetate (2×200 mL), washed with brine (150 mL), dried over anhydrous sodium sulfate and concentrated under reduced pressure to obtain crude compound. The crude material was purified by silica gel (100-200 mesh) column chromatography using 10% ethyl acetate/hexanes to obtain compound (5.8 g, 50%) as an off-white solid. $^1$H NMR (400 MHz, DMSO-$d_6$) δ 8.36 (d, 1H, J=2 Hz), 7.90 (d, 1H, J=2 Hz), 5.89 (s, 1H), 1.82-1.76 (m, 1H), 1.37 (s, 9H), 1.14-1.06 (m, 4H). LCMS: m/z=337.5 [M+], RT=3.72 minutes; (Program P1, Column V).

Step 6: 5-Bromo-3-(5-cyclopropyl-tetrazol-1-yl)-pyridin-2-yl-amine

To a solution of compound VI (5.8 g, 17.2 mmol, 1 eq) in methanol (150 mL) was added 6 N HCl dropwise (150 mL), with stirring at 0° C. After the addition, the mixture was heated at reflux for 2 h. The mixture was concentrated in vacuo and the residue was diluted with saturated aqueous sodium bicarbonate solution to adjust the pH to 8. The organic components were extracted with 10% MeOH/CH$_2$Cl$_2$ (3×200 mL). The combined organic layers were washed with brine (200 mL), dried over anhydrous sodium sulfate and concentrated under reduced pressure to obtain the title compound (4.6 g, 95%) as an off-white solid. $^1$H NMR (400 MHz, DMSO-$d_6$) δ 8.28 (d, 1H, J=2 Hz), 7.98 (d, 1H, J=2 Hz), 6.58 (s, 2H), 1.84-1.77 (m, 1H), 1.11-1.06 (m, 4H). LCMS: m/z=281.0 [M+], 283.2 [M+2], RT=2.69 minutes; (Program P1, Column V).

Step 7:
6-Amino-5-(5-cyclopropyl-tetrazol-1-yl)-nicotinic acid methyl ester

To a solution of compound VII (4.6 g, 16.4 mmol, 1 eq) in methanol (140 mL) was added DIPEA (18.6 mL, 106.4 mmol, 6.5 eq) and the resulting mixture was degassed under argon in a Parr autoclave vessel. After 10 min, $PdCl_2$ (dppf).$CH_2Cl_2$ (1.6 g, 2 mmol, 0.12 eq) was added to the mixture and degassing with argon was continued for another 10 min. The mixture was stirred at 90° C. under 50 psi pressure of CO gas in a Parr autoclave for 16 h. The mixture was filtered through a Celite® pad and the filtrate was concentrated in vacuo to obtain crude product. The crude material was purified by silica gel (100-200 mesh) column chromatography using 5% MeOH/$CH_2Cl_2$ to obtain the title compound (3.8 g, 89%) as an off-white solid. $^1$H NMR (400 MHz, DMSO-$d_6$) δ 8.72 (d, 1H, J=2 Hz), 8.08 (d, 1H, J=2 Hz), 7.24 (brs, 2H), 3.80 (s, 3H), 1.83-1.75 (m, 1H), 1.08-1.06 (m, 4H). LCMS: m/z=261.4 [M+H], RT=2.44 minutes; (Program R1, Column Y).

Step 8: 8-(5-Cyclopropyl-tetrazol-1-yl)-imidazo[1,2-a]pyridine-6-carboxylic acid methyl ester To a stirred solution of compound VIII (3.8 g, 14.6 mmol, 1 eq) in ethanol (140 mL) were added sodium bicarbonate (12.4 g, 146 mmol, 10 eq), a 55% aqueous solution of chloroacetaldehyde (38 mL, 584 mmol, 40 eq) and the resulting mixture was heated at reflux for 16 h. The mixture was filtered through a Celite® pad and the filtrate was concentrated under reduced pressure. The residue was diluted with ice-cold water (100 mL) and the organic components were extracted with ethyl acetate (2×100 mL) and 5% MeOH/$CH_2Cl_2$ (50 mL). The combined organic layers were washed with brine (150 mL), dried over anhydrous sodium sulfate and concentrated in vacuo. The crude material was purified by silica gel (100-200 mesh) column chromatography using 10% MeOH/$CH_2Cl_2$ to obtain the title compound as brown sticky solid (7 g, impure), which was carried forward for the next step. LCMS: m/z=285.2 [M+H], RT=2.42 minutes; (Program P1, Column W)

Step 9: 3-Bromo-8-(5-cyclopropyl-tetrazol-1-yl)-imidazo[1,2-a]pyridine-6-carboxylic acid methyl ester To a stirred solution of compound IX (7 g impure) in THF (300 mL) was added N-bromosuccinimide (3.1 g, 17.3 mmol, 0.7 eq) portionwise at 0° C. After completion of the addition, the mixture was stirred at 23° C. for 1.5 h. The mixture was concentrated under reduced pressure and diluted with aqueous sodium bicarbonate adjusting the pH to 8. The organic components were extracted with ethyl acetate (2×150 mL) and the combined organic layers were washed with brine (150 mL), dried over anhydrous sodium sulfate and concentrated in vacuo to obtain crude compound. The crude material was purified by silica gel (100-200 mesh) column chromatography using 20% EtOAc/hexanes to obtain the title compound (4 g, 75%) as brownish sticky solid. $^1$H NMR (400 MHz, DMSO-$d_6$) δ 8.98 (d, 1H, J=1 Hz), 8.24 (d, 1H, J=1 Hz), 7.98 (s, 1H), 3.96 (s, 3H), 1.99-1.94 (m, 1H), 1.10-1.04 (m, 4H). LCMS: m/z=363.1 [M+], 365.0 [M+2], RT=3.33 minutes; (Program R1, Column Y).

Step 10: 3-Bromo-8-(5-cyclopropyl-tetrazol-1-yl)-imidazo[1,2-a]pyridine-6-carboxylic acid To a solution of compound X (4 g, 11 mmol, 1 eq) in THF (200 mL) was added an aqueous solution of LiOH.$H_2O$ (1.4 g, 33 mmol, 3 eq) dropwise, followed by an addition of methanol (6 mL) and the mixture was stirred at 23° C. for 2 h. The solvents were removed in vacuo and the solid residue was diluted with water (100 mL). The aqueous layer was washed with EtOAc (50 mL) and a saturated aqueous solution of citric acid was added to the aqueous phase adjusting the pH to1. The organic component was then extracted from the aqueous layer with 10% MeOH/$CH_2Cl_2$ (100 mL), dried over anhydrous sodium sulfate, filtered and concentrated under reduced pressure to obtain the title compound (3.5 g, 91%) as a deep brown solid. $^1$H NMR (400 MHz, DMSO-$d_6$) δ 13.87 (brs, 1H), 8.96 (d, 1H, J=1 Hz), 8.18 (d, 1H, J=1 Hz), 7.97 (s, 1H), 1.99-1.96 (m, 1H), 1.10-1.04 (m, 4H). LCMS: m/z=349.0 [M+], 351.0 [M+2], RT=2.77 minutes; (Program R1, Column Y).

Step 11: 3-Bromo-8-(5-cyclopropyl-tetrazol-1-yl)-imidazo[1,2-a]pyridine-6-carboxylic acid (6-methyl-pyridin-3-ylmethyl)-amide To a solution of compound XI (1 g, 2.86 mmol, 1 eq) in DMF (100 mL) were added HATU (1.41 g, 3.72 mmol, 1.3 eq) and DIPEA (4 mL) at 0° C. under argon. After 10 min, a DMF solution of C-(6-methyl-pyridin-3-yl)-methylamine (524 mg, 4.3 mmol, 1.5 eq) was added to the mixture and the resulting mixture was stirred at 23° C. for 16 h. The mixture was diluted with ice cold water (50 mL) and the organic components were extracted with ethyl acetate (2×50 mL) and 10% MeOH/$CH_2Cl_2$ (50 mL). The combined organic layers were washed with brine (100 mL), dried over anhydrous sodium sulfate, filtered and concentrated under reduced pressure to obtain crude compound. The crude product was purified by flash Combiflash™ chromatography using 100-200 mesh silica gel eluting with 9% MeOH/$CH_2Cl_2$ to obtain the title compound (660 mg, 52%) as an orange solid. $^1$H NMR (400 MHz, DMSO-$d_6$) δ 9.48 (t, 1H, J=5 Hz), 9.13 (s, 1H), 8.47 (s, 1H), 8.25 (s, 1H), 7.94 (s, 1H), 7.67 (d, 1H, J=8 Hz), 7.23 (d, 1H, J=8 Hz), 4.53 (d, 2H, J=5 Hz), 2.44 (s, 3H), 2.02-1.93 (m, 1H), 1.11-1.01 (m, 4H). LCMS: m/z=453.2 [M+], 455.0 [M+2], RT=2.13 minutes; (Program R1, Column Y)

Step 12: 8-(5-Cyclopropyl-1H-tetrazol-1-yl)-N-((6-methylpyridin-3-yl)methyl)-3-(5-methylthiophen-2-yl)imidazo[1,2-a]pyridine-6-carboxamide To a DMF (30 mL) solution of compound XII (650 mg, 1.44 mmol, 1 eq) degassed with argon in a reaction tube was added compound VIa (832 mg, 2.2 mmol, 1.5 eq) and the resulting mixture was degassed with argon for 10 min, before the addition of Pd(PPh$_3$)$_4$ (162 mg, 0.14 mmol, 0.1 eq). Degassing with argon was done for another 15 min, the reaction tube was sealed, then heated at 120° C. for 4 h. The mixture was filtered through a Celite® pad and the filtrate was concentrated under reduced pressure to provide a solid residue. The organic components were then extracted with EtOAc (2×100 mL) and 10% MeOH/$CH_2Cl_2$ (100 mL), and the combined organic layers were washed with brine (100 mL), dried over anhydrous sodium sulfate, filtered and concentrated to provide crude compound. The crude product was purified by flash Combiflash™ chromatography using 100-200 mesh silica gel eluting with 4% MeOH/$CH_2Cl_2$ to obtain the title compound (400 mg, 59%) as an off-white solid. $^1$H NMR (400 MHz, DMSO-$d_6$) δ 9.39 (m, 1H), 9.22 (s, 1H), 8.44 (s, 1H), 8.21 (s, 1H), 7.91 (s, 1H), 7.64 (d, 1H, J=8 Hz), 7.46 (d, 1H, J=3 Hz), 7.21 (d, 1H, J=8 Hz), 7.05 (d, 1H, J=3 Hz), 4.50 (d, 2H, J=6 Hz), 2.56 (s, 3H), 2.44 (s, 3H), 2.06-1.96 (m, 1H), 1.11-1.06 (m, 4H). LCMS: m/z=471.0 [M+H]$^+$, RT=6.07 minutes; (Program R1, Column Y).

Example 17: 8-(5-(Hydroxymethyl)-1H-tetrazol-1-yl)-N-((6-methylpyridin-3-yl)methyl)-3-(5-methylthiophen-2-yl)imidazo[1,2-a]pyridine-6-carboxamide
Scheme 33
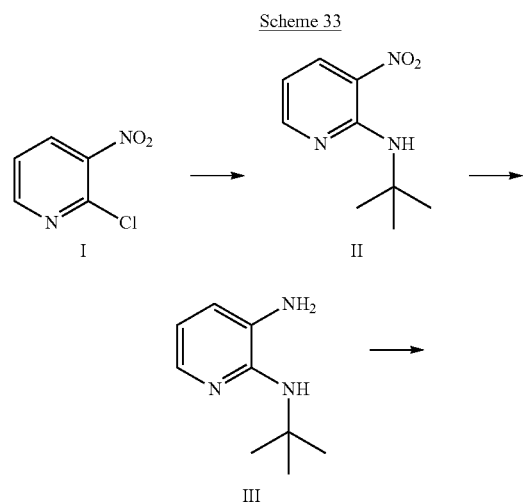
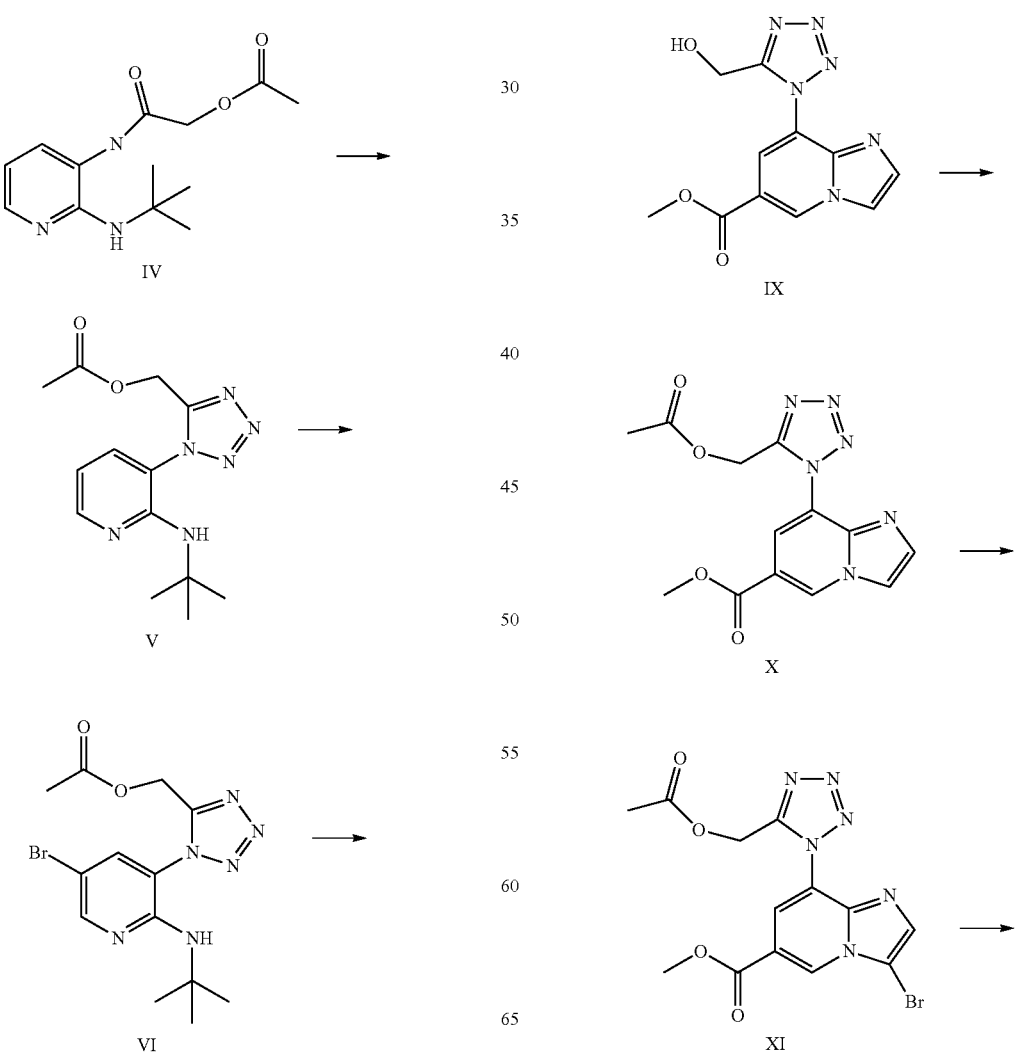

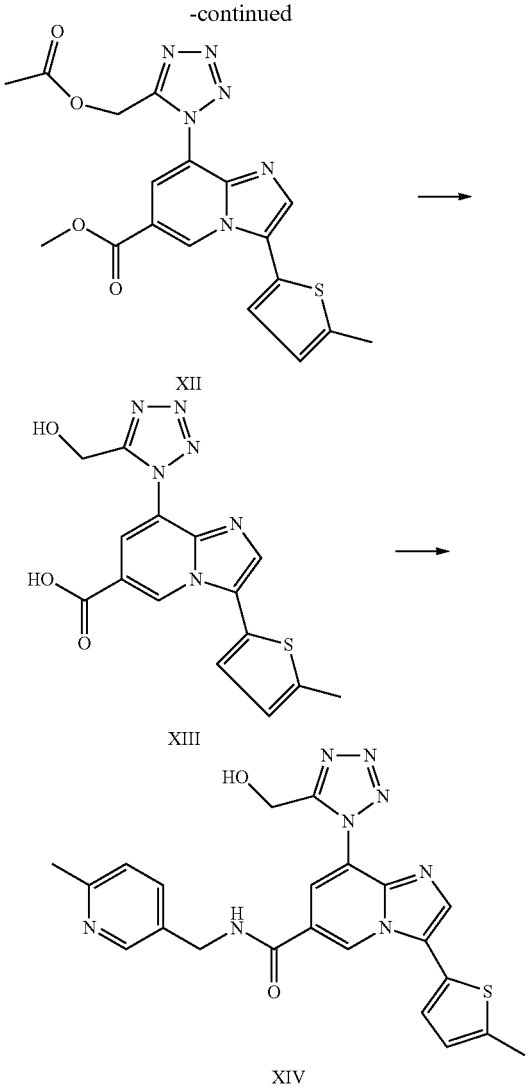

Compound III was prepared as discussed in scheme 32.

Step 1: Acetic acid (2-tert-butylamino-pyridin-3-ylcarbamoyl)-methyl ester

To a solution of compound III (3 g, 18.2 mmol, 1 eq) in CH$_2$Cl$_2$ (100 mL) was added DIPEA (9.52 mL, 54.5 mmol, 3 eq) dropwise at 0° C. and the resulting mixture was stirred for 10 min. To the mixture was then added a solution of acetoxy acetylchloride (1.95 mL, 18.2 mmol, 1 eq) in CH$_2$Cl$_2$ (5 mL) dropwise and continued stirring at 0° C. for 3 h. The mixture was diluted with ice-cold water (50 mL) and the organic components were extracted with CH$_2$Cl$_2$ (2×70 mL). The combined organic layers were washed with brine (100 mL), dried over anhydrous sodium sulfate and concentrated under reduced pressure to get crude compound. The crude material was purified by silica gel (100-200 mesh) column chromatography with 30% ethyl acetate/hexanes to obtain the title compound (3 g, 60%) as brownish solid. $^1$H NMR (400 MHz, DMSO-d$_6$) δ 9.39 (s, 1H), 7.90 (d, 1H, J=5 Hz), 7.36 (d, 1H, J=7 Hz), 6.52 (dd, 1H, J=5, 7 Hz), 5.10 (s, 1H), 4.66 (s, 2H), 2.12 (s, 3H), 1.41 (s, 9H). LCMS: m/z=266.0 [M+H], RT=1.20 minutes; (Program R1, Column Y).

Step 2: Acetic acid 1-(2-tert-butylamino-pyridin-3-yl)-1H-tetrazol-5-ylmethyl ester To a stirred solution of compound IV (3 g, 11.3 mmol, 1 eq) in acetonitrile (100 mL) were added sodium azide (7.35 g, 113 mmol, 10 eq) and silicon tetrachloride (3.9 mL, 33.9 mmol, 3 eq) at 0° C. and the resulting mixture was stirred at 90° C. for 16 h. The mixture was poured into ice cold water and solid NaHCO$_3$ was added in portions to adjust the pH to 8. The resulting mixture was filtered through a Celite® pad and the filtrate was collected. The organic components were extracted with ethyl acetate (200 mL) and washed with brine (100 mL). The organic layer was dried over anhydrous sodium sulfate, filtered and concentrated in vacuo to provide crude title compound (4 g) as an off-white sticky solid. $^1$H NMR (400 MHz, DMSO-d$_6$) δ 8.27 (dd, 1H, J=2, 5 Hz), 7.54 (dd, 1H, J=2, 8 Hz), 6.71 (dd, 1H, J=5, 8 Hz), 5.56 (s, 1H), 5.28 (s, 2H), 1.91 (s, 3H), 1.38 (s, 9H). LCMS: m/z=291.1 [M+H], RT=3.82 minutes; (Program R1, Column Y).

Step 3: Acetic acid 1-(5-bromo-2-tert-butylamino-pyridin-3-yl)-1H-tetrazol-5-ylmethyl ester To a solution of compound V (4 g, 13.8 mmol, 1 eq) in THF (100 mL) was added N-bromosuccinimide (2.2 g, 12.4 mmol, 0.9 eq) in small portions with stirring at 0° C. After completion of the addition, the mixture was stirred at 23° C. for 2 h. The mixture was concentrated in vacuo and the residue was diluted with aqueous sodium bicarbonate to adjust the pH to 8. The organic components were extracted with ethyl acetate (2×100 mL), the combined extracts were washed with brine (100 mL), dried over anhydrous sodium sulfate, filtered and concentrated under reduced pressure to obtain crude compound. The crude material was purified by silica gel (100-200 mesh) column chromatography using 20% ethyl acetate/hexanes to obtain the title compound (3.0 g, 72%, two steps) as a brown solid. $^1$H NMR (400 MHz, DMSO-d$_6$) δ 8.37 (d, 1H, J=2 Hz), 7.89 (d, 1H, J=2 Hz), 5.88 (s, 1H), 5.30 (s, 2H), 1.93 (s, 3H), 1.36 (s, 9H). LCMS: m/z=371.0 [M+2], RT=4.11 minutes; (Program R1, Column Y).

Step 4: Acetic acid 1-(2-amino-5-bromo-pyridin-3-yl)-1H-tetrazol-5-ylmethyl ester To a stirred solution of compound VI (3 g, 8.13 mmol, 1 eq) in CH$_2$Cl$_2$ (100 mL) was added trifluoroacetic acid (100 mL) dropwise at 23° C. and the resulting mixture was stirred at 23° C. for 16 h. The mixture was cooled to 0° C. and diluted with saturated aqueous sodium bicarbonate solution to adjust the pH to 8. The organic components were extracted with CH$_2$Cl$_2$ (2×70 mL) and the combined extracts were washed with brine (75 mL). The organic layer was dried over anhydrous sodium sulfate, filtered and concentrated under reduced pressure to obtain the title compound (1.7 g, 68%) as an off-white solid. $^1$H NMR (400 MHz, DMSO-d$_6$) δ 8.29 (d, 1H, J=2 Hz), 7.94 (d, 1H, J=2 Hz), 6.60 (s, 2H), 5.32 (s, 2H), 1.93 (s, 3H). LCMS: m/z=313.0 [M+], 315.2 [M+2], RT=3.09 minutes; (Program R1, Column Y).

Step 5: Acetic acid 1-(6-bromo-imidazo[1,2-a]pyridin-8-yl)-1H-tetrazol-5-ylmethyl ester To a stirred solution of compound VII (1.7 g, 5.4 mmol, 1 eq) in ethanol (100 mL) were added sodium bicarbonate (4.6 g, 54 mmol, 10 eq) and a 55% aqueous solution of chloroacetaldehyde (26 mL, 216 mmol, 40 eq), and the resulting mixture was heated at reflux for 16 h. The mixture was filtered through a Celite® pad and the filtrate was concentrated under reduced pressure. The filtrate was diluted with ice-cold water (100 mL) and the organic components were extracted with ethyl acetate (2×70 mL) and 5% MeOH/$CH_2Cl_2$ (75 mL). The combined organic layers were washed with brine (100 mL), dried over anhydrous sodium sulfate and concentrated in vacuo. The crude material was purified by silica gel (100-200 mesh) column chromatography using 10% MeOH/$CH_2Cl_2$ to obtain the title compound as a brown sticky solid (1.4 g, 75%), which was carried forward for the next step. $^1$H NMR (400 MHz, DMSO-$d_6$) δ 9.24 (d, 1H, J=1 Hz), 8.16 (s, 1H), 8.02 (d, 1H, J=2 Hz), 7.70 (s, 1H), 5.45 (s, 2H), 1.84 (s, 3H). LCMS: m/z=337.0 [M+], 339.0 [M+2], RT=2.94 minutes; (Program R1, Column Y)

Step 6: 8-(5-Hydroxymethyl-tetrazol-1-yl)-imidazo[1,2-a]pyridine-6-carboxylic acid methyl ester To a solution of compound VIII (1.4 g, 4.15 mmol, 1 eq) in MeOH (100 mL) was added DIPEA (5 mL, 27 mmol, 6.5 eq) and the resulting mixture was degassed with argon for 10 min. To the mixture was then added $PdCl_2$(dppf) and $CH_2Cl_2$ (408 mg, 0.5 mmol, 0.12 eq) and the resulting mixture was degassed with argon for another 10 min. The mixture was then stirred at 90° C. under CO atmosphere with a pressure of 50 psi in a Parr autoclave for 16 h. The mixture was filtered through a Celite® pad and the filtrate was concentrated in vacuo to obtain crude product. The crude material was purified by silica gel (100-200 mesh) column chromatography using 5% MeOH/$CH_2Cl_2$ to obtain the title compound (0.8 g, 71%) as an off-white solid. $^1$H NMR (400 MHz, DMSO-$d_6$) δ 9.62 (s, 1H), 8.34 (s, 1H), 8.04 (s, 1H), 7.94-7.85 (m, 1H), 7.77 (s, 1H), 4.82 (d, 2H, J=6 Hz), 3.93 (s, 3H). LCMS: m/z=275.4 [M+H], RT=2.44 minutes; (Program R1, Column Y).

Step 7: 8-(5-Acetoxymethyl-tetrazol-1-yl)-imidazo[1,2-a]pyridine-6-carboxylic acid methyl ester To a stirred solution of compound IX (0.8 g, 2.92 mmol, 1 eq) in $CH_2Cl_2$ (50 mL) was added TEA (0.82 mL, 5.84 mmol, 2 eq) dropwise at 0° C., and the resulting mixture was stirred for 15 min. Acetyl chloride (0.42 mL, 5.84 mmol, 2 eq) was added to the mixture and the resulting mixture was stirred at 23° C. for 2 h. The mixture was concentrated under reduced pressure and diluted with water (30 mL). The organic components were extracted with ethyl acetate (2×20 mL) and the combined extracts were washed with brine (30 mL). The organic layer was dried over anhydrous sodium sulfate, filtered and concentrated under reduced pressure to obtain the title compound (1.2 g) crude as an off-white solid. LCMS: m/z=317.2 [M+H], RT=2.76 minutes; (Program R1, Column Y)

Step 8: 8-(5-Acetoxymethyl-tetrazol-1-yl)-3-(5-methyl-thiophen-2-yl)-imidazo[1,2-a]pyridine-6-carboxylic acid methyl ester To a stirred solution of compound X (1.2 g, 3.8 mmol, 1 eq) in THF (100 mL) was added N-bromosuccinimide (0.61 g, 3.4 mmol, 0.9 eq) at 0° C. in portions and the resulting mixture was stirred at 23° C. for 1.5 h. The mixture was concentrated under reduced pressure and diluted with aqueous sodium bicarbonate adjusting the pH to 8. The organic components were extracted with ethyl acetate (2×50 mL) and the combined extracts were washed with brine (70 mL), dried over anhydrous sodium sulfate, filtered and concentrated in vacuo to obtain crude compound. The crude material was purified by silica gel (100-200 mesh) column chromatography using 20% EtOAc/hexanes to obtain the title compound (0.8 g, 69%) as greenish yellow solid. $^1$H NMR (400 MHz, DMSO-$d_6$) δ 9.00 (s, 1H), 8.26 (s, 1H), 7.99 (s, 1H), 5.41 (s, 2H), 3.97 (s, 3H), 1.87 (s, 3H). LCMS: m/z=395.1 [M+], 397.0 [M+2], RT=3.31 minutes; (Program R1, Column Y).

Step 9: 8-(5-Acetoxymethyl-tetrazol-1-yl)-3-bromo-imidazo[1,2-a]pyridine-6-carboxylic acid methyl ester To a DMF (50 mL) solution of compound XI (0.8 g, 2.02 mmol, 1 eq), degassed with argon, in a reaction tube was added compound VIa (1.17 g, 3.03 mmol, 1.5 eq) and the resulting mixture was degassed with argon for 10 min. To the mixture was added Pd(PPh$_3$)$_4$ (0.23 g, 0.2 mmol, 0.1 eq) and the resulting mixture was degassed with argon for another 15 min. The reaction tube was then sealed and heated at 120° C. for 4 h. The mixture was filtered through a Celite® pad and the filtrate was concentrated under reduced pressure to provide a solid residue. The organic components were then extracted with EtOAc (2×50 mL) and 10% MeOH/$CH_2Cl_2$ (50 mL), and the combined extracts were washed with brine (100 mL). The organic layer was dried over anhydrous sodium sulfate, filtered and concentrated to provide crude compound. The crude product was purified by flash Combiflash™ chromatography using 100-200 mesh silica gel eluting with 4% MeOH/$CH_2Cl_2$ to obtain the title compound (0.64 g, 75%) as an off-white solid. $^1$H NMR (400 MHz, DMSO-$d_6$) δ 9.17 (d, 1H, J=1 Hz), 8.20 (s, 1H), 7.97 (s, 1H), 4.45 (d, 1H, J=4 Hz), 7.06 (d, 1H, J=3 Hz), 5.44 (s, 2H), 3.94 (s, 3H), 2.57 (s, 3H), 1.89 (s, 3H). LCMS: m/z=413.0 [M+H], RT=3.73 minutes; (Program R1, Column Y).

Step 10: 8-(5-Hydroxymethyl-tetrazol-1-yl)-3-(5-methyl-thiophen-2-yl)-imidazo[1,2-a]pyridine-6-carboxylic acid To a solution of compound XII (0.64 g, 1.55 mmol, 1 eq) in THF (50 mL) was added an aqueous solution of LiOH.$H_2O$ (0.2 g, 4.66 mmol, 3 eq) dropwise followed by addition of methanol (3 mL) and the resulting mixture was stirred at 23° C. for 2 h. The solvent of the mixture was removed in vacuo and the solid residue was diluted with water (40 mL). The aqueous layer was washed with the EtOAc (30 mL) and a saturated aqueous solution of citric acid was added to the aqueous part adjusting the pH to 1. The organic component was then extracted from the aqueous layer with 10% MeOH/$CH_2Cl_2$ (100 mL), dried over anhydrous sodium sulfate, filtered and concentrated under reduced pressure to obtain the title compound (0.35 g, 63%) as brownish solid. $^1$H NMR (400 MHz, DMSO-$d_6$) δ 12.30 (brs, 1H), 9.15 (s, 1H), 8.08 (s, 1H), 7.95 (s, 1H), 7.44 (d, 1H, J=3 Hz), 7.05 (s, 1H), 5.79-5.69 (m, 1H), 4.85 (d, 2H, J=5 Hz), 2.57 (s, 3H). LCMS: m/z=357.2 [M+H], RT=3.04 minutes; (Program R1, Column W)

Step 11: 8-(5-(Hydroxymethyl)-1H-tetrazol-1-yl)-N-((6-methylpyridin-3-yl)methyl)-3-(5-methylthiophen-2-yl)imidazo[1,2-a]pyridine-6-carboxamide To a solution of compound XIII (0.35 g, 0.98 mmol, 1 eq) in DMF (30 mL) were added HATU (0.48 g, 1.27 mmol, 1.3 eq) and DIPEA (2 mL) at 0° C. under an argon atmosphere. After 10 minutes, a DMF solution of C-(6-methyl-pyridin- 3-yl)-methylamine (0.18 g, 1.47 mmol, 1.5 eq) was added and the resulting mixture was stirred at 23° C. for 16 h. The mixture was diluted with ice cold water (30 mL) and the organic components were extracted with ethyl acetate (2×50 mL) and 10% MeOH/CH$_2$Cl$_2$ (50 mL). The combined organic layers were washed with brine (80 mL), dried over anhydrous sodium sulfate, filtered and concentrated under reduced pressure to obtain crude compound. The crude product was purified by flash Combiflash™ chromatography using 100-200 mesh silica gel eluting with 9% MeOH/CH$_2$Cl$_2$ to obtain the title compound (0.25 g, 55%) as an off-white solid. $^1$H NMR (400 MHz, DMSO-d$_6$) δ 9.46-9.38 (m, 1H), 9.21 (s, 1H), 8.45 (s, 1H), 8.18 (s, 1H), 7.90 (s, 1H), 7.68-7.63 (m, 1H), 7.46 (d, 1H, J=3 Hz), 7.26-7.20 (m, 1H), 7.05 (d, 1H, J=3 Hz), 5.80-5.70 (m, 1H), 4.87 (d, 2H, J=5 Hz), 4.50 (d, 2H, J=5 Hz), 2.56 (s, 3H), 2.44 (s, 3H). LCMS: m/z=461.2 [M+H]$^+$, RT=2.30 minutes; (Program R1, Column W).

Example 18: 8-(5-(Difluoromethyl)-1H-tetrazol-1-yl)-N-((6-methylpyridin-3-yl)methyl)-3-(5-methylthiophen-2-yl)imidazo[1,2-a]pyridine-6-carboxamide

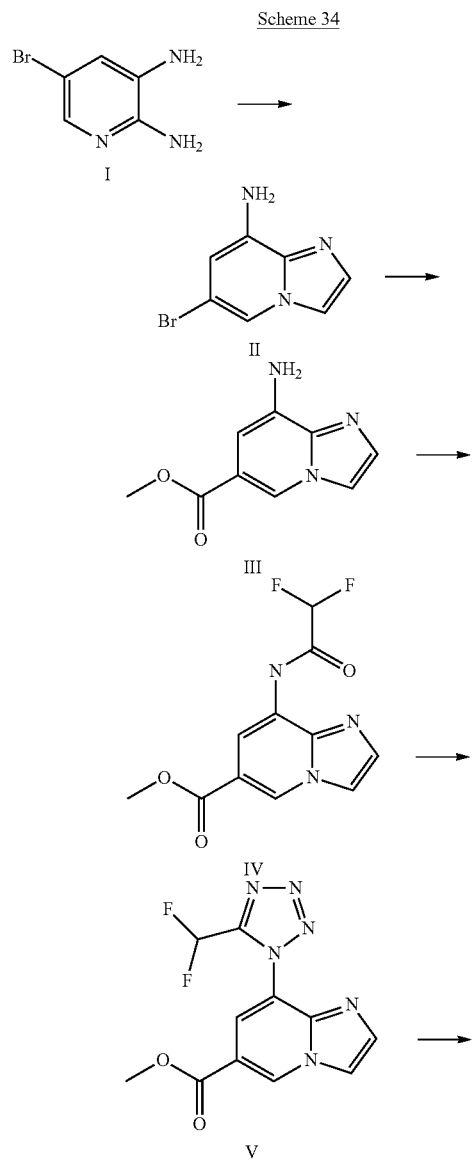

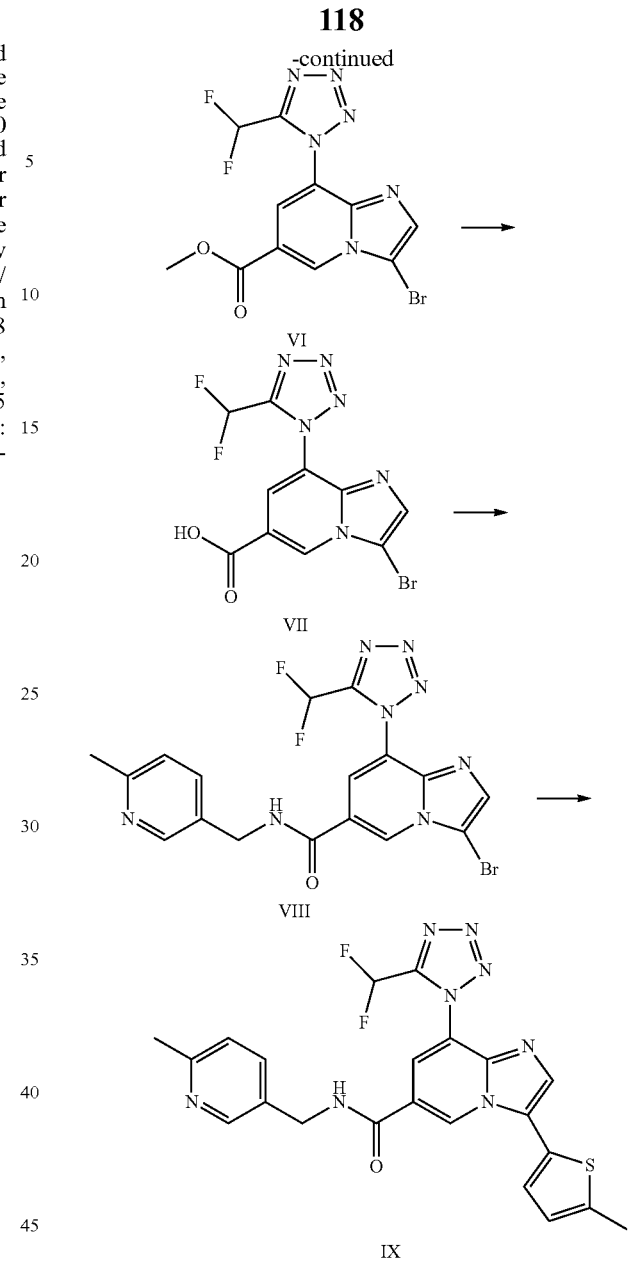

Step 1: 6-Bromo-imidazo[1,2-a]pyridin-8-ylamine

To a solution of compound I (10 g, 53 mmol, 1 eq) in ethanol (200 mL) were added sodium bicarbonate (8.92 g, 106 mmol, 2 eq) and chloroacetaldehyde (8.6 mL, 133 mmol, 2.5 eq) and the resulting mixture was stirred at 120° C. for 16 h. The mixture was filtered and the filtrate was concentrated in vacuo to obtain a solid residue. The residue was then washed with water (200 mL) and organic components were extracted with ethyl acetate (800 mL), dried over anhydrous sodium sulfate, filtered and the solvent was removed under reduced pressure to provide crude compound. The crude product was purified by flash Combiflash™ chromatography using 100-200 mesh silica gel eluting with 2% MeOH/CH$_2$Cl$_2$ to obtain the title compound (6 g, 53%) as a brown solid. $^1$H NMR (400 MHz, DMSO-d$_6$) δ 8.05 (d, 1H, J=2 Hz), 7.77 (d, 1H, J=1 Hz), 7.41 (d, 1H, J=1 Hz), 6.30 (d, 1H, J=2 Hz), 5.98 (s, 2H). LCMS: m/z=213.6 [M+2], RT=0.79 minutes; (Program R1, Column Y).

Step 2: 8-Amino-imidazo[1,2-a]pyridine-6-carboxylic acid methyl ester

To a solution of compound II (6 g, 28 mmol, 1 eq) in MeOH (100 mL) was added DIPEA (26 mL, 140 mmol, 5 eq) and the resulting mixture was degassed with argon for 10 min, then PdCl$_2$(dppf).CH$_2$Cl$_2$ (2.3 g, 2.8 mol, 0.1 eq) was added. Degassing with argon was repeated for 10 min and the reaction vessel was attached to Parr autoclave stirring at 90° C. at 50 psi under CO atmosphere for 16 h. The mixture was filtered through a Celite® pad and the filtrate was concentrated in vacuo to obtain a solid residue. The residue was then washed with water (100 mL) and the organic components were extracted with ethyl acetate (800 mL), dried over anhydrous sodium sulfate and the solvent was removed under reduced pressure to provide crude compound. The crude product was purified by flash Combiflash™ chromatography using 100-200 mesh silica gel eluting with 40% EtOAc/hexanes to obtain the title compound (3.5 g, 65%) as an off-white solid. $^1$H NMR (400 MHz, DMSO-d$_6$) δ 8.57 (d, 1H, J=1 Hz), 7.97 (s, 1H), 7.51 (s, 1H), 6.67 (d, 1H), 5.87 (s, 2H), 3.84 (s, 3H). LCMS: m/z=191.8 [M+H], RT=0.78 minutes; (Program R1, Column Y).

Step 3: 8-(2,2-Difluoro-acetylamino)-imidazo[1,2-a]pyridine-6-carboxylic acid methyl ester To a solution of compound III (4 g, 20 mmol, 1 eq), difluoroacetic acid (17.16 mL, 272 mmol, 13 eq) and TEA (8.82 mL, 62.8 mmol, 3 eq) in DMF (100 mL) was added T3P (16 mL, 26.8 mmol, 1.3 eq) dropwise under nitrogen atmosphere and the mixture was stirred at reflux for 5 h. The mixture was then diluted with water (100 mL) and the organic components were extracted with ethyl acetate (800 mL). The organic layer was washed with brine (300 mL), dried over anhydrous sodium sulfate, filtered and solvent was removed under reduced pressure to provide crude compound. The crude product was purified by flash Combiflash™ chromatography using 100-200 mesh silica gel eluting with 35% EtOAc/hexanes to obtain the title compound (3 g, 53%) as a grey solid. $^1$H NMR (400 MHz, DMSO-d$_6$) δ 11.09 (s, 1H), 9.19 (d, 1H, J=1 Hz), 8.40 (d, 1H, J=1 Hz), 8.18 (d, 1H, J=1 Hz), 7.72 (d, 1H, J=1 Hz), 6.79-6.16 (m, 1H), 3.90 (s, 3H). LCMS: m/z=269.7 [M+H], RT=2.40 minutes; (Program R1, Column W).

Step 4: 8-(5-Difluoromethyl-tetrazol-1-yl)-imidazo[1,2-a]pyridine-6-carboxylic acid methyl ester Route 1
To a solution of compound IV (3 g, 11.15 mmol, 1 eq) in acetonitrile (100 mL) was added sodium azide (29 g, 446.1 mmol, 40 eq) and the resulting mixture was cooled to 0° C. Silicon tetrachloride (13 mL, 111.5 mmol, 10 eq) was added and the resulting mixture was stirred at 90° C. for 9 h. The mixture was poured into ice cold water and solid NaHCO$_3$ was added in portions to adjust the pH to 8. The resulting mixture was then filtered through a Celite® pad and filtrate was collected. The organic components were then extracted with ethyl acetate (400 mL) after washing with water (100 mL). The organic layer was then dried over anhydrous sodium sulfate, filtered and the solvent was removed under reduced pressure to provide crude compound. The crude product was purified by flash Combiflash™ chromatography using 100-200 mesh silica gel eluting with 40% EtOAc/hexanes to obtain the title compound (1 g, 30%) as a brownish sticky solid. $^1$H NMR (400 MHz, DMSO-d$_6$) δ 9.66 (d, 1H, J=1 Hz), 8.36 (s, 1H), 8.26 (d, 1H, J=1 Hz), 7.77 (d, 1H, J=1 Hz), 7.60 (t, 1H, J=51 Hz), 3.94 (s, 3H). LCMS: m/z=295.1 [M+H], RT=3.11 minutes; (Program R1, Column Y).

Route 2

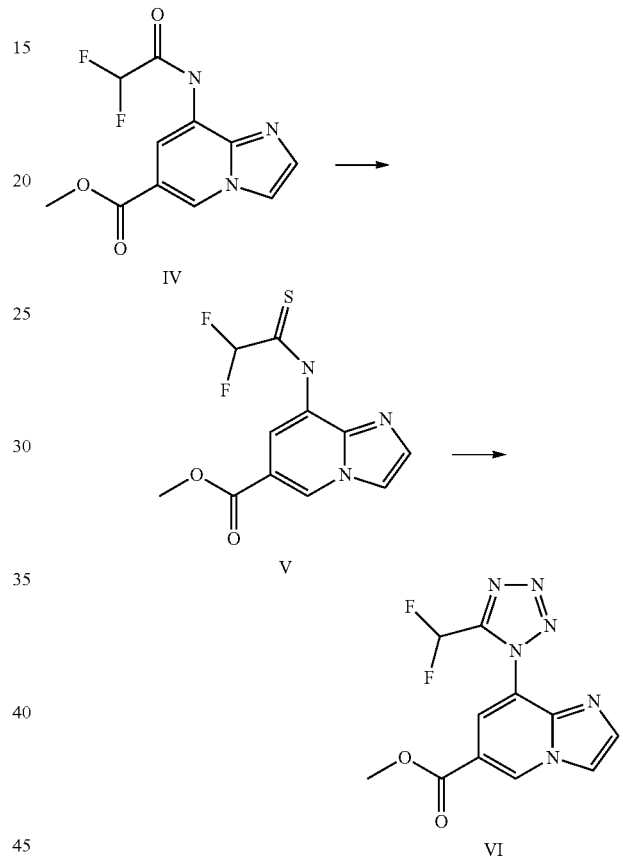

Scheme 34A 8-(2,2-Difluoro-thioacetylamino)-imidazo[1,2-a]pyridine-6-carboxylic acid methyl ester V To a solution of compound IV (26.5 g, 98.5 mmol, 1 eq) in 1,4-dioxane (1.4 L) were added hexamethyldisiloxane (84.19 mL, 394 mmol, 4 eq) and phosphorus pentasulfide (21.89 g, 98.5 mmol, 1 eq) and the mixture refluxed under stirring for 6-8 h. The mixture was cooled to room temperature, quenched with saturated aqueous sodium bicarbonate solution to adjust the pH to 8. The organic components were then extracted with ethyl acetate (2 L), after washing with water (1 L). The organic layer was then dried over anhydrous sodium sulfate and solvent was removed under reduced pressure to get crude compound. The crude was washed with ethanol to afford compound V (21 g, 75%) as brown solid. $^1$H NMR (400 MHz, DMSO-d$_6$) δ 9.31 (s, 1H), 8.57 (s, 1H), 8.21 (s, 1H), 7.73 (t, J=95 Hz, 1H), 6.67 (m, 1H), 5.87 (m, 1H), 3.90 (s, 3H); LCMS: m/z=286.0 [M+H], RT=2.58 minutes; (Program P1, Column Y).

8-(5-Difluoromethyl-tetrazol-1-yl)-imidazo[1,2-a]pyridine-6-carboxylic acid methyl ester VI To a solution of compound V (21 g, 73.6 mmol, 1 eq) in THF (300 mL) at 0° C., were added mercury (II) acetate (46.96 g, 147 mmol, 2 eq) and trimethylsilylazide (24.3 mL, 184 mmol, 2.5 eq) and the mixture was stirred at 0° C. for 1 h. The mixture was quenched with saturated aqueous ammonium chloride solution, filtered and the filtrate was collected. The organic components of the filtrate were then extracted with ethyl acetate (1 L) after washing with water (1 L). The organic layer was then dried over anhydrous sodium sulfate and solvent was removed under reduced pressure to get crude compound. The crude compound was washed with ethanol to afford compound V (21 g, 97%) as off white solid. $^1$H NMR (400 MHz, DMSO-$d_6$) δ 9.66 (s, 1H), 8.35 (s, 1H), 8.26 (s, 1H), 7.77 (s, 1H), 7.60 (t, J=52 Hz, 1H), 3.93 (s, 3H); LCMS: m/z=295.1 [M+H], RT=2.77 minutes; (Program P1, Column V).

Step 5: 3-Bromo-8-(5-difluoromethyl-tetrazol-1-yl)-imidazo[1,2-a]pyridine-6-carboxylic acid methyl ester To a solution of compound V (1 g, 3.4 mmol, 1 eq) in THF (100 mL) was added N-bromosuccinamide (0.6 g, 3.4 mmol, 1 eq) and the resulting mixture was stirred at 23° C. for 3 h. The volatiles of the mixture were removed under reduced pressure and the residue was diluted with aqueous sodium bicarbonate to adjust the pH to 8. The organic components were extracted with ethyl acetate (150 mL) after washing with water (50 mL). The organic layer was dried over anhydrous sodium sulfate, filtered and the solvent was removed under reduced pressure to provide the crude compound. The crude product was purified by flash Combiflash™ chromatography using 100-200 mesh silica gel eluting with 30% EtOAc/hexanes to obtain the title compound (0.8 g, 63%) as a brown solid. $^1$H NMR (400 MHz, DMSO-$d_6$) δ 9.01 (d, 1H, J=1 Hz), 8.40 (d, 1H, J=1 Hz), 7.99 (s, 1H), 7.56 (t, 1H, J=51 Hz), 3.97 (s, 3H). LCMS: m/z=372.9 [M+], 375.0 [M+2], RT=3.52 minutes; (Program R1, Column Y).

Step 6: 3-Bromo-8-(5-difluoromethyl-tetrazol-1-yl)-imidazo[1,2-a]pyridine-6-carboxylic acid methyl ester To a solution of compound VI (0.8 g, 2.14 mmol, 1 eq) in THF (50 mL) and MeOH (4 mL) was added an aqueous solution of LiOH, H$_2$O (0.27 g, 6.42 mmol, 3 eq) and the resulting mixture was stirred at 23° C. for 1 h. The solvent of the mixture was removed in vacuo and the solid residue was diluted with water (50 mL). The residue was washed with EtOAc (30 mL) and the aqueous layer was acidified with citric acid adjusting the pH to 1. The organic components were then extracted with 10% MeOH/CH$_2$Cl$_2$ (100 mL), dried over anhydrous sodium sulfate, filtered and concentrated under reduced pressure to provide the title compound (0.5 g, 66%) as a brown solid. $^1$H NMR (400 MHz, DMSO-$d_6$) δ 9.95 (s, 1H), 8.98 (d, 1H, J=1 Hz), 8.35 (d, 1H, J=1 Hz), 7.97 (s, 1H), 7.56 (t, 1H, J=47 Hz). LCMS: m/z=359.0 [M+], 361.1 [M+2], RT=3.03 minutes; (Program R1, Column Y).

Step 7: 3-Bromo-8-(5-difluoromethyl-tetrazol-1-yl)-imidazo[1,2-a]pyridine-6-carboxylic acid (6-methyl-pyridin-3-ylmethyl)-amide To a solution of compound VII (0.5 g, 1.39 mmol, 1 eq) in DMF (50 mL) were added HATU (0.7 g, 1.8 mmol, 1.3 eq) and DIPEA (0.74 mL, 4.17 mmol, 3 eq) under argon atmosphere at 0° C. A DMF solution of C-(6-methyl-pyridin-3-yl)-methylamine (0.25 g, 2.09 mmol, 1.5 eq) was added and the resulting mixture was stirred at 23° C. for 16 h. The mixture was diluted with ice water (40 mL) and the organic components were extracted with EtOAc (2×50 mL) and 10% MeOH/CH$_2$Cl$_2$ (50 mL), and the combined extracts were washed with brine (50 mL). The organic layer was dried over anhydrous sodium sulfate, filtered and concentrated under reduced pressure to provide the crude compound. The crude product was purified by flash Combiflash chromatography using 100-200 mesh silica gel eluting with 5% MeOH/CH$_2$Cl$_2$ to obtain compound (0.4 g, 62%) as an orange solid. $^1$H NMR (400 MHz, DMSO-$d_6$) δ 9.53 (t, 1H, J=6 Hz), 9.18 (s, 1H), 8.47 (s, 1H), 8.37 (s, 1H), 7.94 (s, 1H), 7.70-7.44 (m, 2H), 7.23 (d, 1H, J=8 Hz), 4.53 (d, 2H, J=5 Hz), 2.45 (s, 3H). LCMS: m/z=463.0 [M+], 465.0 [M+2], RT=1.94 minutes; (Program R1, Column W).

Step 8: 8-(5-(Difluoromethyl)-1H-tetrazol-1-yl)-N-((6-methylpyridin-3-yl)methyl)-3-(5-methylthiophen-2-yl)imidazo[1,2-a]pyridine-6-carboxamide To a DMF (20 mL) solution of compound VIII (0.4 g, 0.86 mmol, 1 eq), degassed with argon, in a reaction tube was added compound VIa (0.50 g, 1.29 mmol, 1.5 eq) and the resulting mixture was degassed with argon for 10 min, followed by the addition of Pd(PPh$_3$)$_4$ (0.1 g, 0.086 mmol, 0.1 eq). Further degassing with argon was done for another 15 min and the reaction tube was sealed then heated at 120° C. for 5 h. The mixture was filtered through a Celite® pad and the filtrate was concentrated under reduced pressure to provide a solid residue. The organic components were then extracted with EtOAc (2×40 mL) and 10% MeOH/CH$_2$Cl$_2$ (50 mL) and the combined extracts were washed with brine (50 mL). The organic layer was dried over anhydrous sodium sulfate, filtered and concentrated to provide crude compound. The crude product was purified by flash Combiflash™ chromatography using 100-200 mesh silica gel eluting with 4% MeOH/CH$_2$Cl$_2$ to obtain the title compound (0.18 g, 44%) as an off-white solid. $^1$H NMR (400 MHz, DMSO-$d_6$) δ 9.45-9.36 (m, 1H), 9.21 (s, 1H), 8.42 (s, 1H), 8.30 (s, 1H), 7.88 (s, 1H), 7.73-7.46 (m, 3H), 7.19 (d, 1H, J=8 Hz), 7.03 (s, 1H), 4.48 (d, 2H, J=5 Hz), 2.53 (s, 3H), 2.41 (s, 3H). LCMS: m/z=481.0 [M+H]$^+$, RT=2.80 minutes; (Program R1, Column W).

Example 19: (R)-8-(5-(Difluoromethyl)-1H-tetrazol-1-yl)-N-(1-(3-methyl-1,2,4-oxadiazol-5-yl)ethyl)-3-(5-methylthiophen-2-yl)imidazo[1,2-a]pyridine-6-carboxamide Scheme 35

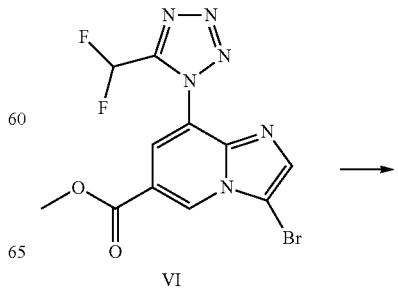

VI

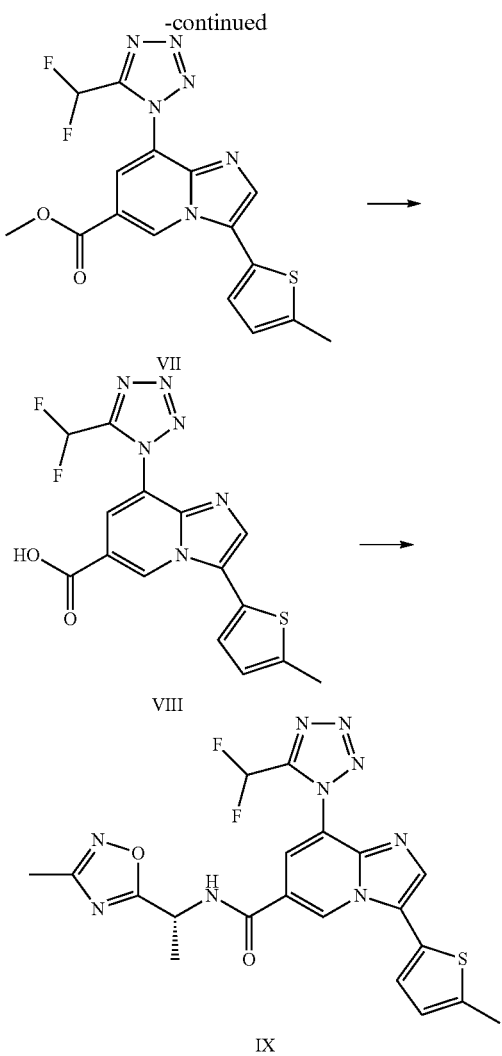

Following the experimental procedure described for Example 18, compound VI was prepared.

Step 6: 8-(5-Difluoromethyl-tetrazol-1-yl)-3-(5-methyl-thiophen-2-yl)-imidazo[1,2-a]pyridine-6-carboxylic acid methyl ester To a toluene-DMF (10:1, 170 mL) solution of compound VI (1.8 g, 4.82 mmol, 1 eq), degassed with argon, was added compound VIa (2.80 g, 7.23 mmol, 1.5 eq) and the resulting mixture was degassed with argon for 10 minutes before the addition of Pd(PPh$_3$)$_4$ (0.55 g, 0.48 mmol, 0.1 eq). Further degassing with argon was done for another 15 min and the resulting mixture was at 120° C. and stirred for 30 min. As the TLC showed the presence of starting material, heating was continued with constant TLC monitoring at 15 minute intervals. After 1 h, as the starting material was found to be consumed completely, the mixture was allowed to cool to room temperature and filtered through a Celite® pad. The filtrate was concentrated under reduced pressure to provide a solid residue from which the organic components were extracted with EtOAc (2×100 mL). The combined organic layers were washed with brine (100 mL), dried over anhydrous sodium sulfate and concentrated to provide a crude solid compound. The crude solid material was washed with 20% EtOAc/hexane (2×50 mL), followed by pentane (2×50 mL) and the residue was dried in vacuo to obtain pure product. The combined organic washes were purified by flash Combiflash™ chromatography using 100-200 mesh silica gel eluting with 20% EtOAc/hexanes to obtain pure product which was combined with the solid residue to provide the title compound (1.4 g, 74%) as a yellow solid. $^1$H NMR (400 MHz, DMSO-d$_6$) δ 9.18 (s, 1H), 8.35 (s, 1H), 7.96 (s, 1H), 7.61 (t, 1H, J=51 Hz), 7.46 (d, 1H, J=3 Hz), 7.06 (d, 1H, J=3 Hz), 3.94 (s, 3H), 2.57 (s, 3H). LCMS: m/z=391.1 [M+H], RT=3.46 minutes; (Program P1, Column V)

Step 7: 8-(5-Difluoromethyl-tetrazol-1-yl)-3-(5-methyl-thiophen-2-yl)-imidazo[1,2-a]pyridine-6-carboxylic acid To a solution of compound VII (0.6 g, 1.54 mmol, 1 eq) in THF (60 mL) was added saturated aqueous solution of LiOH.H$_2$O (0.19 g, 4.61 mmol, 3 eq) and the resulting mixture was stirred at 10° C. for 10 min. To the mixture was then added MeOH (2 mL) to make the mixture a homogeneous solution and stirring was continued at 23° C. for another 2 h. The solvent of the mixture was removed in vacuo and the solid residue was diluted with water and washed with EtOAc. The aqueous layer was acidified with citric acid adjusting the pH to 1 and the organic components were extracted with 20% MeOH/CH$_2$Cl$_2$ (2×30 mL). The combined organic layers were then washed with brine, dried over anhydrous sodium sulfate, filtered and concentrated under reduced pressure to provide the title compound (0.45 g, 78%) as a brownish solid. $^1$H NMR (400 MHz, DMSO-d$_6$) δ 13.88 (brs, 1H), 9.18 (s, 1H), 8.30 (s, 1H), 7.95 (s, 1H), 7.61 (t, 1H, J=51 Hz), 7.45 (d, 1H, J=3 Hz), 7.05 (d, 1H, J=3 Hz), 2.57 (s, 3H). LCMS: m/z=376.9 [M+H], RT=2.52 minutes; (Program P1, Column V)

Step 8: (R)-8-(5-(Difluoromethyl)-1H-tetrazol-1-yl)-N-(1-(3-methyl-1,2,4-oxadiazol-5-yl)ethyl)-3-(5-methylthiophen-2-yl)imidazo[1,2-a]pyridine-6-carboxamide To a stirred solution of compound VIII (0.15 g, 0.4 mmol, 1 eq) in DMF (10 mL) were added HATU (0.2 g, 0.52 mmol, 1.3 eq) and DIPEA (0.7 mL) under argon atmosphere at 0° C. and after 10 minutes 1-(3-methyl-[1,2,4]oxadiazol-5-yl)-ethylamine (0.76 g, 0.6 mmol, 1.5 eq) was added and the resulting mixture was stirred at 23° C. for 16 h. The mixture was diluted with ice water and the organic components were extracted with EtOAc and 10% MeOH/CH$_2$Cl$_2$, then washed with brine. The organic layer was dried over anhydrous sodium sulfate, filtered and concentrated under reduced pressure to give crude compound which was purified by flash Combiflash™ chromatography using 100-200 mesh silica gel eluting with 5% MeOH/CH$_2$Cl$_2$ to obtain the title compound as an off white solid. The racemic compound was resolved by purification with chiral HPLC to obtain the pure (R)-enantiomer (0.10 g, 5.2%) as a yellowish solid. $^1$H NMR (400 MHz, DMSO-d$_6$) δ 9.60 (d, 1H, J=7 Hz), 9.25 (s, 1H), 8.36 (s, 1H), 7.92 (s, 1H), 7.63 (t, 1H, J=51 Hz), 7.49 (d, 1H, J=3 Hz), 7.07 (m, 1H), 5.46-5.33 (m, 1H), 2.56 (s, 3H), 2.33 (s, 3H), 1.62 (d, 3H, J=7 Hz). LCMS: m/z=486.3 [M+H]+, RT=3.31 minutes; (Program P1, Column V).

125

Example 20: (S)—N-(1-(4H-1,2,4-Triazol-3-yl)ethyl)-8-(N-methylisobutyramido)-3-(5-methylthiophen-2-yl)imidazo[1,2-a]pyridine-6-carboxamide Scheme 36

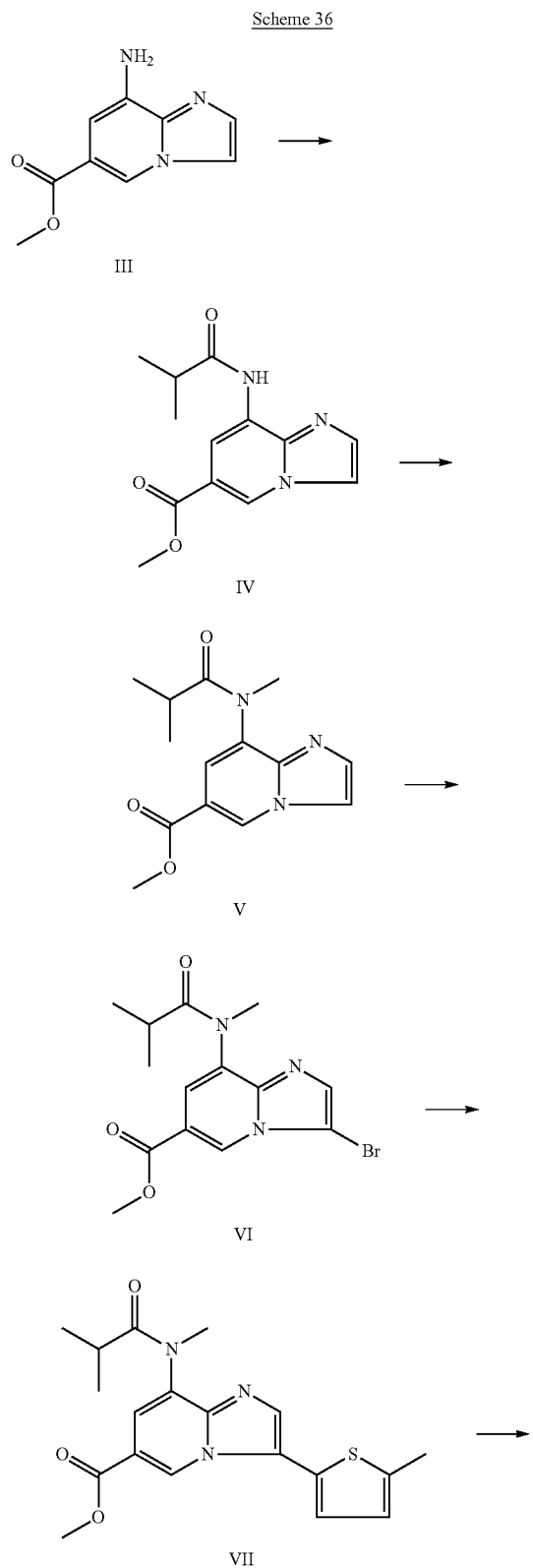

126

-continued

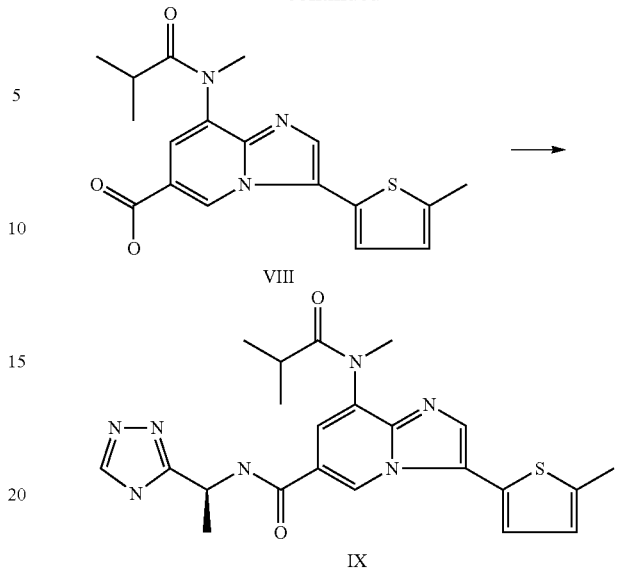

Following the experimental procedure described for Example 2, compound III was prepared.

Step 3: 8-Isobutyrylamino-imidazo[1,2-a]pyridine-6-carboxylic acid methyl ester

To a solution of compound III (2 g, 10.47 mmol, 1 eq) in dry THF (50 mL) was added pyridine (1.6 mL, 20.94 mmol, 2 eq) and isobutyryl chloride (2.2 mL, 20.94 mmol, 2 eq) and the resulting mixture was stirred at 0° C. under an argon atmosphere for 1 h. The mixture was quenched with water (100 mL) and the organic components were extracted with ethyl acetate (2×200 mL). The combined organic layers were washed with brine (100 mL), dried over anhydrous sodium sulfate, filtered and the filtrate was concentrated under reduced pressure to provide crude compound. The crude product was purified by Combiflash™ chromatography eluting with 35% EtOAc/hexanes to obtain the title compound (1 g, 37%) as a grey solid. $^1$H NMR (DMSO-$d_6$) δ 9.97 (s, 1H), 9.06 (s, 1H), 8.45 (s, 1H), 8.13 (s, 1H), 7.66 (s, 1H), 3.88 (s, 3H), 3.02 (m, 1H), 1.11 (d, 6H, J=7 Hz). LCMS: m/z=261.9 [M+H]$^+$, RT=2.90 minutes, (Program P1, Column Y).

Step 4: 8-(Isobutyryl-methyl-amino)-imidazo[1,2-a]pyridine-6-carboxylic acid methyl ester To a stirred solution of compound IV (1 g; 3.83 mmol; 1 eq) in dry DMF (10 mL) was added sodium hydride (60% in mineral oil, 0.13 g; 5.74 mmol; 1.5 eq) in portions at 0° C. and the resulting mixture was stirred for 5 min at 0° C. To the mixture was added methyl iodide (0.47 mL; 7.66 mmol; 2 eq) and stirring was continued at 0° C. for 2 h. The temperature of the mixture was then slowly raised to 23° C. and the mixture was stirred for another 2 h. The mixture was quenched with water (100 mL) and the organic components were extracted with ethyl acetate (2×200 mL). The combined organic layers were washed with brine (100 mL), dried over anhydrous sodium sulfate, filtered and the solvent was removed under reduced pressure to provide crude compound (0.8 g, 76%) as a solid. The crude product was directly used in the next step without further purification. $^1$H NMR (DMSO-$d_6$) δ 9.37 (s, 1H), 8.20 (s, 1H), 7.71 (s, 1H), 7.62 (s, 1H), 3.90 (s, 3H), 3.21 (s, 3H), 2.30 (m, 1H), 0.90 (m, 6H). LCMS: m/z=276.2 [M+], RT=2.40 minutes, (Program P1, Column V).

Step 5: 3-Bromo-8-(isobutyryl-methyl-amino)-imidazo[1,2-a]pyridine-6-carboxylic acid methyl ester To a stirred solution of compound V (0.8 g, 2.9 mmol, 1 eq) in THF (20 mL) was added N-bromosuccinamide (0.51 g, 2.9 mmol, 1 eq) at 0° C. and the resulting mixture was stirred for 30 min. The mixture was quenched with water (100 mL) and the organic components were extracted with ethyl acetate (2×200 mL). The combined organic layers were washed with brine (100 mL), dried over anhydrous sodium sulfate, filtered and solvents were removed under reduced pressure to provide crude compound. The crude product was purified by flash chromatography using 100-200 mesh silica gel eluting with 30% EtOAc/hexanes to obtain the title compound (1 g, 98%) as a brown solid. $^1$H NMR (DMSO-$d_6$) δ 8.77 (s, 1H), 7.91 (s, 1H), 7.77 (s, 1H), 3.93 (s, 3H), 3.21 (s, 3H), 2.38 (m, 1H), 090 (m, 6H). LCMS: m/z=354.0 [M+], 356.0 [M+2], RT=2.86 minutes; (Program P1, Column V).

Step 6: 8-(Isobutyryl-methyl-amino)-3-(5-methyl-thiophen-2-yl)-imidazo[1,2-a]pyridine-6-carboxylic acid methyl ester To a stirred, dry DMF solution of compound VI (1 g; 2.82 mmol; 1 eq) in a reaction tube was added compound VIa (1.6 g; 4.23 mmol; 1.5 eq) and the resulting mixture was degassed with argon for 5 min. To the mixture was added Pd(PPh$_3$)$_4$ (0.32 g; 0.28 mmol; 0.1 eq) and degassing with argon was repeated for about 5 min, then the reaction tube was sealed and heated at 140° C. for 2 h. The mixture was cooled to room temperature, quenched with water (100 mL) and the organic components were extracted with ethyl acetate (2×200 mL). The combined organic layers were washed with water (200 mL), brine and dried over anhydrous Na$_2$SO$_4$, then filtered. The filtrate was evaporated under vacuum to obtain a crude material which was purified by silica gel (230-400 mesh) column chromatography eluting with 10-50% ethyl acetate/hexane to obtain the title compound (0.95 g, 91%) as an off white solid. $^1$H NMR (DMSO-$d_6$) δ 8.98 (s, 1H), 7.89 (s, 1H), 7.72 (s, 1H), 7.38 (d, 1H, J=3 Hz), 7.03 (d, 1H, J=3 Hz), 3.90 (s, 3H), 3.23 (s, 3H), 2.55 (s, 3H), 2.50 (m, 1H), 0.93 (m, 6H). LCMS: m/z=372.4 [M+], RT=3.24 minutes, (Program P1, Column V).

Step 7: 8-(Isobutyryl-methyl-amino)-3-(5-methyl-thiophen-2-yl)-imidazo[1,2-a]pyridine-6-carboxylic acid To a solution of compound VII (0.95 g, 2.56 mmol, 1 eq) in THF:methanol:H$_2$O (40 mL, 5:1:1) at 23° C. was added a solution of lithium hydroxide monohydrate (0.16 g, 3.84 mmol, 1.5 eq) in water (5 mL) and the resulting mixture was stirred at 23° C. for 1 h. The organic solvent was removed under reduced pressure and the residue was diluted with water and acidified with 6N HCl to adjust the pH to about 5-6. The precipitated solid was collected by filtration and the solid was dried under vacuum to afford the title compound (0.8 g, 82%) as an off white solid. $^1$H NMR (DMSO-$d_6$) δ 13.5 (brs, 1H), 8.97 (s, 1H), 7.88 (s, 1H), 7.69 (s, 1H), 7.37 (d, 1H, J=4 Hz), 7.02 (s, 1H), 3.23 (s, 3H), 2.55 (s, 3H), 2.50 (m, 1H), 0.93 (m, 6H). LCMS: m/z=358.0 [M+], RT=2.35 minutes, (Program P1, Column Y).

Step 8: (S)—N-(1-(4H-1,2,4-Triazol-3-yl)ethyl)-8-(N-methylisobutyramido)-3-(5-methylthiophen-2-yl)imidazo[1,2-a]pyridine-6-carboxamide To a stirred solution of compound VIII (0.18 g, 0.50 mmol, 1 eq) in DMF (2 mL) were added TEA (0.21 mL, 1.51 mmol, 3 eq), a DMF (2 mL) solution of (S)-1-(4H-[1,2,4] triazol-3-yl)-ethylamine hydrochloride (0.09 g, 0.60 mmol, 1.2 eq) and T3P (0.23 mL, 0.75 mmol, 1.5 eq) at 23° C. and the resulting mixture was stirred at 120° C. for 2 h. The mixture was cooled to room temperature and quenched with water. The organic components were extracted with ethyl acetate (2×100 mL) and the combined extracts were washed with brine. The organic layer was dried over anhydrous sodium sulfate, filtered and concentrated to dryness to provide crude material which was purified by silica gel (100-200 mesh) column chromatography eluting with 0-5% methanol/CH$_2$Cl$_2$ to obtain the title compound (0.12 g, 53%) as an off white solid. $^1$H NMR (DMSO-$d_6$) δ 13.85 (brs, 1H), 9.13 (brs, 1H), 9.01 (s, 1H), 8.48 (s, 1H), 7.84 (m, 2H), 7.40 (m, 1H), 7.02 (s, 1H), 5.32 (m, 1H), 3.17 (s, 3H), 2.54 (s, 3H), 2.43 (m, 1H), 1.55 (m, 3H), 0.95 (m, 6H). LCMS: m/z=452.3 [M+], RT=2.61 minutes, (Program P1, Column V).

TABLE 1

| Ex. No. | Structure | LCMS | Prepared by method of Example No. |
|---|---|---|---|
| 1 | 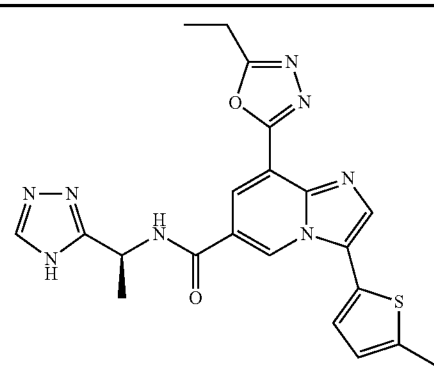 | 449.2 [M + H]$^+$ | 1 |

TABLE 1-continued
| Ex. No. | Structure | LCMS | Prepared by method of Example No. |
|---|---|---|---|
| 2 | 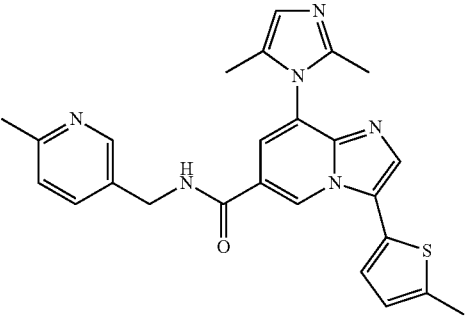 | 457.2 [M + H]⁺ | 2 |
| 3 | 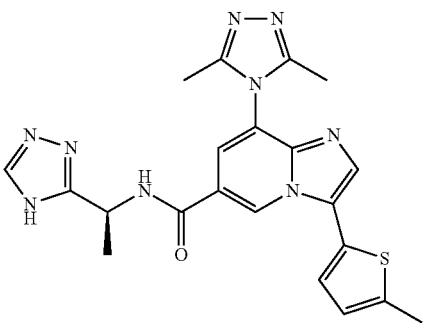 [SMILES: Cc1ccc(-c2cnc3c(-n4c(C)nnc4C)cc(C(=O)N[C@@H](C)c4nnc[nH]4)cn23)s1] | 448.2 [M + H]⁺ | 3 |
| 4 | 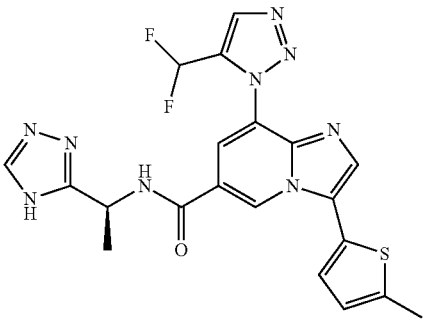 [SMILES: Cc1ccc(-c2cnc3c(-n4nncc4C(F)F)cc(C(=O)N[C@@H](C)c4nnc[nH]4)cn23)s1] | 470.2 [M + H]⁺ | 4 |
| 5 | 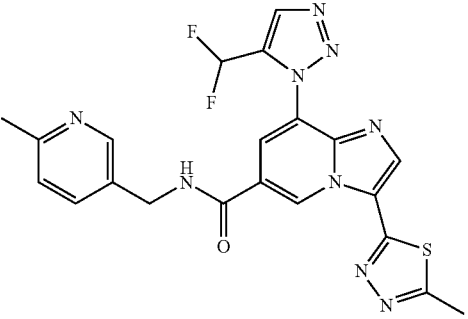 | 482.2 [M + H]⁺ | 5 |

TABLE 1-continued
| Ex. No. | Structure | LCMS | Prepared by method of Example No. |
|---|---|---|---|
| 6 | 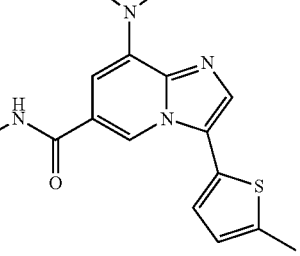 | 457.0 [M + H]+ | 6 |
| 7 | 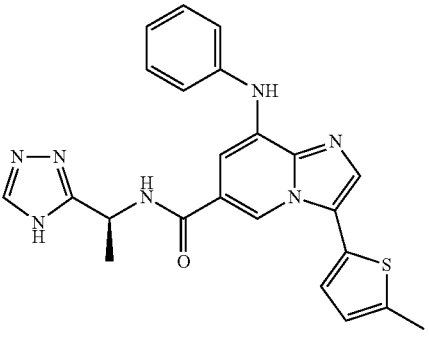 [SMILES: Cc1ccc(-c2cnc3c(Nc4ccccc4)cc(C(=O)N[C@@H](C)c4nnc[nH]4)cn23)s1] | 444.0 [M + H]+ | 7 |
| 8 | 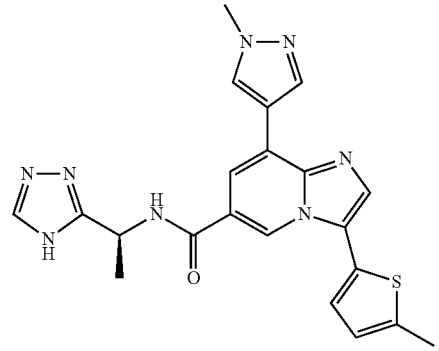 [SMILES: Cc1ccc(-c2cnc3c(-c4cnn(C)c4)cc(C(=O)N[C@@H](C)c4nnc[nH]4)cn23)s1] | 433.2 [M + H]+ | 8 |
| 9 | 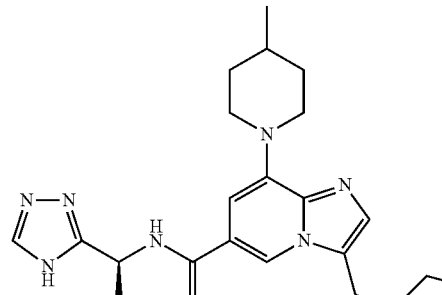 | 409.6 [M + H]+ | 9 |

TABLE 1-continued

| Ex. No. | Structure | LCMS | Prepared by method of Example No. |
|---------|-----------|------|-----------------------------------|
| 10 | 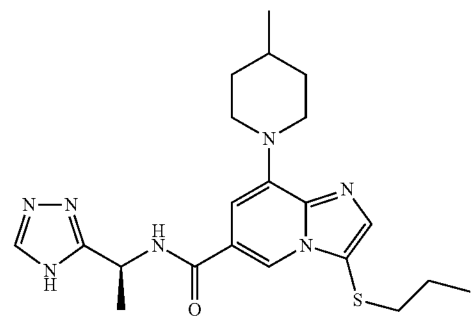 [SMILES: CCCSc1cnc2c(N3CCC(C)CC3)cc(C(=O)N[C@@H](C)c3nnc[nH]3)cn12] | 428.4 [M + H]+ | 10 |
| 11 | 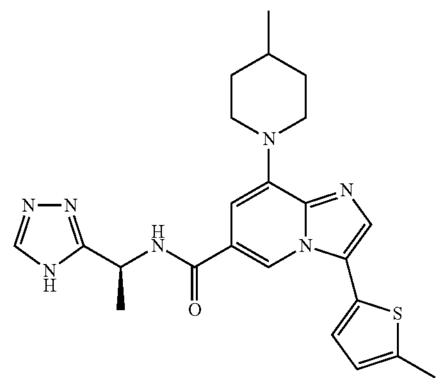 [SMILES: Cc1ccc(-c2cnc3c(N4CCC(C)CC4)cc(C(=O)N[C@@H](C)c4nnc[nH]4)cn23)s1] | 450.0 [M + H]+ | 11 |
| 12 | 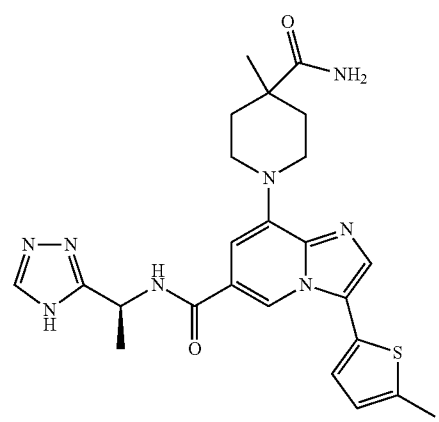 [SMILES: Cc1ccc(-c2cnc3c(N4CCC(C)(C(N)=O)CC4)cc(C(=O)N[C@@H](C)c4nnc[nH]4)cn23)s1] | 493.4 [M + H]+ | 12 |
| 13 | 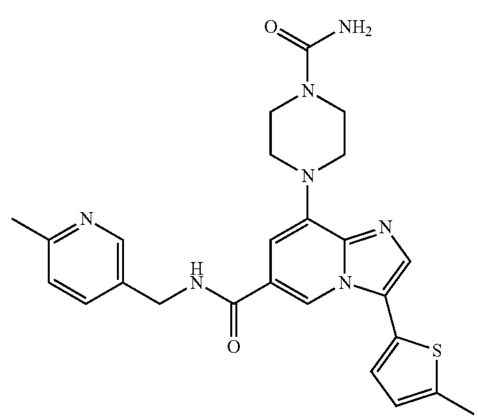 | 490.2 [M + H]+ | 13 |

TABLE 1-continued

| Ex. No. | Structure | LCMS | Prepared by method of Example No. |
|---|---|---|---|
| 14 | 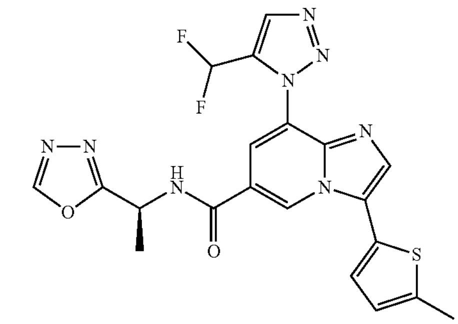 [SMILES: Cc1ccc(-c2cnc3c(-n4nncc4C(F)F)cc(C(=O)N[C@@H](C)c4nnco4)cn23)s1] | 471.0 [M + H]+ | 14 |
| 15 | 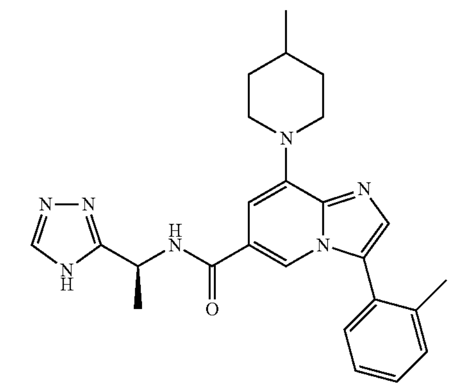 [SMILES: Cc1ccccc1-c1cnc2c(N3CCC(C)CC3)cc(C(=O)N[C@@H](C)c3nnc[nH]3)cn12] | 444.4 [M + H]+ | 15 |
| 16 | 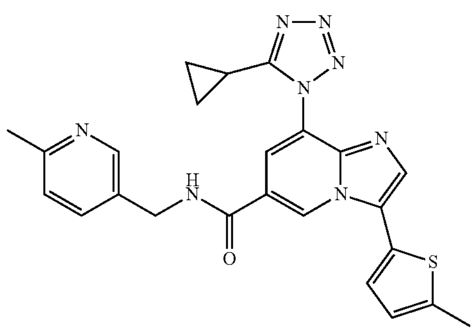 | 471.0 [M + H]+ | 16 |
| 17 | 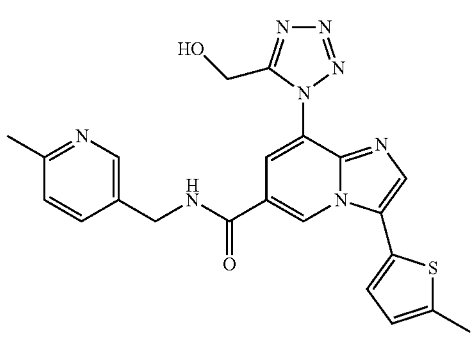 | 461.2 [M + H]+ | 17 |

TABLE 1-continued
| Ex. No. | Structure | LCMS | Prepared by method of Example No. |
|---|---|---|---|
| 18 | 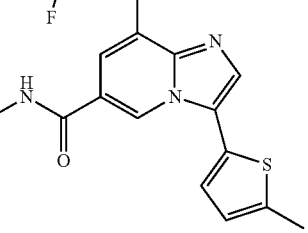 | 481.0 [M + H]+ | 18 |
| 19 | 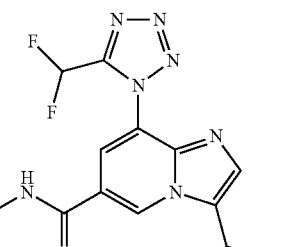 | 486.3 [M + H]+ | 19 |
| 20 | 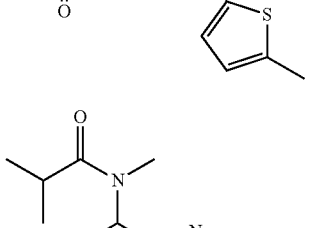 | 452.3 [M + H]+ | 20 |
| 21 | 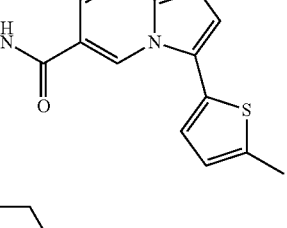 | 459.4 [M + H]+ | 1 |
| 22 | 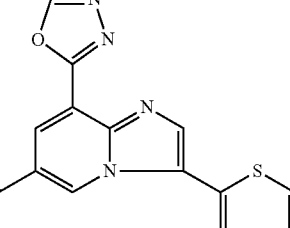 | 458.0 [M + H]+ | 4 |

TABLE 1-continued

| Ex. No. | Structure | LCMS | Prepared by method of Example No. |
|---|---|---|---|
| 23 | 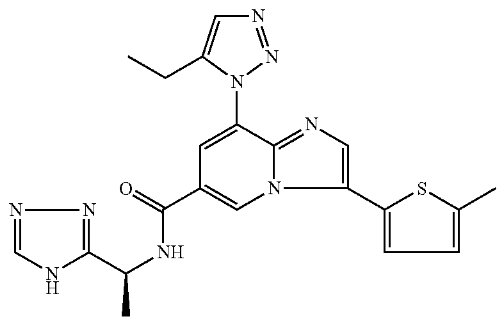 | 448.4 [M + H]+ | 4 |
| 24 | 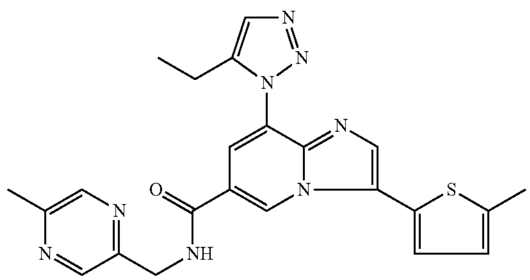 | 458.8 [M + H]+ | 4 |
| 25 | 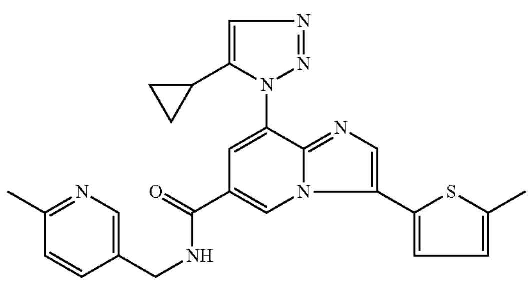 | 470.0 [M + H]+ | 4 |
| 26 | 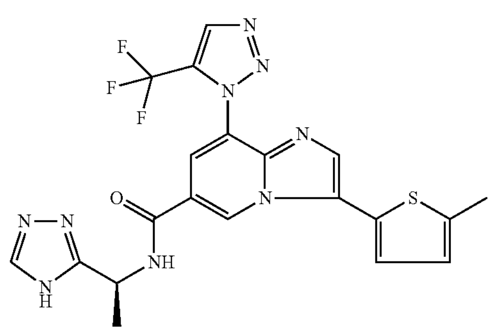 [SMILES: Cc1ccc(-c2cnc3c(-n4nncc4C(F)(F)F)cc(C(=O)N[C@@H](C)c4nnc[nH]4)cn23)s1] | 488.1 [M + H]+ | 4 |
| 27 | 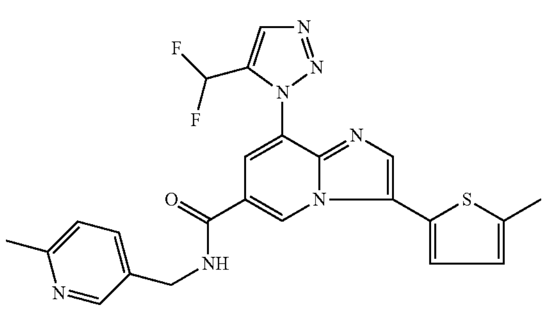 | 480.2 [M + H]+ | 4 |

TABLE 1-continued

| Ex. No. | Structure | LCMS | Prepared by method of Example No. |
|---|---|---|---|
| 28 | 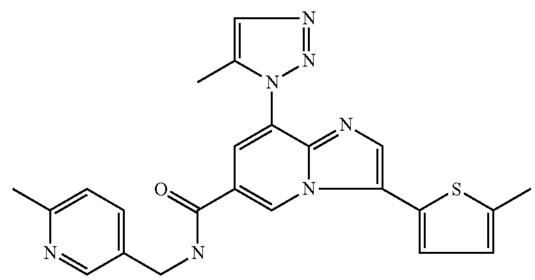 | 444.2 [M + H]⁺ | 4 |
| 29 | 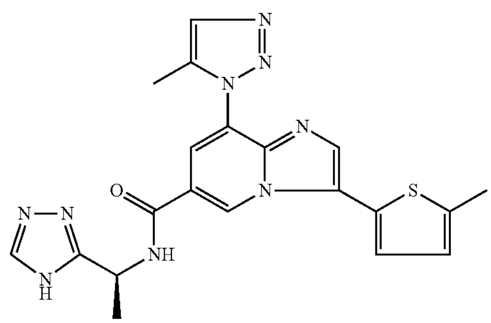 [SMILES: Cc1ccc(-c2cnc3c(-n4nncc4C)cc(C(=O)N[C@@H](C)c4nnc[nH]4)cn23)s1] | 434.2 [M + H]⁺ | 4 |
| 30 | 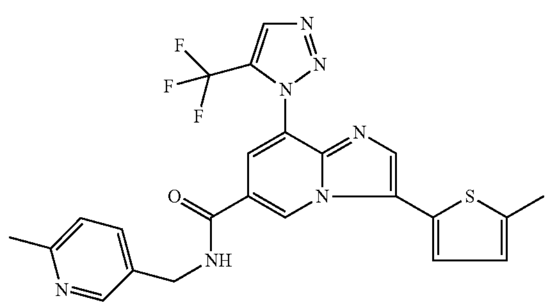 | 498.0 [M + H]⁺ | 4 |
| 31 | 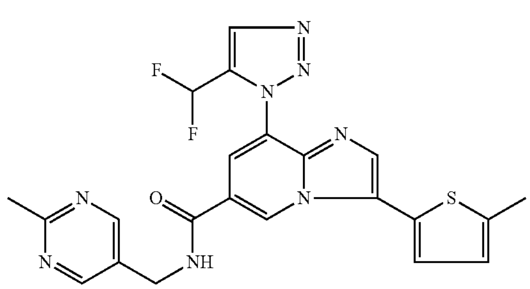 | 481.4 [M + H]⁺ | 4 |
| 32 | 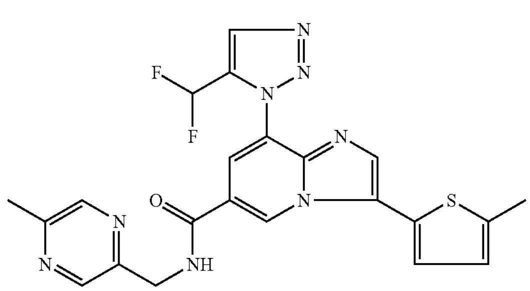 | 481.2 [M + H]⁺ | 4 |

TABLE 1-continued

| Ex. No. | Structure | LCMS | Prepared by method of Example No. |
| --- | --- | --- | --- |
| 33 | 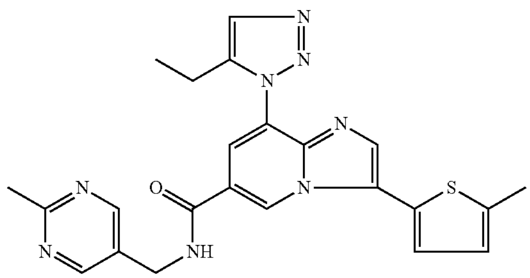 | 459.2 [M + H]⁺ | 4 |
| 34 | 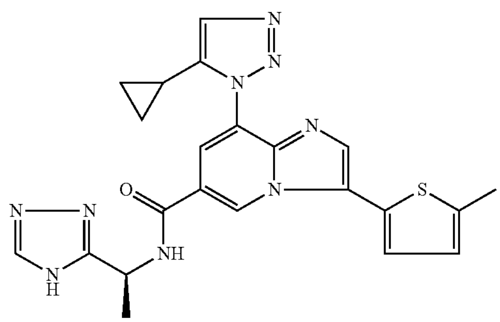 [SMILES: Cc1ccc(-c2cnc3c(-n4nncc4C4CC4)cc(C(=O)N[C@@H](C)c4nnc[nH]4)cn23)s1] | 460.0 [M + H]⁺ | 4 |
| 35 | 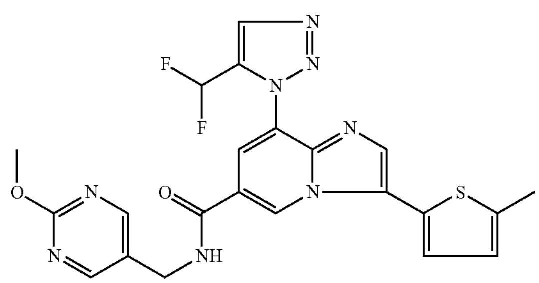 [SMILES: COc1ncc(CNC(=O)c2cc(-n3nncc3C(F)F)c3ncc(-c4ccc(C)s4)n3c2)cn1] | 497.2 [M + H]⁺ | 4 |
| 36 | 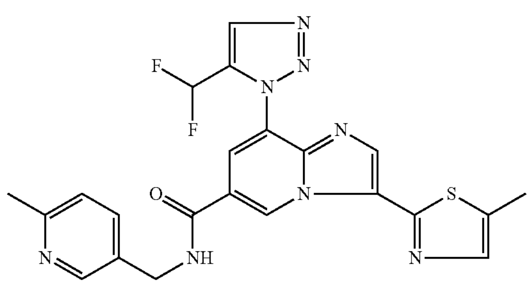 | 481.2 [M + H]⁺ | 4 |
| 37 | 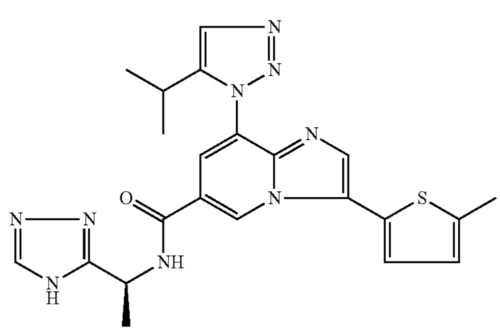 [SMILES: Cc1ccc(-c2cnc3c(-n4nncc4C(C)C)cc(C(=O)N[C@@H](C)c4nnc[nH]4)cn23)s1] | 462.2 [M + H]⁺ | 4 |

TABLE 1-continued
| Ex. No. | Structure | LCMS | Prepared by method of Example No. |
|---|---|---|---|
| 38 | 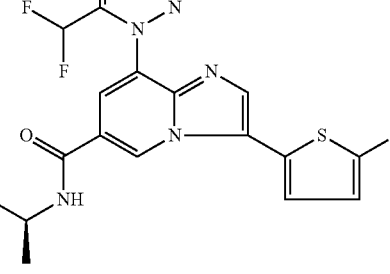 | 490.2 [M + H]+ | 4 |
| 39 | 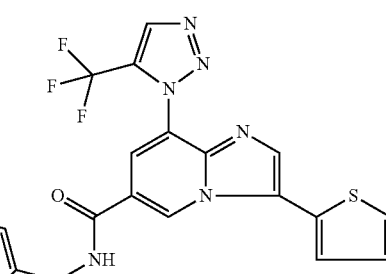 | 499.1 [M + H]+ | 4 |
| 40 | 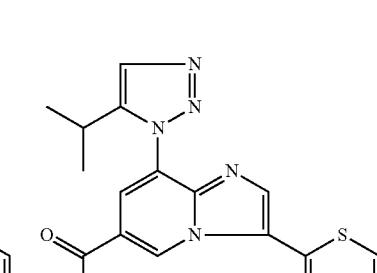 | 473.4 [M + H]+ | 4 |
| 41 | 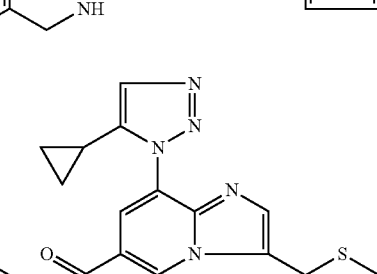 | 471.4 [M + H]+ | 4 |
| 42 | 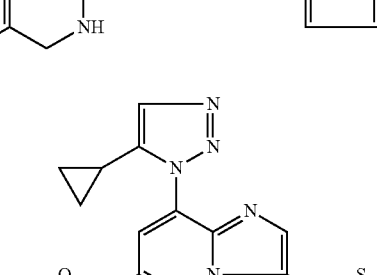 | 487.2 [M + H]+ | 4 |

TABLE 1-continued

| Ex. No. | Structure | LCMS | Prepared by method of Example No. |
|---|---|---|---|
| 43 | 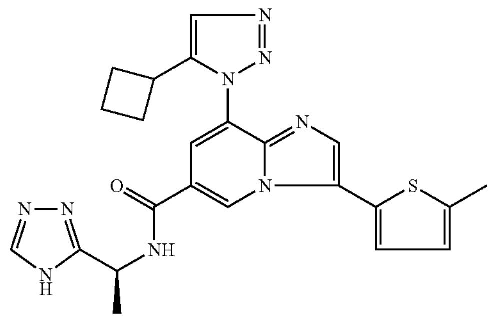 [SMILES: Cc1ccc(-c2cnc3c(-n4nncc4C4CCC4)cc(C(=O)N[C@@H](C)c4nnc[nH]4)cn23)s1] | 474.2 [M + H]+ | 4 |
| 44 | 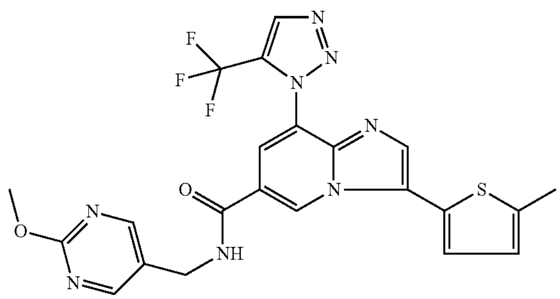 | 515.0 [M + H]+ | 4 |
| 45 | 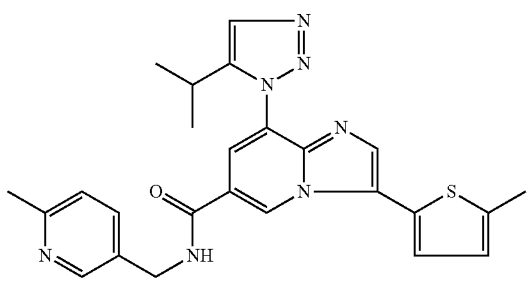 | 472.2 [M + H]+ | 4 |
| 46 | 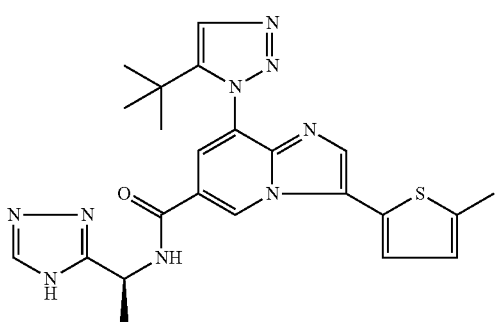 [SMILES: Cc1ccc(-c2cnc3c(-n4nncc4C(C)(C)C)cc(C(=O)N[C@@H](C)c4nnc[nH]4)cn23)s1] | 476.2 [M + H]+ | 4 |
| 47 | 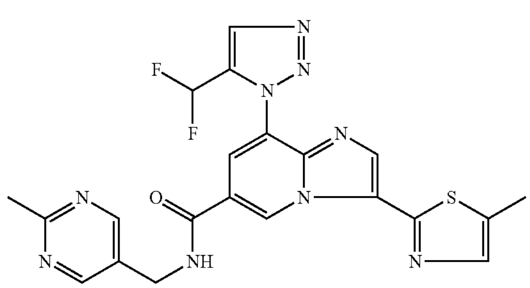 | 482.2 [M + H]+ | 4 |

TABLE 1-continued

| Ex. No. | Structure | LCMS | Prepared by method of Example No. |
|---|---|---|---|
| 48 | 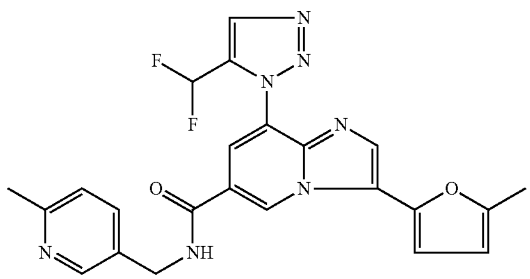 | 464.0 [M + H]+ | 4 |
| 49 | 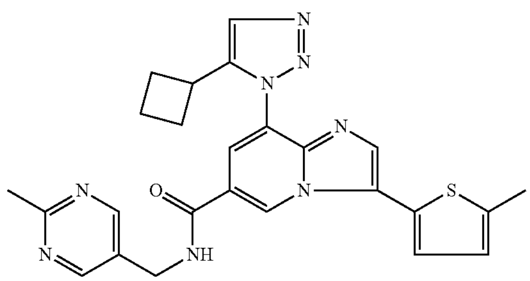 | 485.2 [M + H]+ | 4 |
| 50 | 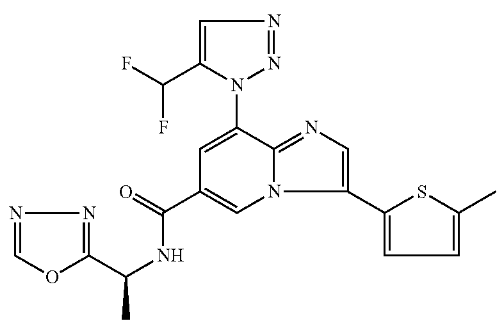 [SMILES: Cc1ccc(-c2cnc3c(-n4nncc4C(F)F)cc(C(=O)N[C@@H](C)c4nnco4)cn23)s1] | 471.0 [M + H]+ | 4 |
| 51 | 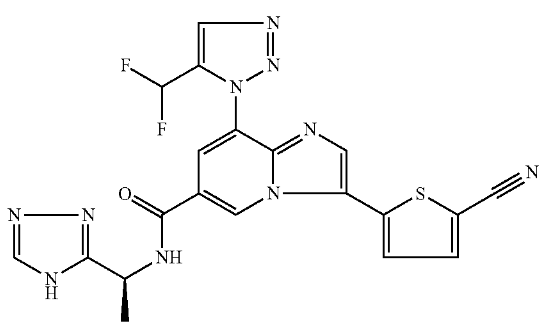 [SMILES: C[C@H](NC(=O)c1cc(-n2nncc2C(F)F)c2ncc(-c3ccc(C#N)s3)n2c1)c1nnc[nH]1] | 481.0 [M + H] + | 4 |
| 52 | 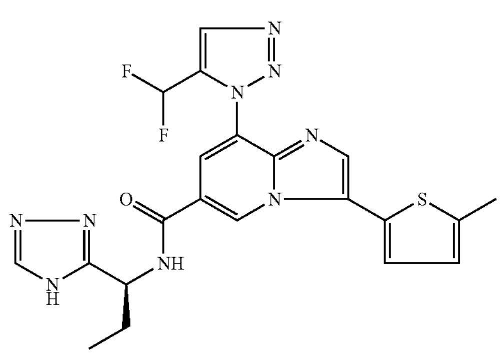 [SMILES: CC[C@H](NC(=O)c1cc(-n2nncc2C(F)F)c2ncc(-c3ccc(C)s3)n2c1)c1nnc[nH]1] | 484.0 [M + H] + | 4 |

TABLE 1-continued

| Ex. No. | Structure | LCMS | Prepared by method of Example No. |
|---|---|---|---|
| 53 | 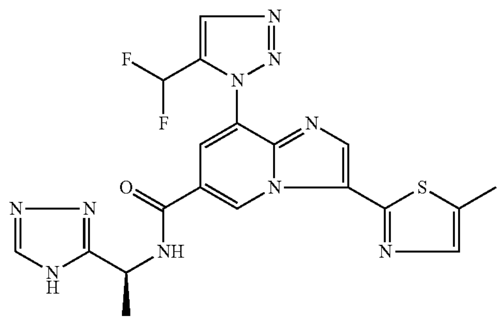 [SMILES: Cc1cnc(-c2cnc3c(-n4nncc4C(F)F)cc(C(=O)N[C@@H](C)c4nnc[nH]4)cn23)s1] | 471.0 [M + H] + | 4 |
| 54 | 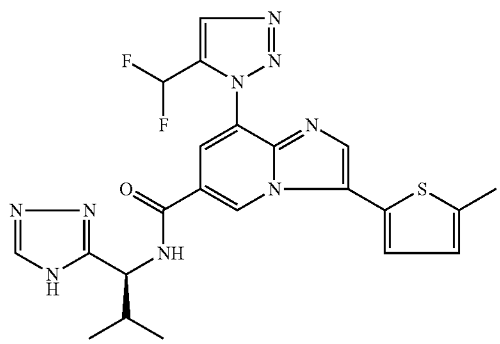 [SMILES: Cc1ccc(-c2cnc3c(-n4nncc4C(F)F)cc(C(=O)N[C@H](c4nnc[nH]4)C(C)C)cn23)s1] | 498.2 [M + H] + | 4 |
| 55 | 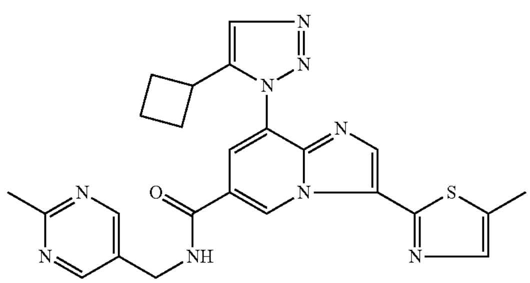 | 486.2 [M + H] + | 4 |
| 56 | 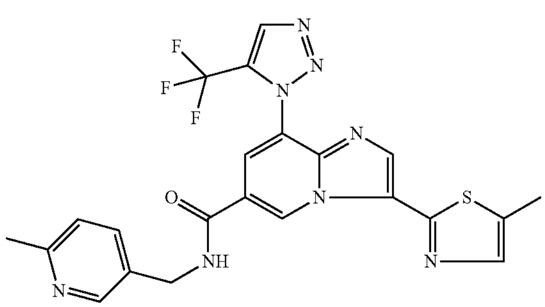 | 499.2 [M + H] + | 4 |
| 57 | 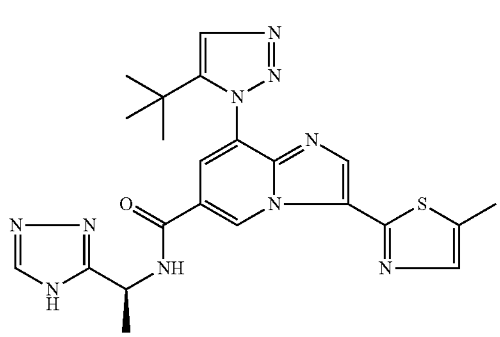 | 477.2 [M + H] + | 4 |

TABLE 1-continued

| Ex. No. | Structure | LCMS | Prepared by method of Example No. |
|---|---|---|---|
| 58 | 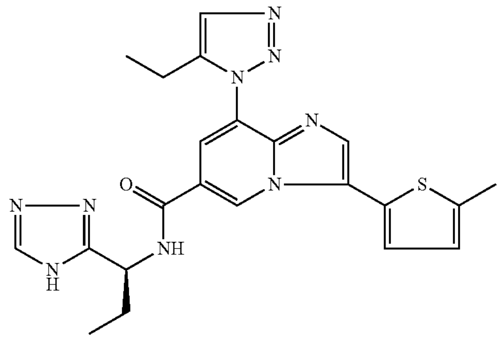 [SMILES: CCc1cnnn1-c1cc(C(=O)N[C@@H](CC)c2nnc[nH]2)cn2c(-c3ccc(C)s3)cnc12] | 462.2 [M + H] + | 4 |
| 59 | 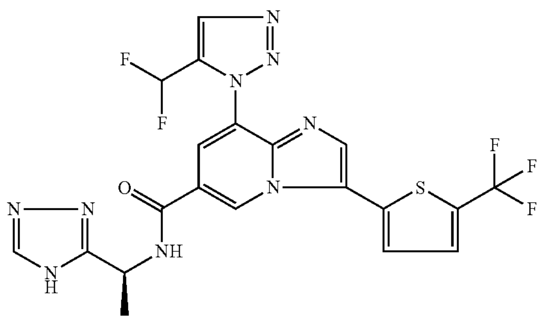 [SMILES: C[C@H](NC(=O)c1cc(-n2nncc2C(F)F)c2ncc(-c3ccc(C(F)(F)F)s3)n2c1)c1nnc[nH]1] | 524.2 [M + H] + | 4 |
| 60 | 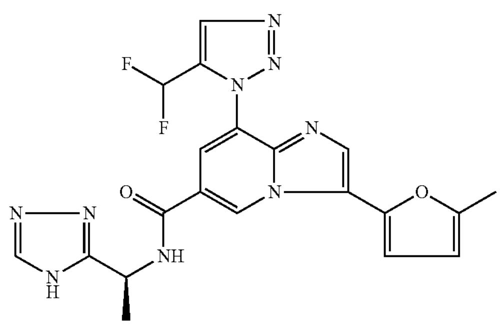 [SMILES: Cc1ccc(-c2cnc3c(-n4nncc4C(F)F)cc(C(=O)N[C@@H](C)c4nnc[nH]4)cn23)o1] | 454.2 [M + H] + | 4 |
| 61 | 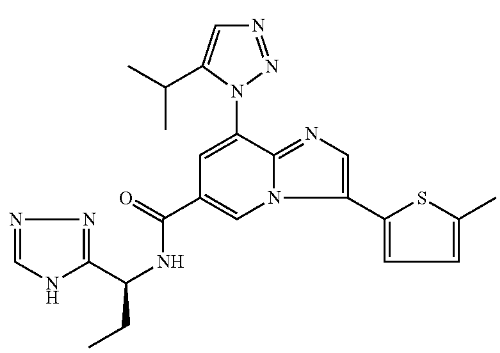 [SMILES: CC[C@H](NC(=O)c1cc(-n2nncc2C(C)C)c2ncc(-c3ccc(C)s3)n2c1)c1nnc[nH]1] | 476.2 [M + H] + | 4 |

TABLE 1-continued

| Ex. No. | Structure | LCMS | Prepared by method of Example No. |
|---|---|---|---|
| 62 | 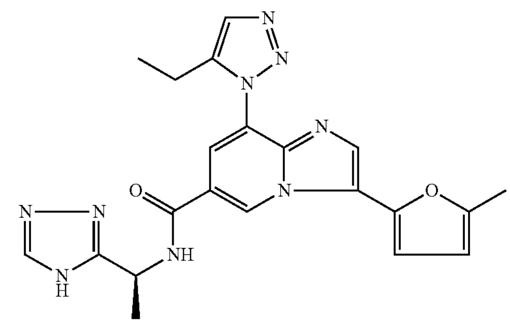 [SMILES: CCc1cnnn1-c1cc(C(=O)N[C@@H](C)c2nnc[nH]2)cn2c(-c3ccc(C)o3)cnc12] | 432.2 [M + H] + | 4 |
| 63 | 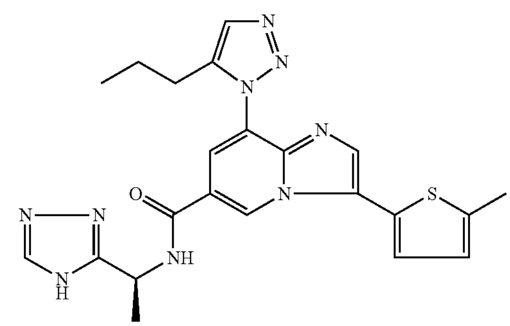 [SMILES: CCCc1cnnn1-c1cc(C(=O)N[C@@H](C)c2nnc[nH]2)cn2c(-c3ccc(C)s3)cnc12] | 462.0 [M + H] + | 4 |
| 64 | 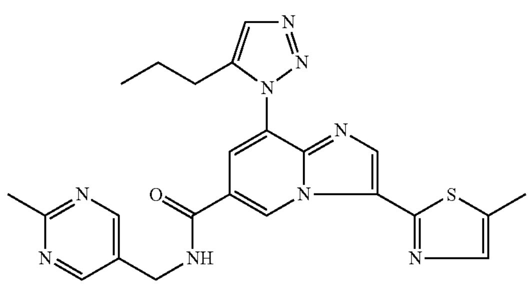 | 474.2 [M + H] + | 4 |
| 65 | 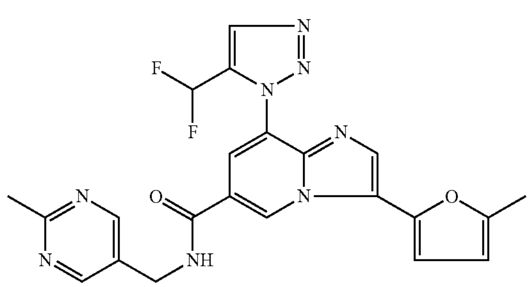 | 465.0 [M + H] + | 4 |
| 66 | 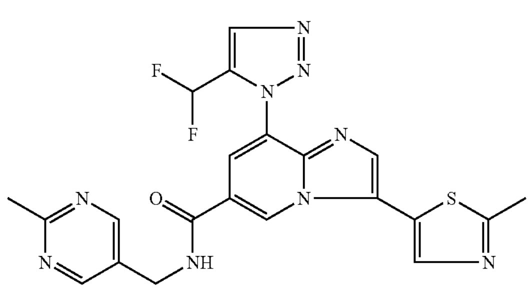 | 482.0 [M + H] + | 4 |

TABLE 1-continued
| Ex. No. | Structure | LCMS | Prepared by method of Example No. |
|---|---|---|---|
| 67 | 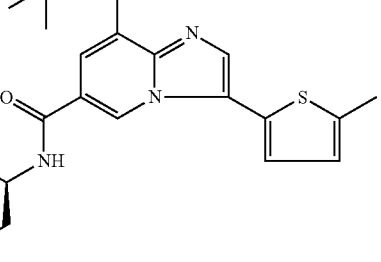 | 490.2 [M + H] + | 4 |
| 68 | 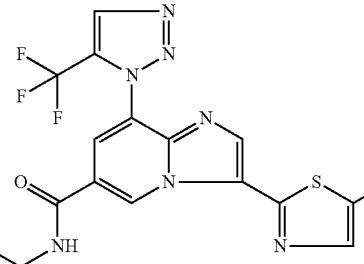 | 500.0 [M + H] + | 4 |
| 69 | 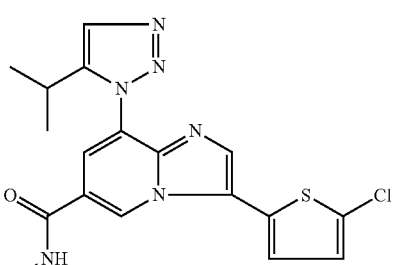 | 496.1 [M + H] + | 4 |
| 70 | 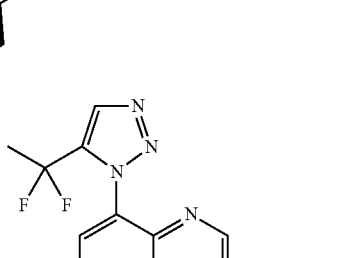 | 484.4 [M + H] + | 4 |
| 71 | 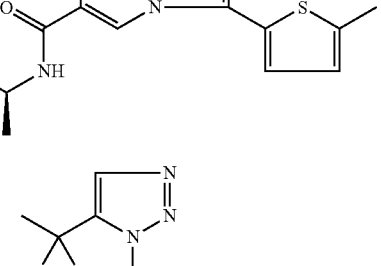 | 496.2 [M + H] + | 4 |

TABLE 1-continued

| Ex. No. | Structure | LCMS | Prepared by method of Example No. |
|---|---|---|---|
| 72 | 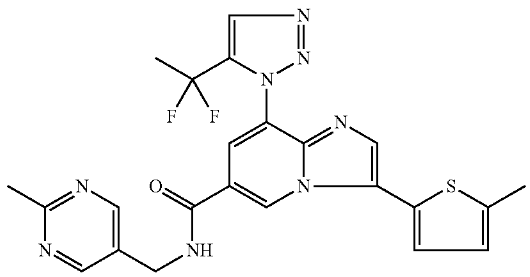 | 495.1 [M + H] + | 4 |
| 73 | 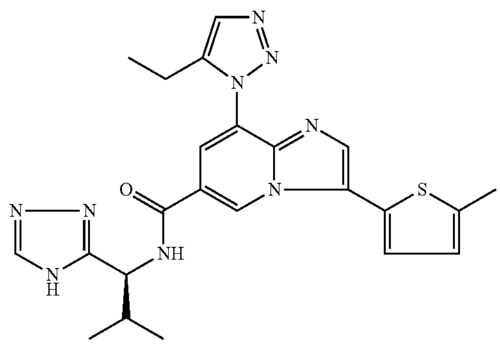 [SMILES: CCc1cnnn1-c1cc(C(=O)N[C@H](c2nnc[nH]2)C(C)C)cn2c(-c3ccc(C)s3)cnc12] | 476.2 [M + H] + | 4 |
| 74 | 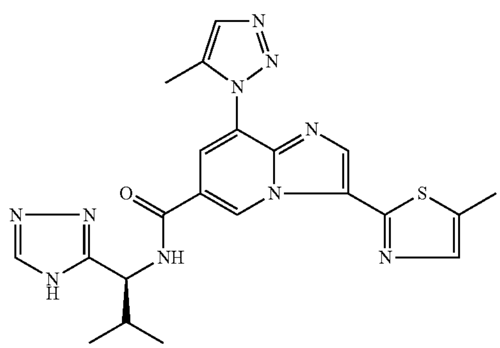 [SMILES: Cc1cnc(-c2cnc3c(-n4nncc4C)cc(C(=O)N[C@H](c4nnc[nH]4)C(C)C)cn23)s1] | 462.4 [M + H] + | 4 |
| 75 | 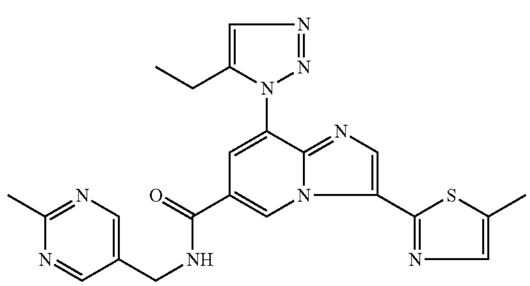 | 460.4 [M + H] + | 4 |
| 76 | 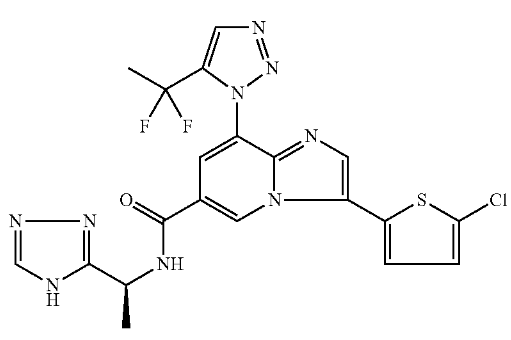 [SMILES: C[C@H](NC(=O)c1cc(-n2nncc2C(C)(F)F)c2ncc(-c3ccc(Cl)s3)n2c1)c1nnc[nH]1] | 504.2 [M + H] + | 4 |

TABLE 1-continued

| Ex. No. | Structure | LCMS | Prepared by method of Example No. |
|---|---|---|---|
| 77 | 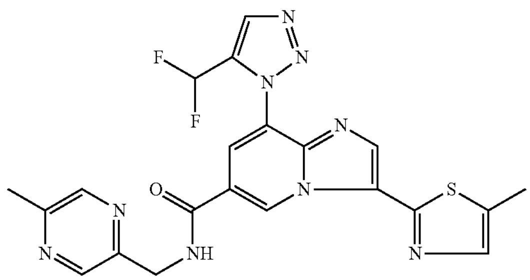 | 482.6 [M + H] + | 4 |
| 78 | 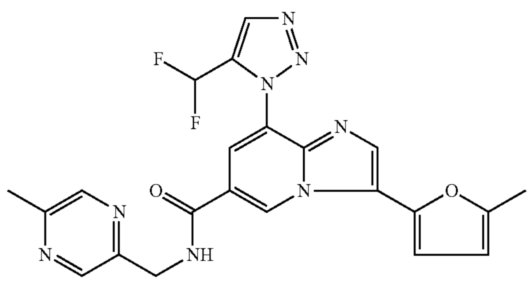 | 465.4 [M + H] + | 4 |
| 79 | 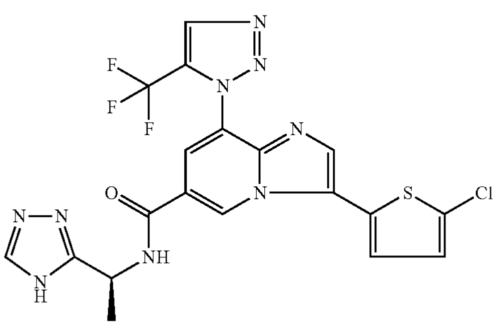 [SMILES: C[C@H](NC(=O)c1cc(-n2nncc2C(F)(F)F)c2ncc(-c3ccc(Cl)s3)n2c1)c1nnc[nH]1] | 508.2 [M + H] + | 4 |
| 80 | 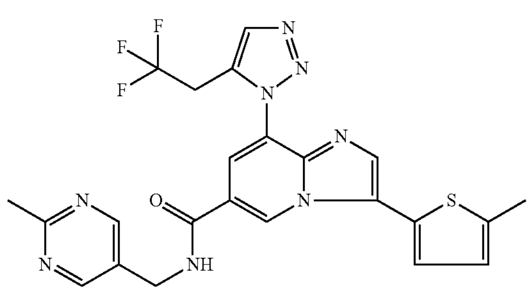 | 513.2 [M + H] + | 4 |
| 81 | 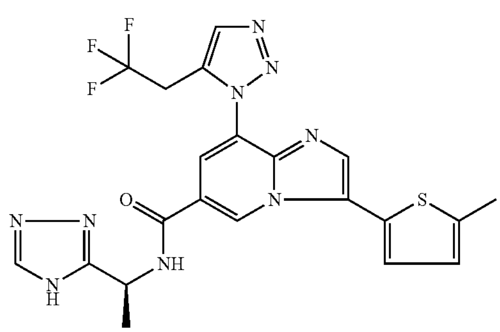 [SMILES: Cc1ccc(-c2cnc3c(-n4nncc4CC(F)(F)F)cc(C(=O)N[C@@H](C)c4nnc[nH]4)cn23)s1] | 502.2 [M + H] + | 4 |

TABLE 1-continued
| Ex. No. | Structure | LCMS | Prepared by method of Example No. |
|---|---|---|---|
| 82 | 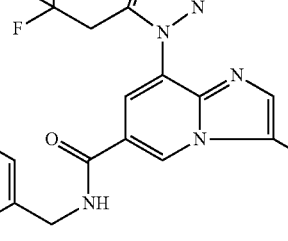 | 514.1 [M + H] + | 4 |
| 83 | 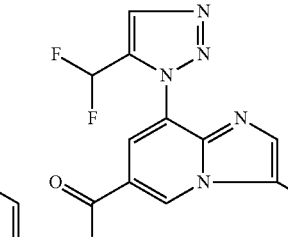 | 496.2 [M + H] + | 4 |
| 84 | 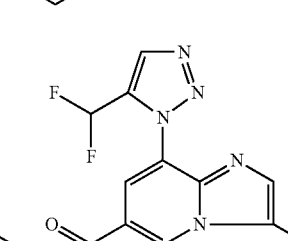 | 496.2 [M + H] + | 4 |
| 85 | 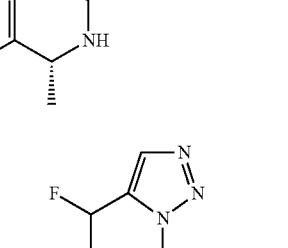 | 485.2 [M + H] + | 4 |
| 86 | 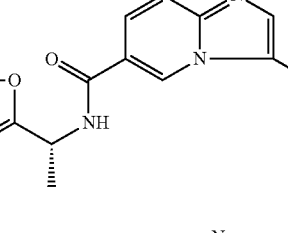 | 516.1 [M + H] + | 4 |

TABLE 1-continued

| Ex. No. | Structure | LCMS | Prepared by method of Example No. |
|---|---|---|---|
| 87 | 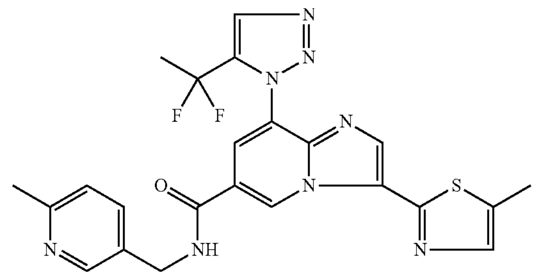 | 495.2 [M + H] + | 4 |
| 88 | 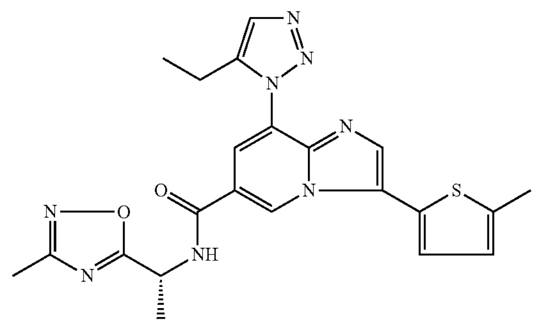 | 463.2 [M + H] + | 4 |
| 89 | 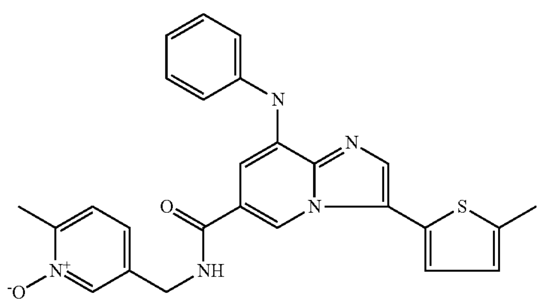 | 470.2 [M + H]+ | 7 |
| 90 | 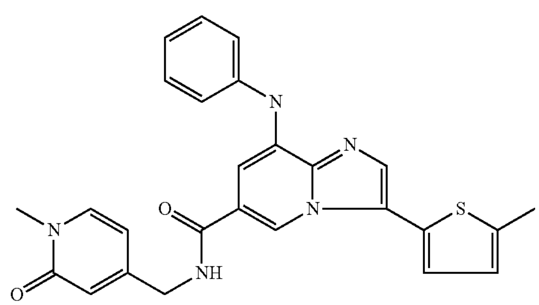 | 470.2 [M + H]+ | 7 |
| 91 | 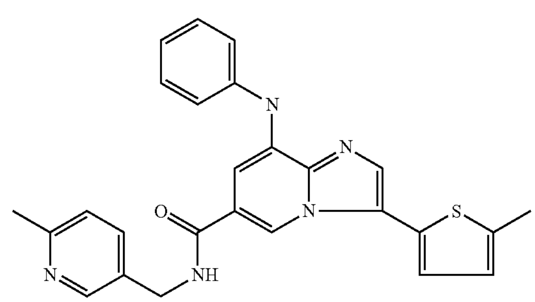 | 454.2 [M + H]+ | 7 |

TABLE 1-continued

| Ex. No. | Structure | LCMS | Prepared by method of Example No. |
|---|---|---|---|
| 92 | 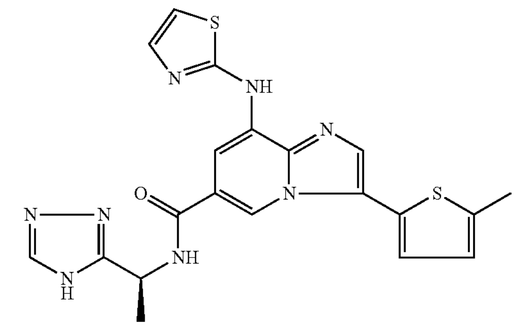 [SMILES: Cc1ccc(-c2cnc3c(Nc4nccs4)cc(C(=O)N[C@@H](C)c4nnc[nH]4)cn23)s1] | 451.2 [M + H]+ | 7 |
| 93 | 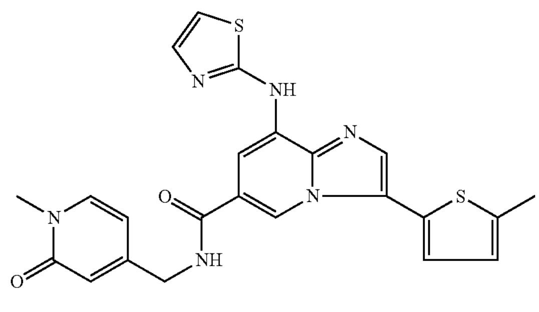 | 477.2 [M + H]+ | 7 |
| 94 | 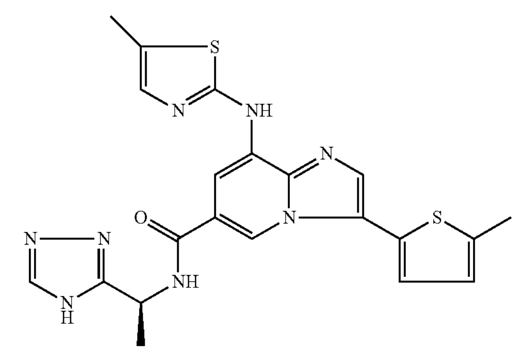 [SMILES: Cc1ccc(-c2cnc3c(Nc4ncc(C)s4)cc(C(=O)N[C@@H](C)c4nnc[nH]4)cn23)s1] | 465.0 [M + H]+ | 7 |
| 95 | 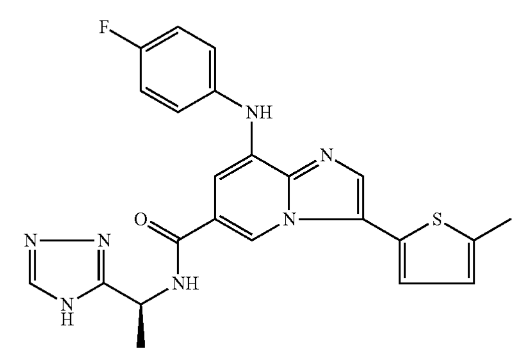 [SMILES: Cc1ccc(-c2cnc3c(Nc4ccc(F)cc4)cc(C(=O)N[C@@H](C)c4nnc[nH]4)cn23)s1] | 462.2 [M + H]+ | 7 |

TABLE 1-continued
| Ex. No. | Structure | LCMS | Prepared by method of Example No. |
|---|---|---|---|
| 96 | 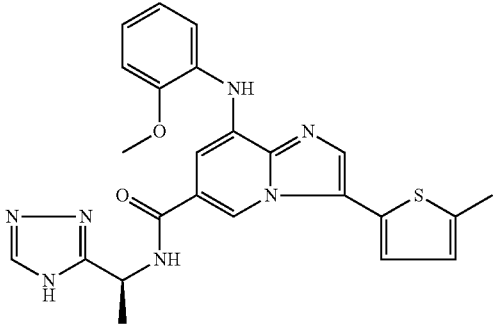 [SMILES: COc1ccccc1Nc1cc(C(=O)N[C@@H](C)c2nnc[nH]2)cn2c(-c3ccc(C)s3)cnc12] | 474.4 [M + H]+ | 7 |
| 97 | 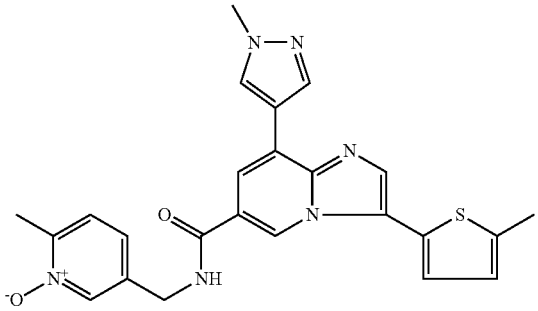 | 454.0 [M + H]+ | 8 |
| 98 | 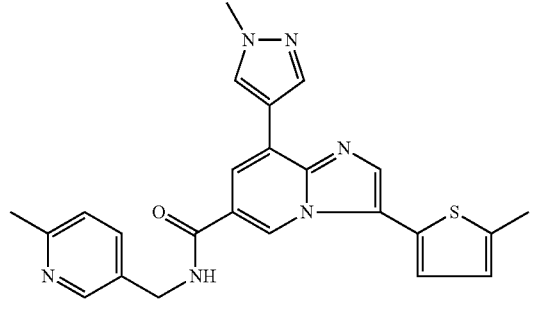 | 443.2 [M + H]+ | 8 |
| 99 | 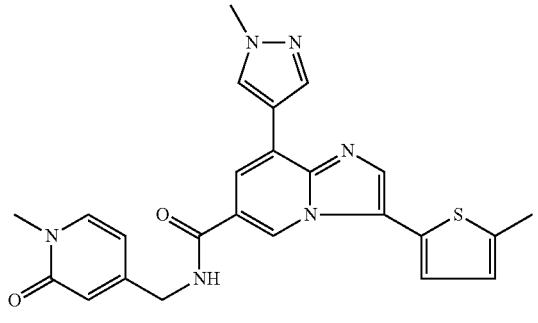 | 459.2 [M + H]+ | 8 |

TABLE 1-continued

| Ex. No. | Structure | LCMS | Prepared by method of Example No. |
|---|---|---|---|
| 100 | 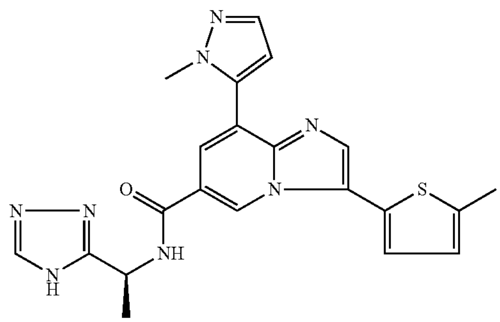 [SMILES: Cc1ccc(-c2cnc3c(-c4ccnn4C)cc(C(=O)N[C@@H](C)c4nnc[nH]4)cn23)s1] | 433.0 [M + H]+ | 8 |
| 101 | 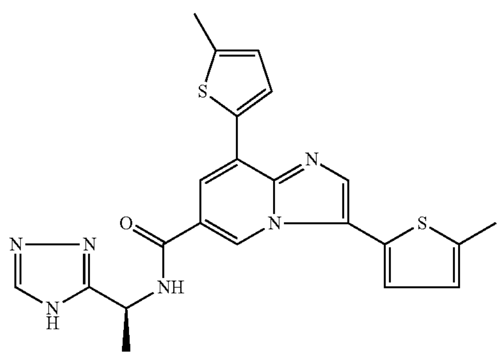 [SMILES: Cc1ccc(-c2cc(C(=O)N[C@@H](C)c3nnc[nH]3)cn3c(-c4ccc(C)s4)cnc23)s1] | 449.0 [M + H]+ | 8 |
| 102 | 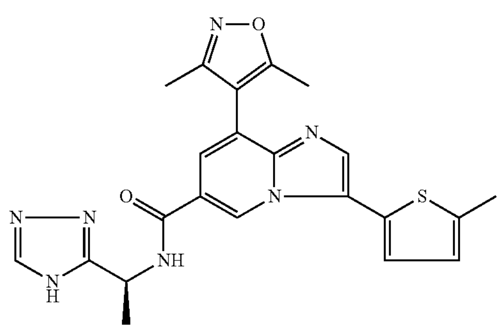 [SMILES: Cc1ccc(-c2cnc3c(-c4c(C)noc4C)cc(C(=O)N[C@@H](C)c4nnc[nH]4)cn23)s1] | 448.0 [M + H]+ | 8 |
| 103 | 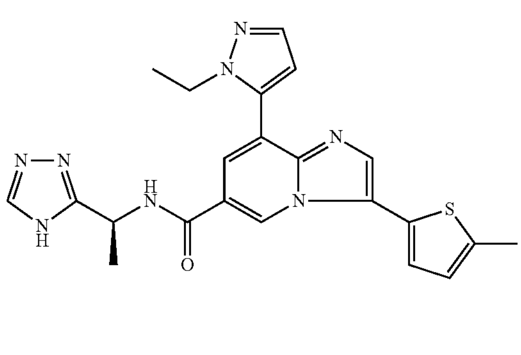 [SMILES: CCn1nccc1-c1cc(C(=O)N[C@@H](C)c2nnc[nH]2)cn2c(-c3ccc(C)s3)cnc12] | 447.0 [M + H]+ | 8 |

TABLE 1-continued

| Ex. No. | Structure | LCMS | Prepared by method of Example No. |
|---|---|---|---|
| 104 | 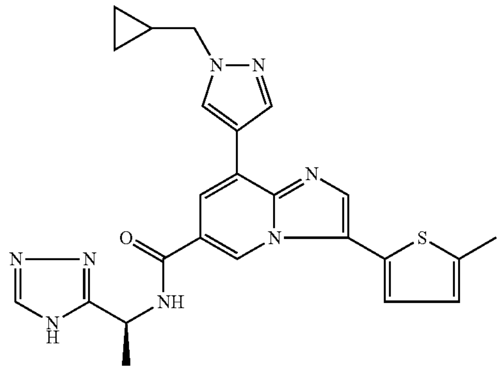 [SMILES: Cc1ccc(-c2cnc3c(-c4cnn(CC5CC5)c4)cc(C(=O)N[C@@H](C)c4nnc[nH]4)cn23)s1] | 473.4 [M + H]+ | 8 |
| 105 | 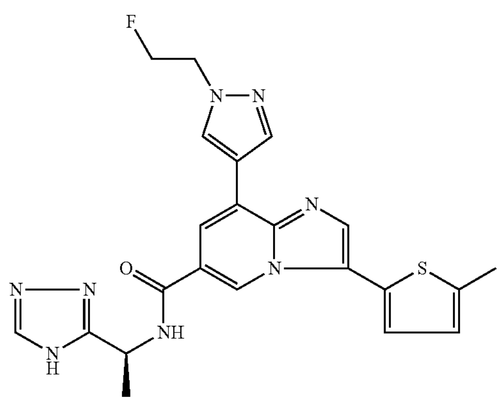 [SMILES: Cc1ccc(-c2cnc3c(-c4cnn(CCF)c4)cc(C(=O)N[C@@H](C)c4nnc[nH]4)cn23)s1] | 465.0 [M + H]+ | 8 |
| 106 | 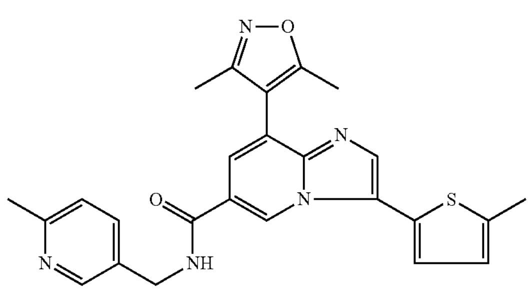 | 458.0 [M + H]+ | 8 |
| 107 | 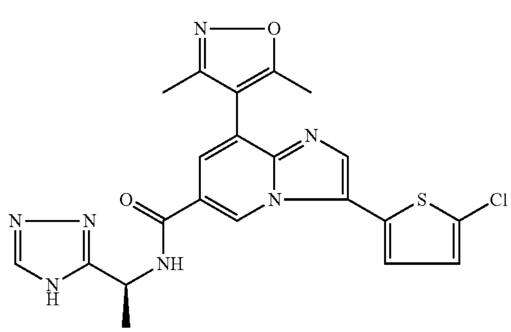 [SMILES: Cc1noc(C)c1-c1cc(C(=O)N[C@@H](C)c2nnc[nH]2)cn2c(-c3ccc(Cl)s3)cnc12] | 468.0 [M + H] + | 8 |

TABLE 1-continued

| Ex. No. | Structure | LCMS | Prepared by method of Example No. |
|---|---|---|---|
| 108 | 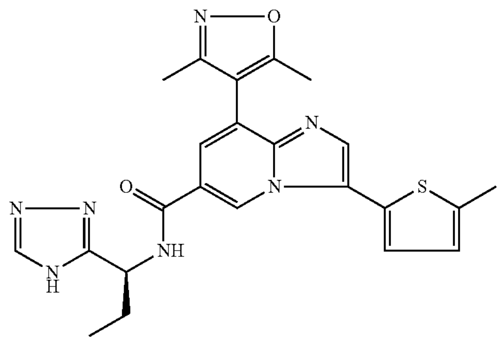 [SMILES: CC[C@H](NC(=O)c1cc(-c2c(C)noc2C)c2ncc(-c3ccc(C)s3)n2c1)c1nnc[nH]1] | 462.2 [M + H] + | 8 |
| 109 | 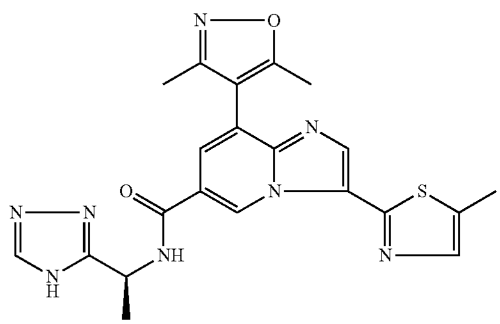 [SMILES: Cc1cnc(-c2cnc3c(-c4c(C)noc4C)cc(C(=O)N[C@@H](C)c4nnc[nH]4)cn23)s1] | 449.2 [M + H] + | 8 |
| 110 | 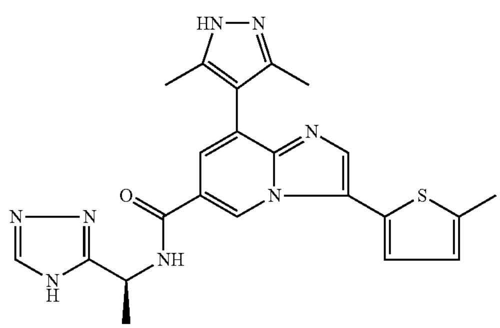 [SMILES: Cc1ccc(-c2cnc3c(-c4c(C)n[nH]c4C)cc(C(=O)N[C@@H](C)c4nnc[nH]4)cn23)s1] | 447.2 [M + H] + | 8 |
| 111 | 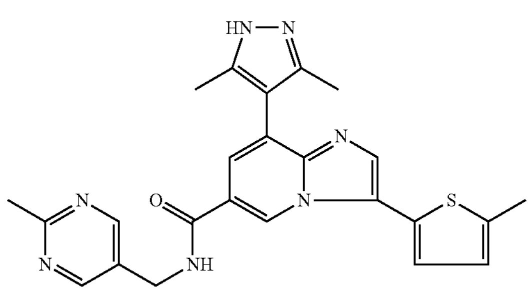 | 458.2 [M + H] + | 8 |

TABLE 1-continued

| Ex. No. | Structure | LCMS | Prepared by method of Example No. |
|---|---|---|---|
| 112 | 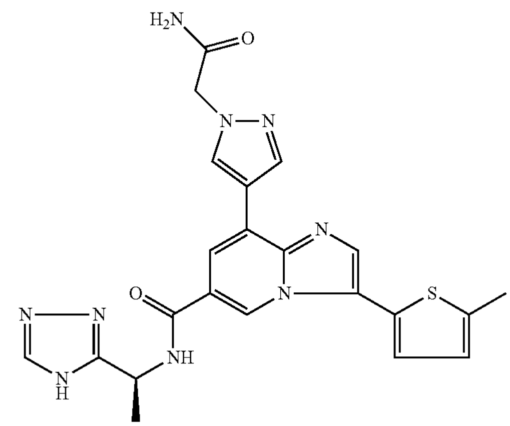 [SMILES: Cc1ccc(-c2cnc3c(-c4cnn(CC(N)=O)c4)cc(C(=O)N[C@@H](C)c4nnc[nH]4)cn23)s1] | 476.4 [M + H]+ | 8 |
| 113 | 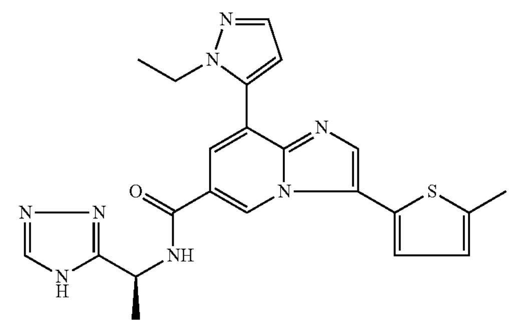 [SMILES: CCn1nccc1-c1cc(C(=O)N[C@@H](C)c2nnc[nH]2)cn2c(-c3ccc(C)s3)cnc12] | 447.0 [M + H]+ | 8 |
| 114 | 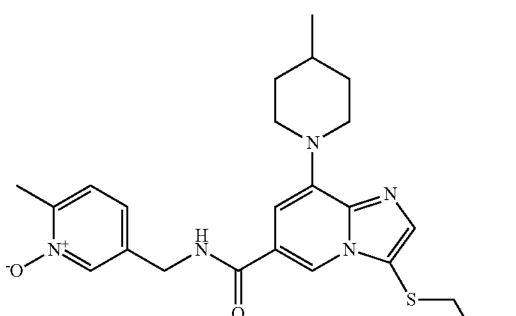 | 454.0 [M + H]+ | 10 |
| 115 | 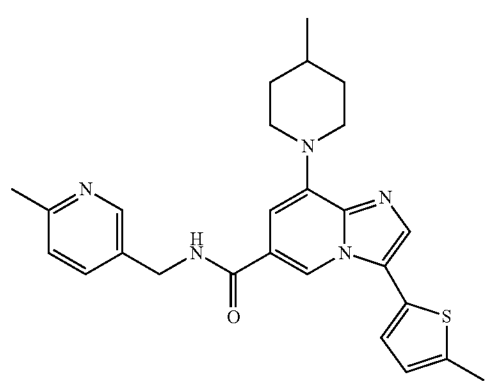 | 460.2 [M + H]+ | 11 |

TABLE 1-continued
| Ex. No. | Structure | LCMS | Prepared by method of Example No. |
|---|---|---|---|
| 116 | 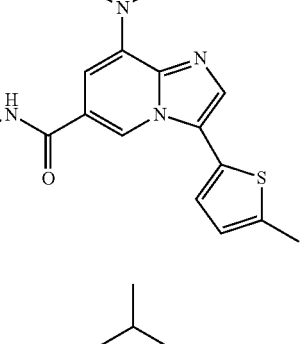 | 461.4 [M + H]+ | 11 |
| 117 | 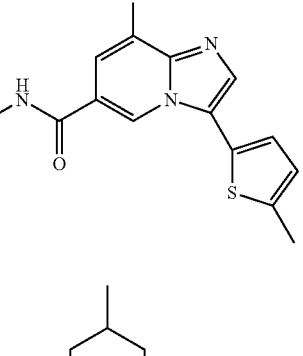 | 476.4 [M + H]+ | 11 |
| 118 | 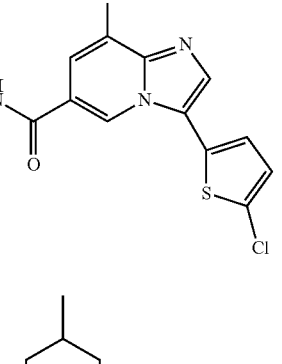 | 470.2 [M + H]+ | 11 |
| 119 | 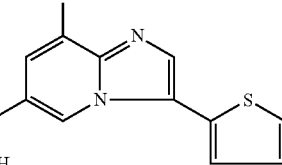 | 496.2 [M + H]+ | 11 |

TABLE 1-continued

| Ex. No. | Structure | LCMS | Prepared by method of Example No. |
|---|---|---|---|
| 120 | 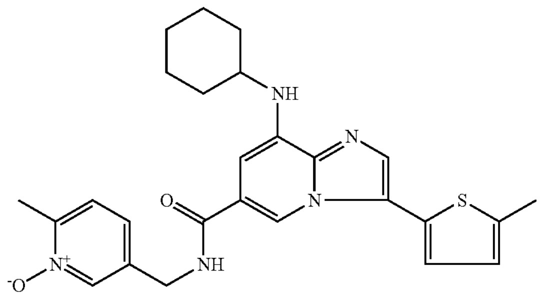 | 476.4 [M + H]+ | 11 |
| 121 | 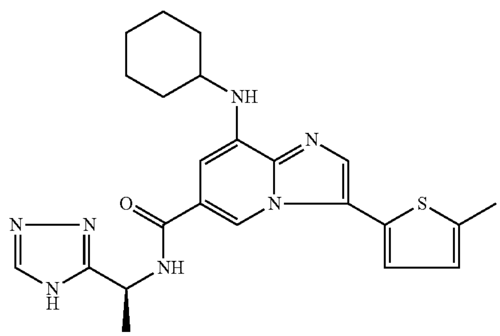 [SMILES: Cc1ccc(-c2cnc3c(NC4CCCCC4)cc(C(=O)N[C@@H](C)c4nnc[nH]4)cn23)s1] | 450.6 [M + H]+ | 11 |
| 122 | 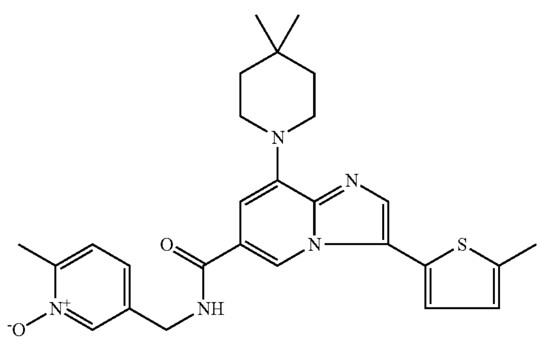 | 490.4 [M + H]+ | 11 |
| 123 | 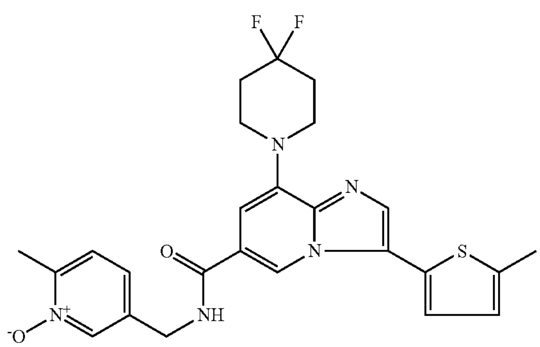 | 498.2 [M + H]+ | 11 |

TABLE 1-continued

| Ex. No. | Structure | LCMS | Prepared by method of Example No. |
|---|---|---|---|
| 124 | 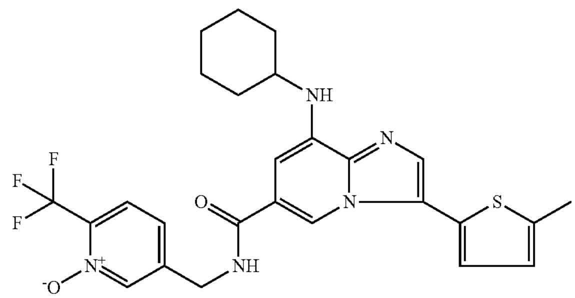 | 530.2 [M + H]+ | 11 |
| 125 | 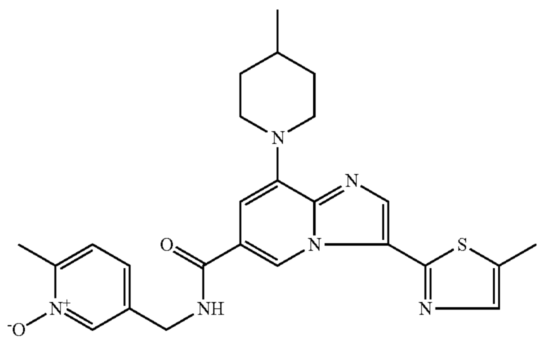 | 477.2 [M + H]+ | 11 |
| 126 | 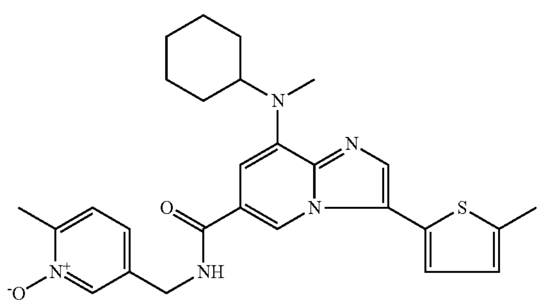 | 490.6 [M + H]+ | 11 |
| 127 | 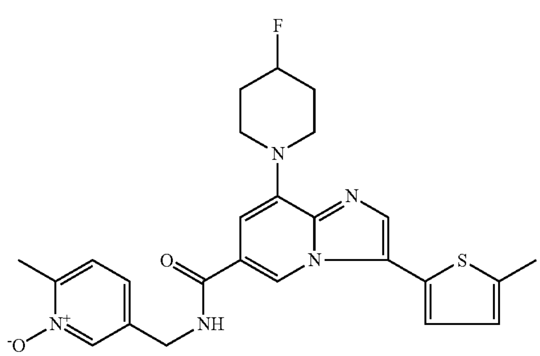 | 480.2 [M + H]+ | 11 |

TABLE 1-continued

| Ex. No. | Structure | LCMS | Prepared by method of Example No. |
|---|---|---|---|
| 128 | 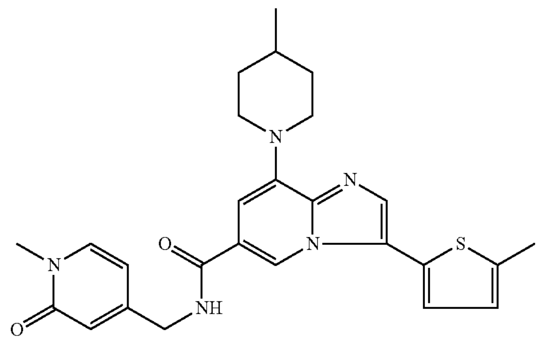 | 476.3 [M + H]+ | 11 |
| 129 | 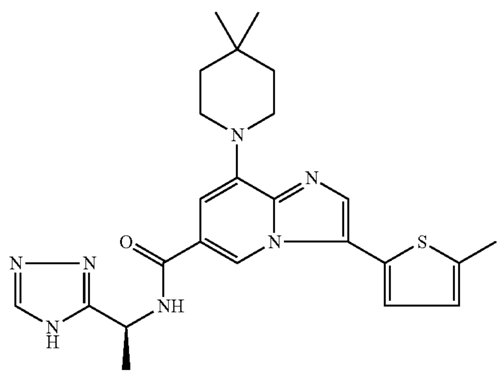 [SMILES: Cc1ccc(-c2cnc3c(N4CCC(C)(C)CC4)cc(C(=O)N[C@@H](C)c4nnc[nH]4)cn23)s1] | 464.0 [M + H]+ | 11 |
| 130 | 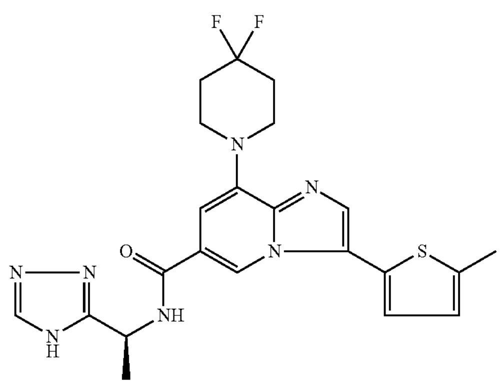 [SMILES: Cc1ccc(-c2cnc3c(N4CCC(F)(F)CC4)cc(C(=O)N[C@@H](C)c4nnc[nH]4)cn23)s1] | 472.2 [M + H]+ | 11 |
| 131 | 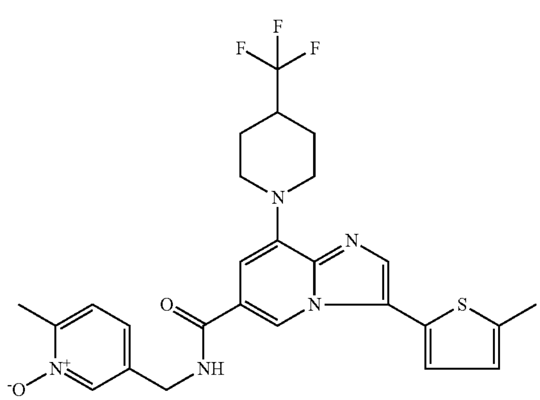 | 530.0 [M + H]+ | 11 |

TABLE 1-continued

| Ex. No. | Structure | LCMS | Prepared by method of Example No. |
|---|---|---|---|
| 132 | 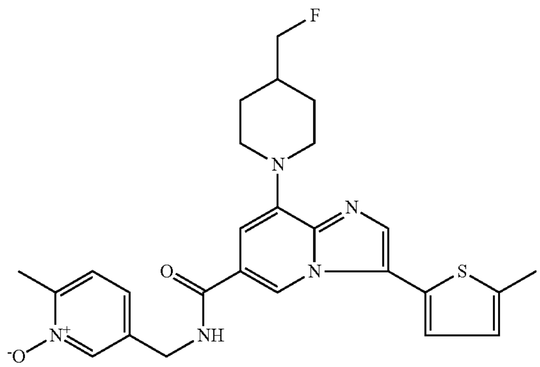 | 494.2 [M + H]+ | 11 |
| 133 | 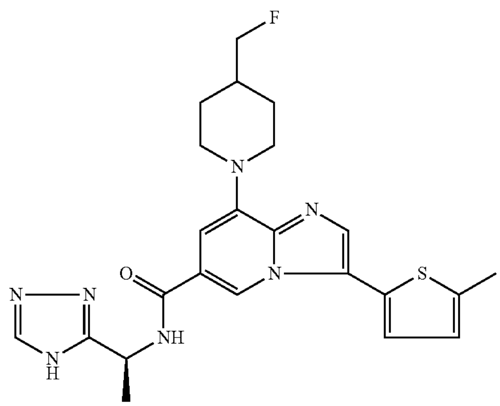 [SMILES: Cc1ccc(-c2cnc3c(N4CCC(CF)CC4)cc(C(=O)N[C@@H](C)c4nnc[nH]4)cn23)s1] | 468.2 [M + H]+ | 11 |
| 134 | 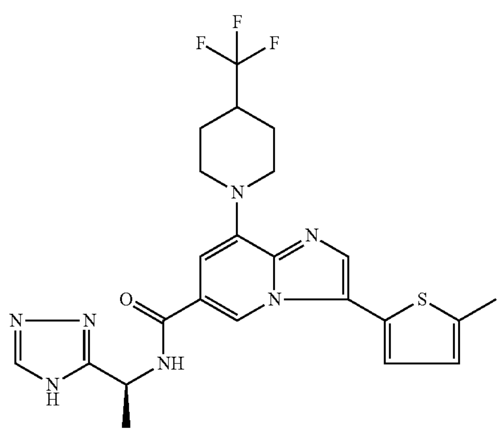 [SMILES: Cc1ccc(-c2cnc3c(N4CCC(C(F)(F)F)CC4)cc(C(=O)N[C@@H](C)c4nnc[nH]4)cn23)s1] | 504.2 [M + H]+ | 11 |
| 135 | 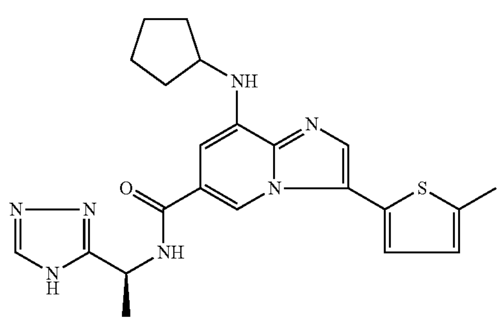 [SMILES: Cc1ccc(-c2cnc3c(NC4CCCC4)cc(C(=O)N[C@@H](C)c4nnc[nH]4)cn23)s1] | 436.4 [M + H]+ | 11 |

TABLE 1-continued

| Ex. No. | Structure | LCMS | Prepared by method of Example No. |
|---|---|---|---|
| 136 | 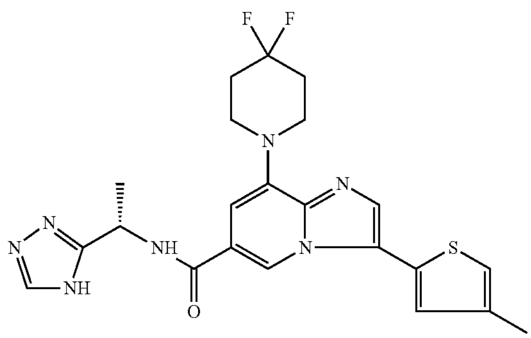 [SMILES: Cc1csc(-c2cnc3c(N4CCC(F)(F)CC4)cc(C(=O)N[C@@H](C)c4nnc[nH]4)cn23)c1] | 472.0 [M + H]+ | 11 |
| 137 | 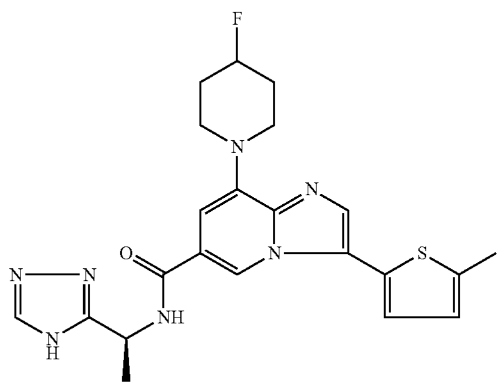 [SMILES: Cc1ccc(-c2cnc3c(N4CCC(F)CC4)cc(C(=O)N[C@@H](C)c4nnc[nH]4)cn23)s1] | 454.2 [M + H]+ | 11 |
| 138 | 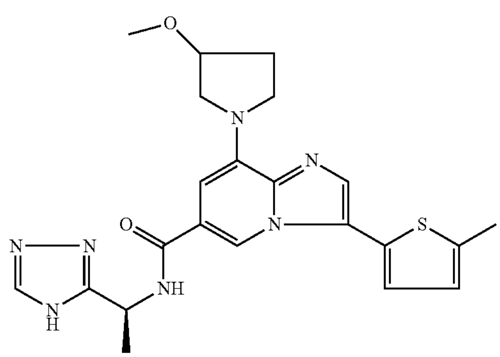 [SMILES: COC1CCN(c2cc(C(=O)N[C@@H](C)c3nnc[nH]3)cn3c(-c4ccc(C)s4)cnc23)C1] | 451.8 [M + H]+ | 11 |
| 139 | 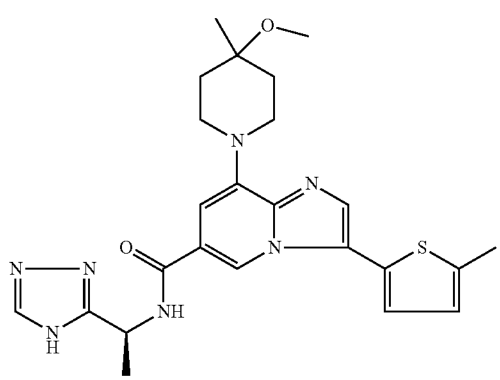 [SMILES: COC1(C)CCN(c2cc(C(=O)N[C@@H](C)c3nnc[nH]3)cn3c(-c4ccc(C)s4)cnc23)CC1] | 480.2 [M + H]+ | 11 |

TABLE 1-continued

| Ex. No. | Structure | LCMS | Prepared by method of Example No. |
|---|---|---|---|
| 140 | 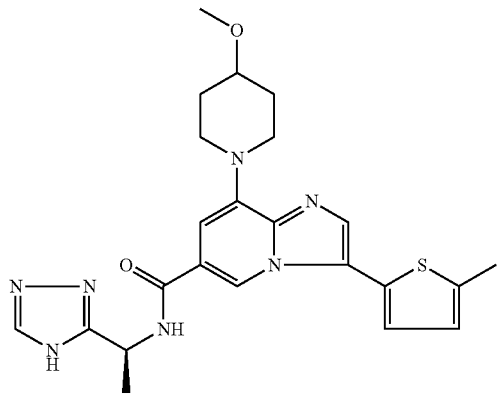 [SMILES: COC1CCN(c2cc(C(=O)N[C@@H](C)c3nnc[nH]3)cn3c(-c4ccc(C)s4)cnc23)CC1] | 466.0 [M + H]+ | 11 |
| 141 | 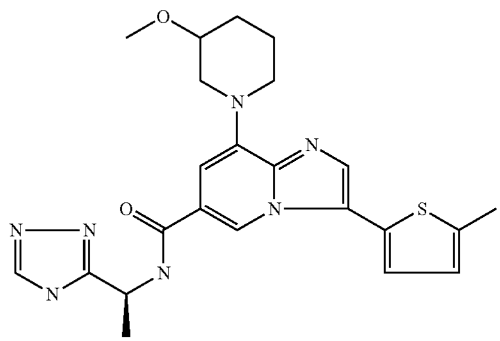 [SMILES: COC1CCCN(c2cc(C(=O)N[C@@H](C)c3nnc[nH]3)cn3c(-c4ccc(C)s4)cnc23)C1] | 466.2 [M + H]+ | 11 |
| 142 | 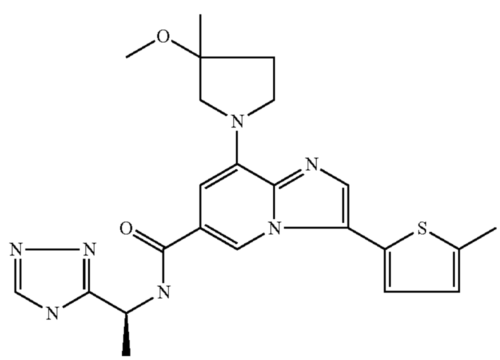 [SMILES: COC1(C)CCN(c2cc(C(=O)N[C@@H](C)c3nnc[nH]3)cn3c(-c4ccc(C)s4)cnc23)C1] | 466.1 [M + H]+ | 11 |
| 143 | 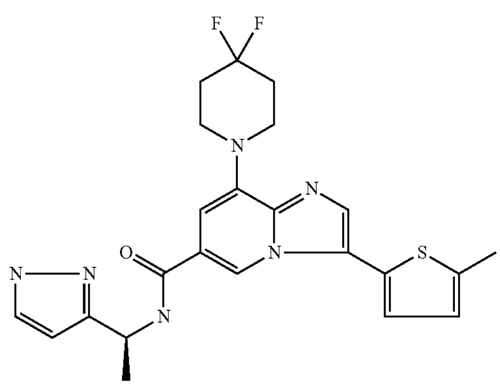 [SMILES: Cc1ccc(-c2cnc3c(N4CCC(F)(F)CC4)cc(C(=O)N[C@@H](C)c4cc[nH]n4)cn23)s1] | 471.2 [M + H] + | 11 |

TABLE 1-continued

| Ex. No. | Structure | LCMS | Prepared by method of Example No. |
|---|---|---|---|
| 144 | 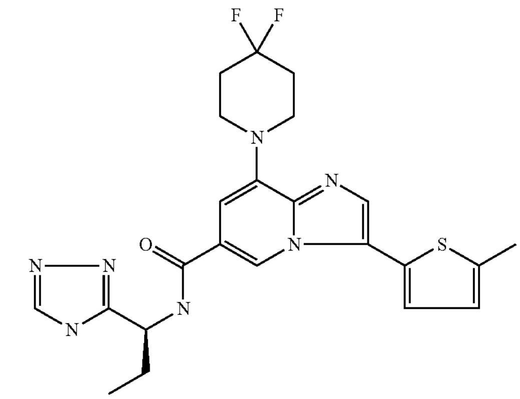 [SMILES: CC[C@H](NC(=O)c1cc(N2CCC(F)(F)CC2)c2ncc(-c3ccc(C)s3)n2c1)c1nnc[nH]1] | 486.2 [M + H] + | 11 |
| 145 | 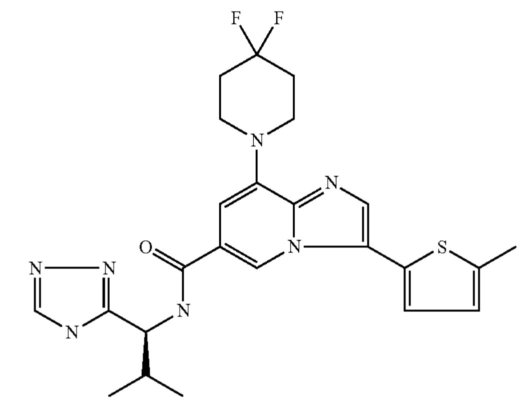 [SMILES: Cc1ccc(-c2cnc3c(N4CCC(F)(F)CC4)cc(C(=O)N[C@H](c4nnc[nH]4)C(C)C)cn23)s1] | 500.0 [M + H] + | 11 |
| 146 | 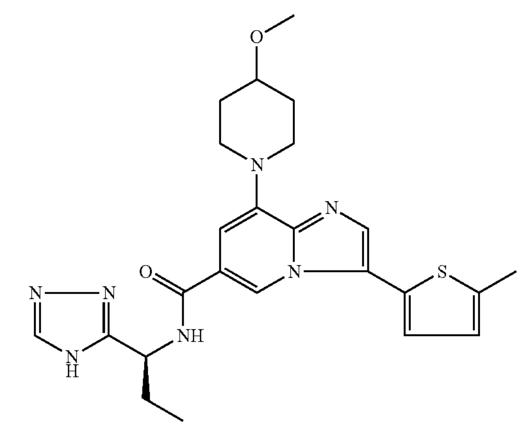 [SMILES: CC[C@H](NC(=O)c1cc(N2CCC(OC)CC2)c2ncc(-c3ccc(C)s3)n2c1)c1nnc[nH]1] | 480.0 [M + H] + | 11 |
| 147 | 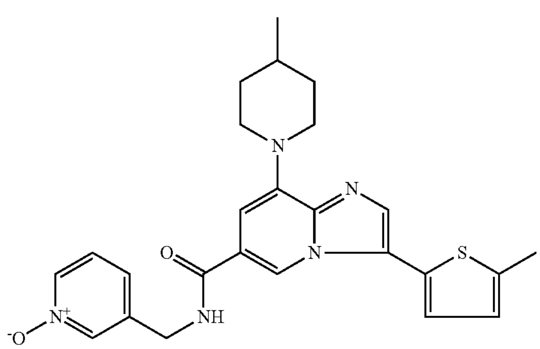 | 462.4 [M + H] + | 11 |

TABLE 1-continued

| Ex. No. | Structure | LCMS | Prepared by method of Example No. |
|---|---|---|---|
| 148 | 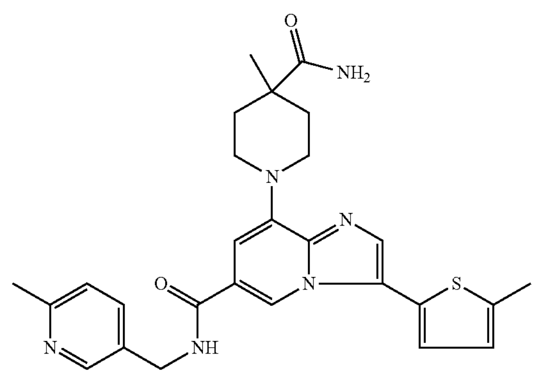 | 503.2 [M + H]+ | 12 |
| 149 | 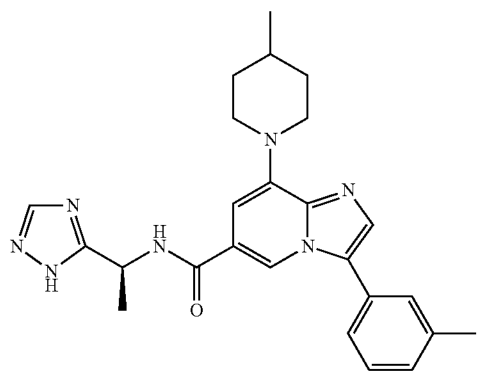 [SMILES: Cc1cccc(-c2cnc3c(N4CCC(C)CC4)cc(C(=O)N[C@@H](C)c4ncn[nH]4)cn23)c1] | 444.4 [M + H]+ | 15 |
| 150 | 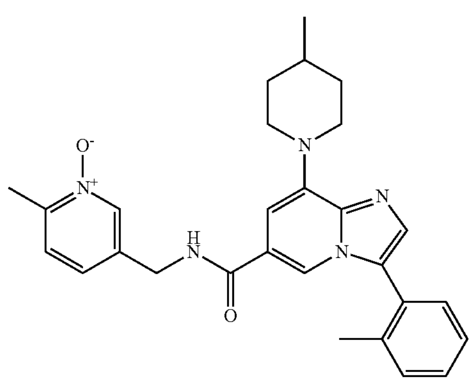 [SMILES: Cc1ccccc1-c1cnc2c(N3CCC(C)CC3)cc(C(=O)NCc3ccc(C)[n+]([O-])c3)cn12] | 470.4 [M + H]+ | 15 |
| 151 | 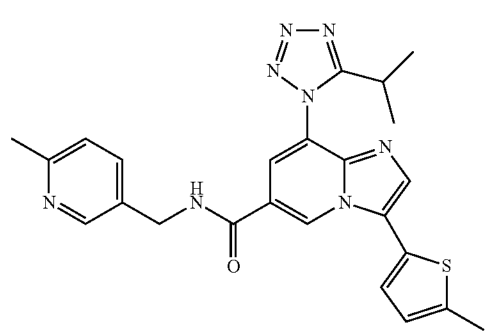 | 473.0 [M + H]+ | 16 |

TABLE 1-continued

| Ex. No. | Structure | LCMS | Prepared by method of Example No. |
|---|---|---|---|
| 152 | 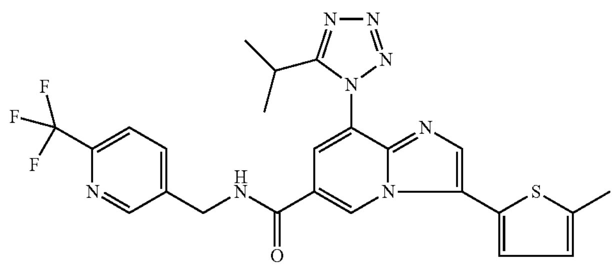 [SMILES: Cc1ccc(-c2cnc3c(-n4nnnc4C(C)C)cc(C(=O)NCc4ccc(C(F)(F)F)nc4)cn23)s1] | 527.4 [M + H]+ | 16 |
| 153 | 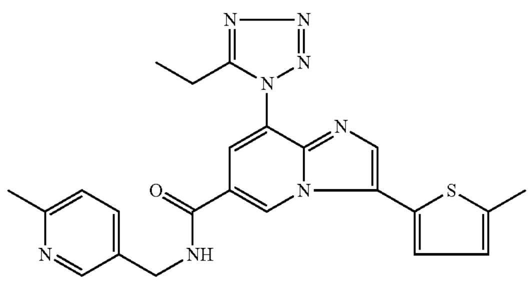 | 459.4 [M + H]+ | 16 |
| 154 | 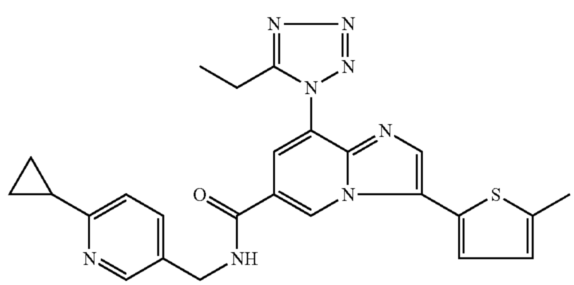 [SMILES: CCc1nnnn1-c1cc(C(=O)NCc2ccc(C3CC3)nc2)cn2c(-c3ccc(C)s3)cnc12] | 485.2 [M + H]+ | 16 |
| 155 | 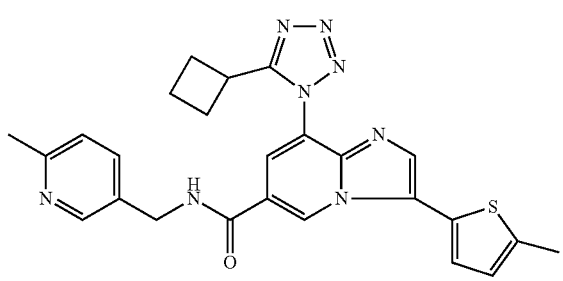 | 485.2 [M + H]+ | 16 |
| 156 | 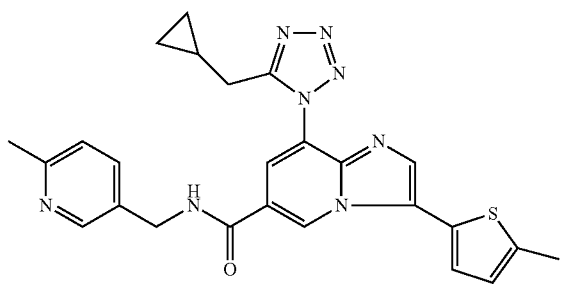 | 485.4 [M + H]+ | 16 |

TABLE 1-continued

| Ex. No. | Structure | LCMS | Prepared by method of Example No. |
|---|---|---|---|
| 157 | 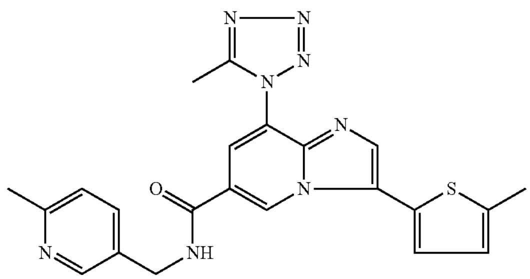 | 445.2 [M + H]+ | 16 |
| 158 | 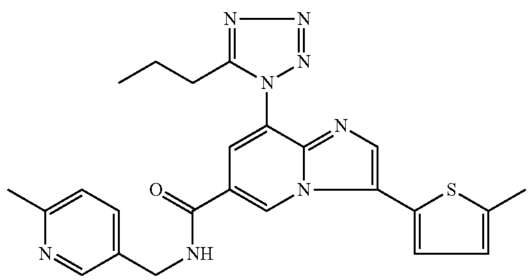 | 473.2 [M + H]+ | 16 |
| 159 | 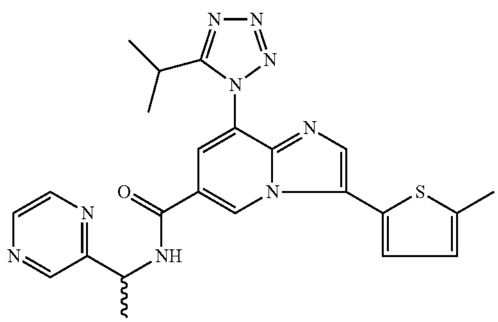 [SMILES: Cc1ccc(-c2cnc3c(-n4nnnc4C(C)C)cc(C(=O)NC(C)c4cnccn4)cn23)s1] | 474.2 [M + H]+ | 16 |
| 160 | 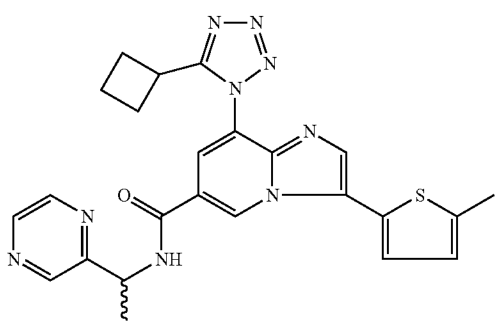 [SMILES: Cc1ccc(-c2cnc3c(-n4nnnc4C4CCC4)cc(C(=O)NC(C)c4cnccn4)cn23)s1] | 486.4 [M + H]+ | 16 |
| 161 | 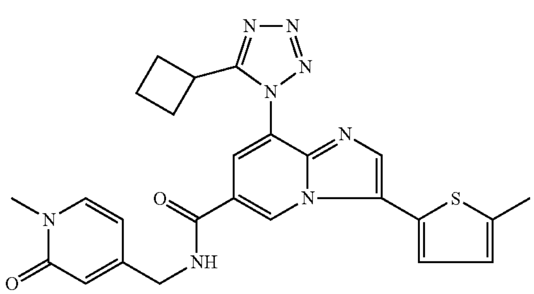 [SMILES: Cc1ccc(-c2cnc3c(-n4nnnc4C4CCC4)cc(C(=O)NCc4ccn(C)c(=O)c4)cn23)s1] | 501.4 [M + H]+ | 16 |

TABLE 1-continued

| Ex. No. | Structure | LCMS | Prepared by method of Example No. |
|---|---|---|---|
| 162 | 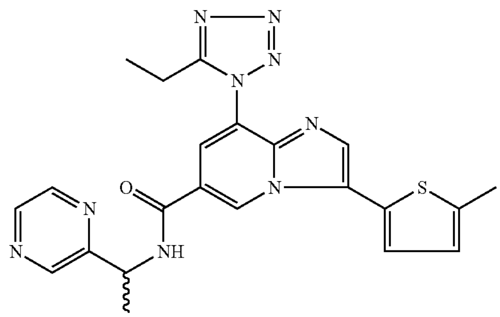 [SMILES: CCc1nnnn1-c1cc(C(=O)NC(C)c2cnccn2)cn2c(-c3ccc(C)s3)cnc12] | 460.2 [M + H]+ | 16 |
| 163 | 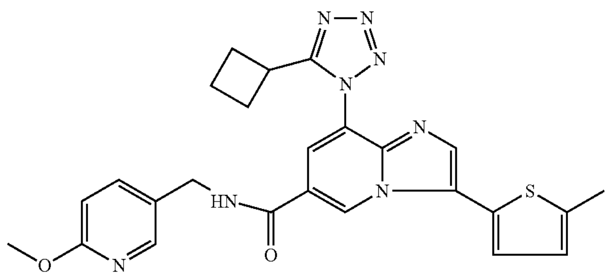 | 500.8 [M + H]+ | 16 |
| 164 | 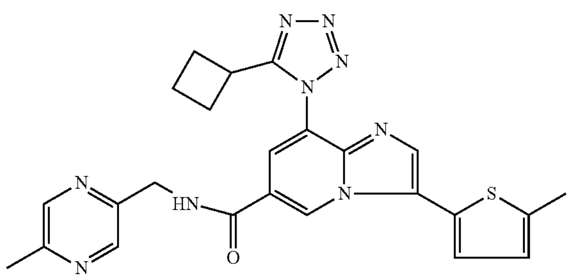 | 485.8 [M + H]+ | 16 |
| 165 | 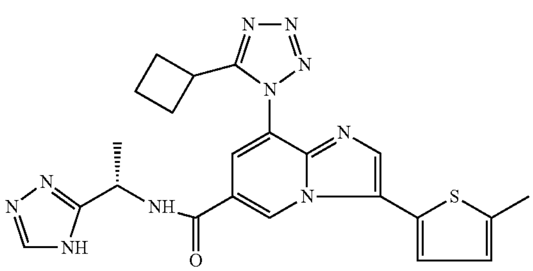 [SMILES: Cc1ccc(-c2cnc3c(-n4nnnc4C4CCC4)cc(C(=O)N[C@@H](C)c4nnc[nH]4)cn23)s1] | 475.4 [M + H]+ | 16 |
| 166 | 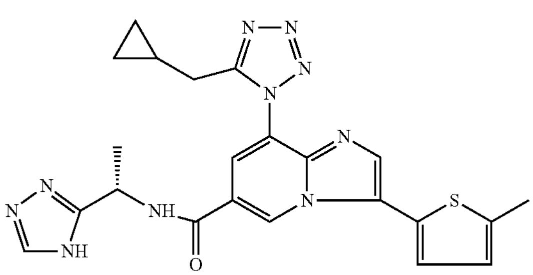 [SMILES: Cc1ccc(-c2cnc3c(-n4nnnc4CC4CC4)cc(C(=O)N[C@@H](C)c4nnc[nH]4)cn23)s1] | 475.2 [M + H]+ | 16 |

TABLE 1-continued

| Ex. No. | Structure | LCMS | Prepared by method of Example No. |
|---|---|---|---|
| 167 | 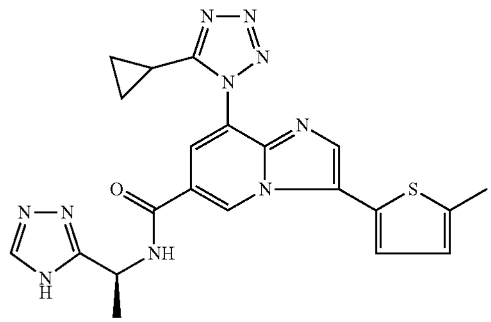 [SMILES: Cc1ccc(-c2cnc3c(-n4nnnc4C4CC4)cc(C(=O)N[C@@H](C)c4nnc[nH]4)cn23)s1] | 461.3 [M + H]+ | 16 |
| 168 | 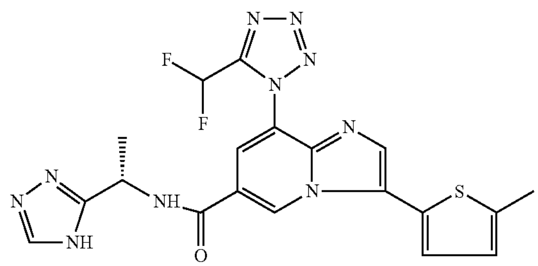 [SMILES: Cc1ccc(-c2cnc3c(-n4nnnc4C(F)F)cc(C(=O)N[C@@H](C)c4nnc[nH]4)cn23)s1] | 471.2 [M + H]+ | 18 |
| 169 | 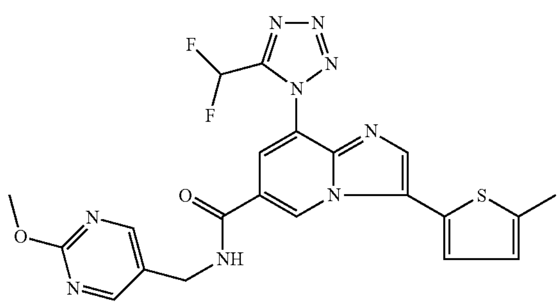 | 498.0 [M + H]+ | 18 |
| 170 | 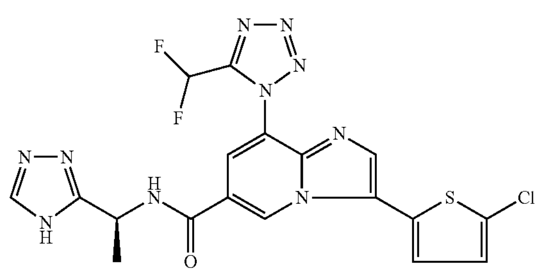 [SMILES: C[C@H](NC(=O)c1cc(-n2nnnc2C(F)F)c2ncc(-c3ccc(Cl)s3)n2c1)c1nnc[nH]1] | 491.3 [M + H]+ | 18 |
| 171 | 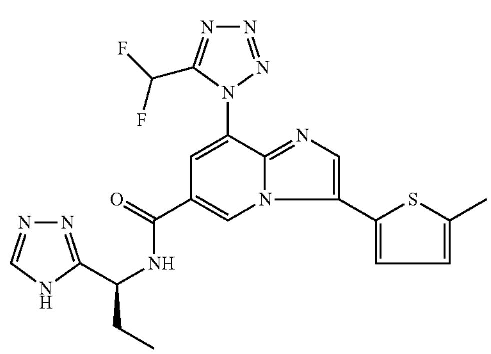 [SMILES: CC[C@H](NC(=O)c1cc(-n2nnnc2C(F)F)c2ncc(-c3ccc(C)s3)n2c1)c1nnc[nH]1] | 485.2 [M + H] + | 18 |

TABLE 1-continued

| Ex. No. | Structure | LCMS | Prepared by method of Example No. |
|---|---|---|---|
| 172 | 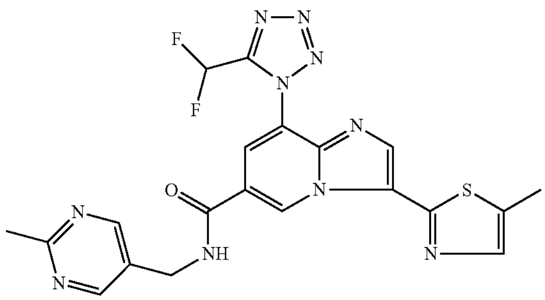 | 483.2 [M + H] + | 18 |
| 173 | 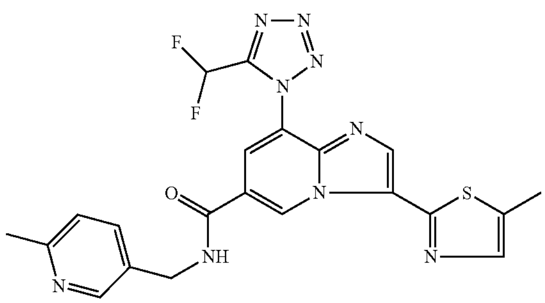 | 482.0 [M + H] + | 18 |
| 174 | 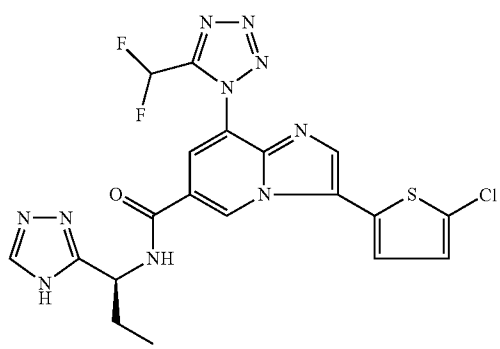 [SMILES: CC[C@H](NC(=O)c1cc(-n2nnnc2C(F)F)c2ncc(-c3ccc(Cl)s3)n2c1)c1nnc[nH]1] | 505.0 [M + H] + | 18 |
| 175 | 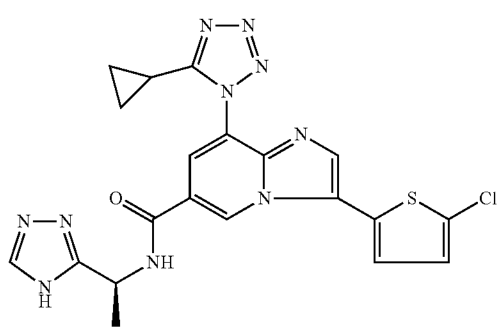 [SMILES: C[C@H](NC(=O)c1cc(-n2nnnc2C2CC2)c2ncc(-c3ccc(Cl)s3)n2c1)c1nnc[nH]1] | 481.0 [M + H] + | 18 |
| 176 | 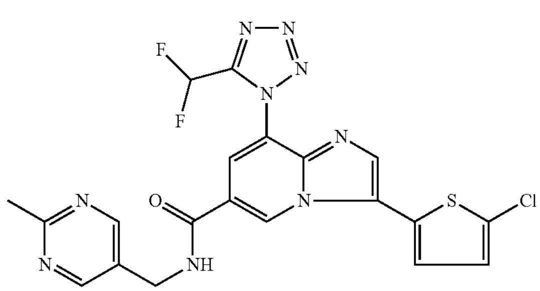 [SMILES: Cc1ncc(CNC(=O)c2cc(-n3nnnc3C(F)F)c3ncc(-c4ccc(Cl)s4)n3c2)cn1] | 502.0 [M + H] + | 18 |

TABLE 1-continued

| Ex. No. | Structure | LCMS | Prepared by method of Example No. |
|---|---|---|---|
| 177 | 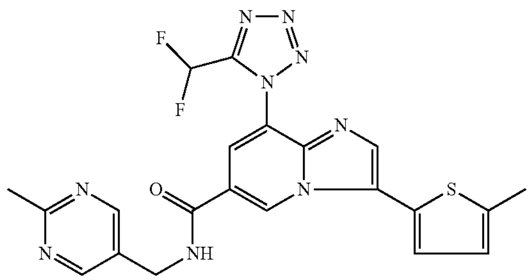 | 482.0 [M + H] + | 18 |
| 178 | 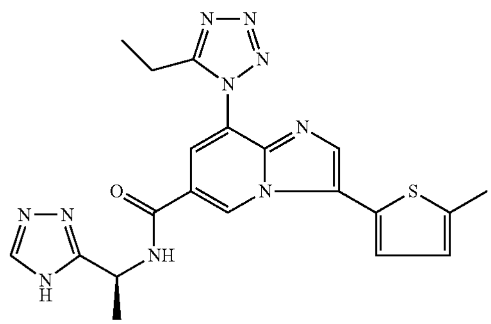 [SMILES: CCc1nnnn1-c1cc(C(=O)N[C@@H](C)c2nnc[nH]2)cn2c(-c3ccc(C)s3)cnc12] | 449.0 [M + H] + | 18 |
| 179 | 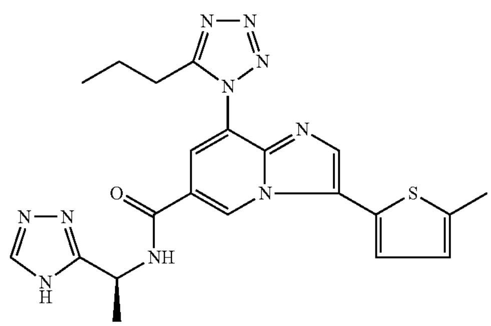 [SMILES: CCCc1nnnn1-c1cc(C(=O)N[C@@H](C)c2nnc[nH]2)cn2c(-c3ccc(C)s3)cnc12] | 463.0 [M + H] + | 18 |
| 180 | 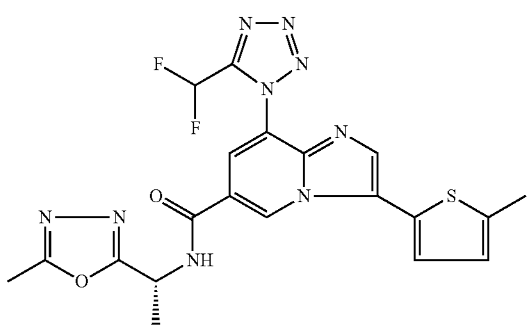 | 486.0 [M + H] + | 18 |
| 181 | 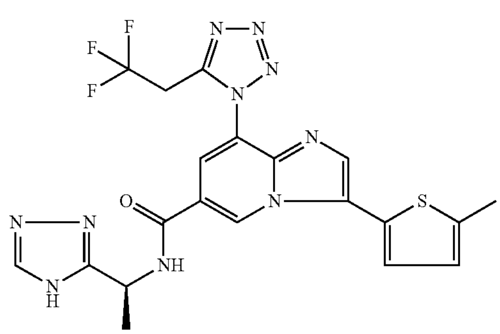 | 503.2 [M + H] + | 18 |

TABLE 1-continued
| Ex. No. | Structure | LCMS | Prepared by method of Example No. |
|---|---|---|---|
| 182 | 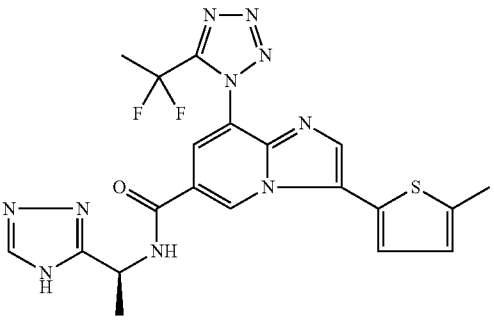 [SMILES: Cc1ccc(-c2cnc3c(-n4nnnc4C(C)(F)F)cc(C(=O)N[C@@H](C)c4nnc[nH]4)cn23)s1] | 485.2 [M + H] + | 18 |
| 183 | 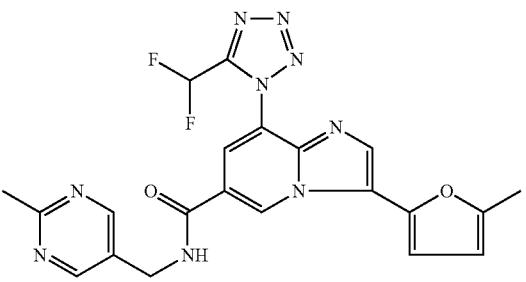 | 466.4 [M + H] + | 18 |
| 184 | 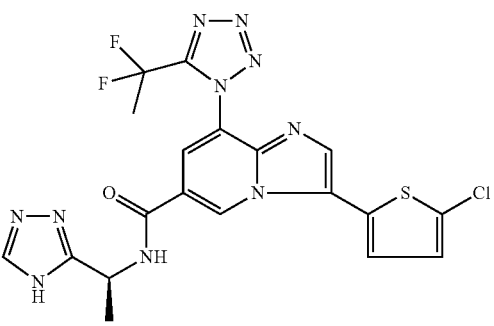 [SMILES: C[C@H](NC(=O)c1cc(-n2nnnc2C(C)(F)F)c2ncc(-c3ccc(Cl)s3)n2c1)c1nnc[nH]1] | 505.2 [M + H] + | 18 |
| 185 | 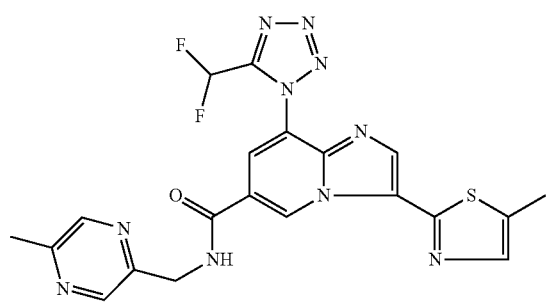 | 483.0 [M + H] + | 18 |
| 186 | 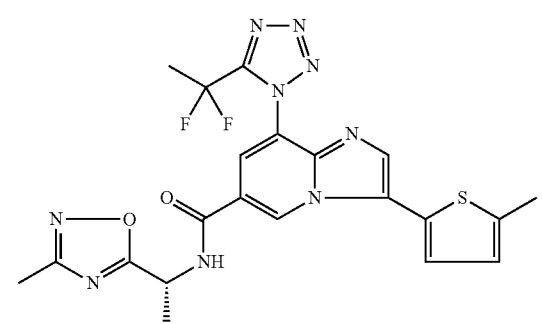 | 500.1 [M + H] + | 19 |

TABLE 1-continued

| Ex. No. | Structure | LCMS | Prepared by method of Example No. |
|---|---|---|---|
| 187 | 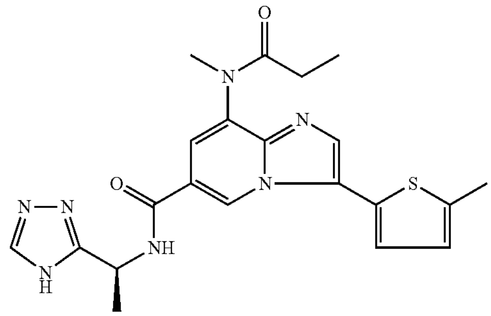 [SMILES: CCC(=O)N(C)c1cc(C(=O)N[C@@H](C)c2nnc[nH]2)cn2c(-c3ccc(C)s3)cnc12] | 438.0 [M + H] + | 20 |
| 188 | 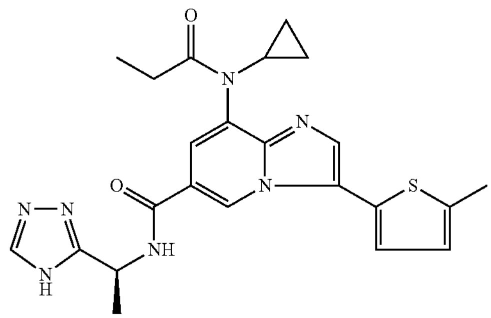 [SMILES: CCC(=O)N(c1cc(C(=O)N[C@@H](C)c2nnc[nH]2)cn2c(-c3ccc(C)s3)cnc12)C1CC1] | 464.2 [M + H] + | 20 |

Example 189: In Vitro Studies

A. Cloning

The FLIPR® assay utilizes cells which express human or rat P2X3 or P2X2/3 receptors. Recombinant cells expressing hP2X3 (Cat#6188) and hP2X2/3 (Cat#6179) were procured from Chantest Corp. Rat P2X2 (NCBI Accession No: U14414) was amplified by PCR from PC12 cDNA (a rat adrenal medulla cell line). The PCR product obtained containing the protein coding sequence of rat P2X2 was cloned into EcoRV-digested and dephosphorylated vector pIRES-puro3 within the multiple cloning site (MCS). See, FIG. 1A.

Figure 1B:
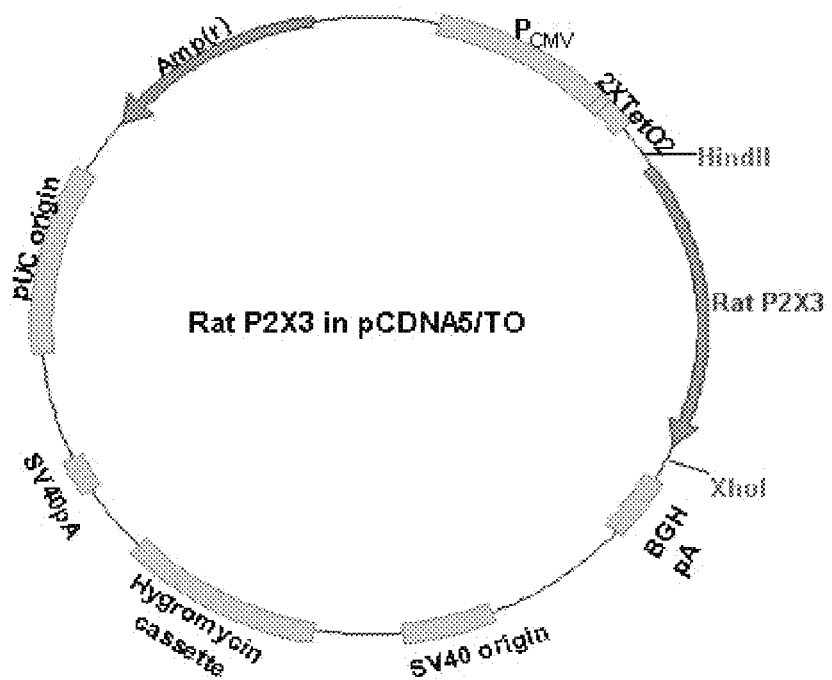
FIG. 1B is a map of a circular plasmid pCDNA-Hygro (Invitrogen) into which the coding sequence of rat P2X3 (NCBI Accession No: X91167), amplified by PCR from rat brain cDNA, has been cloned. The PCR product obtained containing the protein coding sequence of rat P2X3 was cloned into EcoRV-digested and dephosphorylated vector pCDNA-Hygro within the multiple cloning site (MCS).
Figure 1C:
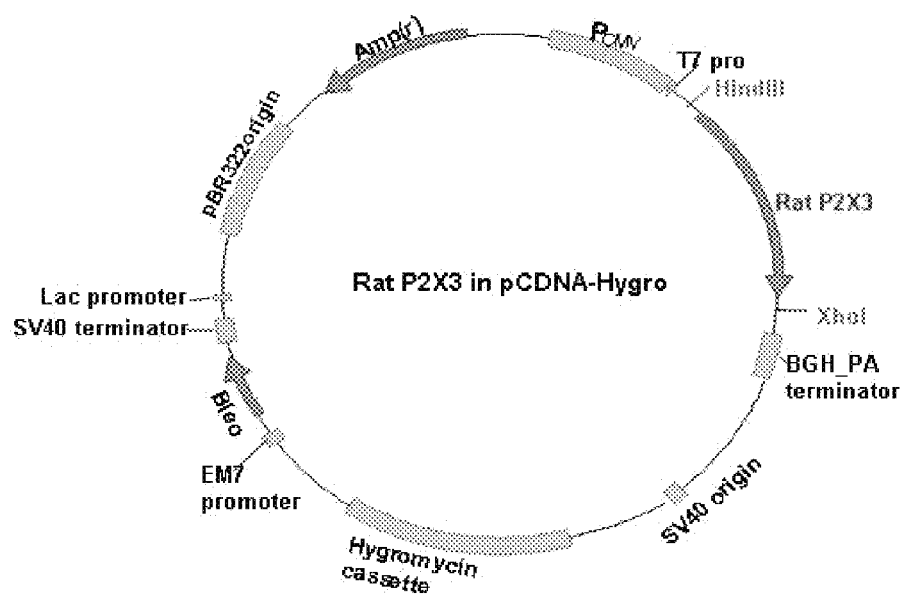
FIG. 1C is a vector generated from the pcDNA-Hygro containing the rat P2X3, which was then subcloned into pcDNA-5/TO (Invitrogen/Life Technologies) at HindIII (5') and XhoI (3') sites within the multiple cloning site (MCS) of the vector.

Rat P2X3 (NCBI Accession No: X91167) was amplified by PCR from rat brain cDNA. The PCR product obtained containing the protein coding sequence of rat P2X3 was cloned into EcoRV-digested and dephosphorylated vector pCDNA-Hygro within the multiple cloning site (MCS) (FIG. 1B). Rat P2X3 cloned into pcDNA-Hygro was then subcloned into pcDNA-5/TO at HindIII (5') and XhoI (3') sites within the multiple cloning site (MCS) of the vector (FIG. 1C).

All the constructs yielding the recombinant vector DNA were used for transfection and generation of the cell lines, after sequence verification.

B. Development of Recombinant TRex293 Cells Expressing rP2X2/3 and CHO-TRex Cells Expressing rP2X3

Transfection was carried out using super-coiled constructs (purified using QIAGEN kit) in antibiotic free, serum free DMEM using Lipofectamine® 2000 (Invitrogen) transfection agent. The DNA constructs rat P2X2 in pIRES-Puro3 and rat P2X3 in pCDNA5/TO were co-transfected into TRex293 cells in order to generate the rP2X2/3 stable line. 50 µg/mL hygromycin (Invitrogen) and 0.5 µg/mL puromycin (Fermentek) were used for selection of stable clones of rP2X2/3. Rat P2X3 in pCDNA5/TO DNA construct was transfected to CHO-TRex cells to generate the rP2×3 stable line and 500 µg/mL hygromycin (Invitrogen) was used as selection antibiotic. Transfected stable colonies were then functionally verified and robust clones suitable for assay were clonally purified through dilutions.

C. Assay Protocols (i) Intracellular Calcium Assay Protocol for Screening Compounds Cryo-vial containing $6 \times 10^6$ cells (human P2X3-HEK/human P2X2/3-TRex293/rat P2X2/3-TRex293/rat P2X3 TRex-CHO) was thawed in a 37° C. water bath. Cells were suspended in 20 mL of respective cell plating media (See annexure for composition) in a 50 mL centrifuge tube. The cell viability was checked with the help of Trypan Blue dye. Upon washing, cells were plated in a black 384-well clear bottomed, sterile poly-D-lysine coated plate such that, each well contained 10,000 cells (15,000/well for hP2X3) in 30 µL cell plating media. The plate was incubated in a 5% $CO_2$ incubator at 37° C. for 24 h.

The next day, prior to the assay, the cell plating media was removed from each well by decanting and gentle tapping. Thirty µL of FLIPR Calcium 4 dye solution was added to each well. The plate was incubated at 37° C. for 45 min (60 min for hP2X3). The plate was next equilibrated at room temperature for 15 minutes before placing it in a 384 well FLIPR for the assay.

Compounds were dissolved in DMSO and serially diluted following 11 point half log (3.16 fold) dilution with a starting concentration of 2 mM. Dilutions were mixed with assay buffer just before performing the assay.

Compounds were added to the respective wells of the assay-ready cell plate with the help of the FLIPR and fluorescence readings were captured for 5 min to observe any possible agonistic property of the compounds. The plate was then incubated at room temperature for 15 min. The cells were stimulated with respective agonist $EC_{75}$ concentration and the fluorescence readings were captured for another 5 min by FLIPR. The difference in fluorescence readings in presence of the compounds were compared with that of the control wells (wells having no compound) to calculate the inhibitory potency of the compounds. The $IC_{50}$ values of the compounds were determined using the Graph pad Prism software.

(ii) Cell Plating Media for hP$_2$X3-HEK and hP$_2$X$_{2/3}$-TRex293 Cells
  DMEM/F12(1:1) HAM media (Invitrogen; Cat#11039)
  1×NEAA (Invitrogen; Cat#11140)
  25 mM HEPES (Invitrogen; Cat#15630)
  1 mM sodium pyruvate (Invitrogen; Cat#11360)
  10% tetracycline negative FBS (PAA; Cat#A15-209)
  1 g/mL doxycycline (Clontech; Cat#63131) [for hP2X2/3-TRex293 cells only]
(iii) Cell Plating Media for rP$_2$X$_{2/3}$-TRex293 Cells
  DMEM media (Invitrogen; Cat#11965)
  25 mM HEPES (Invitrogen; Cat#15630)
  10% tetracycline negative FBS (PAA; Cat#A15-209)
  1 g/mL Doxycycline (Clontech; Cat#63131)
(iv) Cell Plating Media for rP$_2$X$_3$-CHOTRex Cells
  F-12 nutrient mixture (HAM) IX (Invitrogen; Cat#11765)
  1× Glutamax™ (Invitrogen; Cat#35050)
  10% tetracycline negative FBS (PAA; Cat#A15-209)
  1 g/mL doxycycline (Clontech; Cat#63131)
(v) Assay Buffer Composition
  HBSS (Invitrogen Cat#14025)
  20 mM HEPES (Invitrogen Cat#15630)
  0.01% F127 (Sigma Cat#P2443)
  1.8 mM $CaCl_2$ (Sigma Cat#C5080)
  pH adjusted to 7.4
(vi) Dye Solution Composition
  IX FLIPR Calcium 4 dye in assay buffer (Molecular devices Cat#R8141)
  1.8 mM Probenecid (Sigma Cat#P8761)
  pH adjusted to 7.4

Data from the P2X$_3$ and P2X$_{2/3}$ FLIPR assays for Examples 1-188 are shown in Table 2.

TABLE 2

| Example | P2X$_3$ | P2X$_{2/3}$ |
| --- | --- | --- |
| 1 | B | C |
| 2 | D | B |
| 3 | C | B |
| 4 | A | A |
| 5 | B | B |
| 6 | D | B |
| 7 | A | B |
| 8 | A | B |
| 9 | C | C |
| 10 | B | C |
| 11 | A | B |
| 12 | A | A |
| 13 | D | B |
| 14 | A | B |
| 15 | B | C |
| 16 | D | B |
| 17 | B | B |
| 18 | A | A |
| 19 | A | A |
| 20 | A | B |
| 21 | A | B |
| 22 | A | A |
| 23 | A | B |
| 24 | A | A |
| 25 | A | A |
| 26 | A | A |
| 27 | A | A |
| 28 | A | A |
| 29 | A | B |
| 30 | A | A |
| 31 | A | A |
| 32 | A | A |
| 33 | A | A |
| 34 | A | A |
| 35 | A | A |
| 36 | A | A |
| 37 | A | A |
| 38 | A | A |
| 39 | A | A |
| 40 | D | A |
| 41 | A | A |
| 42 | A | A |
| 43 | A | A |
| 44 | A | A |
| 45 | D | A |
| 46 | A | A |
| 47 | A | A |
| 48 | A | A |
| 49 | D | A |
| 50 | A | B |
| 51 | B | C |
| 52 | A | A |
| 53 | A | A |
| 54 | A | A |
| 55 | D | B |
| 56 | A | B |
| 57 | A | B |
| 58 | A | A |
| 59 | B | C |
| 60 | A | A |
| 61 | A | A |
| 62 | A | B |
| 63 | A | A |
| 64 | A | B |
| 65 | A | A |
| 66 | B | B |
| 67 | A | A |
| 68 | A | B |
| 69 | A | B |
| 70 | A | A |
| 71 | A | B |
| 72 | A | A |
| 73 | B | B |
| 74 | B | C |
| 75 | A | B |
| 76 | A | A |
| 77 | A | B |
| 78 | A | A |
| 79 | A | A |
| 80 | A | A |
| 81 | A | A |
| 82 | A | B |
| 83 | A | A |
| 84 | A | A |
| 85 | A | A |
| 86 | B | B |
| 87 | B | B |
| 88 | D | A |
| 89 | A | B |
| 90 | A | C |
| 91 | B | C |
| 92 | B | C |
| 93 | B | C |
| 94 | A | C |
| 95 | A | D |
| 96 | B | B |
| 97 | A | B |
| 98 | C | B |
| 99 | A | C |
| 100 | A | B |
| 101 | A | A |
| 102 | A | A |
| 103 | A | B |
| 104 | A | B |
| 105 | A | B |

TABLE 2-continued

| Example | P2X$_3$ | P2X$_{2/3}$ |
|---|---|---|
| 106 | D | A |
| 107 | A | A |
| 108 | A | A |
| 109 | A | B |
| 110 | A | A |
| 111 | D | A |
| 112 | B | C |
| 113 | A | B |
| 114 | A | V |
| 115 | C | B |
| 116 | C | B |
| 117 | A | A |
| 118 | B | B |
| 119 | A | B |
| 120 | A | A |
| 121 | B | B |
| 122 | A | A |
| 123 | D | A |
| 124 | B | B |
| 125 | B | B |
| 126 | D | A |
| 127 | D | A |
| 128 | A | B |
| 129 | A | B |
| 130 | A | A |
| 131 | A | B |
| 132 | A | A |
| 133 | A | B |
| 134 | A | C |
| 135 | B | B |
| 136 | A | B |
| 137 | A | B |
| 138 | A | B |
| 139 | A | B |
| 140 | A | B |
| 141 | A | B |
| 142 | A | B |
| 143 | C | B |
| 144 | B | A |
| 145 | C | B |
| 146 | A | B |
| 147 | C | B |
| 148 | A | A |
| 149 | B | C |
| 150 | A | B |
| 151 | A | B |
| 152 | D | B |
| 153 | D | A |
| 154 | B | B |
| 155 | D | A |
| 156 | D | A |
| 157 | A | B |
| 158 | D | A |
| 159 | B | C |
| 160 | D | B |
| 161 | D | A |
| 162 | A | C |
| 163 | D | A |
| 164 | D | A |
| 165 | A | A |
| 166 | A | A |
| 167 | A | B |
| 168 | A | A |
| 169 | A | A |
| 170 | A | A |
| 171 | A | A |
| 172 | A | A |
| 173 | B | B |
| 174 | A | A |
| 175 | B | C |
| 176 | B | B |
| 177 | A | A |
| 178 | A | B |
| 179 | A | A |
| 180 | A | A |
| 181 | A | A |
| 182 | A | A |
| 183 | B | B |
| 184 | A | A |
| 185 | B | C |
| 186 | D | A |
| 187 | A | B |
| 188 | A | B |

A: IC$_{50}$ = 1-100 nM
B: IC$_{50}$ = >100-1000 nM
C: IC$_{50}$ = >1000-10,000 nM
D: IC$_{50}$ >10,000 nM

Example 190: In Vivo Thermal Hyperalgesia (Hargreaves Test) Studies in the Rat

Male Sprague Dawley rats of young adult age group and body weight range of 180-200 g were included in the study. Animals were housed under a 12 h light/dark cycle with food and water ad libitum. The animals underwent acclimatization with the observation chambers of the Hargreaves' apparatus for two days, twice daily for 45-60 min each time prior to initiation of study. Animals were also habituated to the apparatus for 15-30 min before each testing. Thermal hyperalgesia was assessed using the rat plantar test (Ugo Basile, Italy) following a modified method of Hargreaves (1988, "A new and sensitive method for measuring thermal nociception in cutaneous hyperalgesia", Pain 32: 77-88).

For measurement of Paw withdrawal latency (PWL) values the rats were exposed to a mobile infrared heat source applied directly below the plantar surface of the rat hind paw. The paw withdrawal latency (PWL) was defined as the time in seconds taken by the rat to remove its hind paw from the heat source. Thirty three percent IR of the instrument was used to measure PWL. Animals showing basal response between 8-14 sec on an untreated paw were included in the study. A cut off point of 20 sec was used to prevent tissue damage.

Following basal readout of PWL values to the thermal stimulus (PWL measurements described previously), 50 μL of complete Freund's Adjuvant (CFA—1 mg/mL suspension—Sigma, USA, Cat #F5881) was injected subcutaneously into the plantar surface of the right hind (ipsilateral) paw of animals under light isoflurane anesthesia. A one mL syringe and 26 g$^{1/2}$-inch needle was used for the injection. CFA suspension was mixed thoroughly before each injection. Light pressure was applied to the injection site for 10 s immediately after the needle was removed from the paw to prevent any leaking out of adjuvant oil from the injection site. The rats were then returned to their housing to recover and kept in soft bedding.

Next day (day 1) after 20-22 h of CFA injection, PWL of animals were recorded. Mean of three readings are taken as PWL recording of ipsilateral paw of each animal for pre and post CFA basal readout. Animals with PWL values of ≤6 sec on day 1 post CFA injection were considered hyperalgesic and selected for randomization into treatment groups and further test sessions following a single blind protocol.

Figure 2:
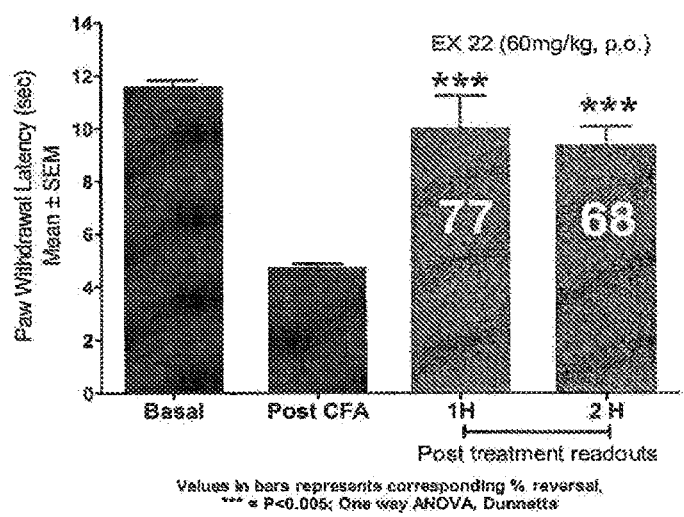
FIG. 2 illustrates the antihyperalgesic effects of the compound of example 22 in a rat model of inflammatory thermal hyperalgesia induced by an intraplantar injection of Complete Freund's Adjuvant (CFA). Thermal hyperalgesia is manifest as a reduction in the time for foot-withdrawal during irradiation with a painful thermal stimulus. The compound of example 22 was administered at a dose of 60 mg/kg, 48 h after footpad injection of CFA and produced a substantial reversal (77% and 68%) of thermal hyperalgesia when assessed at 1 h and 2 h post-dose, respectively.
Figure 5:
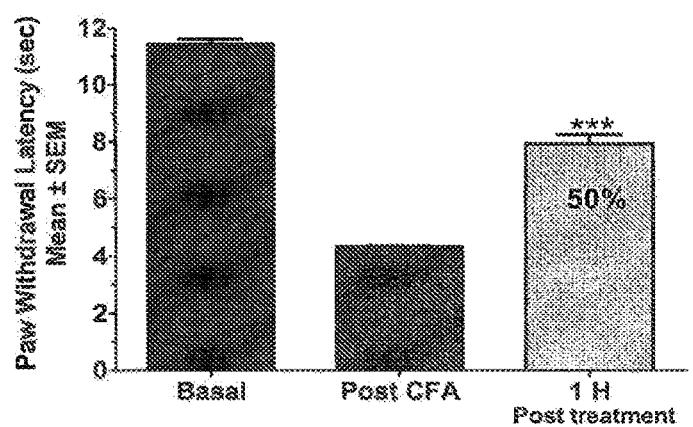
FIG. 5 illustrates the antihyperalgesic effects of the compound of example 38 in a rat model of inflammatory thermal hyperalgesia induced by an intraplantar injection of CFA. Thermal hyperalgesia is manifest as a reduction in the time for foot-withdrawal during irradiation with a painful thermal stimulus. The compound of example 38 was administered at a dose of 60 mg/kg, 48 h after footpad injection of CFA and produced a substantial reversal (50%) of thermal hyperalgesia when assessed at 1 h post-dose.
Figure 6:
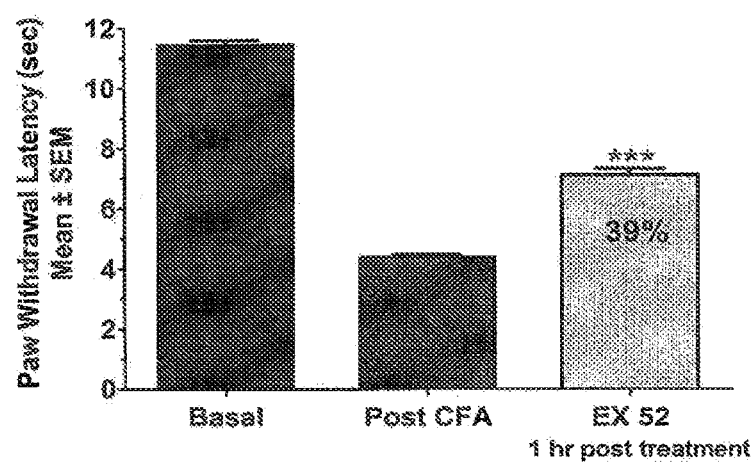
FIG. 6 illustrates the antihyperalgesic effects of the compound of example 52 in a rat model of inflammatory thermal hyperalgesia induced by an intraplantar injection of CFA. Thermal hyperalgesia is manifest as a reduction in the time for foot-withdrawal during irradiation with a painful thermal stimulus. The compound of example 52 was administered at a dose of 60 mg/kg, 48 h after footpad injection of CFA and produced a substantial reversal (39%) of thermal hyperalgesia when assessed at 1 h post-dose.

In the test session, PWL was assessed at 1 h post oral dosing of CE test article, vehicle (20% polyethylene glycol, 1% Tween™ 80, 79% water) and naproxen (positive control). See, e.g., FIG. 2 (compound of Example 22), FIG. 5 (compound of Example 38) and FIG. 6 (compound of Example 52).

Statistical analysis was done with One way ANOVA followed by Dunnett's multiple comparison post test. Post treatment PWL values were compared with pre treatment PWL values and p<0.05 was considered statistically significant. Each group comprised of 8 animals.

Figure 3:
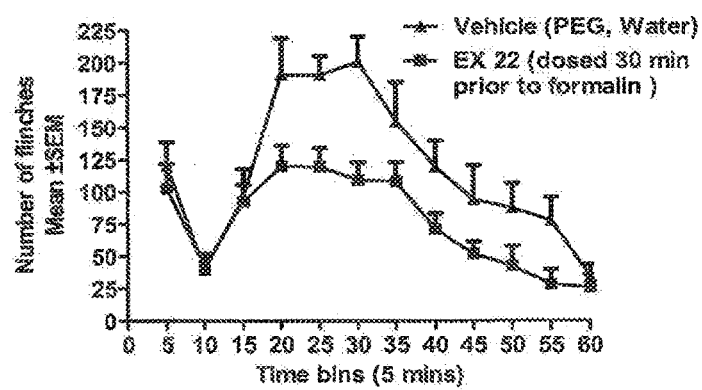
FIG. 3 illustrates the antinociceptive effects of the compound of example 22 in a rat model of ongoing spontaneous pain. The compound of example 22 was administered by oral gavage at a dose of 100 mg/kg followed 30 min later by a footpad injection of a dilute formalin solution. Formalin elicits a typical biphasic nociceptive response that manifests as spontaneous hind limb flinches which are counted and binned over 5 min epochs. The compound of example 22 attenuated the second phase flinching response to formalin a profile that is consistent with an antinociceptive action.

Example 191: Formalin Induced Pain (Automated Nociception Analyzer Test) in the Rat Male Sprague Dawley rats of young adult age group and body weight range of 200-250 g were included in the study. Animals were housed under a 12 h light/dark cycle with food and water ad libitum. Animals were acclimatized in the observation chambers of Automated Nociception Analyzer (ANA) for 45-60 min, twice daily for two days prior to the study day. On the day of the study, metal bands were glued to the plantar surface of the right hind paw of each animal enrolled in the study set and kept in plastic observation chambers for 10-15 min. Formalin injection was done in the animals after 0.5 or 1 h of oral treatment with test compound or vehicle (20% polyethylene glycol, 1% Tween™ 80 reagent, 79% water). Formalin injection of the animals was done with 50 µL of 2.5% formalin (freshly prepared from formaldehyde solution, Sigma, USA, Cat #F8775) injected subcutaneously in to the dorsum of right hind paw. Animals were placed back to their respective recording chambers of ANA immediately after injection. Flinch count data for each animal was recorded from 1 to 60 min post formalin injection, using ANA motion analysis software. The study was analyzed in 2 phases, the early phase extended from 0-10 min and second phase extended from 11-60 min post formalin injection. The data was collected in 5 min time bins and the counts of each bin were added up for total count of the phase. See, e.g., FIG. 3 (test compound of Example 22).

Statistical analysis was done with unpaired t test. Comparison was done between total count of treatment groups and vehicle group and p<0.05 was considered statistically significant. Eight animals were typically used in each of test article and vehicle treated groups.

Example 192: Acetic Acid Induced Writhing Test in Mice

Figure 4:
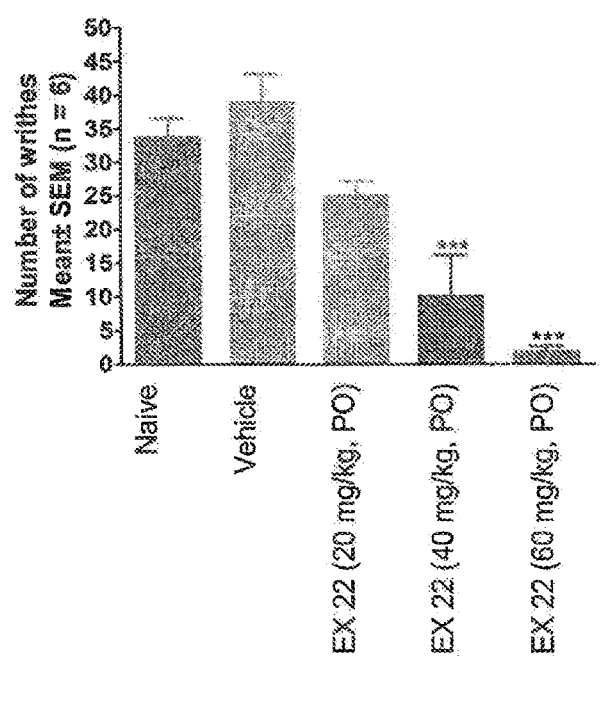
FIG. 4 illustrates the antinociceptive effects of the compound of example 22 in a mouse model of visceral pain. The compound of example 22 was administered by oral gavage at 3 dose levels (20, 40 and 60 mg/kg) 30 min prior to an intraperitoneal injection of a dilute acetic acid solution. When injected into the abdominal cavity, acetic acid induces a distinctive stretching response in the abdomen and at least one hind limb that is assumed to reflect a response to visceral pain. The compound of example 22 produced a clear dose-related reduction in the pain responses when assessed for a total of 15 min post acetic acid injection. Statistical significance is indicated with respect to the vehicle control group and was performed using a one-way ANOVA followed by Dunnett's multiple comparison test.

Swiss albino mice of 30-40 g were included in the study. The mice were given an intraperitoneal injection of 0.7% v/v acetic acid solution at an injection volume of 10 mL/kg, 30 min after oral administration of vehicle or test article control. Test articles were administered, typically, at doses between 20 and 60 mg/kg. The mice were placed individually into glass chambers. The number of writhes produced in these animals was counted for 15 min following acetic acid administration. For scoring purposes writhing was indicated by stretching of the abdomen with simultaneous stretching of at least one hind limb. See, e.g., FIG. 4.

Statistical analysis was done with One way ANOVA followed by Dunnett's multiple comparison tests. Comparison was done between treatment groups and vehicle with respect to total number of writhes and p<0.05 was considered statistically significant. Each group comprised of 6 animals.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A compound of the structure of formula (IV):

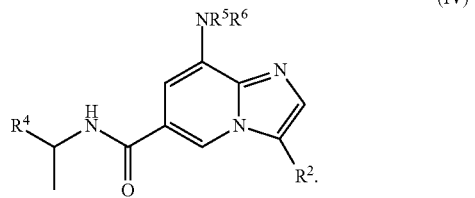

wherein:
$R^1$ is optionally substituted heteroaryl or $NR^5R^6$;
$R^2$ is optionally substituted aryl, optionally substituted heteroaryl, $C_1$ to $C_6$ alkyl, or $S-C_1$ to $C_6$ alkyl;
$R^3$ is H or $C_1$ to $C_6$ alkyl;
$R^4$ is optionally substituted heteroaryl;
$R^5$ and $R^6$ are, independently, selected from the group consisting of H, optionally substituted $C_1$ to $C_6$ alkyl, $C_3$ to $C_6$ cycloalkyl, optionally substituted aryl, optionally substituted heteroaryl, and $CO(C_1$ to $C_6$ alkyl); or
$R^5$ and $R^6$ are joined to form a 5 or 6-membered heterocyclic ring optionally substituted by one or more of halogen, $C_1$ to $C_6$ alkyl, $C_1$ to $C_6$ alkoxy, $C_1$ to $C_6$ hydroxyalkyl, $C_3$ to $C_6$ cycloalkyl, $C_1$ to $C_6$ alkyl containing 1 to 3 fluorine atoms, $C_3$ to $C_6$ cycloalkyl-$C_1$ to $C_6$ alkyl, or $CONH_2$;
or a pharmaceutically acceptable salt or prodrug thereof.

2. A compound of the structure of formula (I):

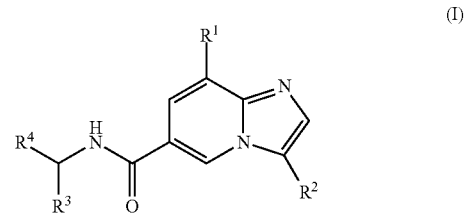

wherein:
$R^1$ is optionally substituted heteroaryl or $NR^5R^6$;
$R^2$ is optionally substituted heteroaryl;
$R^3$ is H or $C_1$ to $C_6$ alkyl;
$R^4$ is optionally substituted heteroaryl;
$R^5$ and $R^6$ are, independently, selected from the group consisting of H, optionally substituted $C_1$ to $C_6$ alkyl, $C_3$ to $C_6$ cycloalkyl, optionally substituted aryl, optionally substituted heteroaryl, and $CO(C_1$ to $C_6$ alkyl); or
$R^5$ and $R^6$ are joined to form a 5 or 6-membered heterocyclic ring optionally substituted by one or more of halogen, $C_1$ to $C_6$ alkyl, $C_1$ to $C_6$ alkoxy, $C_1$ to $C_6$ hydroxyalkyl, $C_3$ to $C_6$ cycloalkyl, $C_1$ to $C_6$ alkyl containing 1 to 3 fluorine atoms, $C_3$ to $C_6$ cycloalkyl-$C_1$ to $C_6$ alkyl, or $CONH_2$;
or a pharmaceutically acceptable salt or prodrug thereof.

3. A compound of the structure of formula (I):

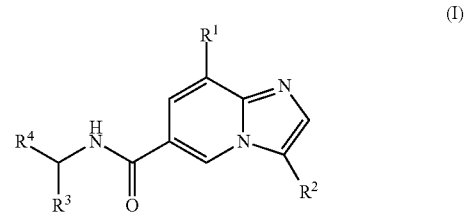

wherein:
$R^1$ is optionally substituted heteroaryl or $NR^5R^6$;
$R^2$ is heteroaryl substituted with one or more halogen, cyano, $C_1$ to $C_6$ alkyl, or $C_1$ to $C_6$ alkyl containing 1-3 fluorine atoms;
$R^3$ is H or $C_1$ to $C_6$ alkyl;
$R^4$ is optionally substituted heteroaryl;

R⁵ and R⁶ are, independently, selected from the group consisting of H, optionally substituted $C_1$ to $C_6$ alkyl, $C_3$ to $C_6$ cycloalkyl, optionally substituted aryl, optionally substituted heteroaryl, and CO($C_1$ to $C_6$ alkyl); or R⁵ and R⁶ are joined to form a 5 or 6-membered heterocyclic ring optionally substituted by one or more of halogen, $C_1$ to $C_6$ alkyl, $C_1$ to $C_6$ alkoxy, $C_1$ to $C_6$ hydroxyalkyl, $C_3$ to $C_6$ cycloalkyl, $C_1$ to $C_6$ alkyl containing 1 to 3 fluorine atoms, $C_3$ to $C_6$ cycloalkyl-$C_1$ to $C_6$ alkyl, or $CONH_2$;

or a pharmaceutically acceptable salt or prodrug thereof.

4. A compound of the structure of formula (I):

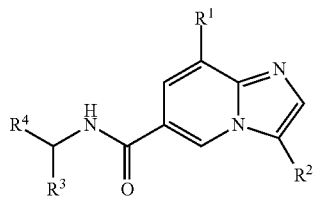

(I)

wherein:
R¹ is optionally substituted heteroaryl or NR⁵R⁶;
R² is thiazole, thiophene, or furan;
R³ is H or $C_1$ to $C_6$ alkyl;
R⁴ is optionally substituted heteroaryl;
R⁵ and R⁶ are, independently, selected from the group consisting of H, optionally substituted $C_1$ to $C_6$ alkyl, $C_3$ to $C_6$ cycloalkyl, optionally substituted aryl, optionally substituted heteroaryl, and CO($C_1$ to $C_6$ alkyl); or
R⁵ and R⁶ are joined to form a 5 or 6-membered heterocyclic ring optionally substituted by one or more of halogen, $C_1$ to $C_6$ alkyl, $C_1$ to $C_6$ alkoxy, $C_1$ to $C_6$ hydroxyalkyl, $C_3$ to $C_6$ cycloalkyl, $C_1$ to $C_6$ alkyl containing 1 to 3 fluorine atoms, $C_3$ to $C_6$ cycloalkyl-$C_1$ to $C_6$ alkyl, or $CONH_2$;

or a pharmaceutically acceptable salt or prodrug thereof.

5. A compound of the structure of formula (I):

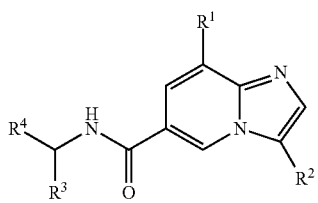

(I)

wherein:
R¹ is optionally substituted heteroaryl or NR⁵R⁶;
R² is thiophene substituted with one or more of halogen, cyano, $C_1$ to $C_6$ alkyl, or $C_1$ to $C_6$ alkyl containing 1-3 fluorine atoms;
R³ is H or $C_1$ to $C_6$ alkyl;
R⁴ is optionally substituted heteroaryl;
R⁵ and R⁶ are, independently, selected from the group consisting of H, optionally substituted $C_1$ to $C_6$ alkyl, $C_3$ to $C_6$ cycloalkyl, optionally substituted aryl, optionally substituted heteroaryl, and CO($C_1$ to $C_6$ alkyl); or
R⁵ and R⁶ are joined to form a 5 or 6-membered heterocyclic ring optionally substituted by one or more of halogen, $C_1$ to $C_6$ alkyl, $C_1$ to $C_6$ alkoxy, $C_1$ to $C_6$ hydroxyalkyl, $C_3$ to $C_6$ cycloalkyl, $C_1$ to $C_6$ alkyl containing 1 to 3 fluorine atoms, $C_3$ to $C_6$ cycloalkyl-$C_1$ to $C_6$ alkyl, or $CONH_2$;

or a pharmaceutically acceptable salt or prodrug thereof.

6. A compound of the structure of formula (I):

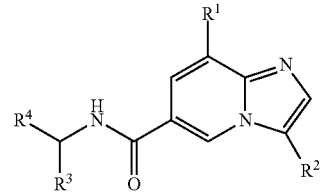

(I)

wherein:
R¹ is optionally substituted heteroaryl or NR R⁶;
R² is 2-chloro-thiophene, 2-methyl-thiophene, 2-cyano-thiophene, 2-trifluoromethyl-thiophene, 5-methyl-thiazole, 2-methyl-thiazole, or 2-methyl-furan;
R³ is H or $C_1$ to $C_6$ alkyl;
R⁴ is optionally substituted heteroaryl;
R⁵ and R⁶ are, independently, selected from the group consisting of H, optionally substituted $C_1$ to $C_6$ alkyl, $C_3$ to $C_6$ cycloalkyl, optionally substituted aryl, optionally substituted heteroaryl, and CO($C_1$ to $C_6$ alkyl); or
R⁵ and R⁶ are joined to form a 5 or 6-membered heterocyclic ring optionally substituted by one or more of halogen, $C_1$ to $C_6$ alkyl, $C_1$ to $C_6$ alkoxy, $C_1$ to $C_6$ hydroxyalkyl, $C_3$ to $C_6$ cycloalkyl, $C_1$ to $C_6$ alkyl containing 1 to 3 fluorine atoms, $C_3$ to $C_6$ cycloalkyl-$C_1$ to $C_6$ alkyl, or $CONH_2$;

or a pharmaceutically acceptable salt or prodrug thereof.

7. A compound selected from the group consisting of
(S)—N-(1-(4H-1,2,4-triazol-3-yl)ethyl)-8-(5-ethyl-1,3,4-oxadiazol-2-yl)-3-(5-methylthiophen-2-yl)imidazo[1,2-a]pyridine-6-carboxamide,
8-(2,5-dimethyl-1H-imidazol-1-yl)-N-((6-methylpyridin-3-yl)methyl)-3-(5-methylthiophen-2-yl)imidazo[1,2-a]pyridine-6-carboxamide,
(S)—N-(1-(4H-1,2,4-triazol-3-yl)ethyl)-8-(3,5-dimethyl-4H-1,2,4-triazol-4-yl)-3-(5-methylthiophen-2-yl)imidazo[1,2-a]pyridine-6-carboxamide,
(S)—N-(1-(4H-1,2,4-triazol-3-yl)ethyl)-8-(5-(difluoromethyl)-1H-1,2,3-triazol-1-yl)-3-(5-methylthiophen-2-yl)imidazo[1,2-a]pyridine-6-carboxamide,
8-(5-(difluoromethyl)-1H-1,2,3-triazol-1l-yl)-3-(5-methyl-1,3,4-thiadiazol-2-yl)-N-((6-methylpyridin-3-yl)methyl)imidazo[1,2-a]pyridine-6-carboxamide,
8-(5-ethyl-1H-pyrazol-1-yl)-N-((6-methylpyridin-3-yl)methyl)-3-(5-methylthiophen-2-yl)imidazo[1,2-a]pyridine-6-carboxamide,
(S)—N-(1-(4H-1,2,4-triazol-3-yl)ethyl)-3-(5-methylthiophen-2-yl)-8-(phenylamino)imidazo[1,2-a]pyridine-6-carboxamide,
(S)—N-(1-(4H-1,2,4-triazol-3-yl)ethyl)-8-(1-methyl-1H-pyrazol-4-yl)-3-(5-methylthiophen-2-yl)imidazo[1,2-a]pyridine-6-carboxamide,
(S)—N-(1-(4H-1,2,4-triazol-3-yl)ethyl)-3-butyl-8-(4-methylpiperidin-1-yl)imidazo[1,2-a]pyridine-6-carboxamide,
(S)—N-(1-(4H-1,2,4-triazol-3-yl)ethyl)-8-(4-methylpiperidin-1-yl)-3-(propylthio)imidazo[1,2-a]pyridine-6-carboxamide, (S)—N-(1-(4H-1,2,4-triazol-3-yl)ethyl)-8-(4-methylpip-eridin-1-yl)-3-(5-methylthiophen-2-yl)imidazo[1,2-a]pyridine-6-carboxamide, (S)—N-(1-(4H-1,2,4-triazol-3-yl)ethyl)-8-(4-carbamoyl-4-methylpiperidin-1-yl)-3-(5-methylthiophen-2-yl)imidazo[1,2-a]pyridine-6-carboxamide, 8-(4-carbamoylpiperazin-1-yl)-N-((6-methylpyridin-3-yl)methyl)-3-(5-methylthiophen-2-yl)imidazo[1,2-a]pyridine-6-carboxamide (S)—N-(1-(1,3,4-oxadiazol-2-yl)ethyl)-8-(5-(difluorom-ethyl)-1H-1,2,3-triazol-1-yl)-3-(5-methylthiophen-2-yl)imidazo[1,2-a]pyridine-6-carboxamide, (S)—N-(1-(4H-1,2,4-triazol-3-yl)ethyl)-8-(4-methylpip-eridin-1-yl)-3-(o-tolyl)imidazo[1,2-a]pyridine-6-car-boxamide, 8-(5-cyclopropyl-1H-tetrazol-1-yl)-N-((6-methylpyridin-3-yl)methyl)-3-(5-methylthiophen-2-yl)imidazo[1,2-a]pyridine-6-carboxamide, 8-(5-(hydroxymethyl)-1H-tetrazol-1-yl)-N-((6-methyl-pyridin-3-yl)methyl)-3-(5-methylthiophen-2-yl)imi-dazo[1,2-a]pyridine-6-carboxamide, 8-(5-(difluoromethyl)-1H-tetrazol-1-yl)-N-((6-methyl-pyridin-3-yl)methyl)-3-(5-methylthiophen-2-yl)imi-dazo[1,2-a]pyridine-6-carboxamide, (R)-8-(5-(difluoromethyl)-1H-tetrazol-1-yl)-N-(1-(3-methyl-1,2,4-oxadiazol-5-yl)ethyl)-3-(5-methylthio-phen-2-yl)imidazo[1,2-a]pyridine-6-carboxamide, (S)—N-(1-(4H-1,2,4-triazol-3-yl)ethyl)-8-(N-methyl-isobutyramido)-3-(5-methylthiophen-2-yl)imidazo[1,2-a]pyridine-6-carboxamide, 8-(5-ethyl-1,3,4-oxadiazol-2-yl)-N-((6-methylpyridin-3-yl)methyl)-3-(5-methylthiophen-2-yl)imidazo[1,2-a]pyridine-6-carboxamide, 8-(5-ethyl-1H-1,2,3-triazol-1-yl)-N-((6-methylpyridin-3-yl)methyl)-3-(5-methylthiophen-2-yl)imidazo[1,2-a]pyridine-6-carboxamide, (S)—N-(1-(4H-1,2,4-triazol-3-yl)ethyl)-8-(5-ethyl-1H-1,2,3-triazol-1-yl)-3-(5-methylthiophen-2-yl)imidazo[1,2-a]pyridine-6-carboxamide, 8-(5-ethyl-1H-1,2,3-triazol-1-yl)-N-((5-methylpyrazin-2-yl)methyl)-3-(5-methylthiophen-2-yl)imidazo[1,2-a]pyridine-6-carboxamide, 8-(5-cyclopropyl-1H-1,2,3-triazol-1-yl)-N-((6-methyl-pyridin-3-yl)methyl)-3-(5-methylthiophen-2-yl)imi-dazo[1,2-a]pyridine-6-carboxamide, (S)—N-(1-(4H-1,2,4-triazol-3-yl)ethyl)-3-(5-methylthio-phen-2-yl)-8-(5-(trifluoromethyl)-1H-1,2,3-triazol-1-yl)imidazo[1,2-a]pyridine-6-carboxamide, 8-(5-(difluoromethyl)-1H-1,2,3-triazol-1-yl)-N-((6-meth-ylpyridin-3-yl)methyl)-3-(5-methylthiophen-2-yl)imi-dazo[1,2-a]pyridine-6-carboxamide, 8-(5-methyl-1H-1,2,3-triazol-1-yl)-N-((6-methylpyridin-3-yl)methyl)-3-(5-methylthiophen-2-yl)imidazo[1,2-a]pyridine-6-carboxamide, (S)—N-(1-(4H-1,2,4-triazol-3-yl)ethyl)-8-(5-methyl-1H-1,2,3-triazol-1-yl)-3-(5-methylthiophen-2-yl)imidazo[1,2-a]pyridine-6-carboxamide, N-((6-methylpyridin-3-yl)methyl)-3-(5-methylthiophen-2-yl)-8-(5-(trifluoromethyl)-1H-1,2,3-triazol-1-yl)imi-dazo[1,2-a]pyridine-6-carboxamide, 8-(5-(difluoromethyl)-1H-1,2,3-triazol-1-yl)-N-((2-meth-ylpyrimidin-5-yl)methyl)-3-(5-methylthiophen-2-yl)imidazo[1,2-a]pyridine-6-carboxamide, 8-(5-(difluoromethyl)-1H-1,2,3-triazol-1-yl)-N-((5-meth-ylpyrazin-2-yl)methyl)-3-(5-methylthiophen-2-yl)imi-dazo[1,2-a]pyridine-6-carboxamide, 8-(5-ethyl-1H-1,2,3-triazol-1-yl)-N-((2-methylpyrimidin-5-yl)methyl)-3-(5-methylthiophen-2-yl)imidazo[1,2-a]pyridine-6-carboxamide, (S)—N-(1-(4H-1,2,4-triazol-3-yl)ethyl)-8-(5-cyclopro-pyl-1H-1,2,3-triazol-1-yl)-3-(5-methylthiophen-2-yl)imidazo[1,2-a]pyridine-6-carboxamide, 8-(5-(difluoromethyl)-1H-1,2,3-triazol-1-yl)-N-((2-methoxypyrimidin-5-yl)methyl)-3-(5-methylthiophen-2-yl)imidazo[1,2-a]pyridine-6-carboxamide, 8-(5-(difluoromethyl)-1H-1,2,3-triazol-1-yl)-N-((6-meth-ylpyridin-3-yl)methyl)-3-(5-methylthiazol-2-yl)imi-dazo[1,2-a]pyridine-6-carboxamide, (S)—N-(1-(4H-1,2,4-triazol-3-yl)ethyl)-8-(5-isopropyl-1H-1,2,3-triazol-1-yl)-3-(5-methylthiophen-2-yl)imi-dazo[1,2-a]pyridine-6-carboxamide, (S)—N-(1-(4H-1,2,4-triazol-3-yl)ethyl)-3-(5-chlorothio-phen-2-yl)-8-(5-(difluoromethyl)-1H-1,2,3-triazol-1-yl)imidazo[1,2-a]pyridine-6-carboxamide, N-((2-methylpyrimidin-5-yl)methyl)-3-(5-methylthio-phen-2-yl)-8-(5-(trifluoromethyl)-1H-1,2,3-triazol-1-yl)imidazo[1,2-a]pyridine-6-carboxamide, 8-(5-isopropyl-1H-1,2,3-triazol-1-yl)-N-((2-methylpy-rimidin-5-yl)methyl)-3-(5-methylthiophen-2-yl)imi-dazo[1,2-a]pyridine-6-carboxamide, 8-(5-cyclopropyl-1H-1,2,3-triazol-1-yl)-N-((2-methylpy-rimidin-5-yl)methyl)-3-(5-methylthiophen-2-yl)imi-dazo[1,2-a]pyridine-6-carboxamide, 8-(5-cyclopropyl-1H-1,2,3-triazol-1-yl)-N-((2-methoxy-pyrimidin-5-yl)methyl)-3-(5-methylthiophen-2-yl)imi-dazo[1,2-a]pyridine-6-carboxamide, (S)—N-(1-(4H-1,2,4-triazol-3-yl)ethyl)-8-(5-cyclobutyl-1H-1,2,3-triazol-1-yl)-3-(5-methylthiophen-2-yl)imi-dazo[1,2-a]pyridine-6-carboxamide, N-((2-methoxypyrimidin-5-yl)methyl)-3-(5-methylthi phen-2-yl)-8-(5-(trifluoromethyl)-1H-1,2,3-triazol-1-yl)imidazo[1,2-a]pyridine-6-carboxamide, 8-(5-isopropyl-1H-1,2,3-triazol-1-yl)-N-((6-methylpyri-din-3-yl)methyl)-3-(5-methylthiophen-2-yl)imidazo[1,2-a]pyridine-6-carboxamide, (S)—N-(1-(4H-1,2,4-triazol-3-yl)ethyl)-8-(5-(tert-butyl)-1H-1,2,3-triazol-1-yl)-3-(5-methylthiophen-2-yl)imi-dazo[1,2-a]pyridine-6-carboxamide, 8-(5-(difluoromethyl)-1H-1,2,3-triazol-1-yl)-N-((2-meth-ylpyrimidin-5-yl)methyl)-3-(5-methylthiazol-2-yl)imi-dazo[1,2-a]pyridine-6-carboxamide, 8-(5-(difluoromethyl)-1H-1,2,3-triazol-1-yl)-3-(5-meth-ylfuran-2-yl)-N-((6-methylpyridin-3-yl)methyl)imi-dazo[1,2-a]pyridine-6-carboxamide, 8-(5-cyclobutyl-1H-1,2,3-triazol-1-yl)-N-((2-methylpy-rimidin-5-yl)methyl)-3-(5-methylthiophen-2-yl)imi-dazo[1,2-a]pyridine-6-carboxamide, (S)—N-(1-(1,3,4-oxadiazol-2-yl)ethyl)-8-(5-(difluorom-ethyl)-1H-1,2,3-triazol-1-yl)-3-(5-methylthiophen-2-yl)imidazo[1,2-a]pyridine-6-carboxamide, (S)—N-(1-(4H-1,2,4-triazol-3-yl)ethyl)-3-(5-cyanothio-phen-2-yl)-8-(5-(difluoromethyl)-1H-1,2,3-triazol-1-yl)imidazo[1,2-a]pyridine-6-carboxamide, (S)—N-(1-(4H-1,2,4-triazol-3-yl)propyl)-8-(5-(difluo-romethyl)-1H-1,2,3-triazol-1-yl)-3-(5-methylthiophen-2-yl)imidazo[1,2-a]pyridine-6-carboxamide, (S)—N-(1-(4H-1,2,4-triazol-3-yl)ethyl)-8-(5-(difluorom-ethyl)-1H-1,2,3-triazol-1-yl)-3-(5-methylthiazol-2-yl)imidazo[1,2-a]pyridine-6-carboxamide, (S)-8-(5-(difluoromethyl)-1H-1,2,3-triazol-1-yl)-N-(2-methyl-1-(4H-1,2,4-triazol-3-yl)propyl)-3-(5-methyl-thiophen-2-yl)imidazo[1,2-a]pyridine-6-carboxamide, 8-(5-cyclobutyl-1H-1,2,3-triazol-1-yl)-N-((2-methylpyrimidin-5-yl)methyl)-3-(5-methylthiazol-2-yl)imidazo[1,2-a]pyridine-6-carboxamide, N-((6-methylpyridin-3-yl)methyl)-3-(5-methylthiazol-2-yl)-8-(5-(trifluoromethyl)-1H-1,2,3-triazol-1-yl)imidazo[1,2-a]pyridine-6-carboxamide, (S)—N-(1-(4H-1,2,4-triazol-3-yl)ethyl)-8-(5-(tert-butyl)-1H-1,2,3-triazol-1-yl)-3-(5-methylthiazol-2-yl)imidazo[1,2-a]pyridine-6-carboxamide, (S)—N-(1-(4H-1,2,4-triazol-3-yl)propyl)-8-(5-ethyl-1H-1,2,3-triazol-1-yl)-3-(5-methylthiophen-2-yl)imidazo[1,2-a]pyridine-6-carboxamide, (S)—N-(1-(4H-1,2,4-triazol-3-yl)ethyl)-8-(5-(difluoromethyl)-1H-1,2,3-triazol-1-yl)-3-(5-(trifluoromethyl)thiophen-2-yl)imidazo[1,2-a]pyridine-6-carboxamide, (S)—N-(1-(4H-1,2,4-triazol-3-yl)ethyl)-8-(5-(difluoromethyl)-1H-1,2,3-triazol-1-yl)-3-(5-methylfuran-2-yl)imidazo[1,2-a]pyridine-6-carboxamide, (S)—N-(1-(4H-1,2,4-triazol-3-yl)propyl)-8-(5-isopropyl-1H-1,2,3-triazol-1-yl)-3-(5-methylthiophen-2-yl)imidazo[1,2-a]pyridine-6-carboxamide, (S)—N-(1-(4H-1,2,4-triazol-3-yl)ethyl)-8-(5-ethyl-1H-1,2,3-triazol-1-yl)-3-(5-methylfuran-2-yl)imidazo[1,2-a]pyridine-6-carboxamide, (S)—N-(1-(4H-1,2,4-triazol-3-yl)ethyl)-3-(5-methylthiophen-2-yl)-8-(5-propyl-1H-1,2,3-triazol-1-yl)imidazo[1,2-a]pyridine-6-carboxamide, N-((2-methylpyrimidin-5-yl)methyl)-3-(5-methylthiazol-2-yl)-8-(5-propyl-1H-1,2,3-triazol-1-yl)imidazo[1,2-a]pyridine-6-carboxamide, 8-(5-(difluoromethyl)-1H-1,2,3-triazol-1-yl)-3-(5-methylfuran-2-yl)-N-((2-methylpyrimidin-5-yl)methyl)imidazo[1,2-a]pyridine-6-carboxamide, 8-(5-(difluoromethyl)-1H-1,2,3-triazol-1-yl)-N-((2-methylpyrimidin-5-yl)methyl)-3-(2-methylthiazol-5-yl)imidazo[1,2-a]pyridine-6-carboxamide, (S)—N-(1-(4H-1,2,4-triazol-3-yl)propyl)-8-(5-(tert-butyl)-1H-1,2,3-triazol-1-yl)-3-(5-methylthiophen-2-yl)imidazo[1,2-a]pyridine-6-carboxamide, N-((2-methylpyrimidin-5-yl)methyl)-3-(5-methylthiazol-2-yl)-8-(5-(trifluoromethyl)-1H-1,2,3-triazol-1-yl)imidazo[1,2-a]pyridine-6-carboxamide, (S)—N-(1-(4H-1,2,4-triazol-3-yl)propyl)-3-(5-chlorothiophen-2-yl)-8-(5-isopropyl-1H-1,2,3-triazol-1-yl)imidazo[1,2-a]pyridine-6-carboxamide, (S)—N-(1-(4H-1,2,4-triazol-3-yl)ethyl)-8-(5-(1,1-difluoroethyl)-1H-1,2,3-triazol-1-yl)-3-(5-methylthiophen-2-yl)imidazo[1,2-a]pyridine-6-carboxamide, 8-(5-(1,1-difluoroethyl)-1H-1,2,3-triazol-1-yl)-N-((2-methylpyrimidin-5-yl)methyl)-3-(5-methylthiazol-2-yl)imidazo[1,2-a]pyridine-6-carboxamide, 8-(5-(1,1-difluoroethyl)-1H-1,2,3-triazol-1-yl)-N-((2-methylpyrimidin-5-yl)methyl)-3-(5-methylthiophen-2-yl)imidazo[1,2-a]pyridine-6-carboxamide, (S)-8-(5-ethyl-1H-1,2,3-triazol-1-yl)-N-(2-methyl-1-(4H-1,2,4-triazol-3-yl)propyl)-3-(5-methylthiophen-2-yl)imidazo[1,2-a]pyridine-6-carboxamide, (S)—N-(2-methyl-1-(4H-1,2,4-triazol-3-yl)propyl)-8-(5-methyl-1H-1,2,3-triazol-1-yl)-3-(5-methylthiophen-2-yl)imidazo[1,2-a]pyridine-6-carboxamide, 8-(5-ethyl-1H-1,2,3-triazol-1-yl)-N-((2-methylpyrimidin-5-yl)methyl)-3-(5-methylthiazol-2-yl)imidazo[1,2-a]pyridine-6-carboxamide, (S)—N-(1-(4H-1,2,4-triazol-3-yl)ethyl)-3-(5-chlorothiophen-2-yl)-8-(5-(1,1-difluoroethyl)-1H-1,2,3-triazol-1-yl)imidazo[1,2-a]pyridine-6-carboxamide, 8-(5-(difluoromethyl)-1H-1,2,3-triazol-1-yl)-N-((5-methylpyrazin-2-yl)methyl)-3-(5-methylthiazol-2-yl)imidazo[1,2-a]pyridine-6-carboxamide, 8-(5-(difluoromethyl)-1H-1,2,3-triazol-1-yl)-3-(5-methylfuran-2-yl)-N-((5-methylpyrazin-2-yl)methyl)imidazo[1,2-a]pyridine-6-carboxamide, (S)—N-(1-(4H-1,2,4-triazol-3-yl)ethyl)-3-(5-chlorothiophen-2-yl)-8-(5-(trifluoromethyl)-1H-1,2,3-triazol-1-yl)imidazo[1,2-a]pyridine-6-carboxamide, N-((2-methylpyrimidin-5-yl)methyl)-3-(5-methylthiophen-2-yl)-8-(5-(2,2,2-trifluoroethyl)-1H-1,2,3-triazol-1-yl)imidazo[1,2-a]pyridine-6-carboxamide, (S)—N-(1-(4H-1,2,4-triazol-3-yl)ethyl)-3-(5-methylthiophen-2-yl)-8-(5-(2,2,2-trifluoroethyl)-1H-1,2,3-triazol-1-yl)imidazo[1,2-a]pyridine-6-carboxamide, N-((2-methylpyrimidin-5-yl)methyl)-3-(5-methylthiazol-2-yl)-8-(5-(2,2,2-trifluoroethyl)-1H-1,2,3-triazol-1-yl)imidazo[1,2-a]pyridine-6-carboxamide, 8-(5-(difluoromethyl)-1H-1,2,3-triazol-1-yl)-N-((6-methoxypyridin-3-yl)methyl)-3-(5-methylthiophen-2-yl)imidazo[1,2-a]pyridine-6-carboxamide, (R)-8-(5-(difluoromethyl)-1H-1,2,3-triazol-1-yl)-N-(1-(2-methylpyrimidin-5-yl)ethyl)-3-(5-methylthiazol-2-yl)imidazo[1,2-a]pyridine-6-carboxamide, (R)-8-(5-(difluoromethyl)-1H-1,2,3-triazol-1-yl)-N-(1-(3-methyl-1,2,4-oxadiazol-5-yl)ethyl)-3-(5-methylthiophen-2-yl)imidazo[1,2-a]pyridine-6-carboxamide, N-((2-methoxypyrimidin-5-yl)methyl)-3-(5-methylthiazol-2-yl)-8-(5-(trifluoromethyl)-1H-1,2,3-triazol-1-yl)imidazo[1,2-a]pyridine-6-carboxamide, 8-(5-(1,1-difluoroethyl)-1H-1,2,3-triazol-1-yl)-N-((6-methylpyridin-3-yl)methyl)-3-(5-methylthiazol-2-yl)imidazo[1,2-a]pyridine-6-carboxamide, (R)-8-(5-ethyl-1H-1,2,3-triazol-1-yl)-N-(1-(3-methyl-1,2,4-oxadiazol-5-yl)ethyl)-3-(5-methylthiophen-2-yl)imidazo[1,2-a]pyridine-6-carboxamide, 2-methyl-5-((3-(5-methylthiophen-2-yl)-8-(phenylamino)imidazo[1,2-a]pyridine-6-carboxamido)methyl)pyridine 1-oxide, N-((1-methyl-2-oxo-1,2-dihydropyridin-4-yl)methyl)-3-(5-methylthiophen-2-yl)-8-(phenylamino)imidazo[1,2-a]pyridine-6-carboxamide, N-((6-methylpyridin-3-yl)methyl)-3-(5-methylthiophen-2-yl)-8-(phenylamino)imidazo[1,2-a]pyridine-6-carboxamide, (S)—N-(1-(4H-1,2,4-triazol-3-yl)ethyl)-3-(5-methylthiophen-2-yl)-8-(thiazol-2-ylamino)imidazo[1,2-a]pyridine-6-carboxamide, N-((1-methyl-2-oxo-1,2-dihydropyridin-4-yl)methyl)-3-(5-methylthiophen-2-yl)-8-(thiazol-2-ylamino)imidazo[1,2-a]pyridine-6-carboxamide, (S)—N-(1-(4H-1,2,4-triazol-3-yl)ethyl)-8-((5-methylthiazol-2-yl)amino)-3-(5-methylthiophen-2-yl)imidazo[1,2-a]pyridine-6-carboxamide, (S)—N-(1-(4H-1,2,4-triazol-3-yl)ethyl)-8-((4-fluorophenyl)amino)-3-(5-methylthiophen-2-yl)imidazo[1,2-a]pyridine-6-carboxamide, (S)—N-(1-(4H-1,2,4-triazol-3-yl)ethyl)-8-((2-methoxyphenyl)amino)-3-(5-methylthiophen-2-yl)imidazo[1,2-a]pyridine-6-carboxamide, 2-methyl-5-((8-(1-methyl-1H-pyrazol-4-yl)-3-(5-methylthiophen-2-yl)imidazo[1,2-a]pyridine-6-carboxamido)methyl)pyridine 1-oxide, 8-(1-methyl-1H-pyrazol-4-yl)-N-((6-methylpyridin-3-yl)methyl)-3-(5-methylthiophen-2-yl)imidazo[1,2-a]pyridine-6-carboxamide, 8-(1-methyl-1H-pyrazol-4-yl)-N-((1-methyl-2-oxo-1,2-dihydropyridin-4-yl)methyl)-3-(5-methylthiophen-2-yl)imidazo[1,2-a]pyridine-6-carboxamide, (S)—N-(1-(4H-1,2,4-triazol-3-yl)ethyl)-8-(1-methyl-1H-pyrazol-5-yl)-3-(5-methylthiophen-2-yl)imidazo[1,2-a]pyridine-6-carboxamide, (S)—N-(1-(4H-1,2,4-triazol-3-yl)ethyl)-3, 8-bis(5-methylthiophen-2-yl)imidazo[1,2-a]pyridine-6-carboxamide, N-((S)-1-(4H-1,2,4-triazol-3-yl)ethyl)-8-(3,5-dimethylisoxazol-4-yl)-3-(5-methylthiophen-2-yl)imidazo[1,2-a]pyridine-6-carboxamide, (S)—N-(1-(4H-1,2,4-triazol-3-yl)ethyl)-8-(1-ethyl-1H-pyrazol-5-yl)-3-(5-methylthiophen-2-yl)imidazo[1,2-a]pyridine-6-carboxamide, (S)—N-(1-(4H-1,2,4-triazol-3-yl)ethyl)-8-(1-(cyclopropylmethyl)-1H-pyrazol-4-yl)-3-(5-methylthiophen-2-yl)imidazo[1,2-a]pyridine-6-carboxamide, (S)—N-(1-(4H-1,2,4-triazol-3-yl)ethyl)-8-(1-(2-fluoroethyl)-1H-pyrazol-4-yl)-3-(5-methylthiophen-2-yl)imidazo[1,2-a]pyridine-6-carboxamide, 8-(3,5-dimethylisoxazol-4-yl)-N-((6-methylpyridin-3-yl)methyl)-3-(5-methylthiophen-2-yl)imidazo[1,2-a]pyridine-6-carboxamide, N—((S)-1-(4H-1,2,4-triazol-3-yl)ethyl)-3-(5-chlorothiophen-2-yl)-8-(3,5-dimethylisoxazol-4-yl)imidazo[1,2-a]pyridine-6-carboxamide, N—((S)-1-(4H-1,2,4-triazol-3-yl)propyl)-8-(3,5-dimethylisoxazol-4-yl)-3-(5-methylthiophen-2-yl)imidazo[1,2-a]pyridine-6-carboxamide, N—((S)-1-(4H-1,2,4-triazol-3-yl)ethyl)-8-(3,5-dimethylisoxazol-4-yl)-3-(5-methylthiazol-2-yl)imidazo[1,2-a]pyridine-6-carboxamide, N—((S)-1-(4H-1,2,4-triazol-3-yl)ethyl)-8-(3,5-dimethyl-1H-pyrazol-4-yl)-3-(5-methylthiophen-2-yl)imidazo[1,2-a]pyridine-6-carboxamide, 8-(3,5-dimethyl-1H-pyrazol-4-yl)-N-((2-methylpyrimidin-5-yl)methyl)-3-(5-methylthiophen-2-yl)imidazo[1,2-a]pyridine-6-carboxamide, (S)—N-(1-(4H-1,2,4-triazol-3-yl)ethyl)-8-(1-(2-amino-2-oxoethyl)-1H-pyrazol-4-yl)-3-(5-methylthiophen-2-yl)imidazo[1,2-a]pyridine-6-carboxamide, (S)—N-(1-(4H-1,2,4-triazol-3-yl)ethyl)-8-(1-ethyl-1H-pyrazol-5-yl)-3-(5-methylthiophen-2-yl)imidazo[1,2-a]pyridine-6-carboxamide, 2-methyl-5-((8-(4-methylpiperidin-1-yl)-3-(propylthio)imidazo[1,2-a]pyridine-6-carboxamido)methyl)pyridine 1-oxide, 8-(4-methylpiperidin-1-yl)-N-((6-methylpyridin-3-yl)methyl)-3-(5-methylthiophen-2-yl)imidazo[1,2-a]pyridine-6-carboxamide, 8-(4-methylpiperidin-1-yl)-N-((5-methylpyrazin-2-yl)methyl)-3-(5-methylthiophen-2-yl)imidazo[1,2-a]pyridine-6-carboxamide, 2-methyl-5-((8-(4-methylpiperidin-1-yl)-3-(5-methylthiophen-2-yl)imidazo[1,2-a]pyridine-6-carboxamido)methyl)pyridine 1-oxide, (S)—N-(1-(4H-1,2,4-triazol-3-yl)ethyl)-3-(5-chlorothiophen-2-yl)-8-(4-methylpiperidin-1-yl)imidazo[1,2-a]pyridine-6-carboxamide, 5-((3-(5-chlorothiophen-2-yl)-8-(4-methylpiperidin-1-yl)imidazo[1,2-a]pyridine-6-carboxamido)methyl)-2-methylpyridine 1-oxide, 5-((8-(cyclohexylamino)-3-(5-methylthiophen-2-yl)imidazo[1,2-a]pyridine-6-carboxamido)methyl)-2-methylpyridine 1-oxide, (S)—N-(1-(4H-1,2,4-triazol-3-yl)ethyl)-8-(cyclohexylamino)-3-(5-methylthiophen-2-yl)imidazo[1,2-a]pyridine-6-carboxamide, 5-((8-(4,4-dimethylpiperidin-1-yl)-3-(5-methylthiophen-2-yl)imidazo[1,2-a]pyridine-6-carboxamido)methyl)-2-methylpyridine 1-oxide, 5-((8-(4,4-difluoropiperidin-1-yl)-3-(5-methylthiophen-2-yl)imidazo[1,2-a]pyridine-6-carboxamido)methyl)-2-methylpyridine 1-oxide, 5-((8-(cyclohexylamino)-3-(5-methylthiophen-2-yl)imidazo[1,2-a]pyridine-6-carboxamido)methyl)-2-(trifluoromethyl)pyridine 1-oxide, 2-methyl-5-((8-(4-methylpiperidin-1-yl)-3-(5-methylthiazol-2-yl)imidazo[1,2-a]pyridine-6-carboxamido)methyl)pyridine 1-oxide, 5-((8-(cyclohexyl(methyl)amino)-3-(5-methylthiophen-2-yl)imidazo[1,2-a]pyridine-6-carboxamido)methyl)-2-methylpyridine 1-oxide, 5-((8-(4-fluoropiperidin-1-yl)-3-(5-methylthiophen-2-yl)imidazo[1,2-a]pyridine-6-carboxamido)methyl)-2-methylpyridine 1-oxide, N-((1-methyl-2-oxo-1,2-dihydropyridin-4-yl)methyl)-8-(4-methylpiperidin-1-yl)-3-(5-methylthiophen-2-yl)imidazo[1,2-a]pyridine-6-carboxamide, (S)—N-(1-(4H-1,2,4-triazol-3-yl)ethyl)-8-(4,4-dimethylpiperidin-1-yl)-3-(5-methylthiophen-2-yl)imidazo[1,2-a]pyridine-6-carboxamide, (S)—N-(1-(4H-1,2,4-triazol-3-yl)ethyl)-8-(4,4-difluoropiperidin-1-yl)-3-(5-methylthiophen-2-yl)imidazo[1,2-a]pyridine-6-carboxamide, 2-methyl-5-((3-(5-methylthiophen-2-yl)-8-(4-(trifluoromethyl)piperidin-1-yl)imidazo[1,2-a]pyridine-6-carboxamido)methyl)pyridine 1-oxide, 5-((8-(4-(fluoromethyl)piperidin-1-yl)-3-(5-methylthiophen-2-yl)imidazo[1,2-a]pyridine-6-carboxamido)methyl)-2-methylpyridine 1-oxide, (S)—N-(1-(4H-1,2,4-triazol-3-yl)ethyl)-8-(4-(fluoromethyl)piperidin-1-yl)-3-(5-methylthiophen-2-yl)imidazo[1,2-a]pyridine-6-carboxamide, (S)—N-(1-(4H-1,2,4-triazol-3-yl)ethyl)-3-(5-methylthiophen-2-yl)-8-(4-(trifluoromethyl)piperidin-1-yl)imidazo[1,2-a]pyridine-6-carboxamide, (S)—N-(1-(4H-1,2,4-triazol-3-yl)ethyl)-8-(cyclopentylamino)-3-(5-methylthiophen-2-yl)imidazo[1,2-a]pyridine-6-carboxamide, (S)—N-(1-(4H-1,2,4-triazol-3-yl)ethyl)-8-(4,4-difluoropiperidin-1-yl)-3-(4-methylthiophen-2-yl)imidazo[1,2-a]pyridine-6-carboxamide, (S)—N-(1-(4H-1,2,4-triazol-3-yl)ethyl)-8-(4-fluoropiperidin-1-yl)-3-(5-methylthiophen-2-yl)imidazo[1,2-a]pyridine-6-carboxamide, N—((S)-1-(4H-1,2,4-triazol-3-yl)ethyl)-8-(3-methoxypyrrolidin-1-yl)-3-(5-methylthiophen-2-yl)imidazo[1,2-a]pyridine-6-carboxamide, (S)—N-(1-(4H-1,2,4-triazol-3-yl)ethyl)-8-(4-methoxy-4-methylpiperidin-1-yl)-3-(5-methylthiophen-2-yl)imidazo[1,2-a]pyridine-6-carboxamide, (S)—N-(1-(4H-1,2,4-triazol-3-yl)ethyl)-8-(4-methoxypiperidin-1-yl)-3-(5-methylthiophen-2-yl)imidazo[1,2-a]pyridine-6-carboxamide, N—((S)-1-(4H-1,2,4-triazol-3-yl)ethyl)-8-(3-methoxypiperidin-1-yl)-3-(5-methylthiophen-2-yl)imidazo[1,2-a]pyridine-6-carboxamide, N—((S)-1-(4H-1,2,4-triazol-3-yl)ethyl)-8-(3-methoxy-3-methylpyrrolidin-1-yl)-3-(5-methylthiophen-2-yl)imidazo[1,2-a]pyridine-6-carboxamide, (S)—N-(1-(1H-pyrazol-3-yl)ethyl)-8-(4,4-difluoropiperi-din-1-yl)-3-(5-methylthiophen-2-yl)imidazo[1,2-a] pyridine-6-carboxamide, (S)—N-(1-(4H-1,2,4-triazol-3-yl)propyl)-8-(4,4-difluoropiperidin-1-yl)-3-(5-methylthiophen-2-yl)imidazo[1,2-a]pyridine-6-carboxamide, (S)-8-(4,4-difluoropiperidin-1-yl)-N-(2-methyl-1-(4H-1,2,4-triazol-3-yl)propyl)-3-(5-methylthiophen-2-yl)imidazo[1,2-a]pyridine-6-carboxamide, 3-((8-(4-methylpiperidin-1-yl)-3-(5-methylthiophen-2-yl)imidazo[1,2-a]pyridine-6-carboxamido)methyl) pyridine 1-oxide, (S)—N-(1-(4H-1,2,4-triazol-3-yl)propyl)-8-(4-methoxypiperidin-1-yl)-3-(5-methylthiophen-2-yl)imidazo[1,2-a]pyridine-6-carboxamide, 8-(4-carbamoyl-4-methylpiperidin-1-yl)-N-((6-methylpyridin-3-yl)methyl)-3-(5-methylthiophen-2-yl)imidazo[1,2-a]pyridine-6-carboxamide, (S)—N-(1-(1H-1,2,4-triazol-5-yl)ethyl)-8-(4-methylpiperidin-1-yl)-3-(m-tolyl)imidazo[1,2-a]pyridine-6-carboxamide, 2-methyl-5-((8-(4-methylpiperidin-1-yl)-3-(o-tolyl)imidazo[1,2-a]pyridine-6-carboxamido)methyl)pyridine 1-oxide, 8-(5-isopropyl-1H-tetrazol-1-yl)-N-((6-methylpyridin-3-yl)methyl)-3-(5-methylthiophen-2-yl)imidazo[1,2-a] pyridine-6-carboxamide, 8-(5-isopropyl-1H-tetrazol-1-yl)-3-(5-methylthiophen-2-yl)-N-((6-(trifluoromethyl)pyridin-3-yl)methyl)imidazo[1,2-a]pyridine-6-carboxamide, 8-(5-ethyl-1H-tetrazol-1-yl)-N-((6-methylpyridin-3-yl)methyl)-3-(5-methylthiophen-2-yl)imidazo[1,2-a]pyridine-6-carboxamide, N-((6-cyclopropylpyridin-3-yl)methyl)-8-(5-ethyl-1H-tetrazol-1-yl)-3-(5-methylthiophen-2-yl)imidazo[1,2-a]pyridine-6-carboxamide, 8-(5-cyclobutyl-1H-tetrazol-1-yl)-N-((6-methylpyridin-3-yl)methyl)-3-(5-methylthiophen-2-yl)imidazo[1,2-a] pyridine-6-carboxamide, 8-(5-(cyclopropylmethyl)-1H-tetrazol-1-yl)-N-((6-methylpyridin-3-yl)methyl)-3-(5-methylthiophen-2-yl)imidazo[1,2-a]pyridine-6-carboxamide, 8-(5-methyl-1H-tetrazol-1-yl)-N-((6-methylpyridin-3-yl)methyl)-3-(5-methylthiophen-2-yl)imidazo[1,2-a]pyridine-6-carboxamide, N-((6-methylpyridin-3-yl)methyl)-3-(5-methylthiophen-2-yl)-8-(5-propyl-1H-tetrazol-1-yl)imidazo[1,2-a]pyridine-6-carboxamide, 8-(5-isopropyl-1H-tetrazol-1-yl)-3-(5-methylthiophen-2-yl)-N-(1-(pyrazin-2-yl)ethyl)imidazo[1,2-a]pyridine-6-carboxamide, 8-(5-cyclobutyl-1H-tetrazol-1-yl)-3-(5-methylthiophen-2-yl)-N-(1-(pyrazin-2-yl)ethyl)imidazo[1,2-a]pyridine-6-carboxamide, 8-(5-cyclobutyl-1H-tetrazol-1-yl)-N-((1-methyl-2-oxo-1,2-dihydropyridin-4-yl)methyl)-3-(5-methylthiophen-2-yl)imidazo[1,2-a]pyridine-6-carboxamide, 8-(5-ethyl-1H-tetrazol-1-yl)-3-(5-methylthiophen-2-yl)-N-(1-(pyrazin-2-yl)ethyl)imidazo[1,2-a]pyridine-6-carboxamide, 8-(5-cyclobutyl-1H-tetrazol-1-yl)-N-((6-methoxypyridin-3-yl)methyl)-3-(5-methylthiophen-2-yl)imidazo[1,2-a]pyridine-6-carboxamide, 8-(5-cyclobutyl-1H-tetrazol-1-yl)-N-((5-methylpyrazin-2-yl)methyl)-3-(5-methylthiophen-2-yl)imidazo[1,2-a]pyridine-6-carboxamide, (S)—N-(1-(4H-1,2,4-triazol-3-yl)ethyl)-8-(5-cyclobutyl-1H-tetrazol-1-yl)-3-(5-methylthiophen-2-yl)imidazo[1,2-a]pyridine-6-carboxamide, (S)—N-(1-(4H-1,2,4-triazol-3-y)ethyl)-8-(5-(cyclopropylmethyl)-1H-tetrazol-1-yl)-3-(5-methylthiophen-2-yl)imidazo[1,2-a]pyridine-6-carboxamide, (S)—N-(1-(4H-1,2,4-triazol-3-yl)ethyl)-8-(5-cyclopropyl-1H-tetrazol-1-yl)-3-(5-methylthiophen-2-yl)imidazo[1,2-a]pyridine-6-carboxamide, (S)—N-(1-(4H-1,2,4-triazol-3-yl)ethyl)-8-(5-(difluoromethyl)-1H-tetrazol-1-yl)-3-(5-methylthiophen-2-yl)imidazo[1,2-a]pyridine-6-carboxamide, 8-(5-(difluoromethyl)-1H-tetrazol-1-yl)-N-((2-methoxypyrimidin-5-yl)methyl)-3-(5-methylthiophen-2-yl)imidazo[1,2-a]pyridine-6-carboxamide, (S)—N-(1-(4H-1,2,4-triazol-3-yl)ethyl)-3-(5-chlorothiophen-2-yl)-8-(5-(difluoromethyl)-1H-tetrazol-1-yl)imidazo[1,2-a]pyridine-6-carboxamide, (S)—N-(1-(4H-1,2,4-triazol-3-yl)propyl)-8-(5-(difluoromethyl)-1H-tetrazol-1-yl)-3-(5-methylthiophen-2-yl)imidazo[1,2-a]pyridine-6-carboxamide, 8-(5-(difluoromethyl)-1H-tetrazol-1-yl)-N-((2-methylpyrimidin-5-yl)methyl)-3-(5-methylthiazol-2-yl)imidazo[1,2-a]pyridine-6-carboxamide, 8-(5-(difluoromethyl)-1H-tetrazol-1-yl)-N-((6-methylpyridin-3-yl)methyl)-3-(5-methylthiazol-2-yl)imidazo[1,2-a]pyridine-6-carboxamide, (S)—N-(1-(4H-1,2,4-triazol-3-yl)propyl)-3-(5-chlorothiophen-2-yl)-8-(5-(difluoromethyl)-1H-tetrazol-1-yl)imidazo[1,2-a]pyridine-6-carboxamide, (S)—N-(1-(4H-1,2,4-triazol-3-yl)ethyl)-3-(5-chlorothiophen-2-yl)-8-(5-cyclopropyl-1H-tetrazol-1-yl)imidazo[1,2-a]pyridine-6-carboxamide, 3-(5-chlorothiophen-2-yl)-8-(5-(difluoromethyl)-1H-tetrazol-1-yl)-N-((2-methylpyrimidin-5-yl)methyl)imidazo[1,2-a]pyridine-6-carboxamide, 8-(5-(difluoromethyl)-1H-tetrazol-1-yl)-N-((2-methylpyrimidin-5-yl)methyl)-3-(5-methylthiophen-2-yl)imidazo[1,2-a]pyridine-6-carboxamide, (S)—N-(1-(4H-1,2,4-triazol-3-yl)ethyl)-8-(5-ethyl-1H-tetrazol-1-yl)-3-(5-methylthiophen-2-yl)imidazo[1,2-a]pyridine-6-carboxamide, (S)—N-(1-(4H-1,2,4-triazol-3-yl)ethyl)-3-(5-methylthiophen-2-yl)-8-(5-propyl-1H-tetrazol-1-yl)imidazo[1,2-a]pyridine-6-carboxamide, (R)-8-(5-(difluoromethyl)-1H-tetrazol-1-yl)-N-(1-(5-methyl-1,3,4-oxadiazol-2-yl)ethyl)-3-(5-methylthiophen-2-yl)imidazo[1,2-a]pyridine-6-carboxamide, (S)—N-(1-(4H-1,2,4-triazol-3-yl)ethyl)-3-(5-methylthiophen-2-yl)-8-(5-(2,2,2-trifluoroethyl)-1H-tetrazol-1-yl)imidazo[1,2-a]pyridine-6-carboxamide, (S)—N-(1-(4H-1,2,4-triazol-3-yl)ethyl)-8-(5-(1,1-difluoroethyl)-1H-tetrazol-1-yl)-3-(5-methylthiophen-2-yl)imidazo[1,2-a]pyridine-6-carboxamide, 8-(5-(difluoromethyl)-1H-tetrazol-1-yl)-3-(5-methylfuran-2-yl)-N-((2-methylpyrimidin-5-yl)methyl)imidazo[1,2-a]pyridine-6-carboxamide, (S)—N-(1-(4H-1,2,4-triazol-3-yl)ethyl)-3-(5-chlorothiophen-2-yl)-8-(5-(1,1-difluoroethyl)-1H-tetrazol-1-yl)imidazo[1,2-a]pyridine-6-carboxamide, 8-(5-(difluoromethyl)-1H-tetrazol-1-yl)-N-((5-methylpyrazin-2-yl)methyl)-3-(5-methylthiazol-2-yl)imidazo[1,2-a]pyridine-6-carboxamide, (R)-8-(5-(1,1-difluoroethyl)-1H-tetrazol-1-yl)-N-(1-(3-methyl-1,2,4-oxadiazol-5-yl)ethyl)-3-(5-methylthiophen-2-yl)imidazo[1,2-a]pyridine-6-carboxamide, (S)—N-(1-(4H-1,2,4-triazol-3-yl)ethyl)-8-(N-methylpropionamido)-3-(5-methylthiophen-2-yl)imidazo[1,2-a]pyridine-6-carboxamide, (S)—N-(1-(4H-1,2,4-triazol-3-yl)ethyl)-8-(N-cyclopropylpropionamido)-3-(5-methylthiophen-2-yl)imidazo[1,2-a]pyridine-6-carboxamide.

8. A pharmaceutical composition comprising an effective amount of a compound of claim 2 and optionally a pharmaceutically acceptable carrier.

9. A kit comprising a compound of claim 2.

10. A method for regulating one or both of the $P2X_3$ or $P2X_{2/3}$ receptors, said method comprising administering an effective amount of a compound of claim 2 to a patient in need thereof.

11. A method according to claim 10, wherein said regulating comprises inhibition.

12. A method for treating pain in a patient, said method comprising administering an effective amount of a compound of claim 2 to said patient.

13. A method according to claim 12, wherein said pain is nociceptive, dysfunctional, idiopathic, neuropathic, somatic, central, visceral, inflammatory, or procedural.

14. A method according to claim 12, wherein said pain is caused by airway, bladder or visceral organ dysfunction.

15. A method according to claim 12, wherein said pain is a migraine, back pain, neck pain, gynecological pain, pre-labor pain, labor pain, orthopedic pain, post-stroke pain, post-surgical pain, post herpetic neuralgia, sickle cell crises, interstitial cystitis, urological pain, dental pain, headache, wound pain, surgical pain, suturing, fracture setting pain, or biopsy.

16. A method according to claim 12, wherein said pain is due to inflammation, nerve compression, or a mechanical force resulting from tissue distension as a consequence of invasion by a tumor and tumor metastasis into bone or other tissues.

17. A method according to claim 12, wherein said pain is caused by esophageal cancer, colitis, cystitis, irritable bowel syndrome, or idiopathic neuropathy.

18. A method according to claim 13, wherein said somatic pain comprises pain from bone, joint, muscle, skin, or connective tissue.

19. A method according to claim 13, wherein said central pain comprises pain from brain trauma, stroke, or spinal cord injury.

20. A method according to claim 13, wherein said visceral pain comprises pain from the respiratory tract, gastrointestinal tract, pancreas, urinary tract or reproductive organs.

21. A method according to claim 13, wherein said dysfunctional pain comprises pain from a rheumatologic condition, tension type headache, irritable bowel disorder or erythermalgia.

22. A method according to claim 13, wherein said nociceptive pain comprises pain from a cut, bruise, bone fracture, crush injury, burn, trauma, surgery, labor, sprain, bump, injection, dental procedure, skin biopsy, or obstruction.

23. A method according to claim 13, wherein said neuropathic pain comprises pain is due to trauma, surgery, herniation of an intervertebral disk, spinal cord injury, diabetes, infection with herpes zoster, HIV/AIDS, late-stage cancer, amputation, carpal tunnel syndrome, chronic alcohol use, exposure to radiation, or an unintended side-effect of a neurotoxic treatment agent.

24. A method according to claim 13, wherein said inflammatory pain comprises pain is due to joint injury, muscle injury, tendon injury, surgical procedures, infection, or arthritis.

25. A method according to claim 13, wherein said procedural pain comprises pain from medical, dental or surgical procedure.

26. A method according to claim 25, wherein said procedural pain is postoperative pain, associated with an injection, draining an abscess, surgery, dermatological, dental procedure, ophthalmic procedure, arthroscopy, or cosmetic surgery.

27. A method according to claim 12, wherein said pain is caused by cancer.

28. A method according to claim 27, wherein said cancer is bone cancer.

29. A method according to claim 12, wherein said administration is oral, intramuscular, rectal, cutaneous, subcutaneous, topical, transdermal, sublingual, nasal, vaginal, epidural, intrathecal, intravesical, or ocular.

30. A method for modulating one or both of the $P2X_3$ or $P2X_{2/3}$ pathways comprising administering an effective amount of a compound of claim 2 to a patient in need thereof.

* * * * *

UNITED STATES PATENT AND TRADEMARK OFFICE
CERTIFICATE OF CORRECTION

PATENT NO.         : 9,944,637 B2
APPLICATION NO.    : 15/105526
DATED              : April 17, 2018
INVENTOR(S)        : Thompson et al.

It is certified that error appears in the above-identified patent and that said Letters Patent is hereby corrected as shown below:

In the Claims

In Column 220
At Line 20, please change "NR R$^6$" to -- NR$^5$ R$^6$ --; and at Line 50, please change "triazol-11-yl" to -- triazol-1-yl) --

Signed and Sealed this
Thirtieth Day of October, 2018

Andrei Iancu
*Director of the United States Patent and Trademark Office*